US011274094B2

(12) United States Patent
Fatheree et al.

(10) Patent No.: US 11,274,094 B2
(45) Date of Patent: Mar. 15, 2022

(54) SUBSTITUTED BENZENECARBOXAMIDES AS IL-17A MODULATORS

(71) Applicant: DiCE Alpha, Inc., South San Francisco, CA (US)

(72) Inventors: Paul R. Fatheree, South San Francisco, CA (US); Martin S. Linsell, South San Francisco, CA (US); John R. Jacobsen, South San Francisco, CA (US); Wouter A. Van Der Linden, South San Francisco, CA (US); Timothy J. Church, South San Francisco, CA (US); Claudio Aquino, South San Francisco, CA (US); Margot G. Paulick, South San Francisco, CA (US)

(73) Assignee: DICE ALPHA, INC., South San Francisco, CA (US)

( * ) Notice: Subject to any disclaimer, the term of this patent is extended or adjusted under 35 U.S.C. 154(b) by 0 days.

(21) Appl. No.: 17/118,947

(22) Filed: Dec. 11, 2020

(65) Prior Publication Data

US 2021/0101886 A1 Apr. 8, 2021

Related U.S. Application Data

(63) Continuation of application No. PCT/US2020/050924, filed on Sep. 15, 2020, which is a continuation of application No. 16/783,268, filed on Feb. 6, 2020, and a continuation of application No. PCT/US2020/016925, filed on Feb. 6, 2020.

(60) Provisional application No. 63/061,719, filed on Aug. 5, 2020, provisional application No. 62/901,249, filed on Sep. 16, 2019.

(51) Int. Cl.
| | |
|---|---|
| *A61K 31/167* | (2006.01) |
| *C07C 233/07* | (2006.01) |
| *C07D 403/12* | (2006.01) |
| *C07D 241/04* | (2006.01) |
| *C07D 401/12* | (2006.01) |
| *C07D 471/04* | (2006.01) |
| *C07D 413/12* | (2006.01) |
| *C07D 455/02* | (2006.01) |
| *C07D 403/14* | (2006.01) |

(52) U.S. Cl.
CPC ......... *C07D 403/12* (2013.01); *C07D 241/04* (2013.01); *C07D 401/12* (2013.01); *C07D 403/14* (2013.01); *C07D 413/12* (2013.01); *C07D 455/02* (2013.01); *C07D 471/04* (2013.01)

(58) Field of Classification Search
CPC .............................. A61K 31/167; C07C 233/07
USPC .......................................... 514/613; 564/123
See application file for complete search history.

(56) References Cited

U.S. PATENT DOCUMENTS

| | | |
|---|---|---|
| 3,536,809 A | 10/1970 | Applezweig et al. |
| 3,598,123 A | 8/1971 | Zaffaroni |
| 3,710,795 A | 1/1973 | Higuchi et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |
| 5,900,252 A | 5/1999 | Calanchi et al. |
| 5,922,356 A | 7/1999 | Koseki et al. |

(Continued)

FOREIGN PATENT DOCUMENTS

| | | |
|---|---|---|
| WO | WO-2005025506 A2 | 3/2005 |
| WO | WO-2013116682 A1 | 8/2013 |

(Continued)

OTHER PUBLICATIONS

Appel et al. Analysis of IL-17(+) cells in facet joints of patients with spondyloarthritis suggests that the innate immune pathway might be of greater relevance than the Th17-mediated adaptive immune response Arthritis Res Therap 13:R95 (2011-).

(Continued)

*Primary Examiner* — Douglas M Willis

(74) *Attorney, Agent, or Firm* — Wilson Sonsini Goodrich & Rosati

(57) ABSTRACT

The disclosure herein provides compounds and pharmaceutical compositions for the modulation of IL-17A useful for the treatment of inflammatory conditions, such as psoriasis.

60 Claims, No Drawings

(56) References Cited

U.S. PATENT DOCUMENTS

| | | | |
|---|---|---|---|
| 5,948,433 | A | 9/1999 | Burton et al. |
| 5,972,366 | A | 10/1999 | Haynes et al. |
| 5,972,891 | A | 10/1999 | Kamei et al. |
| 5,980,945 | A | 11/1999 | Ruiz |
| 5,983,134 | A | 11/1999 | Ostrow |
| 5,985,307 | A | 11/1999 | Hanson et al. |
| 5,985,317 | A | 11/1999 | Venkateshwaran et al. |
| 5,993,855 | A | 11/1999 | Yoshimoto et al. |
| 6,004,534 | A | 12/1999 | Langer et al. |
| 6,010,715 | A | 1/2000 | Wick et al. |
| 6,024,975 | A | 2/2000 | D'Angelo et al. |
| 6,039,975 | A | 3/2000 | Shah et al. |
| 6,045,830 | A | 4/2000 | Igari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 2020/0247785 | A1 | 8/2020 | Fatheree et al. |

FOREIGN PATENT DOCUMENTS

| | | | |
|---|---|---|---|
| WO | WO-2014066726 | A2 | 5/2014 |
| WO | WO-2020163554 | A1 | 8/2020 |
| WO | WO-2021055376 | A1 | 3/2021 |

OTHER PUBLICATIONS

Brittain Polymorphism in Pharmaceutical Solids, (Brittain, H. ed.), Marcel Dekker, Inc. New York, (1999). Chapter 6, pp. 205-208.
Buchwald et al. Long-term, continuous intravenous heparin administration by an implantable infusion pump in ambulatory patients with recurrent venous thrombosis. Surgery 88:507-516 (1980).
Dudler et al. Effect of interleukin 17 on proteoglycan degradation in murine knee joints. Ann Rheum Dis 59:529-32 (2000).
Fingl et al. Chapter 1: General Principles. In: The Pharmacological basis of therapeutics (pp. 1-46) (1975).
Gaffen. Biology of recently discovered cytokines: interleukin-17—a unique inflammatory cytokine with roles in bone biology and arthritis. Arthritis Res Therapy 6:240-247 (2004).
Gaffen. Structure and signalling in the IL-17 receptor family. Nature Rev Immunol 9:556-567 (2009).
Goodson. Chapter 6: Dental Applications. Medical Applications of Controlled Release 2:115-138 (1984).
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Jens. Chapter 12: Preformulation. Drug Stability: Principles & Practice, 2d. Ed., Marcel Dekker, NY, NY, 1995, pp. 361-385.
Ji et al. Th17 cells: positive or negative role in tumor? Cancer Immunol Immunother 59:979-987 (2010).
Langer. New methods of drug delivery. Science 249:1527-1533 (1990).
Lubberts et al. IL-1-independent role of IL-17 in synovial inflammation and joint destruction during collagen-induced arthritis. J Immunol 167:1004-1013 (2001).
Matthews. Professor Paul Matthews talks 'big data' within multiple sclerosis. Neurodegener Dis Manag 5:101-104 (2015).
Matusevicius et al. Interleukin-17 mRNA expression in blood and CSF mononuclear cells is augmented in multiple sclerosis. Mult Scler 5(2):101-4 (1999).
Nakae et al. Suppression of immune induction of collagen-induced arthritis in IL-17-deficient mice. J Immunol 171:6173-6177 (2003).
PCT/US2020/016925 International Search Report and Written Opinion dated Apr. 17, 2020.
Prabhala et al. Elevated IL-17 produced by Th17 cells promotes myeloma cell growth and inhibits immune function in multiple myeloma. Blood 115(26):5385-5392 (2010).
Saudek et al. A preliminary trial of the programmable implantable medication system for insulin delivery. N. Engl. J. Med. 321:574 (1989).
Sefton. Implantable pumps. Crit Rev Biomed Eng 14(3):201-240 (1987).
Spriggs et al. Interleukin-17 and its receptor. J Clin Immunol 17:366-369 (1997).
Van Bezooijen et al. Interleukin 17 synergises with tumour necrosis factor alpha to induce cartilage destruction in vitro. Ann Rheum Dis 61:870-876 (2002).
Zhang et al. Increased intratumoral IL-17-producing cells correlate with poor survival in hepatocellular carcinoma patients. J Hepatol 50:980-89 (2009).
PCT/US2020/050924 International Search Report and Written Opinion dated Oct. 21, 2020.
2013RN 1469885-68-4, registry database compound (2013).
U.S. Appl. No. 16/783,268 Office Action dated Oct. 12, 2021.

SUBSTITUTED BENZENECARBOXAMIDES AS IL-17A MODULATORS

CROSS-REFERENCE

This application is the by-pass continuation of International Application No. PCT/US2020/050924, filed on Sep. 15, 2020, which application claims the benefit of U.S. Provisional Patent Application No. 62/901,249, filed on Sep. 16, 2019, U.S. Provisional Patent Application No. 63/061,719, filed on Aug. 5, 2020, U.S. Non-Provisional application Ser. No. 16/783,268, filed on Feb. 6, 2020, and International Application No. PCT/US2020/016925, filed on Feb. 6, 2020, the entire contents of each of which are incorporated herein by reference.

BACKGROUND OF THE INVENTION

Interleukin-17A ("IL-17A"), is a pro-inflammatory cytokine, which is a glycoprotein (Spriggs et al., J Clin Immunol, 17: 366-369 (1997)) that stimulates secretion of various other cytokines in a variety of cell types. For example, IL-17A induces IL-6, IL-8, G-CSF, TNF-α, IL-10, PGE2, and IFN-γ, as well as numerous chemokines and other effectors (Gaffen, Arthritis Research & Therapy 6: 240-247 (2004)). IL-17A is expressed by Th17 cells, which are involved in the pathology of inflammation and autoimmunity and also by CD8+ T cells, γδ cells, NK cells, NKT cells, macrophages and dendritic cells. IL-17A and Th17 are also necessary for defense against various microbes despite their involvement in inflammation and autoimmune disorders.

IL-17A can form homodimers or heterodimers with its family member, IL-17F. IL-17A binds to both IL-17 RA and IL-17 RC to mediate signaling. IL-17A, signaling through its receptor, activates the NF-κB transcription factor, as well as various MAPKs (Gaffen, S L, Nature Rev Immunol, 9: 556-567 (2009)). IL-17A can act in cooperation with other inflammatory cytokines such as TNF-α, IFN-γ, and IL-1β to mediate pro-inflammatory effects (Gaffen, Arthritis Research & Therapy 6: 240-247 (2004)). Increased levels of IL-17A have been implicated in numerous diseases, including, but not limited to, rheumatoid arthritis (RA), bone erosion, intraperitoneal abscesses, inflammatory bowel disease, allograft rejection, psoriasis, angiogenesis, atherosclerosis, asthma, and multiple sclerosis. IL-17A and IL-17A-producing Th17 cells have also recently been implicated in certain cancers (Ji and Zhang, Cancer Immunol Immunother 59: 979-987 (2010)). For example, IL-17-expressing Th17 cells were shown to be involved in multiple myeloma (Prabhala et al., Blood, online DOI 10.1182/blood-2009-10-246660, April 15 (2010)) and to correlate with poor prognosis in patients with hepatocellular carcinoma (HCC) (Zhang et al., J Hepatology 50: 980-89 (2009)).

Clearly modulation of IL-17A has important therapeutic implications. However, despite its therapeutic importance relatively few examples of small molecule modulators of IL-17A are known. Accordingly, there is a need for the development of small molecule modulators of IL-17A for use in treating disease.

SUMMARY OF THE INVENTION

In certain aspects, the disclosure provides a compound represented by the structure of Formula I:

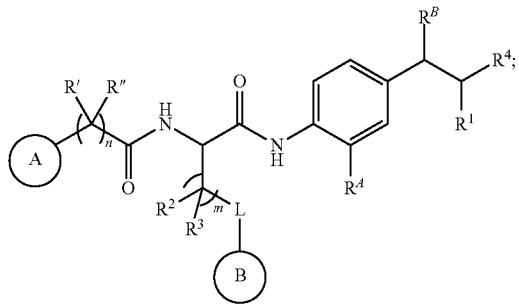

(I)

or a pharmaceutically acceptable salt thereof wherein:

is selected from an optionally substituted $C_{3-12}$ carbocycle and optionally substituted 3- to 12-membered heterocycle wherein one or more substituents on Ring A are independently selected at each occurrence from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$S(O)R^{11}$, —$S(O)_2R^{11}$, —$NO_2$, =O, =S, =$N(R^{11})$, —CN; and $C_{1-10}$ alkyl, $C_{2-10}$ alkenyl, $C_{2-10}$ alkynyl, each of which is optionally substituted with one or more substituents independently selected from halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$S(O)R^{11}$, —$S(O)_2R^{11}$, —$NO_2$, =O, =S, =$N(R^{11})$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =$N(R^{11})$, and —CN; and $C_{3-12}$ carbocycle and 3- to 12-membered heterocycle, each of which is optionally substituted with one or more substituents independently selected from: halogen, —$OR^{11}$, —$SR^{11}$, —$N(R^{11})_2$, —$C(O)R^{11}$, —$C(O)N(R^{11})_2$, $N(R^{11})C(O)R^{11}$, —$C(O)OR^{11}$, —$OC(O)R^{11}$, —$NO_2$, —CN, $C_{1-6}$ alkyl and $C_{1-6}$ haloalkyl;

is selected from an optionally substituted $C_{3-10}$ carbocycle and optionally substituted 3- to 12-membered heterocycle wherein one or more substituents on Ring B are independently selected at each occurrence from: halogen, —$OR^{12}$, —$SR^{12}$, —$N(R^{12})_2$, —$C(O)R^{12}$, —$C(O)N(R^{12})_2$, —$N(R^{12})C(O)R^{12}$, —$C(O)OR^{12}$, —$OC(O)R^{12}$, —$S(O)R^{12}$, —$S(O)_2R^{12}$, —$NO_2$, =O, =S, =$N(R^{12})$, —CN; and C$_{1-10}$ alkyl, C$_{2-10}$ alkenyl, C$_{2-10}$ alkynyl, each of which is optionally substituted with one or more substituents independently selected from halogen, —OR$^{12}$, —SR$^{12}$, —N(R$^{12}$)$_2$, —C(O)R$^{12}$, —C(O)N(R$^{12}$)$_2$, N(R$^{12}$)C(O)R$^{12}$, —C(O)OR$^{12}$, —OC(O)R$^{12}$, —S(O)R$^{12}$, —S(O)$_2$R$^{12}$, —NO$_2$, =O, =S, =N(R$^{12}$), —CN, C$_{3-10}$ carbocycle and 3- to 10-membered heterocycle; wherein the C$_{3-10}$ carbocycle and 3- to 10-membered heterocycle are each optionally substituted with one or more substituents selected from: halogen, —OR$^{12}$, —N(R$^{12}$)$_2$, —C(O)R$^{12}$, —C(O)N(R$^{12}$)$_2$, —N(R$^{12}$)C(O)R$^{12}$, —C(O)OR$^{12}$, —OC(O)R$^{12}$, —NO$_2$, =O, =N(R$^{11}$), and —CN;

R$^4$ is selected from —C(O)N(R$^{23}$)(R$^{24}$) and

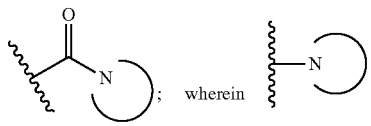; wherein 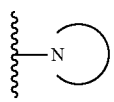

is an optionally substituted 4- to 9-membered heterocycle wherein the optional substituents on are independently selected at each occurrence from:
halogen, —OR$^{13}$, —SR$^{13}$, —N(R$^{13}$)$_2$, —C(O)R$^{13}$, —C(O)N(R$^{13}$)$_2$, —N(R$^{13}$)C(O)R$^{13}$, —C(O)OR$^{13}$, —OC(O)R$^{13}$, —S(O)R$^{13}$, —S(O)$_2$R$^{13}$, —NO$_2$, =O, =S, =N(R$^{13}$), —CN; and C$_{1-10}$ alkyl, C$_{2-10}$ alkenyl, C$_{2-10}$ alkynyl, each of which is optionally substituted with one or more substituents independently selected from halogen, —OR$^{13}$, —SR$^{13}$, —N(R$^{13}$)$_2$, —C(O)R$^{13}$, —C(O)N(R$^{13}$)$_2$, N(R$^{13}$)C(O)R$^{13}$, —C(O)OR$^{13}$, —OC(O)R$^{13}$, —S(O)R$^{13}$, —S(O)$_2$R$^{13}$, —NO$_2$, =O, =S, =N(R$^{13}$), —CN, C$_{3-10}$ carbocycle and 3- to 10-membered heterocycle, wherein the C$_{3-10}$ carbocycle and 3- to 10-membered heterocycle are each optionally substituted with one or more substituents selected from: halogen, —OR$^{13}$, —N(R$^{13}$)$_2$, —C(O)R$^{13}$, —C(O)N(R$^{13}$)$_2$, —N(R$^{13}$)C(O)R$^{13}$, —C(O)OR$^{13}$, —OC(O)R$^{13}$, —NO$_2$, =O, =N(R$^{13}$), and —CN;

L is absent or selected from —O— and —NH—;

R$^A$ is selected from hydrogen, halogen, —OR$^{14}$, —N(R$^{14}$)$_2$, —C(O)R$^{14}$, —C(O)N(R$^{14}$)$_2$, —N(R$^{14}$)C(O)R$^{14}$, —C(O)OR$^{14}$, —OC(O)R$^{14}$, —NO$_2$, —CN, and C$_{1-6}$ alkyl, wherein C$_{1-6}$ alkyl is optionally substituted with one or more substituents selected from: halogen, OR$^{14}$, —N(R$^{14}$)$_2$, —C(O)R$^{14}$, NO$_2$, =O, and —CN;

R$^B$ is selected from hydrogen, halogen, —OR$^{15}$, —N(R$^{15}$)$_2$, —C(O)R$^{15}$, —C(O)N(R$^{15}$)$_2$, —N(R$^{15}$)C(O)R$^5$, —C(O)OR$^{15}$, —OC(O)R$^{15}$, —NO$_2$, —CN, and C$_{1-6}$ alkyl, wherein C$_{1-6}$ alkyl is optionally substituted with one or more substituents selected from: halogen, OR$^{15}$, —N(R$^{15}$)$_2$, —C(O)R$^{15}$, NO$_2$, =O, and —CN, wherein at least one of R$^A$ or R$^B$ is not hydrogen;

R' and R" are independently selected from:
hydrogen, halogen, —OR$^{16}$, and C$_{1-6}$ alkyl; wherein the C$_{1-6}$ alkyl is optionally substituted with one or more substituents selected from: halogen, —OR$^{16}$, —N(R$^{16}$)$_2$, —C(O)R$^{16}$, —NO$_2$, =O, and —CN;

R$^1$ is selected from —OR$^{21}$, —N(R$^{21}$)(R$^{22}$), —N(R$^{21}$)C(O)R$^{22}$, —N(R$^{21}$)C(O)OR$^{22}$, —N(R$^{21}$)C(O)N(R$^{21}$)(R$^{22}$), —N(R$^{21}$)S(=O)$_2$N(R$^{21}$)(R$^{22}$), and —N(R$^{21}$)S(=O)$_2$(R$^{22}$);

each R$^2$ and R$^3$ are independently selected from:
hydrogen, halogen, —OR$^{17}$, C$_{1-6}$ alkyl, and C$_{3-6}$ cycloalkyl; wherein the C$_{1-6}$ alkyl and C$_{3-6}$ cycloalkyl are optionally substituted with one or more substituents selected from: halogen, —OR$^{17}$, —N(R$^{17}$)$_2$, —C(O)R$^{17}$, —NO$_2$, =O, and —CN; or R$^2$ and R$^3$ bound to the same carbon come together to form a C$_{3-6}$ cycloalkyl optionally substituted with one or more substituents selected from halogen, —OR$^{17}$, —N(R$^{17}$)$_2$, —C(O)R$^{17}$, —NO$_2$, =O, and —CN;

R$^{21}$ is independently selected at each occurrence from hydrogen and C$_1$-C$_6$ alkyl optionally substituted by one or more substituents independently selected from halogen, —OR$^{17}$, —N(R$^{17}$)$_2$, —C(O)R$^{17}$, —NO$_2$, =O, and —CN;

R$^{22}$ is selected from:
C$_{1-10}$ alkyl, C$_{2-10}$ alkenyl, C$_{2-10}$ alkynyl, each of which is optionally substituted with one or more substituents independently selected from halogen, —OR$^{18}$, —SR$^{18}$, —N(R$^{18}$)$_2$, —C(O)R$^{18}$, —C(O)N(R$^{18}$)$_2$, —N(R$^{18}$)C(O)Rig, —C(O)OR$^{11}$, —OC(O)R$^{18}$, —S(O)R$^{18}$, —S(O)$_2$R$^{18}$, —NO$_2$, =O, =S, =N(R$^{18}$), —CN, C$_{3-10}$ carbocycle and 3- to 10-membered heterocycle; wherein the C$_{3-10}$ carbocycle and 3- to 10-membered heterocycle are each optionally substituted with one or more substituents selected from: halogen, —OR$^{18}$, —N(R$^{18}$)$_2$, —C(O)R$^{18}$, —C(O)N(R$^{18}$)$_2$, —N(R$^{18}$)C(O)R$^{18}$, —C(O)OR$^{18}$, —OC(O)R$^{18}$, —NO$_2$, =O, =N(R$^{18}$), and —CN; and C$_{3-12}$ carbocycle and 3- to 12-membered heterocycle, each of which is optionally substituted with one or more substituents independently selected from: halogen, —OR$^{18}$, —SR$^{18}$, —N(R$^{18}$)$_2$, —C(O)R$^{11}$, —C(O)N(R$^{11}$)$_2$, —N(R$^{18}$)C(O)R$^{18}$, —C(O)OR$^{18}$, —OC(O)R$^{18}$, —S(O)R$^{18}$, —S(O)$_2$R$^{18}$, —NO$_2$, =O, =S, =N(R$^{18}$), —CN; and C$_{1-10}$ alkyl, C$_{2-10}$ alkenyl, C$_{2-10}$ alkynyl, each of which is optionally substituted with one or more substituents independently selected from halogen, —OR$^{18}$, —SR$^{18}$, —N(R$^{18}$)$_2$, —C(O)R$^{11}$, —C(O)N(R$^{11}$)$_2$, —N(R$^{18}$)C(O)R$^{18}$, —C(O)OR$^{18}$, —OC(O)R$^{18}$, —S(O)R$^{18}$, —S(O)$_2$R$^{18}$, —NO$_2$, =O, =S, =N(R$^{18}$), —CN, C$_{3-10}$ carbocycle and 3- to 10-membered heterocycle; wherein the C$_{3-10}$ carbocycle and 3- to 10-membered heterocycle are each optionally substituted with one or more substituents selected from: halogen, —OR$^{18}$, —N(R$^{18}$)$_2$, —C(O)R$^{18}$, —C(O)N(R$^{11}$)$_2$, —N(R$^{18}$)C(O)R$^{18}$, —C(O)OR$^{18}$, —OC(O)R$^{18}$, —NO$_2$, =O, =N(R$^{18}$), and —CN; and C$_{3-10}$ carbocycle and 3- to 10-membered heterocycle are each optionally substituted with one or more substituents selected from: halogen, —OR$^{18}$, —N(R$^{18}$)$_2$, —C(O)R$^{18}$, —C(O)N(R$^{11}$)$_2$, N(R$^{18}$)C(O)R$^{18}$, —C(O)OR$^{18}$, —OC(O)R$^{18}$, —NO$_2$, =O, =N(R$^{18}$), and —CN;

$R^{23}$ is selected from:
- $C_{1-6}$ alkyl optionally substituted with one or more substituents independently selected from halogen, —$OR^{19}$, —$SR^{19}$, —$N(R^{19})_2$, —$NO_2$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{19}$, —$N(R^{19})_2$, =O, $C_1$-$C_6$ alkyl, $C_1$-$C_6$ haloalkyl, and —CN; and
- $C_{3-12}$ carbocycle and 3- to 12-membered heterocycle, each of which is optionally substituted with one or more substituents independently selected from halogen, —$OR^{19}$, —$N(R^{19})_2$, =O, $C_1$-$C_6$ alkyl, $C_1$-$C_6$ haloalkyl, and —CN;

$R^{24}$ is selected from hydrogen and $C_{1-6}$ alkyl optionally substituted with one or more substituents independently selected from halogen, —$OR^{19}$, —$SR^{19}$, —$N(R^{19})_2$, —$NO_2$, —CN, $C_{3-6}$ carbocycle and 3- to 6-membered heterocycle;

$R^{11}$, $R^{12}$, $R^{13}$, $R^{14}$, $R^{15}$, $R^{16}$, $R^{17}$, $R^{18}$, and $R^{19}$ are independently selected at each occurrence from:
hydrogen; and
- $C_{1-6}$ alkyl optionally substituted with one or more substituents independently selected from halogen, —OH, —O—$C_1$-$C_6$ alkyl, —O—$C_1$-$C_6$ haloalkyl —$NH_2$, —$NO_2$, =O, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —OH, —O—$C_1$-$C_6$ alkyl, —O—$C_1$-$C_6$ haloalkyl —$NH_2$, —$NO_2$, =O, and —CN; and
- $C_{3-12}$ carbocycle and 3- to 12-membered heterocycle, each of which is optionally substituted with one or more substituents independently selected from: halogen, —OH, —O—$C_1$-$C_6$ alkyl, —O—$C_1$-$C_6$ haloalkyl —$NH_2$, —$NO_2$, =O, —CN; and
- $C_{1-6}$ alkyl optionally substituted with one or more substituents independently selected from halogen, —OH, —O—$C_1$-$C_6$ alkyl, —O—$C_1$-$C_6$ haloalkyl —$NH_2$, —$NO_2$, =O, and —CN;

n is selected from 0 and 1; and
m is selected from 0, 1, and 2.

In certain embodiments, the disclosure provides a compound or salt of Formula (I), represented by any one of Formulas (IA), (IB), (IC), (ID), (II), (III), or (IV).

In certain embodiments, the disclosure provides a pharmaceutical composition comprising a compound or salt of any one of Formulas (I'), (IA), (IB), (IC), (ID), (II), (III), or (IV) and a pharmaceutically acceptable excipient.

In certain embodiments, the disclosure provides method of treating an inflammatory disease or condition comprising administering to a subject in there thereof a compound or salt of any one of Formulas (I'), (IA), (IB), (IC), (ID), (II), (III), or (IV). In certain embodiments, the inflammatory disease or condition is selected from, plaque psoriasis, guttate psoriasis, inverse psoriasis, pustular psoriasis, erythrodermic psoriasis, aspsoriatic arthritis, ankyslosing spondylitis, hidradenitis suppurutiva, rheumatoid arthritis, Palmoplantar Psoriasis, Spondyloarthritis, and Non-infectious Uveitis. In certain embodiments, the inflammatory disease or condition is psoriasis.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "$C_{x-y}$" when used in conjunction with a chemical moiety, such as alkyl, alkenyl, or alkynyl is meant to include groups that contain from x to y carbons in the chain. For example, the term "$C_{1-6}$ alkyl" refers to saturated hydrocarbon groups, including straight-chain alkyl and branched-chain alkyl groups that contain from 1 to 6 carbons. The term —$C_{x-y}$alkylene- refers to a substituted or unsubstituted alkylene chain with from x to y carbons in the alkylene chain. For example —$C_{1-6}$alkylene- may be selected from methylene, ethylene, propylene, butylene, pentylene, and hexylene, any one of which is optionally substituted.

The terms "$C_{x-y}$alkenyl" and "$C_{x-y}$alkynyl" refer to unsaturated aliphatic groups analogous in length and possible substitution to the alkyls described above, but that contain at least one double or triple bond, respectively. The term —$C_{x-y}$alkenylene- refers to a substituted or unsubstituted alkenylene chain with from x to y carbons in the alkenylene chain. For example, —$C_{2-6}$alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene-refers to a substituted or unsubstituted alkynylene chain with from x to y carbons in the alkynylene chain. For example, —$C_{2-6}$alkynylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a straight divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. Alkylene chain may be optionally substituted by one or more substituents such as those substituents described herein.

"Alkenylene" refers to a straight divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. Alkenylene chain may be optionally substituted by one or more substituents such as those substituents described herein.

"Alkynylene" refers to a straight divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. Alkynylene chain may be optionally substituted by one or more substituents such as those substituents described herein.

The term "carbocycle" as used herein refers to a saturated, unsaturated or aromatic ring in which each atom of the ring is carbon. Carbocycle include 3- to 10-membered monocyclic rings and 6- to 12-membered bicyclic rings. Each ring of a bicyclic carbocycle may be selected from saturated, unsaturated, and aromatic rings. Bicyclic carbocycles may be fused, bridged or spiro-ring systems. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Carbocycle may be optionally substituted by one or more substituents such as those substituents described herein.

The term "cycloalkyl" as used herein refers to a saturated carbocycle. Exemplary cycloalkyl rings include cyclopropyl, cyclohexyl, and norbornane. Cycloalkyl may be optionally substituted by one or more substituents such as those substituents described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings and 6- to 12-membered bicyclic rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. Bicyclic heterocycles may be fused, bridged or spiro-ring systems. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Heterocycle may be optionally substituted by one or more substituents such as those substituents described herein.

The term "heteroaryl" includes aromatic single ring structures, preferably 5- to 6-membered rings, whose ring structures include at least one heteroatom, preferably one to four heteroatoms, more preferably one or two heteroatoms. The term "heteroaryl" also includes polycyclic ring systems having two or more rings in which two or more atoms are common to two adjoining rings wherein at least one of the rings is heteroaromatic, e.g., the other rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like. Heteroaryl may be optionally substituted by one or more substituents such as those substituents described herein.

The term "heterocycloalkyl" as used herein refers to a saturated heterocycle. Exemplary heterocycloalkyl rings include morpholinyl, piperidinyl, and piperazinyl. Heterocycloalkyl may be optionally substituted by one or more substituents such as those substituents described herein.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^b$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2), and —$R^b$—S(O)$_t$N($R^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain. It will be understood by those skilled in the art that substituents can themselves be substituted, if appropriate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

The terms "administer", "administered", "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The terms "administer", "administered", "administers" and "administering" a compound should be understood to mean providing a compound of the invention or a prodrug of a compound of the invention to the individual in need.

The term "effective amount" or "therapeutically effective amount" refers to that amount of a compound or salt described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term can also apply to a dose that can induce a particular response in target cells, e.g., reduction of proliferation or down regulation of activity of a target protein. The specific dose can vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition, and can contemplate a range of results directed to that end, including but not restricted to prevention of the condition entirely.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

Compounds

In some aspects, the present disclosure provides a compound represented by the structure of Formula (I):

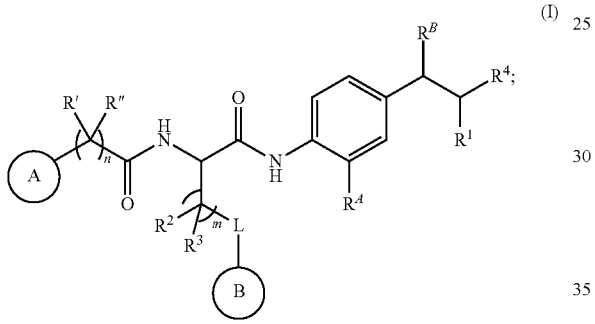

or a pharmaceutically acceptable salt thereof wherein:

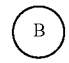

is selected from an optionally substituted $C_{3-12}$ carbocycle and optionally substituted 3- to 12-membered heterocycle wherein one or more substituents on Ring A are independently selected at each occurrence from: halogen, $-OR^{11}$, $-SR^{11}$, $-N(R^{11})_2$, $-C(O)R^{11}$, $-C(O)N(R^{11})_2$, $-N(R^{11})C(O)R^{11}$, $-N(R^{11})S(O)_2R^{11}$, $-C(O)OR^{11}$, $-OC(O)R^{11}$, $-S(O)R^{11}$, $-S(O)_2R^{11}$, $-NO_2$, $=O$, $=S$, $=N(R^{11})$, $-CN$; and $C_{1-10}$ alkyl, $C_{2-10}$ alkenyl, $C_{2-10}$ alkynyl, each of which is optionally substituted with one or more substituents independently selected from halogen, $-OR^{11}$, $-SR^{11}$, $-N(R^{11})_2$, $-C(O)R^{11}$, $-C(O)N(R^{11})_2$, $-N(R^{11})C(O)R^{11}$, $-C(O)OR^{11}$, $-OC(O)R^{11}$, $-S(O)R^{11}$, $-S(O)_2R^{11}$, $-NO_2$, $=O$, $=S$, $=N(R^{11})$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{11}$, $-N(R^{11})_2$, $-C(O)R^{11}$, $-C(O)N(R^{11})_2$, $-N(R^{11})C(O)R^{11}$, $-C(O)OR^{11}$, $-OC(O)R^{11}$, $-NO_2$, $=O$, $=N(R^{11})$, and $-CN$; and $C_{3-12}$ carbocycle and 3- to 12-membered heterocycle, each of which is optionally substituted with one or more substituents independently selected from: halogen, $-OR^{11}$, $-SR^{11}$, $-N(R^{11})_2$, $-C(O)R^{11}$, $-C(O)N(R^{11})_2$, $N(R^{11})C(O)R^{11}$, $-C(O)OR^{11}$, $-OC(O)R^{11}$, $-NO_2$, $-CN$, $C_{1-6}$ alkyl and $C_{1-6}$ haloalkyl;

B as selected from an optionally substituted $C_{3-10}$ carbocycle and optionally substituted 3- to 12-membered heterocycle wherein one or more substituents on Ring B are independently selected at each occurrence from: halogen, $-OR^{12}$, $-SR^{12}$, $-N(R^{12})_2$, $-C(O)R^{12}$, $-C(O)N(R^{12})_2$, $-N(R^{12})C(O)R^2$, $-C(O)OR^{12}$, $-OC(O)R^{12}$, $-S(O)R^{12}$, $-S(O)_2R^{12}$, $-NO_2$, $=O$, $=S$, $=N(R^{12})$, $-CN$; and $C_{1-10}$ alkyl, $C_{2-10}$ alkenyl, $C_{2-10}$ alkynyl, each of which is optionally substituted with one or more substituents independently selected from halogen, $-OR^{12}$, $-SR^{12}$, $-N(R^{12})_2$, $-C(O)R^{12}$, $-C(O)N(R^1)_2$, $N(R^{12})C(O)R^{12}$, $-C(O)OR^{12}$, $-OC(O)R^{12}$, $-S(O)R^{12}$, $-S(O)_2R^{12}$, $-NO_2$, $=O$, $=S$, $=N(R^{12})$, $-CN$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, $-OR^{12}$, $-N(R^{12})_2$, $-C(O)R^{12}$, $-C(O)N(R^1)_2$, $-N(R^{12})C(O)R^2$, $-C(O)OR^{12}$, $-OC(O)R^{12}$, $-NO_2$, $=O$, $=N(R^{11})$, and $-CN$;

$R^4$ is selected from $-C(O)N(R^{23})(R^{24})$ and

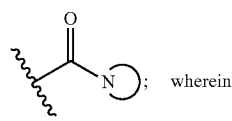 [SMILES: *C(N)=O]; wherein wherein

is an optionally substituted 4- to 9-membered heterocycle wherein the optional substituents on

are independently selected at each occurrence from: halogen, $-OR^{13}$, $-SR^{13}$, $-N(R^{13})_2$, $-C(O)R^{13}$, $-C(O)N(R^{13})_2$, $-N(R^{13})C(O)R^{13}$, $-C(O)OR^{13}$, $-OC(O)R^{13}$, $-S(O)R^{13}$, $-S(O)_2R^{13}$, $-NO_2$, $=O$, $=S$, $=N(R^{13})$, $-CN$; and $C_{1-10}$ alkyl, $C_{2-10}$ alkenyl, $C_{2-10}$ alkynyl, each of which is optionally substituted with one or more substituents independently selected from halogen, —$OR^{13}$, —$SR^{13}$, —$N(R^{13})_2$, —$C(O)R^{13}$, —$C(O)N(R^{13})_2$, $N(R^{13})C(O)R^{13}$, —$C(O)OR^{13}$, —$OC(O)R^{13}$, —$S(O)R^{13}$, —$S(O)_2R^{13}$, —$NO_2$, $=O$, $=S$, $=N(R^{13})$, —CN, $C_{3-10}$ carbocycle and 3- to 10-membered heterocycle, wherein the $C_{3-10}$ carbocycle and 3- to 10-membered heterocycle are each optionally substituted with one or more substituents selected from: halogen, —$OR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, $=O$, $=N(R^{13})$, and —CN;

L is absent or selected from —O— and —NH—;

$R^A$ is selected from hydrogen, halogen, —$OR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, —CN, and $C_{1-6}$ alkyl, wherein $C_{1-6}$ alkyl is optionally substituted with one or more substituents selected from: halogen, $OR^{14}$, —$N(R^{14})_2$, —$C(O)R^{14}$, $NO_2$, $=O$, and —CN;

$R^B$ is selected from hydrogen, halogen, —$OR^{15}$, —$N(R^{15})_2$, —$C(O)R^{15}$, —$C(O)N(R^{15})_2$, —$N(R^{15})C(O)R^5$, —$C(O)OR^{15}$, —$OC(O)R^{15}$, —$NO_2$, —CN, and $C_{1-6}$ alkyl, wherein $C_{1-6}$ alkyl is optionally substituted with one or more substituents selected from: halogen, $OR^{15}$, —$N(R^{15})_2$, —$C(O)R^{15}$, $NO_2$, $=O$, and —CN, wherein at least one of $R^A$ or $R^B$ is not hydrogen;

R' and R" are independently selected from:
hydrogen, halogen, —$OR^{16}$, and $C_{1-6}$ alkyl; wherein the $C_{1-6}$ alkyl is optionally substituted with one or more substituents selected from: halogen, —$OR^{16}$, —$N(R^{16})_2$, —$C(O)R^{16}$, —$NO_2$, $=O$, and —CN;

$R^1$ is selected from —$OR^{21}$, —$N(R^{21})(R^{22})$, —$N(R^{21})C(O)R^{22}$, —$N(R^{21})C(O)OR^{22}$, —$N(R^{21})C(O)N(R^{21})(R^{22})$, —$N(R^{21})S(=O)_2N(R^{21})(R^{22})$, and —$N(R^{21})S(=O)_2(R^{22})$;

each $R^2$ and $R^3$ are independently selected from:
hydrogen, halogen, —$OR^{17}$, $C_{1-6}$ alkyl, and $C_{3-6}$ cycloalkyl; wherein the $C_{1-6}$ alkyl and $C_{3-6}$ cycloalkyl are optionally substituted with one or more substituents selected from: halogen, —$OR^{17}$, —$N(R^{17})_2$, —$C(O)R^{17}$, —$NO_2$, $=O$, and —CN; or
$R^2$ and $R^3$ bound to the same carbon come together to form a $C_{3-6}$ cycloalkyl optionally substituted with one or more substituents selected from halogen, —$OR^{17}$, —$N(R^{17})_2$, —$C(O)R^{17}$, —$NO_2$, $=O$, and —CN;

$R^{21}$ is independently selected at each occurrence from hydrogen and $C_1$-$C_6$ alkyl optionally substituted by one or more substituents independently selected from halogen, —$OR^{17}$, —$N(R^{17})_2$, —$C(O)R^{17}$, —$NO_2$, $=O$, and —CN;

$R^{22}$ is selected from:
$C_{1-10}$ alkyl, $C_{2-10}$ alkenyl, $C_{2-10}$ alkynyl, each of which is optionally substituted with one or more substituents independently selected from halogen, —$OR^{18}$, —$SR^{18}$, —$N(R^{18})_2$, —$C(O)R^{18}$, —$C(O)N(R^{18})_2$, —$N(R^{18})C(O)Rig$, —$C(O)OR^{11}$, —$OC(O)R^{18}$, —$S(O)R^{18}$, —$S(O)_2R^{18}$, —$NO_2$, $=O$, $=S$, $=N(R^{18})$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{18}$, —$N(R^{18})_2$, —$C(O)R^{18}$, —$C(O)N(R^{18})_2$, —$N(R^{18})C(O)R^{18}$, —$C(O)OR^{18}$, —$OC(O)R^{18}$, —$NO_2$, $=O$, $=N(R^{18})$, and —CN; and $C_{3-12}$ carbocycle and 3- to 12-membered heterocycle, each of which is optionally substituted with one or more substituents independently selected from:
halogen, —$OR^{18}$, —$SR^{18}$, —$N(R^{18})_2$, —$C(O)R^{11}$, —$C(O)N(R^{11})_2$, —$N(R^{18})C(O)R^{18}$, —$C(O)OR^{18}$, —$OC(O)R^{18}$, —$S(O)R^{18}$, —$S(O)_2R^{18}$, —$NO_2$, $=O$, $=S$, $=N(R^{18})$, —CN; and $C_{1-10}$ alkyl, $C_{2-10}$ alkenyl, $C_{2-10}$ alkynyl, each of which is optionally substituted with one or more substituents independently selected from halogen, —$OR^{18}$, —$SR^{18}$, —$N(R^{18})_2$, —$C(O)R^{18}$, —$C(O)N(R^{11})_2$, —$N(R^{18})C(O)R^{18}$, —$C(O)OR^{18}$, —$OC(O)R^{18}$, —$S(O)R^{18}$, —$S(O)_2R^{18}$, —$NO_2$, $=O$, $=S$, $=N(R^{18})$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{18}$, —$N(R^{18})_2$, —$C(O)R^{18}$, —$C(O)N(R^{11})_2$, —$N(R^{18})C(O)R^{18}$, —$C(O)OR^{18}$, —$OC(O)R^{18}$, —$NO_2$, $=O$, $=N(R^{18})$, and —CN; and $C_{3-10}$ carbocycle and 3- to 10-membered heterocycle are each optionally substituted with one or more substituents selected from: halogen, —$OR^{18}$, —$N(R^{18})_2$, —$C(O)R^{18}$, —$C(O)N(R^{11})_2$, $N(R^{18})C(O)R^{18}$, —$C(O)OR^{18}$, —$OC(O)R^{18}$, —$NO_2$, $=O$, $=N(R^{18})$, and —CN;

$R^{23}$ is selected from:
$C_{1-6}$ alkyl optionally substituted with one or more substituents independently selected from halogen, —$OR^{19}$, —$SR^{19}$, —$N(R^{19})_2$, —$NO_2$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{19}$, —$N(R^{19})_2$, $=O$, $C_1$-$C_6$ alkyl, $C_1$-$C_6$ haloalkyl, and —CN; and $C_{3-12}$ carbocycle and 3- to 12-membered heterocycle, each of which is optionally substituted with one or more substituents independently selected from halogen, —$OR^{19}$, —$N(R^{19})_2$, $=O$, $C_1$-$C_6$ alkyl, $C_1$-$C_6$ haloalkyl, and —CN;

$R^{24}$ is selected from hydrogen and $C_{1-6}$ alkyl optionally substituted with one or more substituents independently selected from halogen, —$OR^{19}$, —$SR^{19}$, —$N(R^{19})_2$, —$NO_2$, —CN, $C_{3-6}$ carbocycle and 3- to 6-membered heterocycle;

$R^{11}$, $R^{12}$, $R^{13}$, $R^{14}$, $R^{15}$, $R^{16}$, $R^{17}$, $R^{18}$, and $R^{19}$ are independently selected at each occurrence from:
hydrogen; and
$C_{1-6}$ alkyl optionally substituted with one or more substituents independently selected from halogen, —OH, —O—$C_1$-$C_6$ alkyl, —O—$C_1$-$C_6$ haloalkyl —$NH_2$, —$NO_2$, $=O$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —OH, —O—$C_1$-$C_6$ alkyl, —O—$C_1$-$C_6$ haloalkyl —$NH_2$, —$NO_2$, $=O$, and —CN; and $C_{3-12}$ carbocycle and 3- to 12-membered heterocycle, each of which is optionally substituted with one or more substituents independently selected from:

halogen, —OH, —O—C$_1$-C$_6$ alkyl, —O—C$_1$-C$_6$ haloalkyl —NH$_2$, —NO$_2$, =O, —CN; and C$_{1-6}$ alkyl optionally substituted with one or more substituents independently selected from halogen, —OH, —O—C$_1$-C$_6$ alkyl, —O—C$_1$-C$_6$ haloalkyl —NH$_2$, —NO$_2$, =O, and —CN;

n is selected from 0 and 1; and m is selected from 0, 1, and 2.

In some embodiments, for a compound or salt of Formula (I), R$^A$ is selected from hydrogen, fluorine, —OR$^{14}$, and C$_{1-6}$ alkyl optionally substituted with one or more substituents selected from: halogen, —OR$^{14}$, —NO$_2$, =O, and —CN. In some embodiments, R$^A$ is selected from hydrogen, fluorine, chlorine, bromine, iodine, —OR$^{14}$, and C$_{1-6}$ alkyl optionally substituted with one or more substituents selected from: halogen, —OR$^{14}$, —NO$_2$, =O, and —CN. In some embodiments, R$^A$ is selected from hydrogen, fluorine and chlorine. In some embodiments, R$^A$ is fluorine.

In certain embodiments, a compound of Formula (I) is selected from Formula (II):

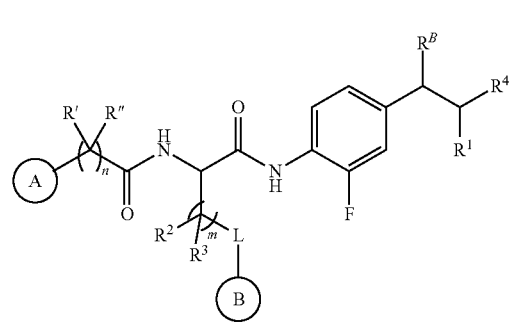

or a salt thereof.

In some embodiments, for a compound or salt of Formula (I) or (II), R$^B$ is selected from hydrogen, —OR$^1$, and C$_{1-6}$ alkyl optionally substituted with one or more substituents selected from: halogen, —OR$^1$, —NO$_2$, =O, and —CN. In some embodiments, R$^B$ is selected from —OMe, —OEt, —CF$_3$, —CHF$_2$, —CH$_2$F, methyl, ethyl, propyl, and isopropyl. In some embodiments, R$^B$ is selected from methyl, —CF$_3$, —CHF$_2$, and —CH$_2$F. In some embodiments, R$^B$ is selected from methyl, ethyl, propyl, and isopropyl. In some embodiments, R$^B$ is methyl.

In certain embodiments, a compound of Formula (I) is represented by Formula (III):

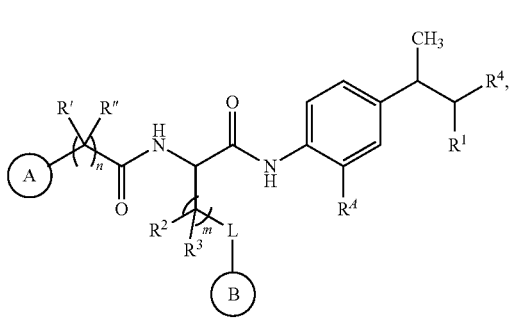

or a salt thereof.

In some embodiments, for a compound or salt of Formula (I), R$^A$ is fluorine and R$^B$ is methyl. In some embodiments, a compound Formula (I) is represented by Formula (IV):

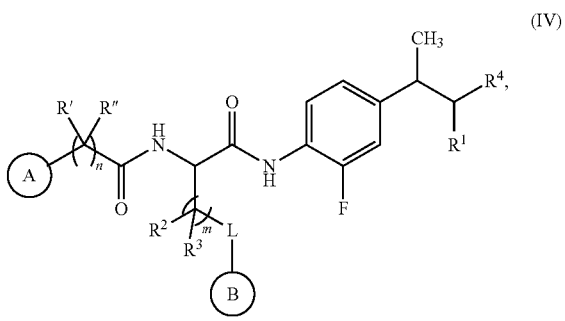

or a salt thereof.

In some embodiments, a compound or salt of the disclosure is represented by Formula (I'):

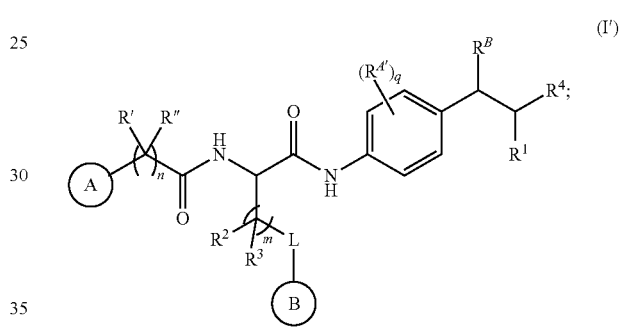

wherein Ring A, Ring B, n, m, R', R", R$^2$, R$^3$, L, R$^B$, R$^1$, and R$^4$ are as described for Formula (I); q is selected from 0, 1, 2, 3, or 4; and R$^{A'}$ is independently selected at each occurrence from halogen, —OR$^{14}$, —N(R$^{14}$)$_2$, —C(O)R$^{14}$, —C(O)N(R$^{14}$)$_2$, —N(R$^{14}$)C(O)R$^{14}$, —C(O)OR$^{14}$, —OC(O)R$^{14}$, —NO$_2$, —CN, and C$_{1-6}$ alkyl, wherein C$_{1-6}$ alkyl is optionally substituted with one or more substituents selected from: halogen, —OR$^{14}$, —N(R$^{14}$)$_2$, —C(O)R$^{14}$, —NO$_2$, =O, and —CN; wherein q is at least 1 when R$^B$ is hydrogen. In certain embodiments, for a compound or salt of Formula (I'), R$^{A'}$ is independently selected at each occurrence from halogen, —OR$^{14}$, —N(R$^{14}$)$_2$, —C(O)R$^{14}$, —NO$_2$, —CN, C$_{1-6}$ alkyl, and C$_{1-6}$ haloalkyl. In certain embodiments, for a compound or salt of Formula (I'), R$^{A'}$ is independently selected at each occurrence from halogen, —OR$^{14}$, —N(R$^{14}$)$_2$, —CN, C$_{1-3}$ alkyl, and C$_{1-3}$ haloalkyl. In certain embodiments, q is selected from 0, 1, or 2. In certain embodiments, q is 1.

In some embodiments, for the compound or salt of Formula (I), (I'), (II), (III), and (IV), Ring A is selected from an optionally substituted C$_{3-12}$ carbocycle. In some embodiments, the optionally substituted C$_{3-12}$ carbocycle of Ring A is saturated. In some embodiments, the optionally substituted C$_{3-12}$ carbocycle of Ring A is unsaturated. In some embodiments, the optionally substituted C$_{3-12}$ carbocycle of Ring A is selected from C$_{3-6}$ carbocycle, C$_{3-7}$ carbocycle, or C$_{3-9}$ carbocycle, any of which is optionally substituted. In some embodiments, the optionally substituted C$_{3-12}$ carbocycle of Ring A is a C$_{5-12}$ carbocycle selected from a spirocycle, fused bicycle, and bridged bicycle. In some embodiments, the optionally substituted $C_{3-12}$ carbocycle of Ring A is an optionally substituted $C_{3-6}$ carbocycle. In some embodiments, the optionally substituted $C_{3-6}$ carbocycle of Ring A is selected from an optionally substituted $C_{3-6}$ cycloalkyl and optionally substituted phenyl.

In some embodiments, for the compound or salt of Formula (I), (I'), (II), (III), and (IV), Ring A is selected from an optionally substituted 3- to 12-membered heterocycle. In some embodiments, the optionally substituted 3- to 12-membered heterocycle of Ring A is saturated. In some embodiments, the optionally substituted 3- to 12-membered heterocycle is unsaturated. In certain embodiments, the optionally substituted 3-12-membered heterocycle is a 5-9-membered heterocyle such as a 5-9-membered heteroaromatic compounds. In some embodiments, the 5- to 12-membered heterocycle of Ring A is selected from a spirocycle, fused bicycle, and bridged bicycle. In some embodiments, the optionally substituted 3- to 12-membered heterocycle is of Ring A is selected from an optionally substituted 5-, 6- or 9-membered heteroaryl or optionally substituted 9- to 10-membered heterocycle.

In some embodiments, for a compound or salt of Formula (I), (I'), (II), (III), and (IV), the optionally substituted 3- to 12-membered heterocycle of Ring A comprises at least one heteroatom selected from oxygen, nitrogen, and sulfur. In some embodiments, the optionally substituted 3- to 12-membered heterocycle of Ring A comprises at least one heteroatom selected from oxygen, and nitrogen. In some embodiments, Ring A is selected from an optionally substituted 5- to 10-membered heteroaryl comprising at least one heteroatom selected from oxygen, nitrogen, and sulfur.

In some embodiments, for the compound or salt of Formula (I), (I'), (II), (III), and (IV), substituents on Ring A are independently selected from:
halogen, —$OR^{11}$, —$N(R^{11})_2$, —$N(R^{11})C(O)R^{11}$, —$N(R^{11})S(O)_2R^{11}$, —$NO_2$, =O, and —CN; and
$C_{1-6}$ alkyl optionally substituted with one or more substituents independently selected from halogen, —$OR^{11}$, —$N(R^{11})_2$, —CN, $C_{3-6}$ carbocycle and 3- to 6-membered heterocycle; wherein the $C_{3-6}$ carbocycle and 3- to 6-membered heterocycle are each optionally substituted with one or more substituents selected from: halogen, —$OR^{11}$, —$N(R^{11})_2$, —$NO_2$, =O, —CN; and $C_{3-6}$ carbocycle and 3- to 6-membered heterocycle, each of which is optionally substituted with one or more substituents independently selected from: halogen, —$OR^{11}$, —$NO_2$, —CN, $C_{1-6}$ alkyl and $C_{1-6}$ haloalkyl.

In some embodiments, for the compound or salt of Formula (I), (I'), (II), (III), and (IV), Ring A is selected from an optionally substituted $C_3$-$C_6$ carbocycle, optionally substituted 5- to 6-membered monocyclic heterocycle, and an optionally substituted 8- to 9-membered bicyclic heterocycle. In some embodiments, Ring A is selected from optionally substituted cyclopropyl, optionally substituted cyclohexyl, optionally substituted phenyl, optionally substituted 5- to 6-membered heteroaryl, and optionally substituted 8- to 9-membered bicyclic heterocycle.

In some embodiments, for the compound or salt of Formula (I), (I'), (II), (III), and (IV), Ring A is selected from cyclopropyl, cyclohexyl, phenyl, pyridine, pyrimidine, pyrazole, thiazole, thiophene, indazole, tetrazole, oxadiazole, oxazole, isoxazole, imidazole, pyrrole, furan, benzothiophene, benzofuran, thieno[2,3-c]pyridine, thieno[2,3-b]pyridine, furo[3,2-c]pyridine, 4,6-dihydrofuro[3,4-b]furan, and benzodioxole any one of which is optionally substituted.

In some embodiments, for the compound or salt of Formula (I), (I'), (II), (III), and (IV), n is 0. In some embodiments, for the compound or salt of Formula (I), (I'), (II), (III), and (IV), n is 1.

In some embodiments, for the compound or salt of Formula (I), (I'), (II), (III), and (IV), n is 0 and Ring A is selected from an optionally substituted 5-membered monocyclic heterocycle, and an optionally substituted 8- to 9-membered bicyclic heterocycle. In some embodiments, Ring A is selected from optionally substituted 5-membered monocyclic heteroaryl, and optionally substituted 8- to 9-membered bicyclic heterocycle. In some embodiments, the optionally substituted 5-membered monocyclic heteroaryl and optionally substituted 8- to 9-membered bicyclic heterocycle comprise at least one heteroatom selected from nitrogen, oxygen, and sulfur.

In some embodiments, for the compound or salt of Formula (I), (I'), (II), (III), and (IV), Ring A is selected from an optionally substituted 5-membered monocyclic heteroaryl. In some embodiments, the optionally substituted 5-membered monocyclic heteroaryl is optionally substituted with one or more substituents independently selected from halogen, —$OR^{11}$, —$N(R^{11})_2$, —$N(R^{11})S(O)_2R^{11}$, —$NO_2$, —CN, $C_{1-6}$ alkyl, —$C_{1-6}$ alkyl-$C_{3-5}$ carbocycle, $C_{3-5}$ carbocycle, and 3- to 5-membered heterocycle. In some embodiments, the optionally substituted 5-membered monocyclic heteroaryl is substituted by a single substituent, wherein the single substituent is selected from halogen, —$OR^{11}$, —$N(R^{11})_2$, —$C(O)R^{11}$, —$NO_2$, —CN, $C_{1-6}$ alkyl, —$C_{1-6}$ alkyl-$C_{3-5}$ carbocycle, $C_{3-5}$ carbocycle, and 3- to 5-membered heterocycloalkyl.

In some embodiments, for the compound or salt of Formula (I), (I'), (II), (III), and (IV), the optionally substituted 5-membered monocyclic heteroaryl is selected from pyrazole, tetrazole, oxadiazole, isoxazole, pyrrole, and furan, any one of which is optionally substituted. In some embodiments, the optionally substituted 5-membered monocyclic heteroaryl is selected from pyrazole, tetrazole, oxadiazole, isoxazole, pyrrole, and furan are optionally substituted with one or more substituents independently selected from halogen, —$OR^{11}$, —$N(R^{11})_2$, —$N(R^{11})S(O)_2R^{11}$, —$NO_2$, —CN, $C_{1-6}$ alkyl, —$C_{1-6}$ alkyl-$C_{3-5}$ carbocycle, $C_{3-5}$ carbocycle, and 3- to 5-membered heterocycle. In some embodiments, the optionally substituted 5-membered monocyclic heteroaryl is selected from pyrazole, tetrazole, oxadiazole, isoxazole, pyrrole, and furan any one of which is substituted by a single substituent, wherein the single substituent is selected from halogen, —$OR^{11}$, —$N(R^{11})_2$, —$C(O)R^{11}$, —$NO_2$, —CN, $C_{1-6}$ alkyl, —$C_{1-6}$ alkyl-$C_{3-5}$ carbocycle, $C_{3-5}$ carbocycle, and 3- to 5-membered heterocycloalkyl.

In some embodiments, for the compound or salt of Formula (I), (I'), (II), (III), and (IV), the 5-membered monocyclic heteroaryl of Ring A is substituted with a single substituent selected from —$OR^{11}$, $C_{1-6}$ alkyl, —$C_{1-6}$ alkyl-$C_{3-5}$ carbocycle, $C_{3-5}$ carbocycle, 3- to 5-membered heterocycloalkyl, wherein $R^{11}$ is selected from $C_{1-6}$ alkyl. In some embodiments, Ring A is selected from pyrazole, tetrazole, oxadiazole, isoxazole, pyrrole, and furan any of which is substituted with a single substituent selected from —$OR^{11}$, $C_{1-6}$ alkyl, —$C_{1-6}$ alkyl-$C_{3-5}$ carbocycle, $C_{3-5}$ carbocycle, 3- to 5-membered heterocycloalkyl, wherein $R^{11}$ is selected from $C_{1-6}$ alkyl. In some embodiments, Ring A is selected from:

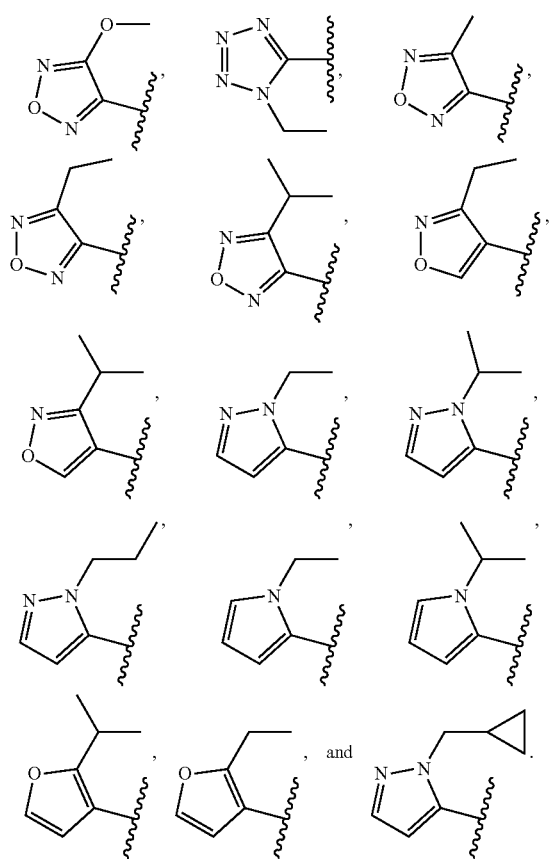

In some embodiments, Ring A is selected from

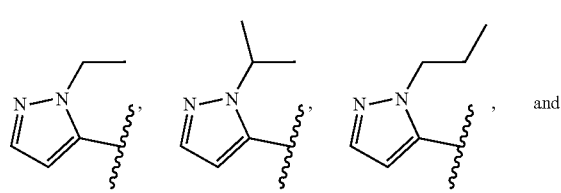

In some embodiments, Ring A is selected from

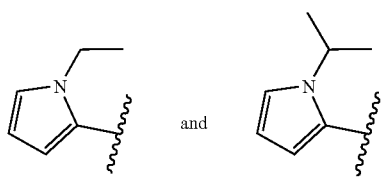

In some embodiments, Ring A is selected from

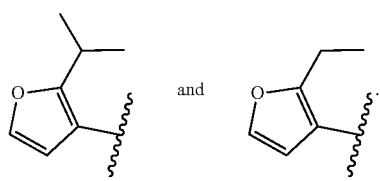

In some embodiments, Ring A is selected from

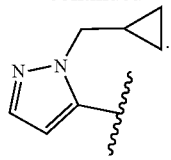

In some embodiments, Ring A is selected from

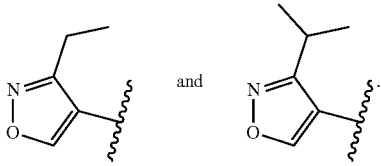

In some embodiments, Ring A is selected from

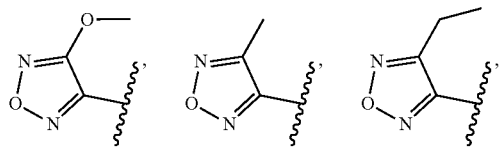

In some embodiments, Ring A is

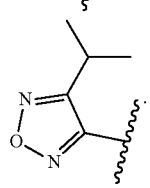

In some embodiments, for the compound or salt of Formula (I), (I'), (II), (III), and (IV), the 5-membered monocyclic heteroaryl of Ring A is substituted with one or more substituents independently selected from optionally substituted $C_{3-6}$ carbocycle and optionally substituted 3- to 6-membered heterocycle. In some embodiments, Ring A is selected from isoxazole and pyrazole each of which is substituted with one or more substituents independently selected from optionally substituted $C_{3-6}$ carbocycle and optionally substituted 3- to 6-membered heterocycle. In some embodiments, Ring A is selected from:

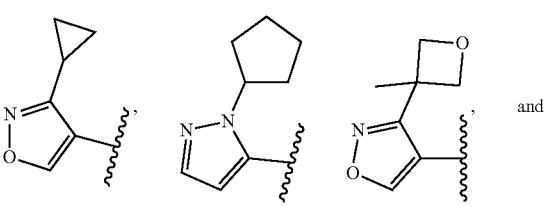

-continued

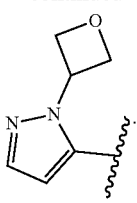

In some embodiments, Ring A is selected from

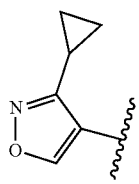 and 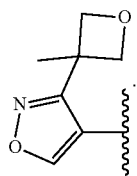

In some embodiments, Ring A is selected from

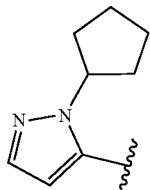 and 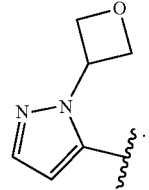

In some embodiments, for the compound or salt of Formula (I), (I'), (II), (III), and (IV), Ring A is an optionally substituted 8- to 9-membered heterocycle. In some embodiments, the 8- to 9-membered heterocycle is optionally substituted by one or more substituents independently selected from halogen, —OR$^{11}$, —NO$_2$, —CN, and C$_{1-6}$ alkyl. In some embodiments, the 8- to 9-membered heterocycle is aromatic. In some embodiments, Ring A is selected from a bicyclic ring, wherein the bicyclic ring is a 5-6 fused ring system and the 5-membered ring contains no more than one nitrogen. In some embodiments, Ring A is selected from a bicyclic ring, wherein the bicyclic ring is a 5-6 fused ring system and the 5-membered ring contains at least one heteroatom selected from oxygen, sulfur, and any combination thereof. In some embodiments, Ring A is selected from a bicyclic ring, wherein the bicyclic ring is selected from an optionally substituted fused furan or an optionally substituted fused thiophene. In some embodiments, Ring A is selected from a bicyclic ring, wherein the bicyclic ring is not selected from a fused pyrazole. In some embodiments, Ring A is selected from:

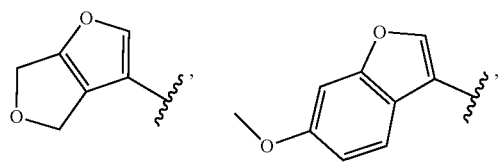

-continued

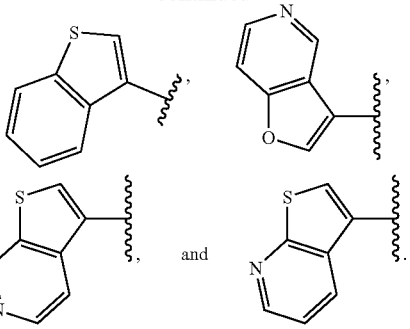

In some embodiments, Ring A is selected from

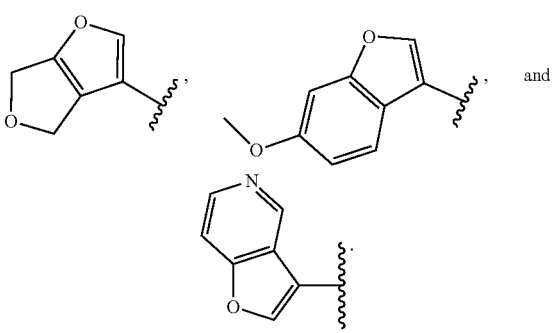

In some embodiments, Ring A is selected from

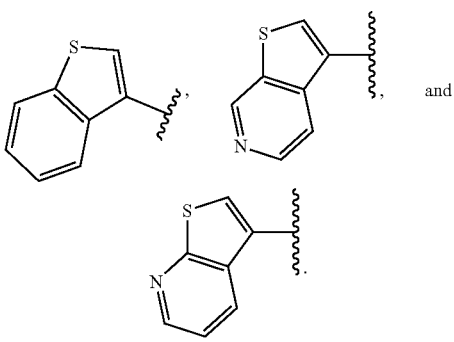

In some embodiments, for the compound or salt of Formula (I), (I'), (II), (III), and (IV), each of R' and R" are independently selected from halogen, —OR$^{16}$, and optionally substituted C$_{1-6}$ alkyl with one or more substituents selected from halogen, —OR$^{16}$, —N(R$^{16}$)$_2$, —C(O)R$^{16}$, —NO$_2$, =O, and —CN. In some embodiments, each of R' and R" are independently selected from fluorine and —OR$^{16}$, wherein R$^{16}$ is selected from optionally substituted C$_{1-6}$ alkyl. In some embodiments, each of R' and R" are fluorine.

In some embodiments, for the compound or salt of Formula (I), (I'), (II), (III), and (IV), n is 1 and Ring A is selected from optionally substituted C$_{3-6}$ carbocycle, optionally substituted 3- to 6-membered heterocycle, and optionally substituted 8- to 9-membered bicyclic heterocycle. In some embodiments, n is 1 and Ring A is selected from C$_{3-6}$ cycloalkyl, phenyl, 5- or 6-membered heteroaryl, and 8- to 9-membered bicyclic heterocycle, any of which is optionally substituted. In some embodiments, n is 1 and Ring A is selected from C$_{3-6}$ cycloalkyl, phenyl, 5- or 6-membered heteroaryl, and 8- to 9-membered bicyclic heterocycle, wherein any one of which is optionally substituted with one or more substituents independently selected from halogen, —OR$^{11}$, —N(R$^{11}$)$_2$, —N(R$^{11}$)S(O)$_2$R$^{11}$, —NO$_2$, —CN, and C$_{1-6}$ alkyl.

In some embodiments, for the compound or salt of Formula (I), (I'), (II), (III), and (IV), n is 1 and Ring A is an optionally substituted C$_{3-6}$ carbocycle with one or more substituents independently selected from: halogen, —OR$^{11}$, —N(R$^{11}$)$_2$, —C(O)R$^{11}$, —C(O)N(R$^{11}$)$_2$, —N(R$^{11}$)C(O)R$^{11}$, —N(R$^{11}$)S(O)$_2$R$^{11}$, —C(O)OR$^{11}$, —OC(O)R$^{11}$, —NO$_2$, and —CN.

In some embodiments, for the compound or salt of Formula (I), (I'), (II), (III), and (IV), n is 1 and Ring A is selected from unsubstituted cyclopropyl, cyclobutyl, cyclopentyl, and cyclohexyl. In some embodiments, n is 1; Ring A is selected from unsubstituted cyclopropyl, cyclobutyl, cyclopentyl, and cyclohexyl; and each of R' and R'' are fluorine. In some embodiments,

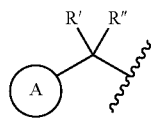

is selected from:

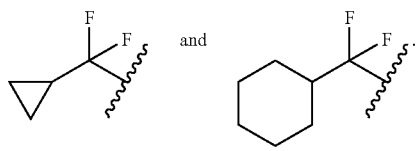 [SMILES: *C(F)(F)C1CC1 ; *C(F)(F)C1CCCCC1]

In some embodiments, for the compound or salt of Formula (I), (I'), (II), (III), and (IV), n is 1 and Ring A is phenyl substituted by one or more substituents. In some embodiments, n is 1 and Ring A is phenyl with one more substituents independently selected from —OR$^{11}$, —N(R$^{11}$)S(O)$_2$R$^{11}$, and —CN; wherein each R$^{11}$ is independently selected from hydrogen and C$_{1-6}$ alkyl. In some embodiments, n is 1; Ring A is phenyl with one more substituents independently selected from —OR$^{11}$, —N(R$^{11}$)S(O)$_2$R$^{11}$, and —CN; wherein each R$^{11}$ is independently selected from hydrogen and C$_{1-6}$ alkyl; and each of R' and R'' are fluorine. In some embodiments,

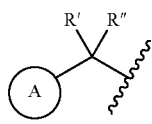

is selected from:

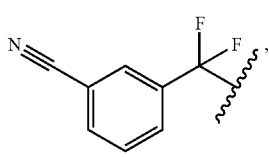

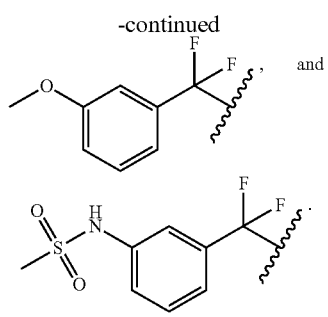

In some embodiments, for the compound or salt of Formula (I), (I'), (II), (III), and (IV), Ring A is an optionally substituted 5- to 6-membered heteroaryl with one or more substituents independently selected from —OR$^{11}$, —SR$^{11}$, —N(R$^{11}$)$_2$, —C(O)R$^{11}$, —C(O)OR$^{11}$, —OC(O)R$^{11}$, —NO$_2$, —CN; and C$_{1-6}$ alkyl optionally substituted with one or more substituents independently selected from —OR$^{11}$, —SR$^{11}$, —N(R$^{11}$)$_2$, —C(O)R$^{11}$, —C(O)OR$^{11}$, —OC(O)R$^{11}$, —NO$_2$, —CN C$_{3-6}$ carbocycle and 3- to 6-membered heterocycle.

In some embodiments, for the compound or salt of Formula (I), (I'), (II), (III), and (IV), Ring A is 5- to 6-membered heteroaryl substituted with one or more substituents independently selected from —OR$^{11}$, —SR$^{11}$, —N(R$^{11}$)$_2$, —C(O)R$^{11}$, —C(O)OR$^{11}$, —OC(O)R$^{11}$, —NO$_2$, —CN; and C$_{1-6}$ alkyl optionally substituted with one or more substituents independently selected from —OR$^{11}$, —SR$^{11}$, —N(R$^{11}$)$_2$, —C(O)R$^{11}$, —C(O)OR$^{11}$, —OC(O)R$^{11}$, —NO$_2$, —CN C$_{3-6}$ carbocycle and 3- to 6-membered heterocycle.

In some embodiments, for the compound or salt of Formula (I), (I'), (II), (III), and (IV), Ring A is a pyridyl substituted with one or more substituents selected from —OR$^{11}$, —SR$^{11}$, —N(R$^{11}$)$_2$, —C(O)R$^{11}$, —C(O)OR$^{11}$, —OC(O)R$^{11}$, —NO$_2$, and —CN.

In some embodiments, for the compound or salt of Formula (I), (I'), (II), (III), and (IV), Ring A is a 5- to 6-membered heteroaryl optionally substituted with one or more substituents independently selected from —OR$^{11}$ and optionally substituted C$_{1-6}$ alkyl. In some embodiments, n is 1; Ring A is a 5- to 6-membered heteroaryl optionally substituted with one or more substituents independently selected from —OR$^{11}$ and optionally substituted C$_{1-6}$ alkyl; and both of R' and R'' are fluorine. In some embodiments,

is selected from:

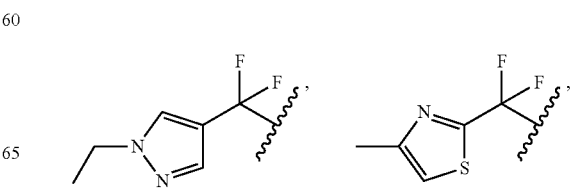

-continued

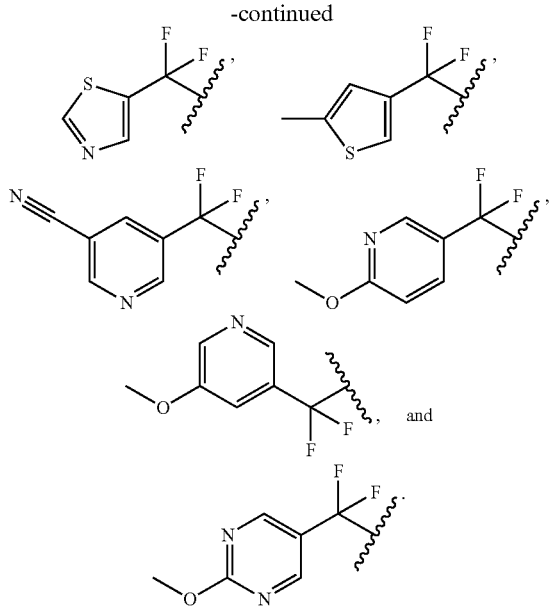

In some embodiments,

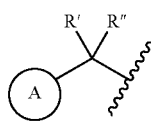

is selected from:

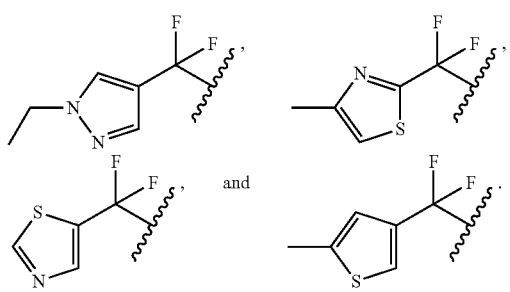

In some embodiments,

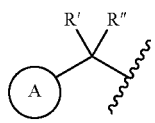

is selected from:

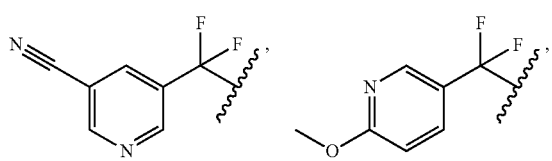

-continued

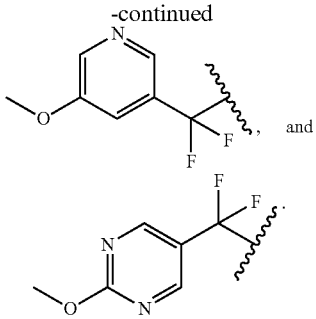

In some embodiments, for the compound or salt of Formula (I), (I'), (II), (III), and (IV), n is 1 and Ring A is an optionally substituted 8- to 9-membered bicyclic heterocycle with one or more substituents independently selected from: —OR[11], —NO$_2$, —CN; and C$_{1-6}$ alkyl optionally substituted with one or more substituents independently selected from OR[11], —NO$_2$, and —CN. In some embodiments, n is 1 and Ring A is an optionally substituted 9-membered bicyclic, wherein the optionally substituted 9-membered bicyclic is a 5-6 bicyclic fused ring system and the 6-membered ring contains no heteroatoms. In some embodiments, n is 1 and Ring A is an unsubstituted 8- to 9-membered bicyclic ring. In some embodiments, n is 1; Ring A is an unsubstituted 8- to 9-membered bicyclic ring; and both of R' and R" are fluorine. In some embodiments,

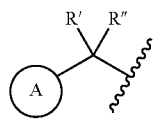

is selected from:

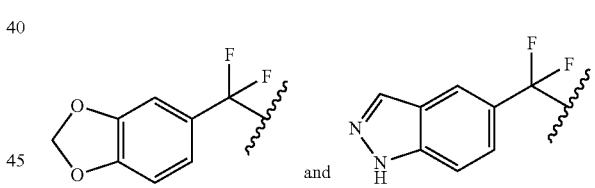

In some embodiments, for the compound or salt of Formula (I), (I'), (II), (III), and (IV), m is 0. In some embodiments, m is 1. In some embodiments, m is 2. In some embodiments, L is —O—. In some embodiments, L is —NH—. In some embodiments, L is absent.

In some embodiments, for the compound or salt of Formula (I), (I'), (II), (III), and (IV), m is 0 and L is absent.

In some embodiments, for the compound or salt of Formula (I), (I'), (II), (III), and (IV), Ring B is selected from an optionally substituted C$_{3-10}$ carbocycle. In some embodiments, the optionally substituted C$_{3-10}$ carbocycle of Ring B is saturated. In some embodiments, the optionally substituted C$_{3-10}$ carbocycle of Ring B is unsaturated. In some embodiments, the optionally substituted C$_{3-10}$ carbocycle of Ring B is selected from C$_{3-9}$ carbocycle or C$_{5-9}$ carbocycle. In some embodiments, the optionally substituted C$_{3-10}$ carbocycle of Ring B is an optionally substituted monocyclic C$_{3-8}$ carbocycle. In some embodiments Ring B is selected from cyclopropyl, cyclobutyl, cyclopentyl, cyclohexyl, cycloheptyl, cyclooctyl, and phenyl, each of which is optionally substituted with one or more substituents independently selected from fluorine, $C_{1-3}$ alkyl, $C_{1-3}$ haloalkyl, and $C_{1-3}$ alkoxyl.

In some embodiments, for the compound or salt of Formula (I), (I'), (II), (III), and (IV), the optionally substituted 3- to 12-membered heterocycle of Ring B comprises at least one heteroatom selected from oxygen, nitrogen, and sulfur. In some embodiments, the optionally substituted 3- to 12-membered heterocycle of Ring B comprises at least one heteroatom selected from oxygen, nitrogen, and any combination thereof.

In some embodiments, for the compound or salt of Formula (I), (I'), (II), (III), and (IV), Ring B is selected from an optionally substituted monocyclic $C_{3-9}$ cycloalkyl and optionally substituted 8- to 10-membered bicyclic carbocycle, wherein one or more substituents on Ring B are independently selected at each occurrence from: halogen, —$OR^{12}$, —$NO_2$, and —CN; and $C_{1-6}$ alkyl optionally substituted with one or more substituents independently selected from halogen, —$OR^{12}$, —$NO_2$, =O, and —CN.

In some embodiments, for the compound or salt of Formula (I), (I'), (II), (III), and (IV), Ring B is a saturated $C_{3-9}$ monocyclic cycloalkyl optionally substituted with one or more substituents independently selected from: halogen, and $C_{1-6}$ alkyl optionally substituted with one or more substituents independently selected from halogen, —$OR^{12}$, and —CN. In some embodiments, Ring B is selected from cyclopentyl, cyclohexyl, and cycloheptyl each of which is optionally substituted with one or more substituents independently selected from halogen, —$OR^{12}$ and optionally substituted $C_{1-3}$ alkyl. In some embodiments, Ring B is cyclohexyl optionally substituted with one or more substituents independently selected from halogen, $C_{1-3}$ alkyl, and $C_{1-3}$ haloalkyl. In some embodiments, Ring B is selected from:

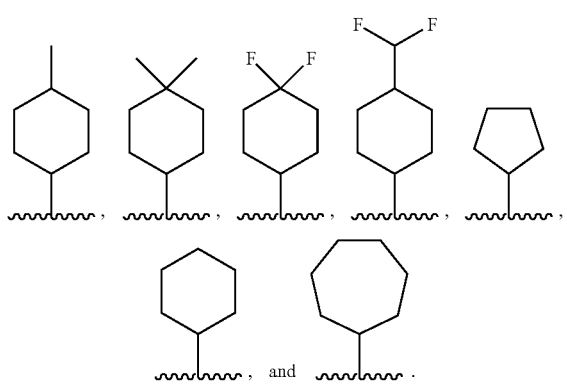

In some embodiments, Ring B is selected from:

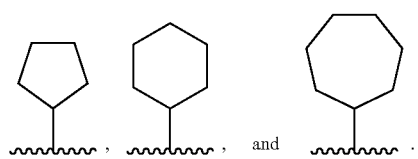

In some embodiments, Ring B is selected from:

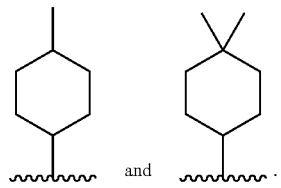

In some embodiments, Ring B is selected from:

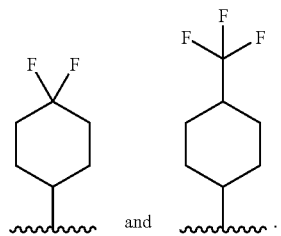 [SMILES: *C1CCC(F)(F)CC1 ; *C1CCC(C(F)(F)F)CC1]

In some embodiments, for the compound or salt of Formula (I), (I'), (II), (III), and (IV), Ring B is an optionally substituted 9- or 10-membered bicyclic carbocycle. In some embodiments, Ring B is an optionally substituted 9-membered bicyclic carbocycle selected from a 5-6 fused ring system and the optional substituents are independently selected from halogen, —$OR^{12}$, $C_{1-6}$ alkyl, and $C_{1-6}$ haloalkyl. In some embodiments, Ring B is indane optionally substituted with one or more substituents independently selected from fluorine, chlorine, —$OR^{12}$ and $C_{1-6}$ alkyl optionally substituted with one or more substituents selected from halogen and —$OR^{12}$. In some embodiments, Ring B is selected from

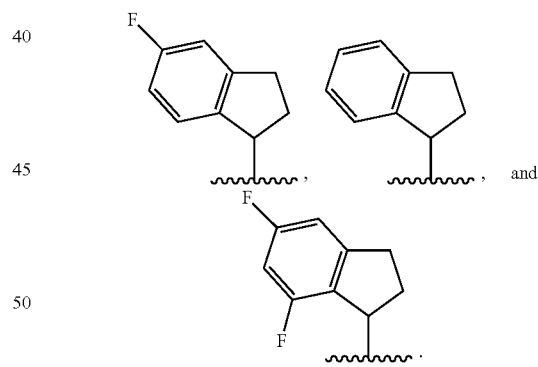

In some embodiments, for the compound or salt of Formula (I), (I'), (II), (III), and (IV), m is 1 and L is absent. In some embodiments, m is 1 and L is —O—.

In some embodiments, for the compound or salt of Formula (I), (I'), (II), (III), and (IV), each $R^2$ and $R^3$ are independently selected from: hydrogen, halogen, —$OR^{17}$, $C_{1-6}$ alkyl, and $C_{3-6}$ cycloalkyl; wherein the $C_{1-6}$ alkyl and $C_{3-6}$ cycloalkyl are optionally substituted with one or more substituents selected from: halogen, —$OR^{17}$, —$N(R^{17})_2$, —$C(O)R^{17}$, —$NO_2$, =O, and —CN. In some embodiments, each $R^2$ and $R^3$ are independently selected from hydrogen, —$OR^{17}$, and $C_{1-6}$ alkyl; wherein the $C_{1-6}$ alkyl is optionally substituted with one or more substituents selected from: halogen, —$OR^{17}$, and —CN. In some embodiments, at least one of $R^2$ and $R^3$ is selected from —$OR^{17}$ and $C_{1-6}$ alkyl; wherein the $C_{1-6}$ alkyl is optionally substituted with one or more substituents selected from: halogen, —$OR^{17}$, and —CN. In some embodiments, $R^2$ and $R^3$ are each independently selected from hydrogen, —O—$C_{1-3}$ alkyl, and $C_{1-3}$ alkyl optionally substituted with one or more substituents selected from —O—$C_{1-3}$ alkyl. In some embodiments, Ring B is selected from $C_{3-8}$ carbocycle each of which is optionally substituted with one or more substituents independently selected from fluorine, $C_{1-3}$ alkyl, $C_{1-3}$ haloalkyl, and $C_{1-3}$ alkoxyl. In some embodiments, the $C_{3-8}$ carbocycle of Ring B is selected from an optionally substituted phenyl, optionally substituted saturated $C_{3-8}$ carbocycle, and optionally substituted saturated $C_{5-8}$ carbocycle. In some embodiments, the $C_{3-8}$ carbocycle of Ring B is selected from optionally substituted phenyl and optionally substituted cyclohexyl. In some embodiments, the $C_{3-8}$ carbocycle of Ring B is selected from optionally substituted phenyl and optionally substituted cyclohexyl; m is 1; and L is absent or —O—. In some embodiments,

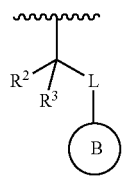

is selected from:

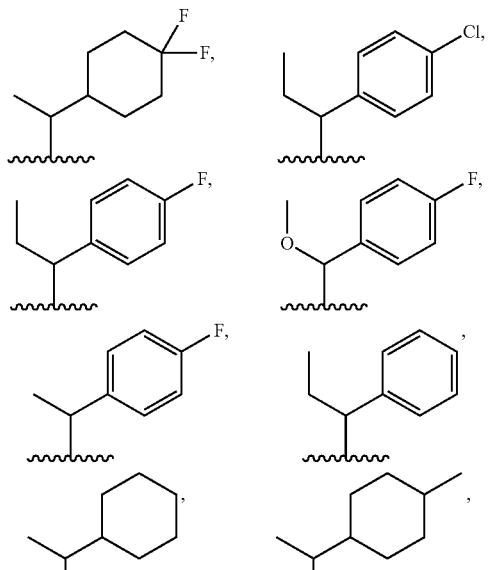

In some embodiments,

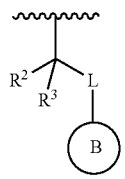

is selected from:

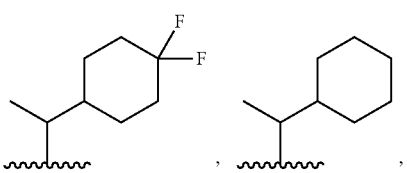

In some embodiments,

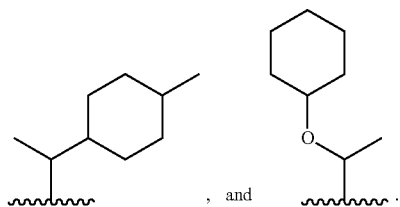

is selected from:

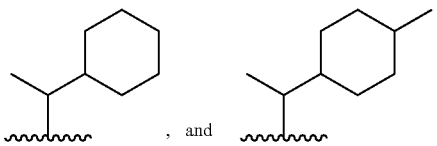

In some embodiments,

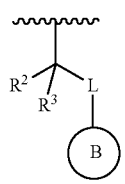

is selected from:

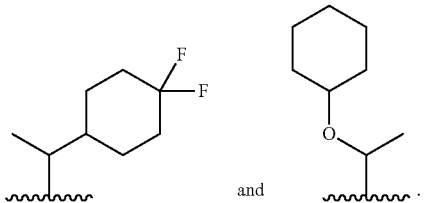

and

In some embodiments,

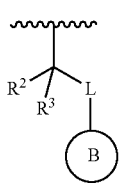

is selected from:

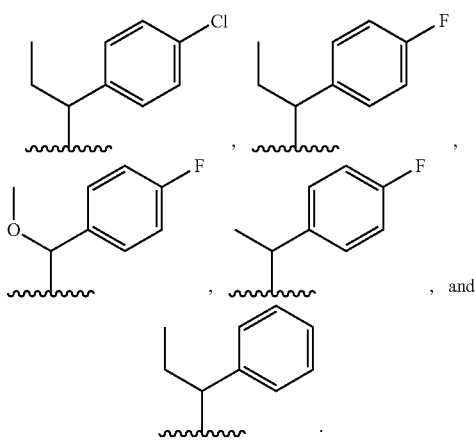

, and

In some embodiments,

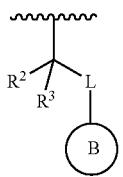

is selected from:

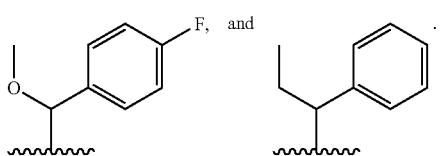

In some embodiments,

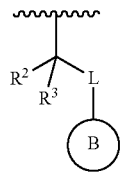

is selected from:

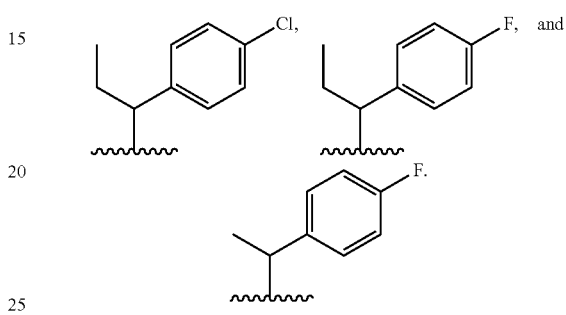

In some embodiments, for the compound or salt of Formula (I), (I'), (II), (III), and (IV), $R^1$ is selected from —N($R^{21}$)C(O)$R^{22}$, —N($R^{21}$)C(O)O$R^{22}$, and —N($R^{21}$)C(O)N($R^{21}$)($R^{22}$). In some embodiments, $R^{21}$ at each occurrence is selected from hydrogen and $C_1$-$C_3$ alkyl. In some embodiments, $R^{21}$ at each occurrence is hydrogen. In some embodiments, $R^{21}$ at each occurrence is selected from methyl, ethyl, and propyl.

In some embodiments, for the compound or salt of Formula (I), (I'), (II), (III), and (IV), $R^{22}$ of $R^1$ is selected from optionally substituted $C_{1-6}$ alkyl, optionally substituted $C_{3-8}$ carbocycle, and optionally substituted 3- to 10-membered heterocycle. In some embodiments, $R^{22}$ of $R^1$ is selected from optionally substituted $C_{1-6}$ alkyl, optionally substituted monocyclic $C_{3-7}$ carbocycle, and optionally substituted 3- to 6-membered monocyclic heterocycle, and optionally substituted 8- to 10-membered bicyclic heterocycle.

In some embodiments, for the compound or salt of Formula (I), (I'), (II), (III), and (IV), $R^{22}$ of $R^1$ is selected from:
  $C_{1-6}$ alkyl optionally substituted by one or more substituents independently selected from halogen, —C(O)O$R^{11}$, —O$R^{18}$, and $C_{3-6}$ cycloalkyl;
  $C_{3-6}$ cycloalkyl optionally substituted by halogen, —O$R^{18}$, $C_{1-6}$ alkyl, and $C_{1-6}$ haloalkyl;
  3- to 6-membered monocyclic heterocycle optionally substituted with halogen, —O$R^{18}$, $C_{1-6}$ alkyl, $C_{3-6}$ cycloalkyl, $C_{3-6}$ cycloalkyl-$C_{1-6}$ alkyl, $C_{1-6}$ alkyl-(3- to 6-membered heterocycloalkyl); and
  8- to 10-membered bicyclic heterocycle optionally substituted with halogen, —O$R^{18}$, $C_{1-6}$ haloalkyl.

In some embodiments, for the compound or salt of Formula (I), (I'), (II), (III), and (IV), $R^{22}$ of $R^1$ is selected from:
  $C_{1-4}$ alkyl optionally substituted by one or more substituents independently selected from halogen, —C(O)O$R^{18}$, and $C_{3-6}$ cycloalkyl;
  $C_{3-6}$ cycloalkyl optionally substituted by halogen;
  3- to 6-membered monocyclic heterocycle optionally substituted with —O$R^{18}$, $C_{1-6}$ alkyl, $C_{3-6}$ cycloalkyl, $C_{3-6}$ cycloalkyl-$C_{1-6}$ alkyl, $C_{1-6}$ alkyl-(3- to 6-membered heterocycloalkyl); and In some embodiments,
8- to 10-membered bicyclic heterocycle.
In some embodiments, for the compound or salt of Formula (I), (II), (III), and (IV), $R^1$ is selected from:
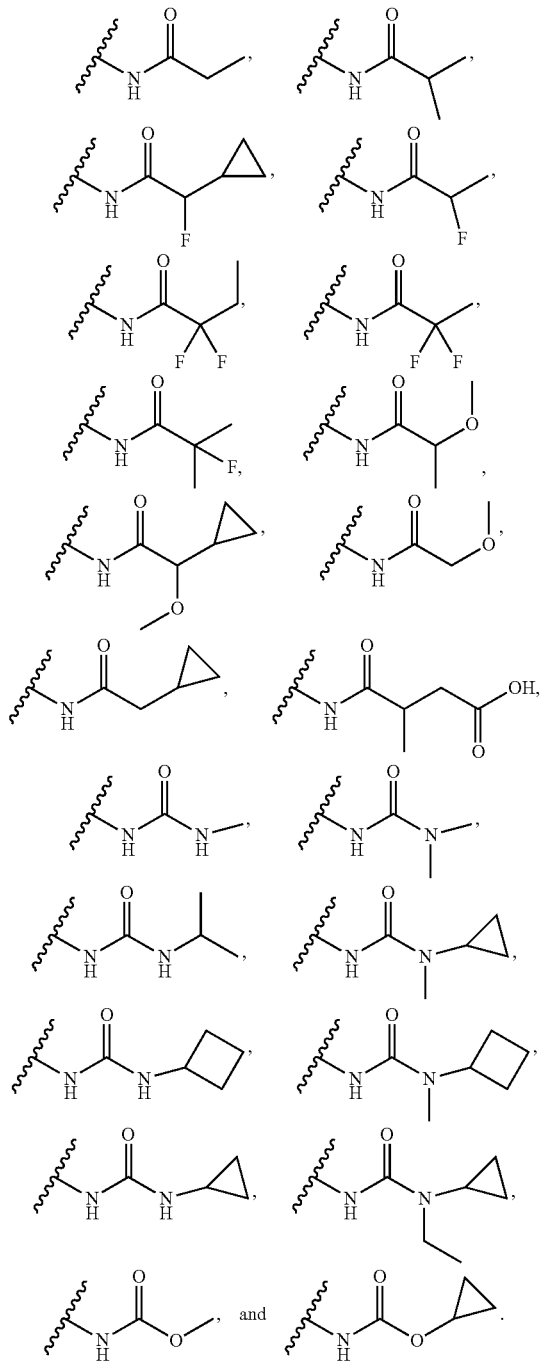
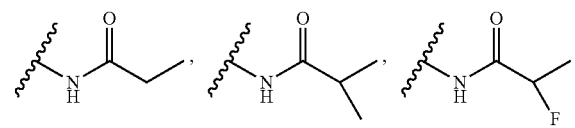
In some embodiments, $R^1$ is selected from:
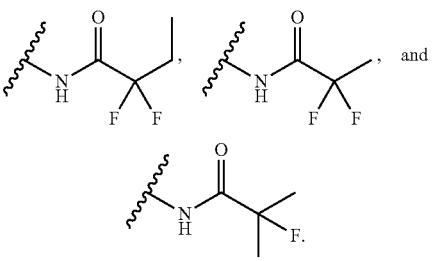
In some embodiments, $R^1$ is selected from:
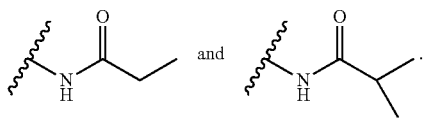
In some embodiments, $R^1$ is selected from:
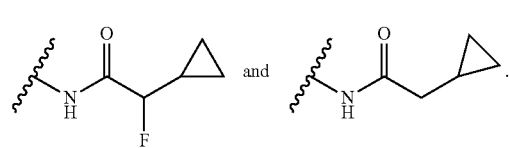 [SMILES: *NC(=O)C(F)C1CC1 ; *NC(=O)CC1CC1]
In some embodiments, $R^1$ is selected from:
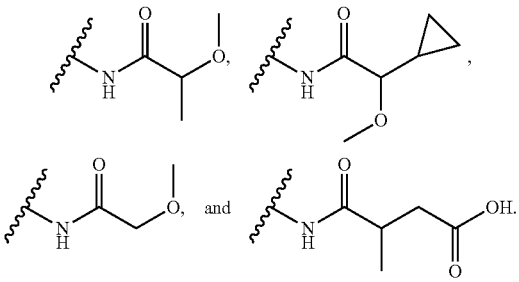
In some embodiments, $R^1$ is selected from:
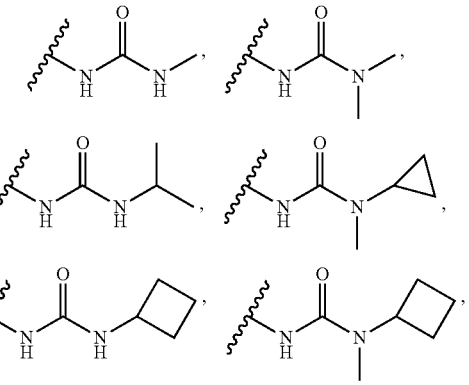

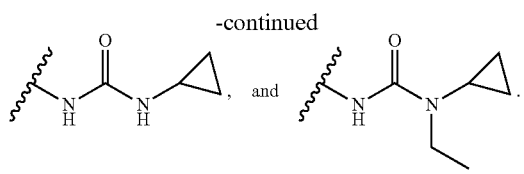

In some embodiments, $R^1$ is selected from:

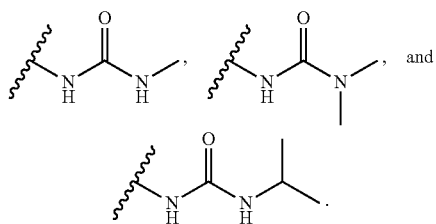

In some embodiments, $R^1$ is selected from:

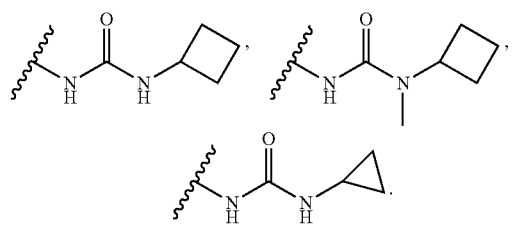

In some embodiments, $R^1$ is selected from:

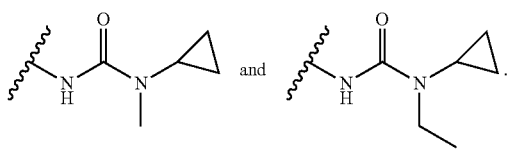

In some embodiments, $R^1$ is selected from:

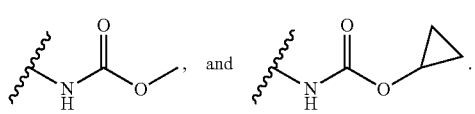

In some embodiments, for the compound or salt of Formula (I), (I'), (II), (III), and (IV), $R^{22}$ of $R^1$ is selected from $C_{1-4}$ alkyl optionally substituted with one or more substituents independently selected from halogen, —$OR^{18}$, —$SR^{18}$, —$N(R^{18})_2$, —$C(O)R^{18}$, —$C(O)OR^{18}$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{18}$—$NO_2$, =O, and —CN. In some embodiments. $R^{22}$ of $R^1$ is selected from $C_{1-4}$ alkyl optionally substituted with one or two substituents independently selected from halogen, —$OR^{18}$, —$SR^{18}$, —$N(R^{18})_2$, —$C(O)R^{18}$, —$C(O)OR^{18}$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{18}$, and —$NO_2$. In some embodiments, $R^{22}$ is selected from unsubstituted methyl, ethyl, propyl, and isopropyl. In some embodiments, $R^{22}$ is ethyl.

In some embodiments, for the compound or salt of Formula (I), (I'), (II), (III), and (IV), $R^1$ is selected from —$N(R^{21})C(O)R^{22}$ and $R^{22}$ of $R^1$ is selected from $C_{1-4}$ alkyl optionally substituted with one or more substituents independently selected from halogen, —$OR^{18}$, —$SR^{18}$, —$N(R^{18})_2$, —$C(O)R^{18}$, —$C(O)OR^{18}$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^8$—$NO_2$, =O, and —CN. In some embodiments, $R^1$ is selected from:

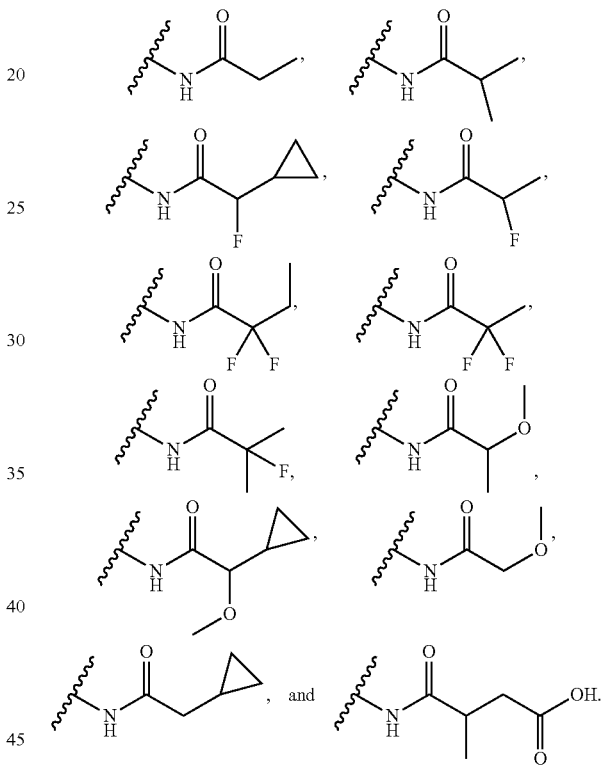

In some embodiments, for the compound or salt of Formula (I), (I'), (II), (III), and (IV), $R^1$ is selected from —$N(R^{21})C(O)R^{22}$ and $R^{22}$ of $R^1$ is an optionally substituted $C_{3-6}$ carbocycle. In some embodiments, $R^{22}$ of $R^1$ is selected from cyclopropyl, cyclobutyl, cyclopentyl, cyclohexyl, and phenyl any of which is optionally substituted by one or more substituents independently selected from halogen and —$OR^{18}$. In some embodiments, $R^{22}$ is selected from cyclopropyl and cyclobutyl each of which is optionally substituted with one or more fluorines. In some embodiments, $R^1$ is selected from

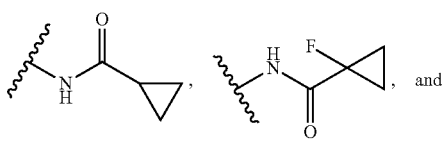

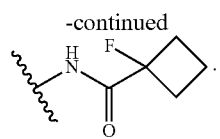

In some embodiments, R¹ is

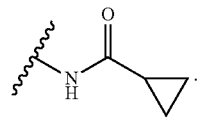 [SMILES: *NC(=O)C1CC1]

In some embodiments, R¹ is selected from:

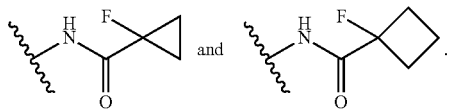 [SMILES: *NC(=O)C1(F)CC1 ; *NC(=O)C1(F)CCC1]

In some embodiments, for the compound or salt of Formula (I), (I'), (II), (III), and (IV), $R^{22}$ of $R^1$ is selected from optionally substituted 5- to 6-membered monocyclic heterocycle, and optionally substituted 8- to 10-membered bicyclic heterocycle, any of which comprising at least one heteroatom selected from nitrogen, oxygen, and sulfur.

In some embodiments, for the compound or salt of Formula (I), (I'), (II), (III), and (IV), $R^{22}$ is selected from an optionally substituted saturated 5- to 6-membered monocyclic heterocycle. In some embodiments, $R^{22}$ is selected from tetrahydrofuran, pyrrolidine, and tetrahydrothiophene any of which is optionally substituted. In some embodiments, $R^{22}$ is selected from unsubstituted tetrahydrofuran and unsubstituted pyrrolidine. In some embodiments, $R^1$ is selected from:

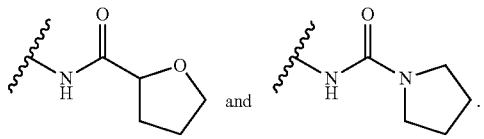 [SMILES: *NC(=O)C1CCCO1 ; *NC(=O)N1CCCC1]

In some embodiments, for the compound or salt of Formula (I), (I'), (II), (III), and (IV), $R^{22}$ of $R^1$ is selected from a 5- to 6-membered monocyclic heteroaryl optionally substituted with one or more substituents selected from:
halogen, —OR¹⁸, —NO₂, —CN;
—C₁₋₆ alkyl which is optionally substituted with one or more substituents independently selected from —OR¹⁸, —SR¹⁸, —N(R¹⁸)₂, —NO₂, =O, =S, =N(R¹⁸), —CN, C₃₋₆ carbocycle and 3- to 6-membered heterocycle; wherein the C₃₋₆ carbocycle and 3- to 6-membered heterocycle are each optionally substituted with one or more substituents selected from: halogen, —OR¹⁸, —NO₂, and —CN;
C₃₋₆ carbocycle and 3- to 6-membered heterocycle, each of which is optionally substituted with one or more substituents independently selected from: halogen, —OR¹⁸, and optionally substituted C₁₋₃ alkyl.

In some embodiments, for the compound or salt of Formula (I), (I'), (II), (III), and (IV), $R^{22}$ of $R^1$ is selected from pyrazole and isoxazole substituted with one or more substituents selected from: halogen, —OR¹⁸, and —NO₂;
—C₁ alkyl which is substituted with one or more substituents independently selected from —OR¹⁸, —SR¹⁸, —N(R¹⁸)₂, —NO₂, =O, =S, =N(R¹⁸), —CN, C₃₋₆ carbocycle and 3- to 6-membered heterocycle; wherein the C₃₋₆ carbocycle and 3- to 6-membered heterocycle are each optionally substituted with one or more substituents selected from: halogen, —OR¹⁸, —NO₂, and —CN;
—C₂₋₆ alkyl which is optionally substituted with one or more substituents independently selected from —OR¹⁸, —SR¹⁸, —N(R¹⁸)₂, —NO₂, =O, =S, =N(R¹⁸), —CN, C₃₋₆ carbocycle and 3- to 6-membered heterocycle; wherein the C₃₋₆ carbocycle and 3- to 6-membered heterocycle are each optionally substituted with one or more substituents selected from: halogen, —OR¹⁸, —NO₂, and —CN;
C₃₋₆ carbocycle and 3- to 6-membered heterocycle, each of which is optionally substituted with one or more substituents independently selected from: halogen, —OR¹⁸, and optionally substituted C₁₋₃ alkyl.

In some embodiments, for the compound or salt of Formula (I), (I'), (II), (III), and (IV), $R^{22}$ of $R^1$ is selected from pyrazole and isoxazole substituted with one or more substituents selected from: halogen, —OR¹⁸, and —NO₂;
—C₁ alkyl which is substituted with one or more substituents independently selected from —OR¹⁸, —SR¹⁸, —N(R¹¹)₂, —NO₂, =O, =S, =N(R¹⁸), —CN, C₃₋₆ carbocycle and 3- to 6-membered heterocycle; wherein the C₃₋₆ carbocycle and 3- to 6-membered heterocycle are each optionally substituted with one or more substituents selected from: halogen, —OR¹⁸, —NO₂, and —CN; and
—C₂₋₆ alkyl which is optionally substituted with one or more substituents independently selected from —OR¹⁸, —SR¹⁸, —N(R⁸)₂, —NO₂, =O, =S, =N(R¹⁸), —CN, C₃₋₆ carbocycle and 3- to 6-membered heterocycle; wherein the C₃₋₆ carbocycle and 3- to 6-membered heterocycle are each optionally substituted with one or more substituents selected from: halogen, —OR¹⁸, —NO₂, and —CN.

In some embodiments, for the compound or salt of Formula (I), (I'), (II), (III), and (IV), $R^{22}$ of $R^1$ is selected from 1,2,3-thiadiazole, isothiazole, thiazole, and thiophene any of which is optionally substituted.

In some embodiments, for the compound or salt of Formula (I), (I'), (II), (III), and (IV), $R^1$ is selected from

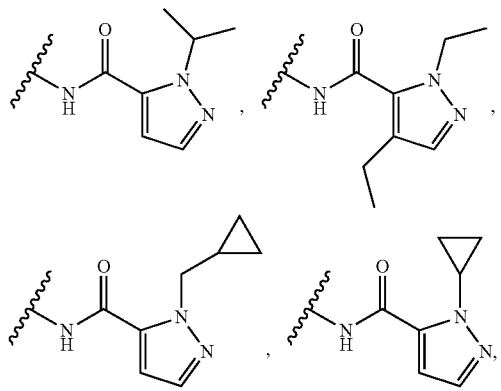

-continued

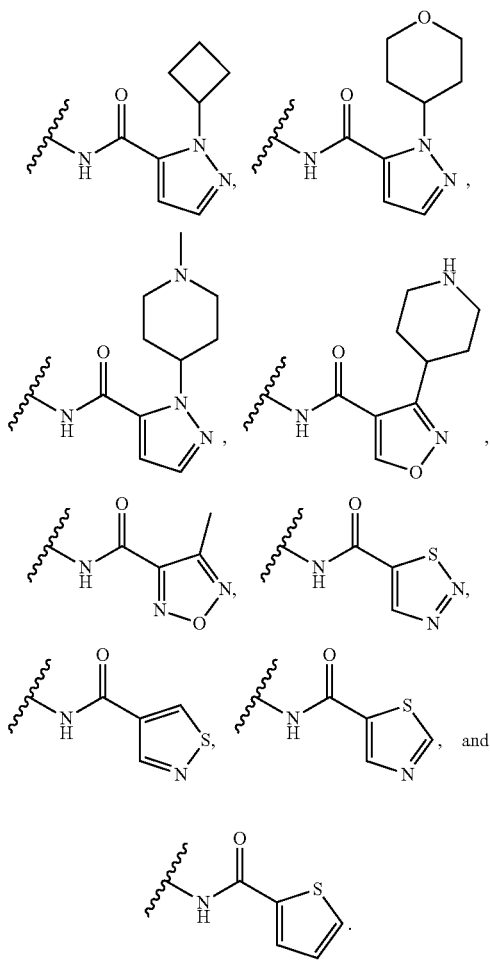

In some embodiments, $R^1$ is selected from:

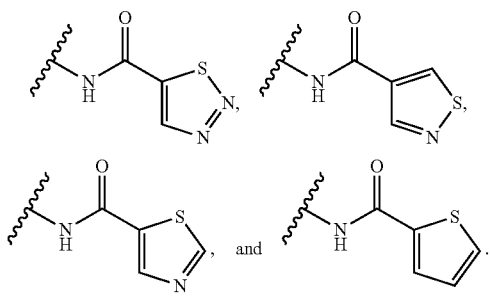

In some embodiments, $R^1$ is selected from:

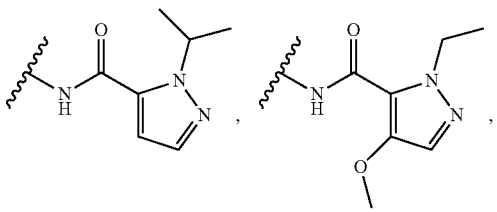

-continued

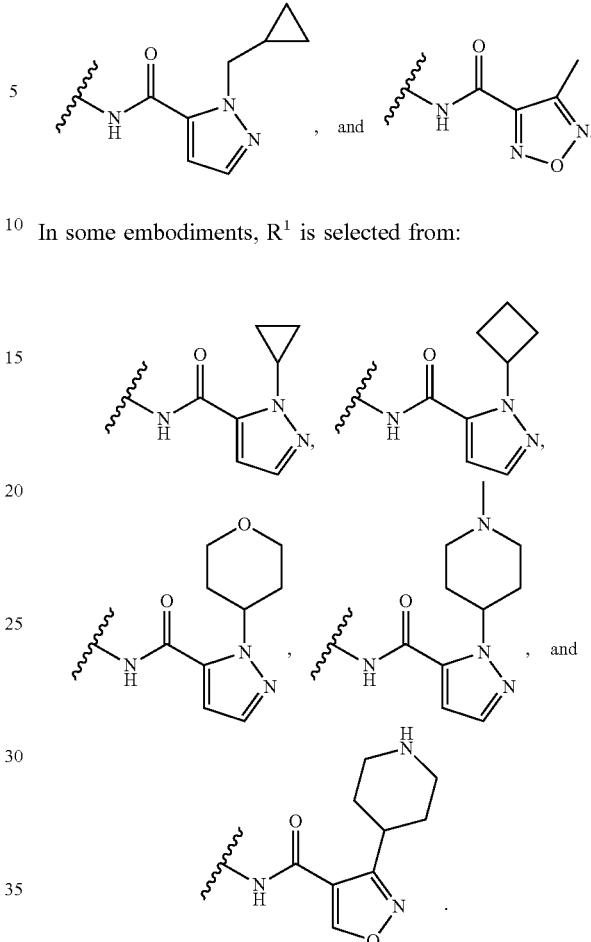

In some embodiments, $R^1$ is selected from:

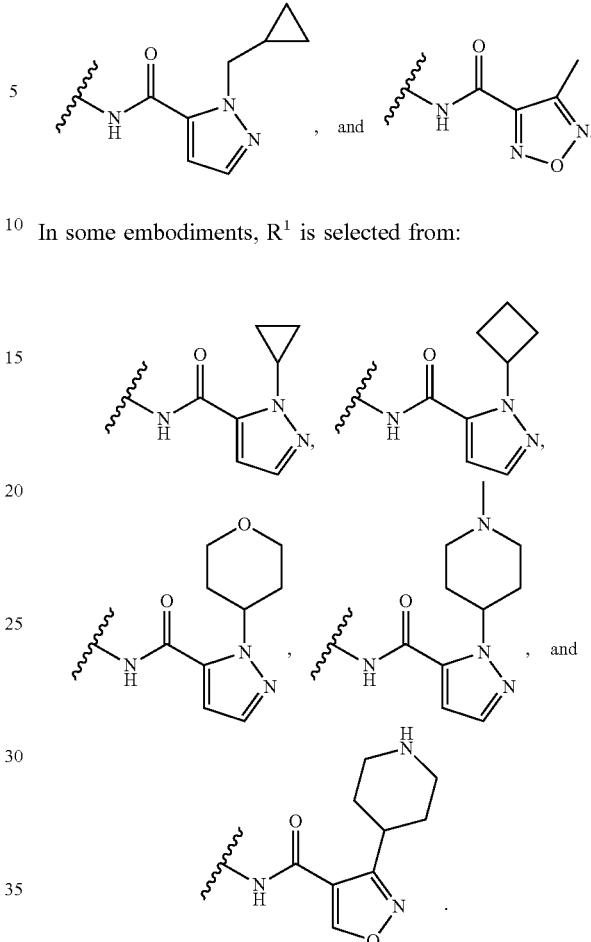

In some embodiments, for the compound or salt of Formula (I), (I'), (II), (III), and (IV), $R^{22}$ is a 6-membered heteroaryl with one or more substituents independently selected from —$OR^{18}$, $C_{1-6}$ alkyl optionally substituted with one or more substituents selected from —$OR^{18}$, optionally substituted $C_{3-6}$ carbocycle and optionally substituted 3- to 6-membered heterocycle. In some embodiments, $R^{22}$ is pyridine optionally substituted with one or more substituents selected from —$OR^{18}$ and $C_{1-6}$ alkyl optionally substituted with one or more substituents selected from —$OR^{18}$. In some embodiments, $R^1$ is

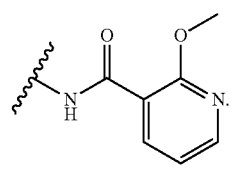

In some embodiments, for the compound or salt of Formula (I), (I'), (II), (III), and (IV), $R^1$ is —$N(R^{21})C(O)OR^{22}$ and $R^{22}$ is selected from $C_{1-6}$ alkyl optionally substituted with one or more substituents selected from $C_{1-4}$ alkyl optionally substituted with one or more substituents independently selected from halogen, —$OR^{18}$, —$SR^{18}$, —$N(R^{18})_2$, —$C(O)R^{18}$, —$C(O)OR^{18}$, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —OR$^{18}$—NO$_2$, =O, and —CN; and C$_{3-6}$ carbocycle optionally substituted with one or more substituents selected from: halogen, —OR$^{18}$—NO$_2$, =O, and —CN. In some embodiments, R$^1$ is selected from

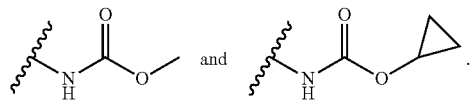

In some embodiments, for the compound or salt of Formula (I), (I'), (II), (III), and (IV), R$^1$ is N(R$^{21}$)C(O)N (R$^{21}$)(R$^{22}$) and R$^{22}$ is selected from methyl, ethyl, propyl, isopropyl, cyclopropyl and cyclobutyl any one of which is optionally substituted with or more substituents selected from halogen, —OR$^8$, —NO$_2$, —CN, and —C$_{1-6}$ haloalkyl. In some embodiments, R$^1$ is selected from:

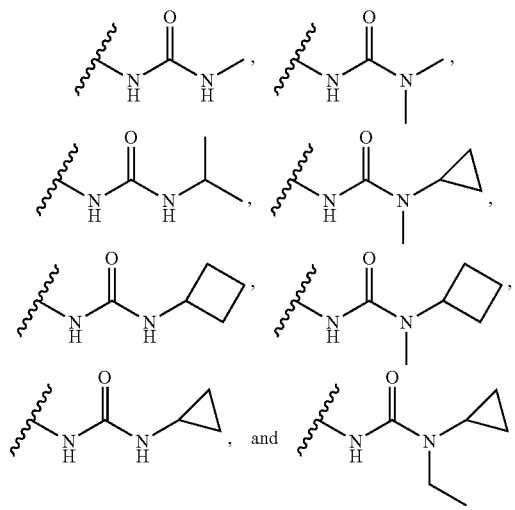

In some embodiments, for the compound or salt of Formula (I), (I'), (II), (III), and (IV), R$^1$ is —N(R$^{21}$)S(=O)$_2$ (R$^{22}$) or —N(R$^{21}$)S(=O)$_2$N(R$^{21}$)(R$^{22}$), and R$^{22}$ is C$_{1-6}$ alkyl or C$_{3-6}$ cycloalkyl any one of which is optionally substituted with one or more substituents independently selected from halogen, —OR$^{18}$, —NO$_2$, =O, and —CN. In some embodiments, R$^1$ is

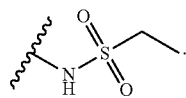 [SMILES: *NS(=O)(=O)CC]

In some embodiments, for the compound or salt of Formula (I), (I'), (II), (III), and (IV), R$^4$ is —C(=O)N(R$^{23}$) (R$^{24}$) and R$^{23}$ is 3- to 12-membered heterocycle, e.g., a 7- to 10-membered bicyclic heterocycle, optionally substituted with one or more substituents independently selected from halogen, —OR$^{19}$, —N(R$^{19}$)$_2$, =O, C$_1$-C$_6$ alkyl, C$_1$-C$_6$ haloalkyl, and —CN and R$^{24}$ of R$^4$ is C$_{1-6}$ alkyl or hydrogen.

In some embodiments, for the compound or salt of Formula (I), (I'), (II), (III), and (IV), R$^4$ is —C(=O)N(R$^{23}$) (R$^{24}$) and R$^{23}$ is C$_{1-6}$ alkyl optionally substituted with one or more substituents independently selected from halogen, —O—C$_{1-6}$ alkyl, C$_{1-6}$ haloalkyl, —NO$_2$, CN, C$_{3-10}$ carbocycle and 3- to 10-membered heterocycle; wherein the C$_{3-10}$ carbocycle and 3- to 10-membered heterocycle are each optionally substituted with one or more substituents selected from: halogen, —OR$^{19}$, —N(R$^{19}$)$_2$, =O, C$_1$-C$_6$ haloalkyl, and CN; optionally substituted C$_{3-6}$ carbocycle and optionally substituted 3- to 6-membered heterocycle. In some embodiments, R$^{24}$ of R$^4$ is hydrogen. In some embodiments, R$^4$ is selected from:

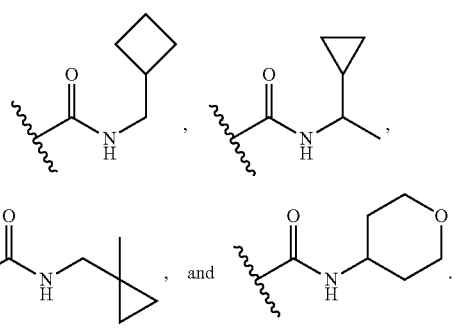

In some embodiments, R$^4$ is selected from:

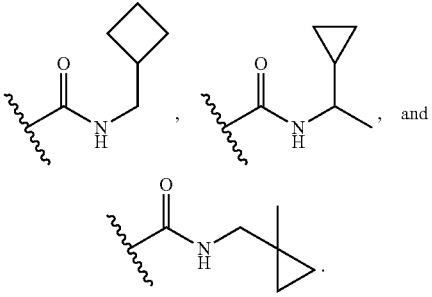

In some embodiments, R$^4$ is

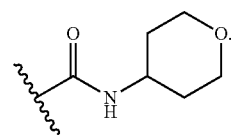 [SMILES: *C(=O)NC1CCOCC1]

In some embodiments, for the compound or salt of Formula (I), (I'), (II), (III), and (IV), R$^4$ is

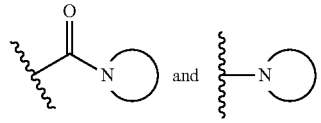

is selected from an optionally substituted saturated 4- to 9-membered heterocycloalkyl. In some embodiments,

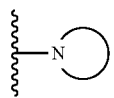

is selected from an optionally substituted 4- to 8-membered heterocycloalkyl. In some embodiments,

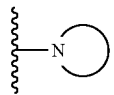

is selected from 4- to 5-membered heterocycloalkyl, 4- to 6-membered heterocycloalkyl. 4- to 7-membered heterocycloalkyl, and 4- to 8-membered heterocycloalkyl any of which is optionally substituted. In some embodiments,

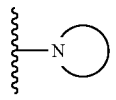

is selected from a 4-membered heterocycloalkyl, 5-membered heterocycloalkyl, 6-membered heterocycloalkyl, 7-membered heterocycloalkyl, 8-membered heterocycloalkyl any of which is optionally substituted. In certain embodiments,

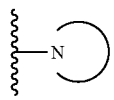

is selected from a 7- to 9-membered bicyclic heterocycloalkyl, such as a bridged bicyclic or a spiro bicyclic. In some embodiments,

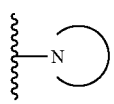

comprises at least one other heteroatom selected from oxygen, nitrogen, sulfur, or any combination thereof. In some embodiments,

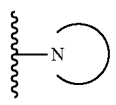

comprises a singular nitrogen heteroatom. In some embodiments,

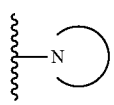

is optionally substituted with one or more substitutents selected from halogen, —C(O)$R^{13}$, —C(O)N($R^{13}$)$_2$, —N($R^{13}$)C(O)$R^{13}$, —C(O)O$R^{13}$, —OC(O)$R^{13}$, —O$R^{13}$, —NO$_2$, =O, and C$_{1-6}$ alkyl optionally substituted with one or more substitutents selected from halogen, —C(O)$R^{13}$, —C(O)N($R^{13}$)$_2$, —N($R^{13}$)C(O)$R^{13}$, —C(O)O$R^{13}$, —OC(O)$R^{13}$, —O$R^{13}$, —NO$_2$, =O, and C$_{3-8}$ carbocycle and 3- to 8-membered heterocycle.

In some embodiments, for the compound or salt of Formula (I), (I'), (II), (III), and (IV),

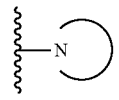

is a optionally substituted saturated heterocycle is a 4- to 6-membered heterocycloalkyl optionally substituted with one or more substituents independently selected from:
halogen, —O$R^{13}$, —N($R^{13}$)$_2$, —C(O)$R^{13}$, —C(O)N($R^{13}$)$_2$, N($R^{13}$)C(O)$R^{13}$, —C(O)O$R^{13}$, —OC(O)$R^{13}$, —S(O)$R^{13}$, —NO$_2$, =O, =S, =N($R^{13}$), —CN;
C$_{1-10}$ alkyl optionally substituted with one or more substituents selected from —O$R^{13}$, C(O)$R^{13}$, —C(O)O$R^{13}$, —NO$_2$, =O, —CN, C$_{3-10}$ carbocycle and wherein the C$_{3-10}$ carbocycle is each optionally substituted with one or more substituents selected from: halogen, —O$R^{13}$, —N($R^{13}$)$_2$, —C(O)$R^{13}$, —C(O)N($R^{13}$)$_2$, N($R^{13}$)C(O)$R^{13}$, —C(O)O$R^{13}$, —OC(O)$R^{13}$, —NO$_2$, =O, =N($R^{13}$), and —CN.

In some embodiments, for the compound or salt of Formula (I), (I'), (II), (III), and (IV), $R^4$ is

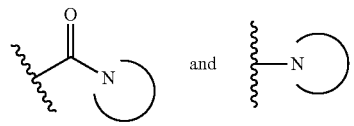

and is selected from azetidine, piperidine, piperazine, morpholine, thiomorpholine, thiomorpholine 1,1-dioxide, and azaspiro[3.3]heptane any of which is optionally substituted. In some embodiments, wherein when $R^4$ is

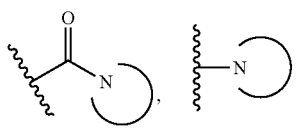

is selected from azetidine, piperidine, piperazine, morpholine, thiomorpholine, and thiomorpholine 1,1-dioxide any of which is optionally substituted. In some embodiments, $R^4$ is selected from:

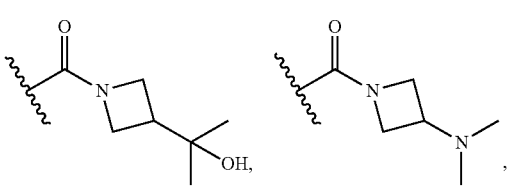

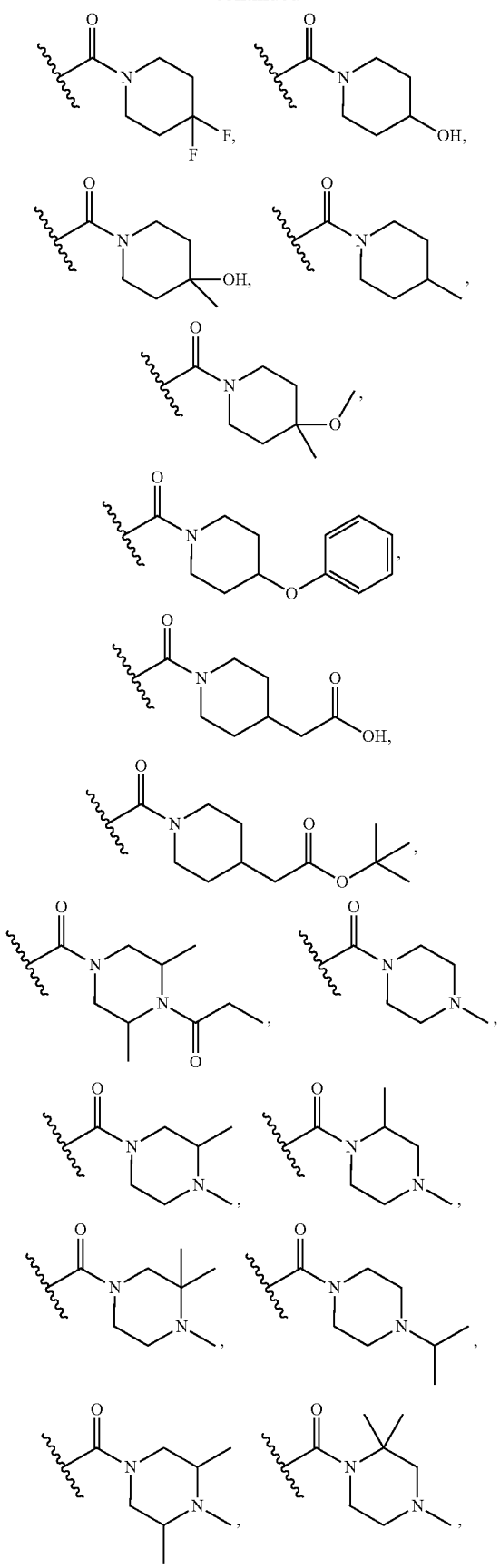
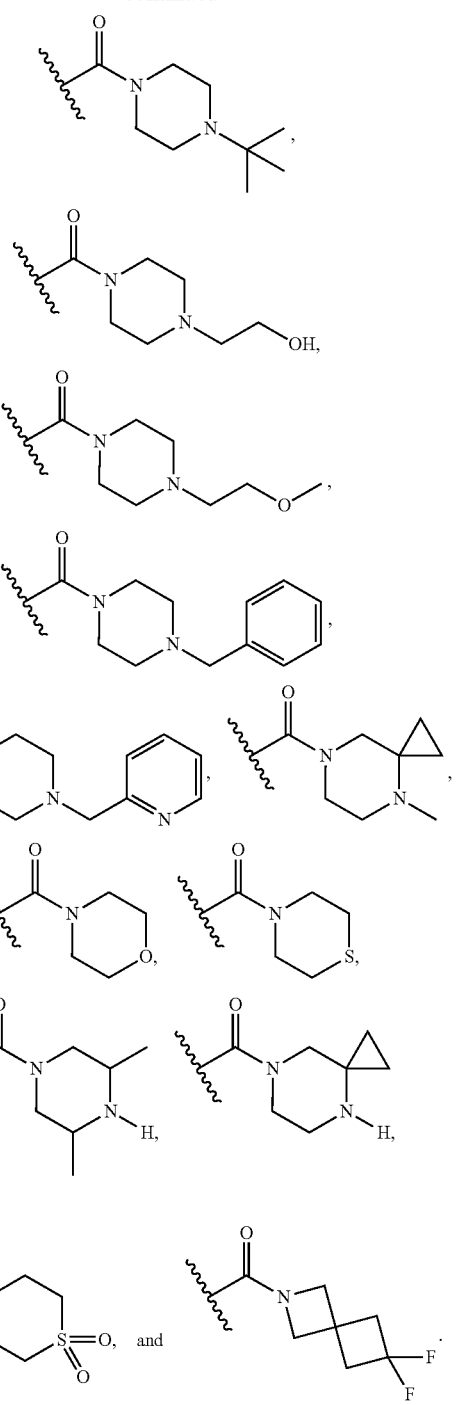
In some embodiments, R⁴ is selected from:
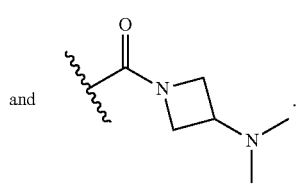

In some embodiments, R$^4$ is selected from:
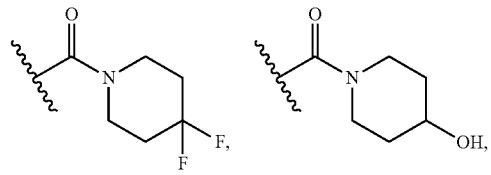
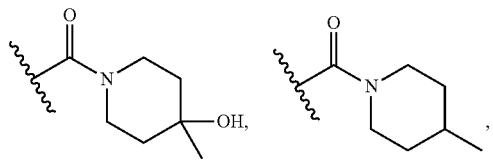
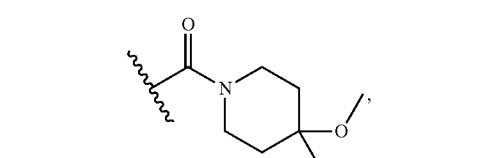
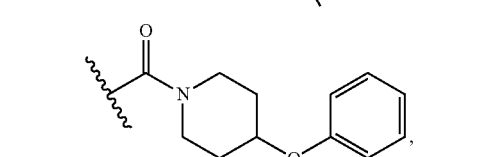
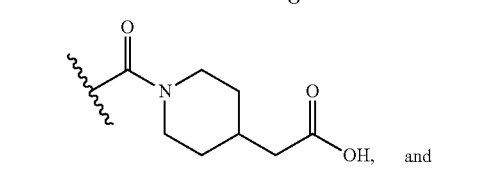
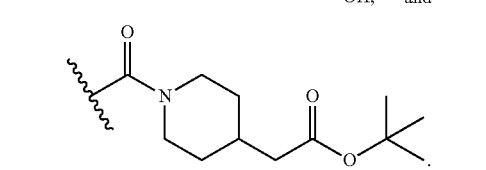
In some embodiments R$^4$ is selected from:
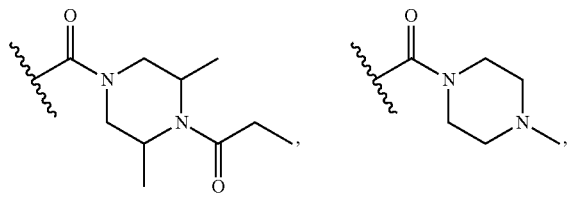
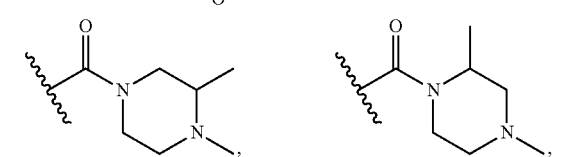
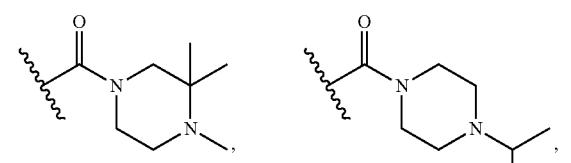
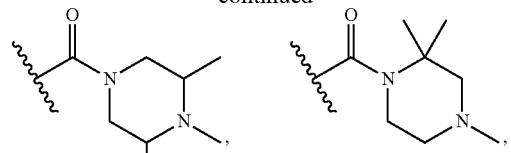
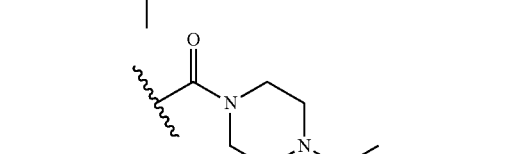

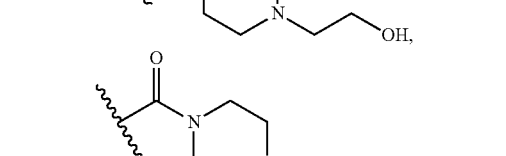
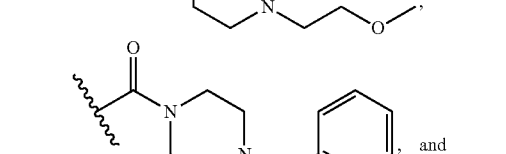
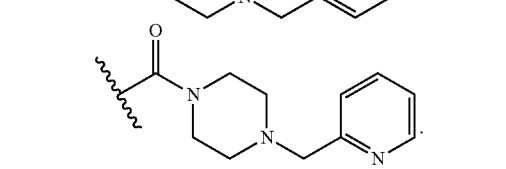
In some embodiments, R$^4$ is selected from:
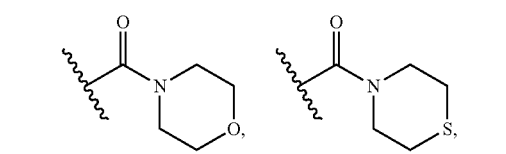
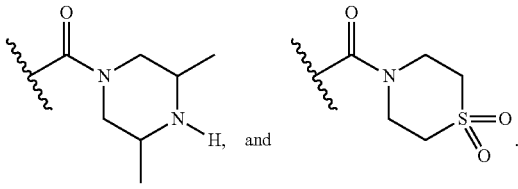
In some embodiments, R$^4$ is
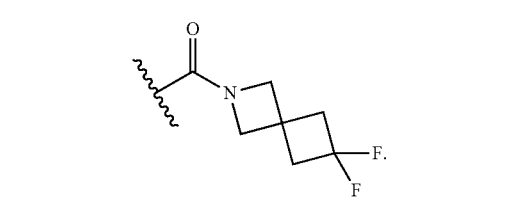 [SMILES: *C(=O)N1CC2(C1)CC(F)(F)C2]

In some embodiments, for the compound or salt of Formula (I), (I'), (II), (III), and (IV), $R^4$ is

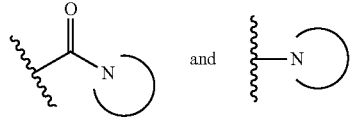

and is selected from an optionally substituted saturated 8-membered bicyclic heterocycle. In some embodiments, the saturated 8-membered bicyclic heterocycle is optionally substituted with one or more substituents selected from halogen, —C(O)$R^{13}$, —C(O)N($R^{13}$)$_2$, N($R^{13}$)C(O)$R^{13}$, —C(O)O$R^{13}$, —OC(O)$R^{13}$, —O$R^{13}$, —NO$_2$, =O, and $C_{1-6}$ alkyl optionally substituted with one or more substitutents selected from halogen, —C(O)$R^{13}$, —C(O)N($R^{13}$)$_2$, N($R^{13}$) C(O)$R^{13}$, —C(O)O$R^{13}$, —OC(O)$R^{13}$, —O$R^{13}$, —NO$_2$, =O, and $C_{3-8}$ carbocycle and 3- to 8-membered heterocycle. In some embodiments, $R^4$ is

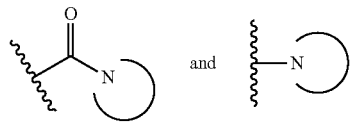

is and selected from an unsubstituted saturated 8-membered bicyclic heterocycle. In some embodiments, $R^4$ is

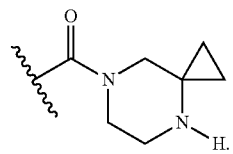

In some embodiments, the compound of Formula (I) is represented by Formula (IA):

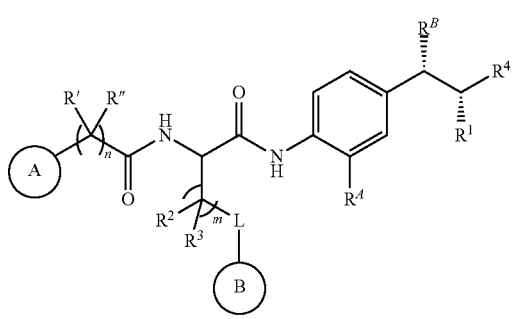

(IA)

or a salt thereof.

In some embodiments, the compound of Formula (I) is represented by Formula (IB):

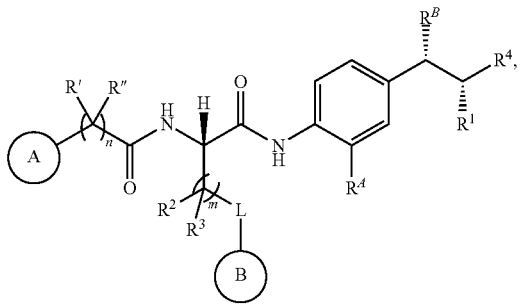

(IB)

or a salt thereof.

In some embodiments, the compound of Formula (I) is represented by Formula (IC):

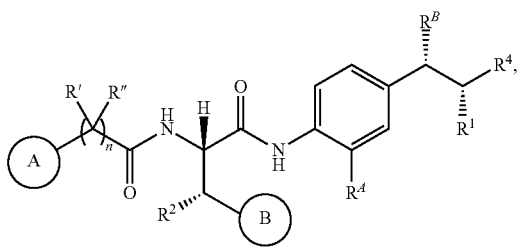

(IC)

or a salt thereof;

wherein $R^2$ is independently selected from —O$R^{17}$, $C_{1-6}$ alkyl, and $C_{3-6}$ cycloalkyl; wherein the $C_{1-6}$ alkyl and $C_{3-6}$ cycloalkyl are optionally substituted with one or more substituents selected from: halogen, —O$R^{17}$, —N($R^{17}$)$_2$, —C(O)$R^{17}$, —NO$_2$, =O, and —CN.

In some embodiments, the compound of Formula (I) is represented by Formula (ID):

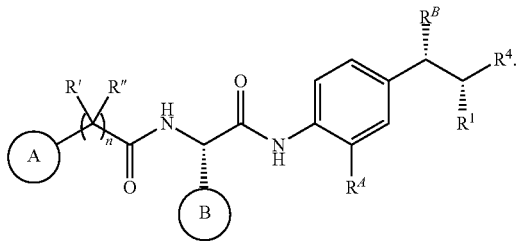

(ID)

In certain embodiments, a compound of the disclosure is selected from a compound described in the Examples herein or a salt thereof.

In certain aspects, the disclosure provides a compound or salt represented by the structure of Formula (I), (I'), (IA), (IB), (IC), or (ID) wherein:

is selected from an 5-membered monocyclic heteroaryl optionally substituted with one or more substituents independently selected from halogen, —OR$^{11}$, —N(R$^{11}$)$_2$, —N(R$^{11}$)S(O)$_2$R$^{11}$, —NO$_2$, —CN, C$_{1-6}$ alkyl, —C$_{1-6}$ alkyl-C$_{3-5}$ carbocycle, C$_{3-5}$ carbocycle, and 3- to 5-membered heterocycle;

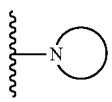

is selected from C$_{3-8}$ monocyclic cycloalkyl optionally substituted with one or more substituents independently selected from: halogen, and C$_{1-6}$ alkyl optionally substituted with one or more substituents independently selected from halogen, —OR$^{12}$, and —CN;

R$^4$ is selected from

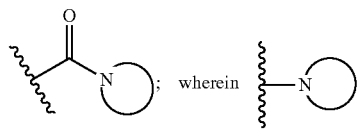

is an optionally substituted saturated 4- to 8-membered heterocycle wherein the optional substituents on are independently selected at each occurrence from: halogen, —OR$^{13}$, —N(R$^{13}$)$_2$, —C(O)R$^{13}$, —C(O)OR$^{13}$, —OC(O)R$^{13}$, =O, and —CN; and C$_{1-6}$ alkyl optionally substituted with one or more substituents independently selected from halogen, —OR$^{13}$, —N(R$^{13}$)$_2$, —C(O)R$^{13}$, —C(O)OR$^{13}$, —OC(O)R$^{13}$, =O, and —CN, C$_{3-10}$ carbocycle and 3- to 10-membered heterocycle, wherein the C$_{3-10}$ carbocycle and 3- to 10-membered heterocycle are each optionally substituted with one or more substituents selected from: halogen, —OR$^{13}$, —N(R$^{13}$)$_2$, —C(O)R$^{13}$, —C(O)OR$^{13}$, —OC(O)R$^{13}$, =O, and —CN;

L is absent;

R$^A$ is selected from hydrogen and halogen, e.g., fluorine;

R$^B$ is selected from hydrogen, —OMe, —OEt, —CF$_3$, —CHF$_2$, —CH$_2$F, methyl, ethyl, propyl, and isopropyl, wherein at least one of R$^A$ or R$^B$ is not hydrogen;

R' and R" are each halogen;

R$^1$ is selected from —N(R$^{21}$)C(O)R$^{22}$, —N(R$^{21}$)C(O)OR$^{22}$, and —N(R$^{21}$)C(O)N(R$^{21}$)(R$^{22}$);

each R$^2$ and R$^3$ are independently selected from hydrogen, —OR$^{17}$, C$_{1-6}$ alkyl, and C$_{3-6}$ cycloalkyl; wherein the C$_{1-6}$ alkyl and C$_{3-6}$ cycloalkyl are optionally substituted with one or more substituents selected from: halogen, —OR$^{17}$, —N(R$^{17}$)$_2$, —C(O)R$^{17}$, —NO$_2$, =O, and —CN;

R$^{21}$ is independently selected at each occurrence from hydrogen and C$_1$-C$_6$ alkyl optionally substituted by one or more substituents independently selected from halogen, —OR$^{17}$, —N(R$^{17}$)$_2$, —C(O)R$^{17}$, —NO$_2$, =O, and —CN;

R$^{22}$ is selected from C$_{1-4}$ alkyl optionally substituted with one or two substituents independently selected from halogen, —OR$^{18}$, —SR$^{18}$, —N(R$^{18}$)$_2$, —C(O)R$^{18}$, —C(O)OR$^{18}$, C$_{3-10}$ carbocycle and 3- to 10-membered heterocycle;

wherein the C$_{3-10}$ carbocycle and 3- to 10-membered heterocycle are each optionally substituted with one or more substituents selected from: halogen, —OR$^{18}$, and —NO$_2$;

R$^{11}$, R$^{12}$, R$^{13}$, R$^{17}$, and R$^{18}$ are independently selected at each occurrence from: hydrogen; and C$_{1-6}$ alkyl optionally substituted with one or more substituents independently selected from halogen, —OH, —O—C$_1$-C$_6$ alkyl, —O—C$_1$-C$_6$ haloalkyl —NH$_2$, —NO$_2$, =O, —CN, C$_{3-10}$ carbocycle and 3- to 10-membered heterocycle; wherein the C$_{3-10}$ carbocycle and 3- to 10-membered heterocycle are each optionally substituted with one or more substituents selected from: halogen, —OH, —O—C$_1$-C$_6$ alkyl, —O—C$_1$-C$_6$ haloalkyl —NH$_2$, —NO$_2$, =O, and —CN; and C$_{3-12}$ carbocycle and 3- to 12-membered heterocycle, each of which is optionally substituted with one or more substituents independently selected from: halogen, —OH, —O—C$_1$-C$_6$ alkyl, —O—C$_1$-C$_6$ haloalkyl —NH$_2$, —NO$_2$, =O, —CN; and C$_{1-6}$ alkyl optionally substituted with one or more substituents independently selected from halogen, —OH, —O—C$_1$-C$_6$ alkyl, —O—C$_1$-C$_6$ haloalkyl —NH$_2$, —NO$_2$, =O, and —CN;

n is selected from 0 and 1; and m is selected from 0, 1, and 2, preferably m is 0 or 1.

In certain aspects, the disclosure provides a compound or salt represented by the structure of Formula (I), (I'), (IA), (IB), (IC), or (ID) wherein:

Ⓐ is selected from pyrazole, tetrazole, oxadiazole, isoxazole, pyrrole, and furan any one of which is optionally substituted with one or more substituents independently selected from halogen, —OR$^{11}$, —N(R$^{11}$)$_2$, —N(R$^{11}$)S(O)$_2$R$^{11}$, —NO$_2$, —CN, C$_{1-6}$ alkyl, —C$_{1-6}$ alkyl-C$_{3-5}$ carbocycle, C$_{3-5}$ carbocycle, and 3- to 5-membered heterocycle, for example,

Ⓐ is pyrazole substituted with C$_{1-6}$ alkyl;

Ⓑ is selected from cyclopentyl, cyclohexyl, and cycloheptyl each of which is optionally substituted with one or more substituents independently selected from halogen, —OR$^{12}$, and optionally substituted C$_{1-3}$ alkyl, for example,

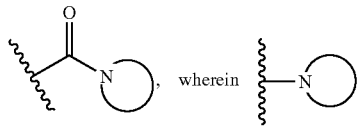

is cyclohexyl optionally substituted with $C_{1-3}$ alkyl;
$R^4$ is

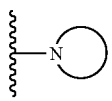

is selected from azetidine, piperidine, piperazine, morpholine, thiomorpholine, thiomorpholine 1,1-dioxide, and azaspiro[3.3]heptane any of which is optionally substituted with one or more substituents independently selected from halogen, —$OR^{13}$, and optionally substituted $C_{1-3}$ alkyl, for example, is piperazine optionally substituted with $C_{1-3}$ alkyl;
L is absent;
$R^A$ is selected from hydrogen and halogen, e.g., fluorine;
$R^B$ is selected from hydrogen, —OMe, —OEt, —$CF_3$, —$CHF_2$, —$CH_2F$, methyl, ethyl, propyl, and isopropyl, wherein at least one of $R^A$ or $R^B$ is not hydrogen, e.g., $R^B$ is methyl;
R' and R" are each halogen;
$R^1$ is selected from —$N(R^{21})C(O)R^{22}$, —$N(R^{21})C(O)OR^{22}$, and —$N(R^{21})C(O)N(R^{21})(R^{22})$, for example, $R^1$ is —$N(R^{21})C(O)R^{22}$;
$R^{21}$ is independently selected at each occurrence from hydrogen and $C_1$-$C_3$ alkyl optionally substituted by one or more substituents independently selected from halogen, —$OR^{17}$, —$N(R^{17})_2$, and —CN, for example, $R^{21}$ is H or $C_1$-$C_3$ alkyl;
$R^{22}$ is selected from $C_{1-4}$ alkyl optionally substituted with one or two substituents independently selected from halogen, —$OR^{18}$, —$SR^{18}$, —$N(R^{18})_2$, —$C(O)R^{18}$, —$C(O)OR^{18}$, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —$OR^{18}$, and —$NO_2$, for example, $R^{22}$ is $C_{1-4}$ alkyl;
$R^{11}$, $R^{12}$, $R^{13}$, $R^{17}$, and $R^{18}$ are independently selected at each occurrence from: hydrogen; and
$C_{1-6}$ alkyl optionally substituted with one or more substituents independently selected from halogen, —OH, —O—$C_1$-$C_6$ alkyl, —O—$C_1$-$C_6$ haloalkyl —$NH_2$, —$NO_2$, =O, —CN, $C_{3-10}$ carbocycle and 3- to 10-membered heterocycle; wherein the $C_{3-10}$ carbocycle and 3- to 10-membered heterocycle are each optionally substituted with one or more substituents selected from: halogen, —OH, —O—$C_1$-$C_6$ alkyl, —O—$C_1$-$C_6$ haloalkyl —$NH_2$, —$NO_2$, =O, and —CN; and $C_{3-12}$ carbocycle and 3- to 12-membered heterocycle, each of which is optionally substituted with one or more substituents independently selected from: halogen, —OH, —O—$C_1$-$C_6$ alkyl, —O—$C_1$-$C_6$ haloalkyl —$NH_2$, —$NO_2$, =O, —CN; and
$C_{1-6}$ alkyl optionally substituted with one or more substituents independently selected from halogen, —OH, —O—$C_1$-$C_6$ alkyl, —O—$C_1$-$C_6$ haloalkyl —$NH_2$, —$NO_2$, =O, and —CN;
n is selected from 0 and 1, e.g., n is 0; and
m is 0.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When stereochemistry is not specified in a chemical structure, molecules with stereocenters described herein include isomers, such as enantiomers and diastereomers, mixtures of enantiomers, including racemates, mixtures of diastereomers, and other mixtures thereof, to the extent they can be made by one of ordinary skill in the art by routine experimentation. In certain embodiments, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration.

In certain embodiments, compositions of the disclosure may comprise two or more enantiomers or diastereomers of a compound wherein a single enantiomer or diastereomer accounts for at least about 70% by weight, at least about 80% by weight, at least about 90% by weight, at least about 98% by weight, or at least about 99% by weight or more of the total weight of all stereoisomers. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) J Chromatogr., 113(3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

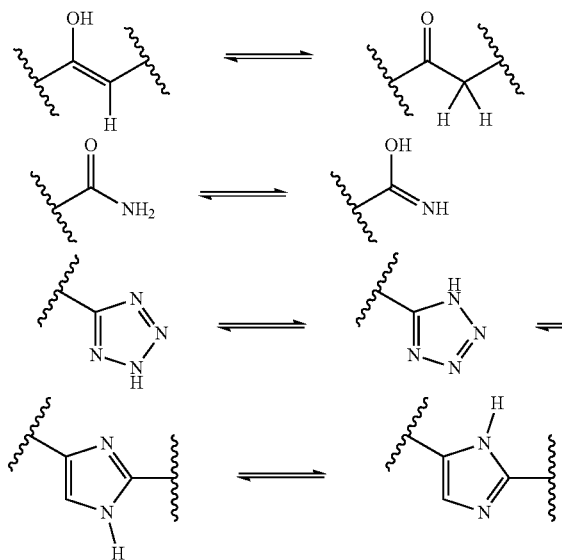
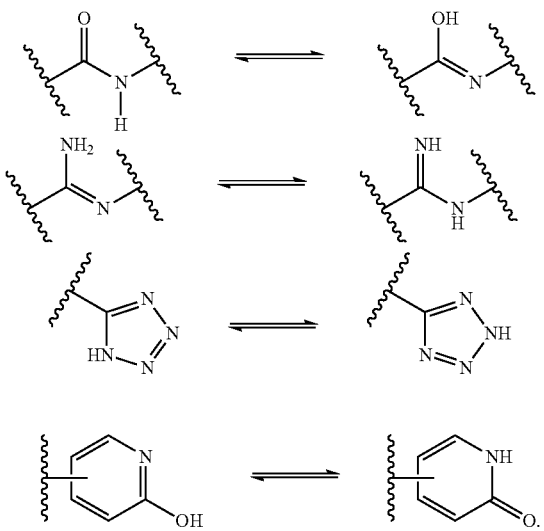

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334, Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In certain embodiments, the prodrug may be converted, e.g., enzymatically or chemically, to the parent compound under the conditions within a cell. In certain embodiments, the parent compound comprises an acidic moiety, e.g., resulting from the hydrolysis of the prodrug, which may be charged under the conditions within the cell. In particular embodiments, the prodrug is converted to the parent compound once it has passed through the cell membrane into a cell. In certain embodiments, the parent compound has diminished cell membrane permeability properties relative to the prodrug, such as decreased lipophilicity and increased hydrophilicity.

In some embodiments, the design of a prodrug increases the lipophilicity of the pharmaceutical agent. In some embodiments, the design of a prodrug increases the effective water solubility. See, e.g., Fedorak et al., *Am. J. Physiol.*, 269:G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as NovelDelivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

In some embodiments, the design of a prodrug increases the lipophilicity of the pharmaceutical agent. In some embodiments, the design of a prodrug increases the effective water solubility. See, e.g., Fedorak et al., *Am. J. Physiol.*, 269:G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as NovelDelivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Formulations

In some aspects, the present disclosure provides a pharmaceutical composition comprising at least one pharmaceutically acceptable excipient and a compound or salt of Formula (I), (I'), (IA), (IB), (IC), (ID), (II), (III), (IV), or a compound or salt described in the examples herein.

Pharmaceutical compositions can be formulated using one or more physiologically-acceptable carriers comprising excipients and auxiliaries. Formulation can be modified depending upon the route of administration chosen. Pharmaceutical compositions comprising a compound or a salt thereof can be manufactured, for example, by lyophilizing the compound or salt thereof, mixing, dissolving, emulsifying, encapsulating or entrapping the compound. The pharmaceutical compositions can also include the compounds or salts thereof, in a free-base form or pharmaceutically-acceptable salt form.

Methods for formulation of the compounds or salts thereof can include formulating any of the compounds or salts with one or more inert, pharmaceutically-acceptable excipients or carriers to form a solid, semi-solid, or liquid composition. Solid compositions can include, for example, powders, tablets, dispersible granules and capsules, and in some aspects, the solid compositions further contain nontoxic, auxiliary substances, for example wetting or emulsifying agents, pH buffering agents, and other pharmaceutically-acceptable additives. Alternatively, the compounds or salts can be lyophilized or in powder form for re-constitution with a suitable vehicle, e.g., sterile pyrogen-free water, before use.

Pharmaceutical compositions can comprise at least one active ingredient (e.g., a compound or salt thereof). The active ingredients can be entrapped in microcapsules prepared, for example, by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nano-particles and nanocapsules) or in macroemulsions.

Pharmaceutical compositions as often further can comprise more than one active compound (e.g., a compound or salt thereof) as necessary for the particular indication being treated. The active compounds can have complementary activities that do not adversely affect each other. Such molecules can be present in combination in amounts that are effective for the purpose intended.

The compositions and formulations can be sterilized. Sterilization can be accomplished by filtration through sterile filtration.

The compositions can be formulated for administration as an injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Injections can be formulated for bolus injection or continuous infusion. Alternatively, the compositions can be lyophilized or in powder form for reconstitution with a suitable vehicle, e.g., sterile pyrogen-free water, before use.

For parenteral administration, the compounds or a salt thereof can be formulated in a unit dosage injectable form (e.g., solution, suspension, emulsion) in association with a pharmaceutically acceptable parenteral vehicle. Such vehicles can be inherently non-toxic, and non-therapeutic. Vehicles can be water, saline, Ringer's solution, dextrose solution, and 5% human serum albumin. Non-aqueous vehicles such as fixed oils and ethyl oleate can also be used. Liposomes can be used as carriers. The vehicle can contain minor amounts of additives such as substances that enhance isotonicity and chemical stability (e.g., buffers and preservatives).

Sustained-release preparations can also be prepared. Examples of sustained-release preparations can include semipermeable matrices of solid hydrophobic polymers that can contain the compound or a salt thereof, and these matrices can be in the form of shaped articles (e.g., films or microcapsules). Examples of sustained-release matrices can include polyesters, hydrogels (e.g., poly(2-hydroxyethyl-methacrylate), or poly (vinyl alcohol)), polylactides, copolymers of L-glutamic acid and γ ethyl-L-glutamate, non-degradable ethylene-vinyl acetate, degradable lactic acid-glycolic acid copolymers such as the LUPRON DEPO™ (i.e., injectable microspheres composed of lactic acid-glycolic acid copolymer and leuprolide acetate), and poly-D-(−)-3-hydroxybutyric acid.

Pharmaceutical formulations can be prepared for storage by mixing a compound or a salt thereof with a pharmaceutically acceptable carrier, excipient, and/or a stabilizer. This formulation can be a lyophilized formulation or an aqueous solution. Acceptable carriers, excipients, and/or stabilizers can be nontoxic to recipients at the dosages and concentrations used. Acceptable carriers, excipients, and/or stabilizers can include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol A compound or salt of any one of Formula (I), (I'), (IA), (IB), (IC), (ID), (II), (III), and (IV), may be formulated in any suitable pharmaceutical formulation. A pharmaceutical formulation of the present disclosure typically contains an active ingredient (e.g., compound or salt of any one of Formula (I), (I'), (IA), (IB), (IC), (ID), (II), (III), and (IV) and one or more pharmaceutically acceptable excipients or carriers, including but not limited to: inert solid diluents and fillers, diluents, sterile aqueous solution and various organic solvents, permeation enhancers, antioxidants, solubilizers, and adjuvants.

In certain embodiments, a compound or salt of Formula (I), (I'), (IA), (IB), (IC), (ID), (II), (III), or (IV) is formulated with an agent that inhibits degradation of the compound or salt. In certain embodiments, the compound or salt is formulated with one or more antioxidants. Acceptable antioxidants include, but are not limited to, citric acid, d,l-α-tocopherol, BHA, BHT, monothioglycerol, ascorbyl palmitate, ascorbic acid, and propyl gallate. In certain embodiments, the formulation contains from 0.1 to 30%, from 0.5 to 25%, from 1 to 20%, from 5 to 15%, or from 7 to 12% (wt/wt) CCI-779, from 0.5 to 50%, from 1 to 40%, from 5 to 35%, from 10 to 25%, or from 15 to 20% (wt/wt) water soluble polymer, from 0.5 to 10%, 1 to 8%, or 3 to 5% (wt/wt) surfactant, and from 0.001% to 1%, 0.01% to 1%, or 0.1% to 0.5% (wt/wt) antioxidant. In certain embodiments, the antioxidants of the formulations of this invention will be used in concentrations ranging from 0.001% to 3% wt/wt.

In certain embodiments, a compound or salt of Formula (I), (I'), (IA), (IB), (IC), (ID), (II), (III), or (IV) is formulated with a pH modifying agent to maintain a pH of about 4 to about 6. Acceptable pH modifying agents include, but are not limited to citric acid, sodium citrate, dilute HCl, and other mild acids or bases capable of buffering a solution containing a compound or a salt of the disclosure to a pH in the range of about 4 to about 6.

In certain embodiments, a compound or salt of Formula (I), (I'), (IA), (IB), (IC), (ID), (II), (III), or (IV) is formulated with a chelating agent or other material capable of binding metal ions, such as ethylene diamine tetra acetic acid (EDTA) and its salts are capable of enhancing the stability of a compound or salt of Formula (I), (I'), (IA), (IB), (IC), (ID), (II), (III), or (IV).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of compound or salt of any one of Formula (I), (I'), (IA), (IB), (IC), (ID), (II), (III), or (IV) will be dependent on the mammal being treated, the severity of the disorder or condition, the rate of administration, the disposition of the compound or salt of any one of Formula (I), (I'), (IA), (IB), (IC), (ID), (II), (III), and (IV) and the discretion of the prescribing physician.

In some embodiments, pharmaceutically acceptable carriers of Formula (I), (I'), (IA), (IB), (IC), (ID), (II), (III), and (IV), can include a physiologically acceptable compound that is an antioxidant.

In some embodiments, the disclosure provides a pharmaceutical composition for oral administration containing at least one compound or salt of any one of Formula (I), (I'), (IA), (IB), (IC), (ID), (II), (III), and (IV) and a pharmaceutical excipient suitable for oral administration. The composition may be in the form of a solid, liquid, gel, semi-liquid, or semi-solid. In some embodiments, the composition further comprises a second agent.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound or salt of any one of Formula (I), (I'), (IA), (IB), (IC), (ID), (II), (III), and (IV) moistened with an inert liquid diluent.

In some embodiments, the disclosure provides a pharmaceutical composition for injection containing a compound or salt of any one of Formula (I), (I'), (IA), (IB), (IC), (ID), (II), (III), and (IV) disclosed herein and a pharmaceutical excipient suitable for injection. Components and amounts of agents in the composition are as described herein.

In certain embodiments, the compound or salt of any one of Formula (I), (I'), (IA), (IB), (IC), (ID), (II), (III), and (IV) may be formulated for injection as aqueous or oil suspensions, emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Pharmaceutical compositions may also be prepared from a compound or salt of any one of Formula (I), (I'), (IA), (IB), (IC), (ID), (II), (III), and (IV) and one or more pharmaceutically acceptable excipients suitable for transdermal, inhalative, sublingual, buccal, rectal, intraosseous, intraocular, intranasal, epidural, or intraspinal administration. Preparations for such pharmaceutical composition are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999).

The disclosure also provides kits. The kits may include a compound or salt of any one of Formula (I), (I'), (IA), (IB), (IC), (ID), (II), (III), and (IV) and one or more additional agents in suitable packaging with written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound or salt of any one of Formula (I), (I'), (IA), (IB), (IC), (ID), (II), (III), and (IV) and the agent are provided as separate compositions in separate containers within the kit. In some embodiments, the compound or salt of any one of Formula (I), (I'), (IA), (IB), (IC), (ID), (II), (III), and (IV) and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN©, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the U.S. Pharmacopeia (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/ vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MILV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known agents by comparing the $IC_{50}$, MIC and/or $I_{100}$ of the specific compound disclosed herein with that of a known agent and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, In: *The Pharmacological Basis of Therapeutics*, Ch. 1, p. 1).

The therapy may be repeated intermittently. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months. In other embodiments, administrations may be separated by Therapeutic Applications In certain embodiments, a compound or salt of Formula (I), (I'), (IA), (IB), (IC), (ID), (II), (III), (IV), or a compound described in the Examples or a salt thereof, can be used to treat or prevent a disease or condition that is mediated directly or indirectly by IL-17A. Such diseases include inflammatory diseases and conditions, proliferative diseases (e.g., cancer), autoimmune diseases and other disease described herein. The methods generally involve administering therapeutically effective amounts of compounds disclosed herein or a pharmaceutical composition thereof to the subject.

Increased levels of IL-17A have been associated with several conditions including airway inflammation, rheumatoid arthritis (RA), osteoarthritis, bone erosion, intraperitoneal abscesses and adhesions, inflammatory bowel disorder (IBD), allograft rejection, psoriasis, psoriatic arthritis, ankylosing spondylitis, certain types of cancer, angiogenesis, atherosclerosis and multiple sclerosis (MS). Both IL-17A and IL-17R are upregulated in the synovial tissue of RA patients. IL-17A exerts its role in pathogenesis of RA through IL-1-β and TNF-α dependent and independent pathways. IL-17A stimulates secretion of other cytokines and chemokines, e.g., TNF-α, IL-1β, IL-6, IL-8 and Gro-α. IL-17A directly contributes to disease progression in RA. Injection of IL-17A into the mouse knee promotes joint destruction independently of IL-I β activity (Ann Rheum Dis 2000, 59:529-32). Anti-IL-1β antibody has no effect on IL-17A induced inflammation and joint damage (J Immunol 2001, 167:1004-1013). In an SCW-induced murine arthritis model, IL-17A induced inflammatory cell infiltration and proteoglycan depletion in wild-type and IL-1β knockout and TNF-α knockout mice. IL-17A knockout mice are phenotypically normal in the absence of antigenic challenge but have markedly reduced arthritis following type II collagen immunization (J Immunol 2003, 171:6173-6177). Increased levels of IL-17A-secreting cells have also been observed in the facet joints of patients suffering from ankylosing spondylitis (H Appel et al., Arthritis Res Therap 2011, 13:R95).

Multiple sclerosis is an autoimmune disease characterized by central nervous system (CNS) inflammation with damage to the myelin sheath surrounding axons. A hallmark of MS is that T cells infiltrate into the CNS. Higher numbers of IL-17A mRNA-expressing blood mono-nuclear cells (MNC) are detected during MS clinical exacerbation compared to remission (Multiple Sclerosis, 5:101-104, 1999). Furthermore, experimental autoimmune encephalomyelitis ("EAE"), a preclinical animal model for MS is significantly suppressed in IL-17A knockout mice.

In certain aspects, the disclosure provides methods of modulating IL-17A in a subject in need thereof, comprising administering to said subject a compound or salt of any one of Formula (I), (I'), (IA), (IB), (IC), (ID), (II), (III), and (IV). In certain embodiments, a compound or salt of Formula (I), (I'), (IA), (IB), (IC), (ID), (II), (III), or (IV) inhibits the activity of IL-17A in a subject in need thereof.

In certain embodiments, a compound or salt of Formula (I), (I'), (IA), (IB), (IC), (ID), (II), (III), or (IV) is used to treat or prevent an inflammatory disease or condition. In certain embodiments, a compound or salt of Formula (I), (I'), (IA), (IB), (IC), (ID), (II), (III), or (IV) is administered to a subject in need thereof to treat an inflammatory disease or condition, e.g., psoriasis.

In certain embodiments, a compound or salt of Formula (I), (I'), (IA), (IB), (IC), (ID), (II), (III), or (IV) is used to treat or prevent an inflammatory disease or condition is selected from, plaque psoriasis, guttate psoriasis, inverse psoriasis, pustular psoriasis, erythrodermic psoriasis, aspsoriatic arthritis, ankyslosing spondylitis, hidradenitis suppurutiva, rheumatoid arthritis, Palmoplantar Psoriasis, Spondyloarthritis, and Non-infectious Uveitis. In certain embodiments, a compound or salt of Formula (I), (I'), (IA), (IB), (IC), (ID), (II), (III), or (IV) is used to treat or prevent psoriasis.

In certain embodiments, a compound or salt of Formula (I), (I'), (IA), (IB), (IC), (ID), (II), (III), or (IV) is used for the treatment or prevention of a condition including, but not limited to, airway inflammation, ankylosing spondylitis, asthma, RA (including juvenile RA), osteoarthritis, bone erosion, intraperitoneal abscesses and adhesions, IBD, Crohn's disease, allograft rejection, psoriasis, psoriatic arthritis, certain types of cancer, angiogenesis, atherosclerosis and MS, as well as other inflammatory disorders, conditions, diseases or states including without limit: erythematosus, response to allergen exposure, *Helicobacter pylori* associated gastritis, bronchial asthma, allograft rejection (e.g., renal), systemic lupus erythematosus and lupus nephritis.

In certain embodiments, a compound or salt of Formula (I), (I'), (IA), (IB), (IC), (ID), (II), (III), or (IV) is used for the treatment or prevention of a condition including, but not limited to, Behcet's disease, ulcerative colitis, Wegener's granulomatosis, sarcoidosis, systemic sclerosis, insulin-dependent diabetes mellitus, septic shock syndrome, Alzheimer's disease, an inflammatory eye disease, and uveitis is provided.

In some embodiments, a compound or salt of Formula (I), (I'), (IA), (IB), (IC), (ID), (II), (III), or (IV) is used for treating a patient suffering from a disease or condition associated with elevated levels of IL-17A comprising the steps of: a) determining whether the patient has an elevated level of one or more IL-17A-induced chemokine or effector; and b) if the patient does have an elevated level of the one or more IL-17A chemokine or effector, administering to the patient an effective amount of a compound or salt of Formula (I), (I'), (IA), (IB), (IC), (ID), (II), (III), or (IV) for a time sufficient to treat the disease or condition is provided. The IL-17A chemokine or effector may be one or more of IL-6, IL-8, G-CSF, TNF-α, IL-1β, PGE2 or IFN-γ.

Methods for determining the levels of IL-17A or any of its chemokines or effectors in a patient are well-known in the art. Typically, a tissue or biological fluid sample is obtained from the patient and is subject to ELISA with commercially available antibodies or kits (e.g., Quantikine IL-17A ELISA; R&D Systems, Minneapolis, Minn., USA). Commercially available antibodies and kits are available for IL-6, IL-8, G-CSF, TNF-α, IL-1β, PGE2, and IFN-γ.

General Synthetic Schemes and Examples

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Examples 1-39 show the general procedure for the preparation of the claimed IL-17A modulators. Example 40 shows IL-17A/A inhibition data for selected compounds.

Example 1: Exemplary Scheme—Synthesis of Intermediate Compounds 62a-62d

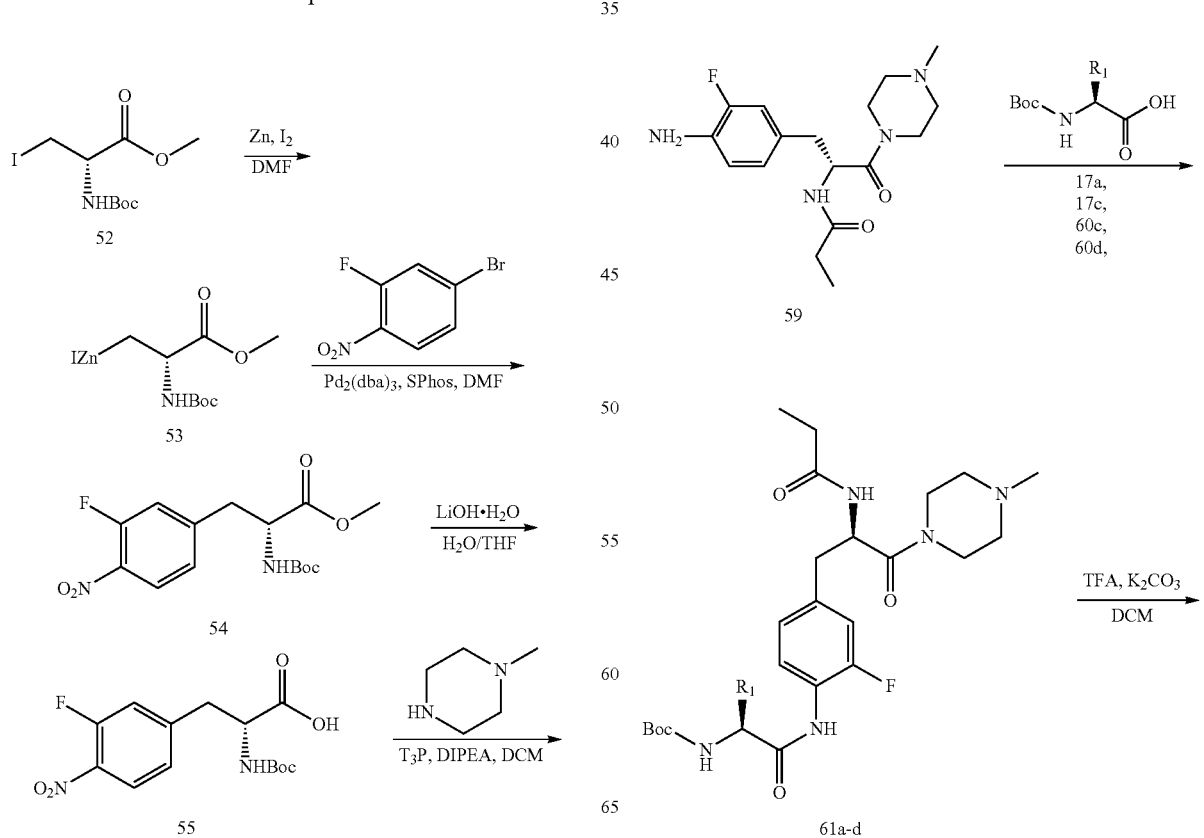

-continued

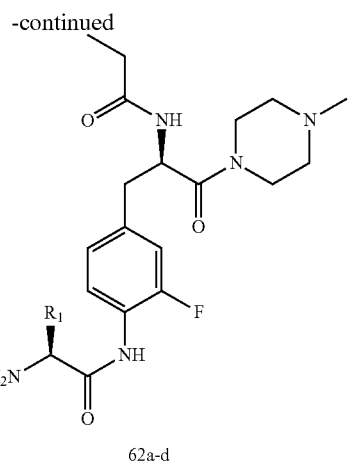

62a-d

Step 1: To a suspension of Zn (28.4 g, 434 mmol, 1.78 eq) in DMF (200 mL) was added $I_2$ (6.17 g, 24.3 mmol, 4.90 mL, 0.100 eq) at 20° C., then the mixture was stirred for 0.2 hr while the color changed from brown to grey. Then to the suspension was added compound 52 (80.0 g, 243 mmol, 1.00 eq) along with $I_2$ (6.17 g, 24.3 mmol, 4.90 mL, 0.100 eq) at 20° C. which was stirred at 20° C. for 2 hrs. The iodozinc compound 53 was not isolated.

Step 2: To compound 53 in DMF (200 mL) was added to a mixture of 3-fluoro, 4-nitro bromobenzene (53.5 g, 243 mmol, 1.00 eq), SPhos (5.99 g, 14.6 mmol, 0.060 eq) and $Pd_2(dba)_3$ (6.68 g, 7.29 mmol, 0.030 eq) in DMF (400 mL) at 20° C., and the solution was then stirred at 65° C. under $N_2$ for 6 hrs. TLC (plate 1, Petroleum ether:Ethyl acetate=5:1, $R_f$=0.23) showed that some 3-fluoro, 4-nitro bromobenzene remained, and one other major spot had formed. LCMS indicated the formation of desired product. The reaction mixture was concentrated under reduced pressure to remove most of the DMF, diluted with ethyl acetate (500 mL) and water (300 mL), and filtered and extracted with ethyl acetate (200 mL (3×)). The combined organic layer was washed with water (300 mL) and brine (300 mL), dried over $Na_2SO_4$ and concentrated under reduced pressure to give a residue. The residue was purified by column ($SiO_2$, Petroleum ether:Ethyl acetate=1:0 to 10:1; plate 2, Petroleum ether:Ethyl acetate=5:1) to provide the desired product, compound 54 (36.0 g, 105 mmol, 43.3% yield), as a yellow solid, which was used in the next step. LCMS: (M-99)+: 243.2.

Step 3: To a solution of compound 54 (36.0 g, 105 mmol, 1.00 eq) in THF (300 mL) was added a solution of LiOH $H_2O$ (8.83 g, 210 mmol, 2.00 eq) in $H_2O$ (300 mL), and the mixture was stirred at 20° C. for 12 hrs. LCMS indicated the presence of the desired product. The reaction mixture was diluted with water (150 mL), and then the pH of the solution was adjusted to 3 by 1 M HCl and extracted with ethyl acetate (200 mL (3×)). The combined organic layers were washed with brine (300 mL (2×)), dried over $Na_2SO_4$, and concentrated under reduced pressure to give a crude product, compound 55 (36.8 g, crude), as a brown gum. LCMS: (M-99)+: 229.1.

Step 4: To a solution of compound 55 (36.8 g, 106 mmol, 1.00 eq) in DCM (350 mL) was added N-methyl piperazine (12.8 g, 127 mmol, 14.1 mL, 1.20 eq), followed with $T_3P$ (81.0 g, 127 mmol, 75.7 mL, 50.0% purity, 1.20 eq) and DIEA (20.6 g, 159 mmol, 27.7 mL, 1.50 eq) at −20° C., and then the mixture was stirred at −20° C. for 1.5 hrs. LCMS showed compound 55 was completely consumed, and the desired product was formed. The reaction mixture was diluted with sat. aq. $NaHCO_3$ (300 mL), and the organic layer was washed with water (200 mL) and brine (200 mL), dried over $Na_2SO_4$, and concentrated under reduced pressure to give the crude product, compound 56 (41.4 g, crude), as a yellow gum. A sample was obtained by prep-TLC (plate 1, DCM:MeOH=10:1, $R_f$=0.47) whose structure was confirmed by LCMS: (M+1)+: 411.3.

Step 5: To a solution of compound 56 (41.4 g, 101 mmol, 1.00 eq) in DCM (250 mL) was added HCl/dioxane (4.00 M, 250 mL, 9.93 eq) at 0° C. Then the mixture was warmed to 20° C. and stirred for 1 hr. LCMS showed compound 56 was completely consumed to provide the desired product. The reaction mixture was concentrated under reduced pressure to give a crude product, compound 57 (40.9 g, crude, 2HCl), as a yellow solid. LCMS: (M+1)+: 311.3.

Step 6: To a solution of compound 57 (40.9 g, 107 mmol, 1.00 eq, 2HCl) in DCM (400 mL) was added TEA (32.4 g, 320 mmol, 44.5 mL, 3.00 eq) and propanoyl propanoate (16.7 g, 128 mmol, 16.5 mL, 1.20 eq) at 0° C. in turn. Then the mixture was warmed to 20° C. and stirred for 2 hrs. LCMS indicated the formation of the desired product. The reaction mixture was diluted with sat. aq. $NaHCO_3$ (100 mL) and extracted with further DCM (50.0 mL*2) The combined organic layers were washed with brine (50.0 mL), dried over $Na_2SO_4$, and concentrated under reduced pressure to give the desired product, compound 58 (36.7 g, crude), as a yellow solid. LCMS: (M+1)+: 367.3.

Step 7: To a solution of compound 58 (35.7 g, 97.6 mmol, 1.00 eq) in MeOH (350 mL) was added Raney Ni (7.00 g, 119 mmol, 1.22 eq) under $N_2$ at 20° C., and then the mixture was degassed and purged with $H_2$ (50 psi) and stirred for 4 hrs. LCMS indicated the presence of the desired product. The reaction mixture was filtered and concentrated under reduced pressure to give a residue. The residue was purified by Reverse-MPLC ($NH_4OH$) on Xtimate C-18 (20/40 um, 120A) gel eluted with $H_2O$:MeCN (75:25) to give the desired product 59 (21.3 g, 61.3 mmol, 62.8% yield, 96.8% purity) as a yellow solid. LCMS: (M+1)+: 337.3.

Example 2: General Scheme Synthesis of Intermediates 61a-d (Step 8)

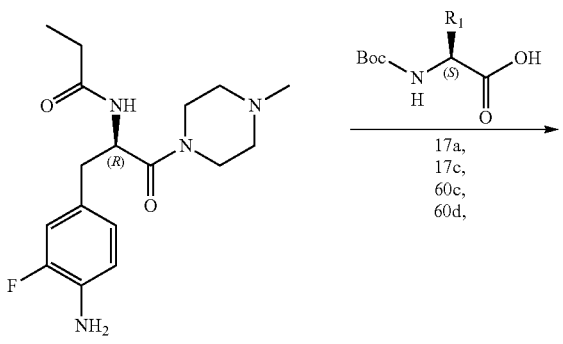

59

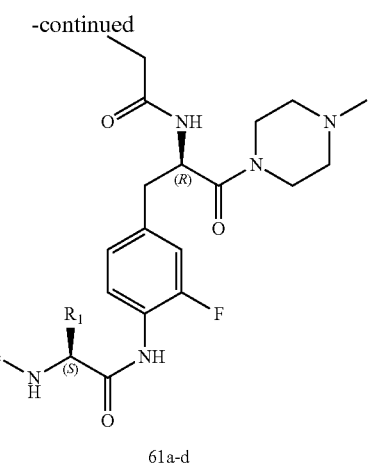

61a-d

Reagents

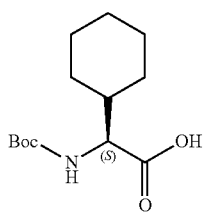
17a

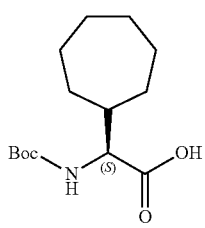
17c

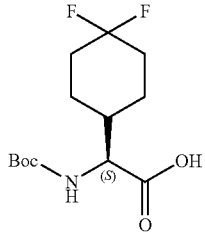
60c

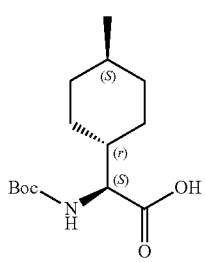
60d

To a solution of N-[(2R)-3-(4-amino-3-fluorophenyl)-1-(4-methylpiperazin-1-yl)-1-oxopropan-2-yl]propanamide 59 (1.0 eq.) in DMF were added 17a, 17c, 60c, or 60d (1.2 eq.), DIPEA (4.0-8.0 eq.) and HATU (1.5-2.0 eq.), and the resulting mixture was stirred for 1 h. Aqueous saturated sodium bicarbonate solution was added and then the product was extracted with EtOAc. The combined organic phases were washed with brine, dried over sodium sulfate, and then concentrated to afford 61a-d which was used in the next step without further purification.

Step 8a: Compound 59 (2.69 g, 8.00 mmol, 1.0 eq.) was reacted with (2S)-2-{[(tert-butoxy)carbonyl]amino}-2-cyclohexylacetic acid 17a (2.47 g, 9.60 mmol, 1.2 eq.), HATU (6.08 g, 16.0 mmol, 2.0 eq.) and DIPEA (5.6 mL, 32.0 mmol, 4.0 eq.) in DMF (27 mL) to afford, after aqueous work-up, 61a (4.41 g, 96% yield) as a yellow solid which was used in the next step without further purification. UPLC-MS (basic 2 min): rt=1.09 min; m/z=576.3 for $[M+H]^+$.

Step 8b: Compound 59 (0.200 g, 0.595 mmol, 1.0 eq.) was reacted with (2S)-2-{[(tert-butoxy)carbonyl]amino}-2-cycloheptylacetic acid) 17c (0.194 g, 0.713 mmol, 1.2 eq.), HATU (0.339 g, 0.892 mmol, 1.5 eq.) and DIPEA (0.83 mL, 4.76 mmol, 8.0 eq.) in DMF (2 mL) to afford, after aqueous work-up, 61b (0.140 g, 40% yield) as a yellow-orange gummy solid which was used in the next step without further purification. UPLC-MS (basic 2 min): rt=1.12 min; m/z=590.2 for $[M+H]^+$.

Step 8c: Compound 59 (0.300 g, 0.892 mmol, 1.0 eq.) was reacted with (2S)-2-{[(tert-butoxy)carbonyl]amino}-2-(4,4-difluorocyclohexyl)acetic acid) 60c (0.314 g, 1.07 mmol, 1.2 eq.), HATU (0.678 g, 1.78 mmol, 2.0 eq.) and DIPEA (1.2 mL, 7.13 mmol, 8.0 eq.) in DMF (6 mL) to afford, after aqueous work-up, 61c (0.284 g, 52% yield) as a yellow gummy solid which was used in the next step without further purification. UPLC-MS (basic 2 min): rt=1.04 min; m/z=612.3 for $[M+H]^+$.

Step 8d: Compound 59 (0.200 g, 0.595 mmol, 1.0 eq.) was reacted with (2S)-2-{[(tert-butoxy)carbonyl]amino}-2-[(1r,4S)-4-methylcyclohexyl]acetic acid 60d (0.194 g, 0.713 mmol, 1.2 eq.), HATU (0.339 g, 0.892 mmol, 1.5 eq.) and DIPEA (0.83 mL, 4.76 mmol, 8.0 eq.) in DMF (2 mL) to afford, after aqueous work-up, 61d (0.184 g, 53% yield) as a yellow gummy solid which was used in the next step without further purification. UPLC-MS (basic 2 min): rt=1.14 min; m/z=590.2 for $[M+H]^+$.

Example 3: General Scheme—Synthesis of Intermediates 62a-d (Step 9)

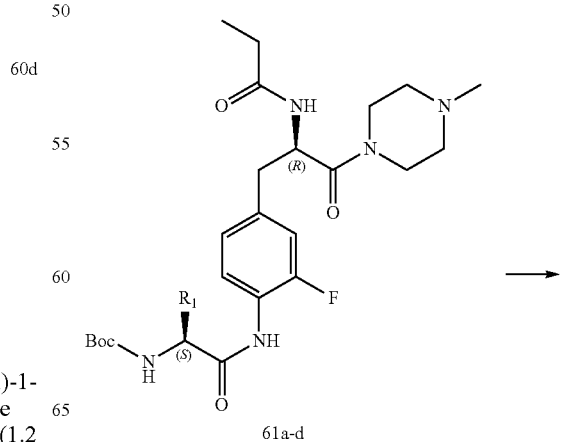

61a-d

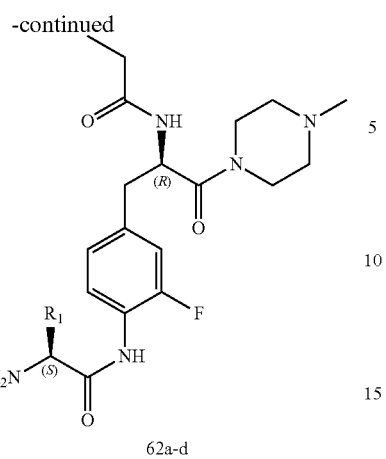

62a-d

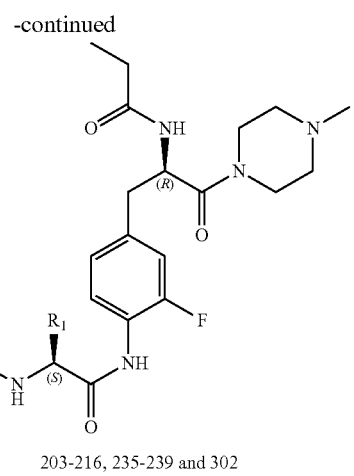

203-216, 235-239 and 302

To a solution of 61a-d (1.0 eq.) in DCM was added TFA, and the resulting mixture was stirred at RT for 0.5 h. The reaction mixture was concentrated to dryness and the residue was stirred in aq. sat. $K_2CO_3$ solution and then extracted with DCM to afford 62a-d which was used in the next step without further purification.

Step 9a: Compound 61a (3.11 g, 5.40 mmol, 1.0 eq.) was reacted with TFA (10 mL) in DCM (10 mL) to afford, after aqueous work-up, 62a (2.54 g, 99% yield) as a yellow solid which was used in the next step without further purification. UPLC-MS (basic 2 min): rt=0.93 min; m z=476.3 for $[M+H]^+$.

Step 9b: Compound 61b (0.140 g, 0.237 mmol, 1.0 eq.) was reacted with TFA (1 mL) in DCM (2 mL) to afford, after aqueous work-up, 62b (0.084 g, 72% yield) as a yellow gummy solid which was used in the next step without further purification. UPLC-MS (basic 2 min): rt=0.99 min; m/z=490.3 for $[M+H]^+$.

Step 9c: Compound 61c (0.284 g, 0.464 mmol, 1.0 eq.) was reacted with TFA (2 mL) in DCM (4 mL) to afford, after aqueous work-up, 62c (0.190 g, 80% yield) as a yellow gummy solid which was used in the next step without further purification. UPLC-MS (basic 2 min): rt=0.88 min; m/z=512.2 for $[M+H]^+$.

Step 9d: Compound 61d (0.160 g, 0.271 mmol, 1.0 eq.) was reacted with TFA (1 mL) in DCM (2 mL) to afford, after aqueous work-up, 62d (0.090 g, 68% yield) as a yellow gummy solid which was used in the next step without further purification. UPLC-MS (basic 2 min): rt=0.99 min; m/z=490.3 for $[M+H]^+$.

Example 4: General Scheme—Synthesis of Compounds 203-216, 235-239, and 302

To a solution of 62a-d (1.0 eq) in DMF were added the required carboxylic acid (1.2 eq.), DIPEA (3.0-8.0 eq.), and then HATU (1.5-2.0 eq.), and the resulting mixture was stirred at RT for 1 h. The mixture was concentrated to dryness and the residue was purified via reverse phase column chromatography on a 120 g C18 cartridge eluting with a 5-95% $H_2O$:MeCN eluent (0.1% ammonia) to afford compounds 203-216, 235-239 and 302.

The following compounds were made following a procedure analogous to Example 4 starting from 62a-d and reacting with the appropriate carboxylic acid.

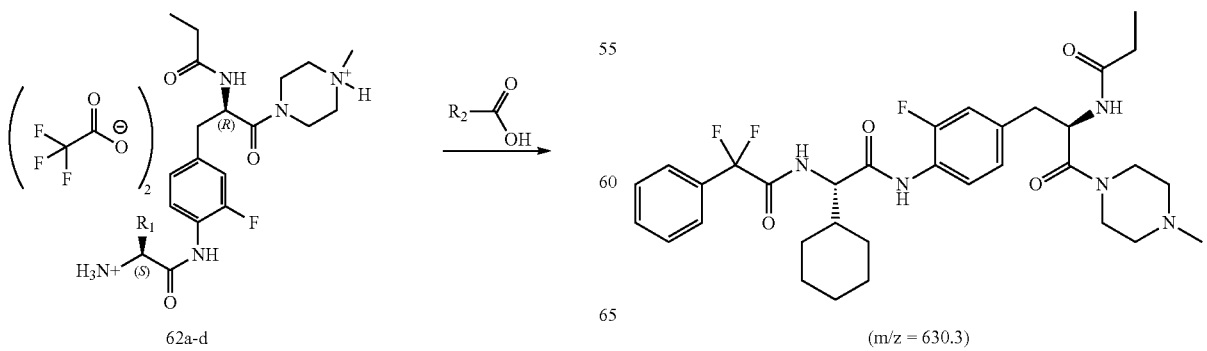

203

(m/z = 661.4)

204

(m/z = 630.3)

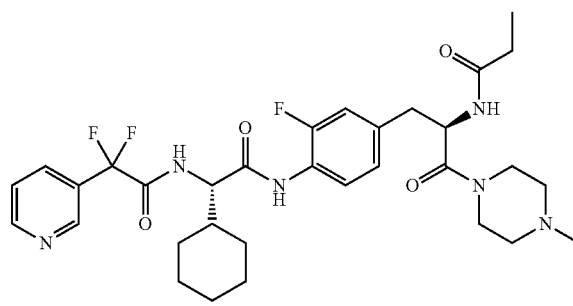
205
(m/z = 631.3)
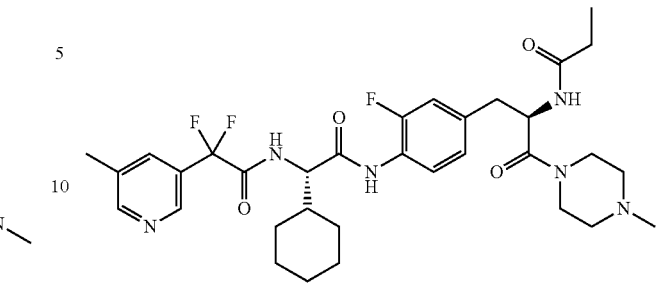
209
(m/z = 645.4)
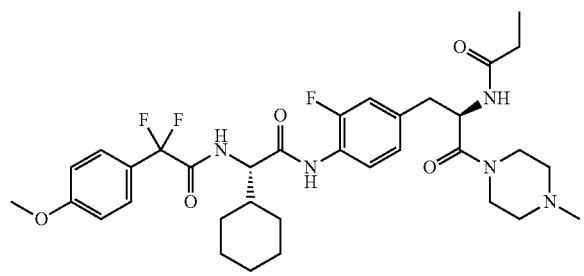
206
(m/z = 666.3)
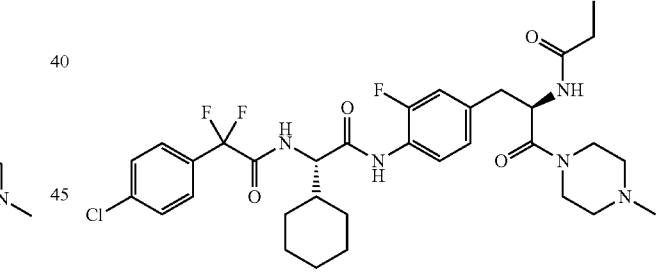
210
(m/z = 644.4)
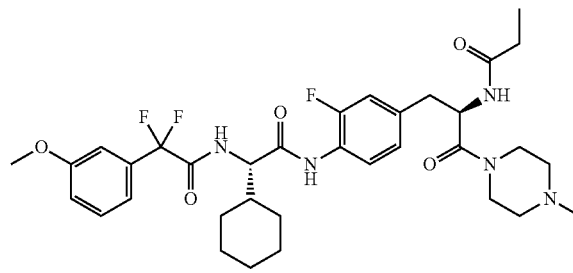
207
(m/z = 660.4)
211
(m/z = 664.35)
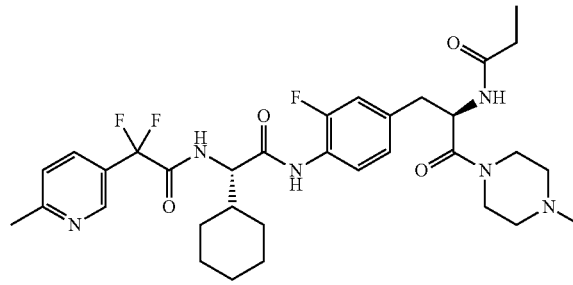
208
(m/z = 645.3)
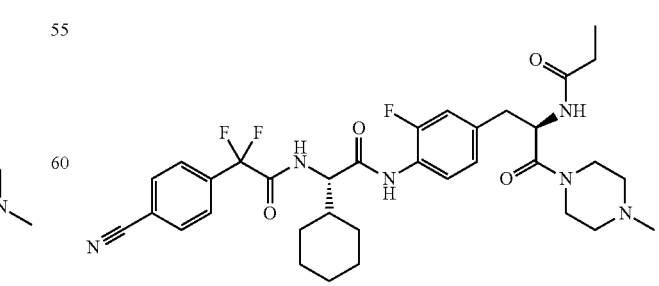
212
(m/z = 655.3)

213
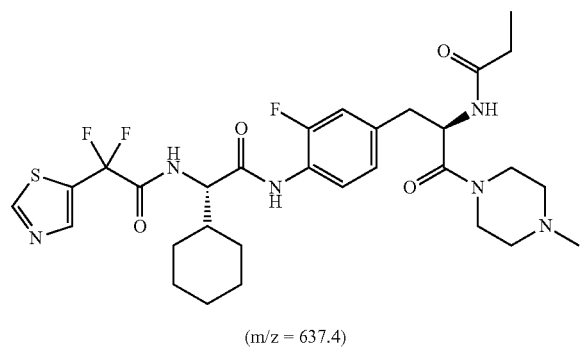
(m/z = 637.4)
214
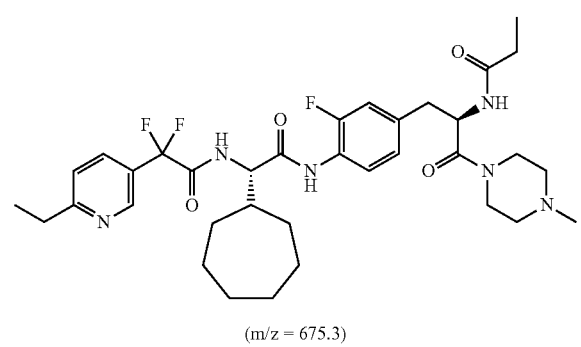
(m/z = 675.3)
215
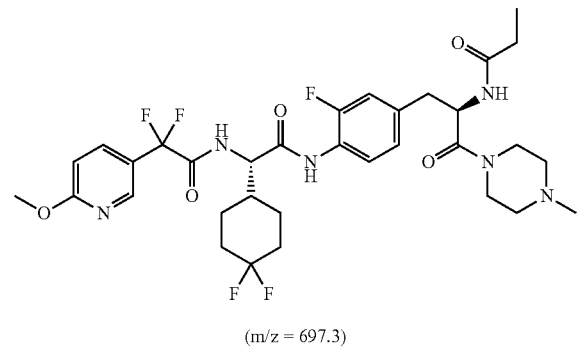
(m/z = 697.3)
216
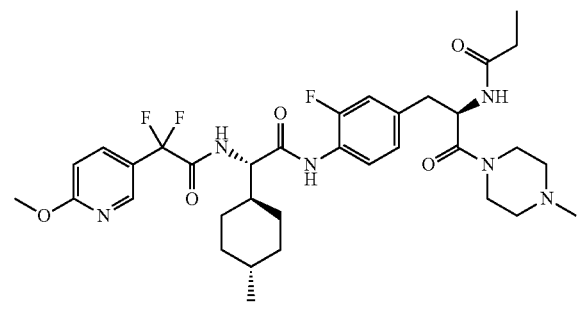
(m/z = 675.3)
235
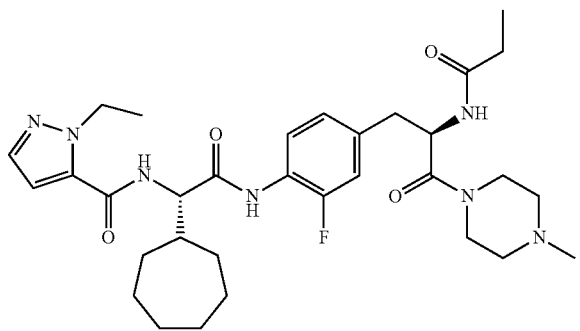
(m/z = 612.4)
236
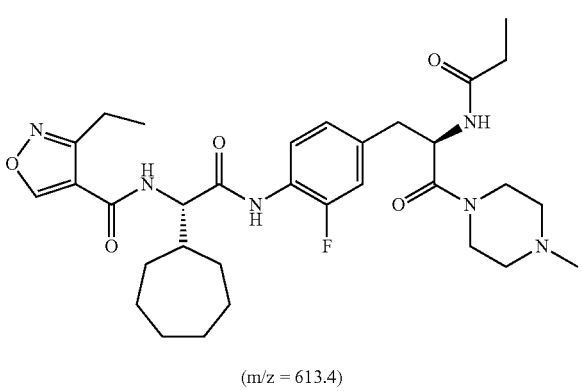
(m/z = 613.4)
237
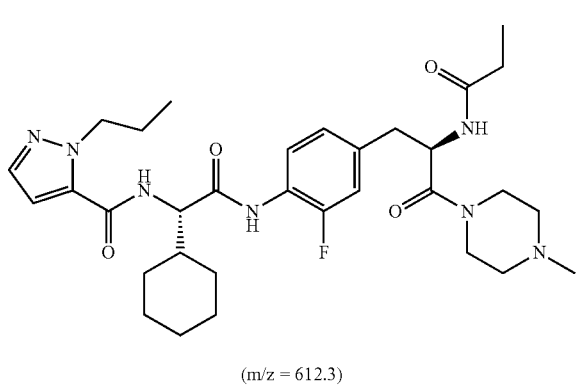
(m/z = 612.3)
238
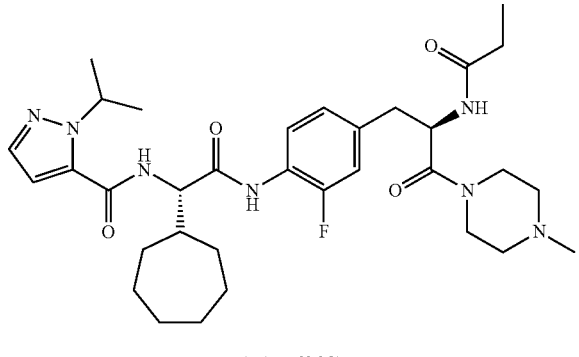
(m/z = 626.3)

-continued

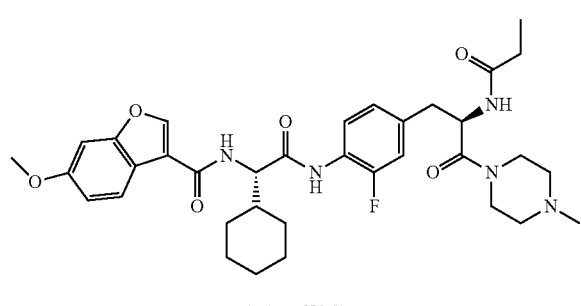

(m/z = 650.3)

239

To a solution of 203 (0.063 g, 0.095 mmol, 1.0 eq.) in DCM (1.89 mL) was added iodotrimethylsilane (14 μL, 0.100 mmol, 1.05 eq.), and the resulting mixture was stirred at RT for 18 h. Methanol (0.2 mL) was added to the reaction mixture and then the solution was concentrated to dryness. The residue was purified via reverse phase column chromatography on a 120 g C18 cartridge eluting with a 5-95% $H_2O$:MeCN eluent (0.1% ammonia) to afford 217 (24.4 mg) as a white solid. UPLC-MS (basic 2 min): rt=0.87 min; m/z=647.3 for $[M+H]^+$ Example 6: Exemplary Scheme Synthesis of Intermediate Compounds 74 and 75

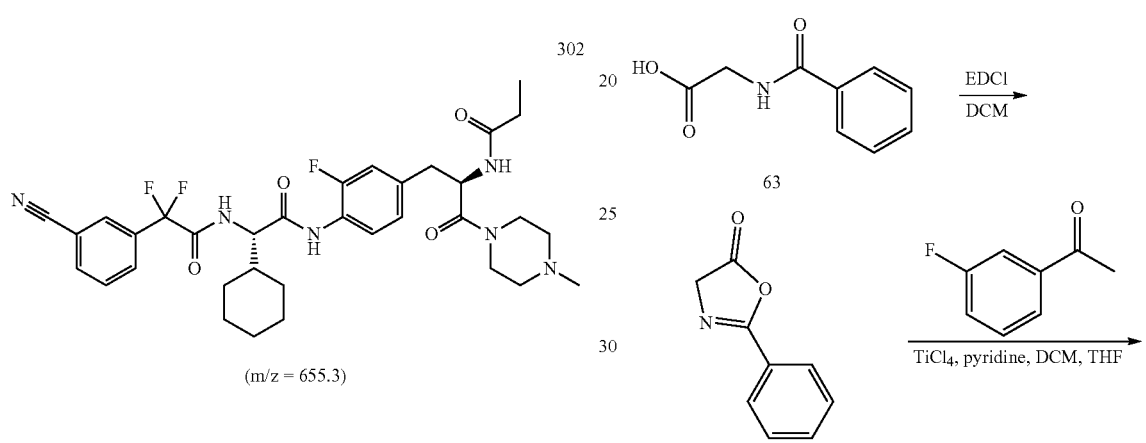

(m/z = 655.3)

Example 5: Exemplary Scheme—Synthesis of Compound 217

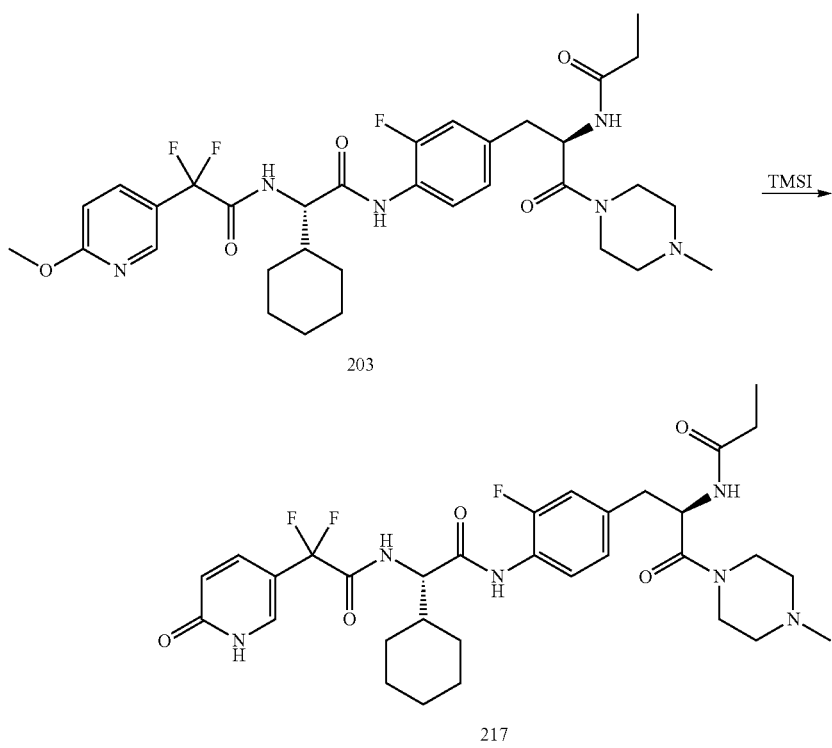

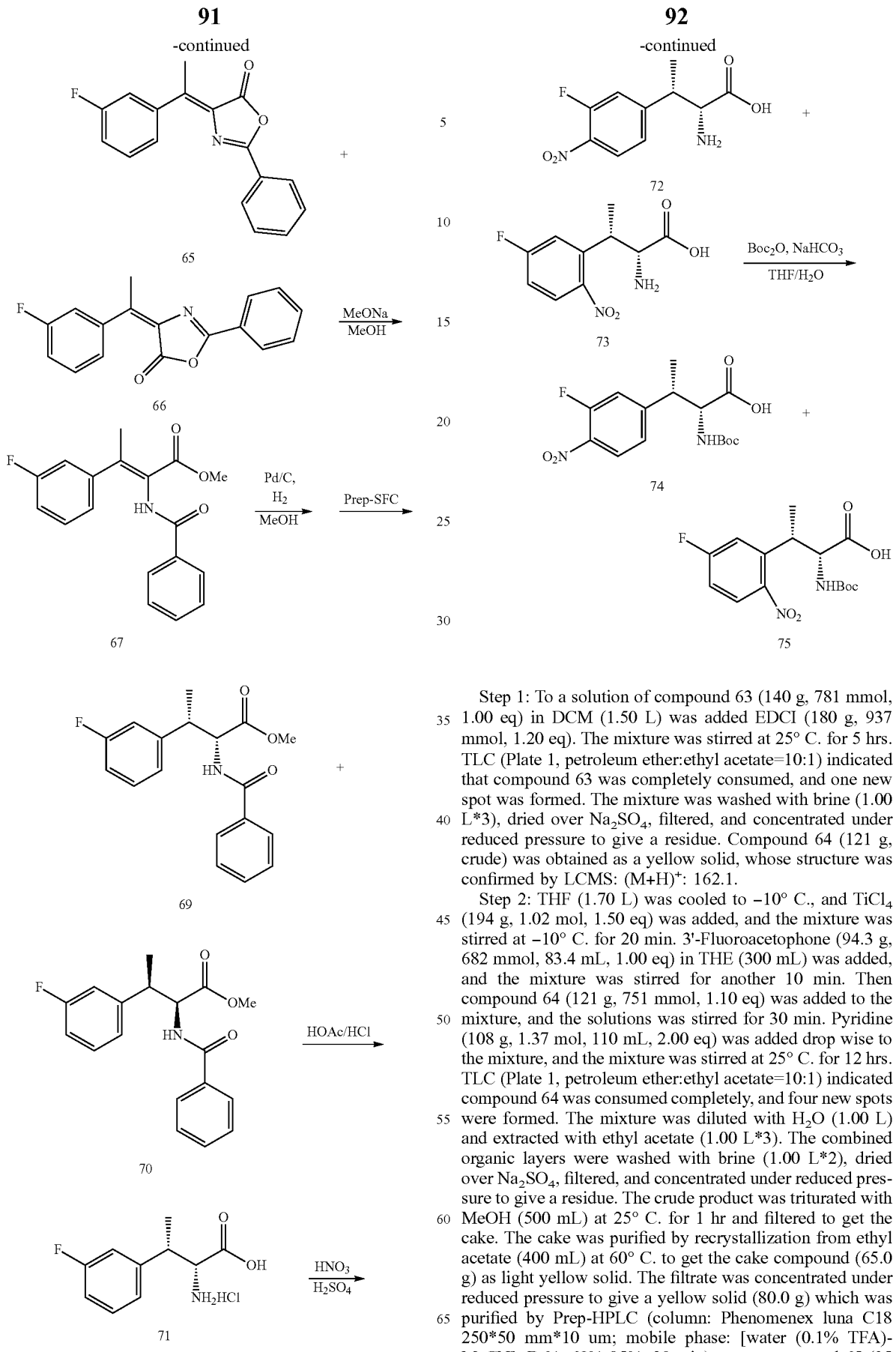

Step 1: To a solution of compound 63 (140 g, 781 mmol, 1.00 eq) in DCM (1.50 L) was added EDCI (180 g, 937 mmol, 1.20 eq). The mixture was stirred at 25° C. for 5 hrs. TLC (Plate 1, petroleum ether:ethyl acetate=10:1) indicated that compound 63 was completely consumed, and one new spot was formed. The mixture was washed with brine (1.00 L*3), dried over $Na_2SO_4$, filtered, and concentrated under reduced pressure to give a residue. Compound 64 (121 g, crude) was obtained as a yellow solid, whose structure was confirmed by LCMS: $(M+H)^+$: 162.1.

Step 2: THF (1.70 L) was cooled to −10° C., and $TiCl_4$ (194 g, 1.02 mol, 1.50 eq) was added, and the mixture was stirred at −10° C. for 20 min. 3'-Fluoroacetophone (94.3 g, 682 mmol, 83.4 mL, 1.00 eq) in THF (300 mL) was added, and the mixture was stirred for another 10 min. Then compound 64 (121 g, 751 mmol, 1.10 eq) was added to the mixture, and the solutions was stirred for 30 min. Pyridine (108 g, 1.37 mol, 110 mL, 2.00 eq) was added drop wise to the mixture, and the mixture was stirred at 25° C. for 12 hrs. TLC (Plate 1, petroleum ether:ethyl acetate=10:1) indicated compound 64 was consumed completely, and four new spots were formed. The mixture was diluted with $H_2O$ (1.00 L) and extracted with ethyl acetate (1.00 L*3). The combined organic layers were washed with brine (1.00 L*2), dried over $Na_2SO_4$, filtered, and concentrated under reduced pressure to give a residue. The crude product was triturated with MeOH (500 mL) at 25° C. for 1 hr and filtered to get the cake. The cake was purified by recrystallization from ethyl acetate (400 mL) at 60° C. to get the cake compound (65.0 g) as light yellow solid. The filtrate was concentrated under reduced pressure to give a yellow solid (80.0 g) which was purified by Prep-HPLC (column: Phenomenex luna C18 250*50 mm*10 um; mobile phase: [water (0.1% TFA)-MeCN]; B %: 60%-85%, 20 min) to get compound 65 (35 g) and compound 66 (33 g). Compound 65 was obtained as a light yellow solid, whose structure was confirmed by LCMS: (M+H)⁺: 282.1.

Step 3: To a solution of compound 65 (65.0 g, 231 mmol, 1.00 eq) in MeOH (420 mL) was added NaOMe (624 mg, 11.5 mmol, 0.05 eq) in MeOH (30.0 mL) at 0° C. The mixture was stirred at 0° C. for 0.5 hr. TLC (Plate 1, petroleum ether:ethyl acetate=10:1) indicated compound 65 was completely consumed, and one new spot was formed. The mixture was added to ice-cold water (600 mL), and extracted with ethyl acetate (1000 mL*2). The combined organic layers were washed with brine (700 mL), then dried over $Na_2SO_4$, filtered, and concentrated under reduced pressure to give a residue. Compound 67 (70.0 g, 223 mmol, 96.7% yield) was obtained as a light yellow solid, whose structure was confirmed by LCMS: (M+H)⁺: 314.0.

Step 4: To a solution of compound 67 (70.0 g, 223 mmol, 1.00 eq) in MeOH (650 mL) was added Pd/C (20.0 g, 10.0% purity). The mixture was degassed and purged with $H_2$ for 3 times, and then the mixture was stirred at 50° C. for 12 hrs under $H_2$ atmosphere. TLC (Plate 1, petroleum ether:ethyl acetate=3:1) indicated compound 67 was completely consumed, and one new spot was formed. The mixture was filtered, and the filtrate was concentrated under reduced pressure to get a white solid. A mixture of compounds 69 and 70 (70.0 g, 222 mmol, 99.4% yield) was obtained as a white solid, whose structure was confirmed by LCMS ((M+H)⁺: 316.1). Compounds 69 and 70 were separated by SFC (column: DAICEL CHIRALPAK AD (250 mm*50 mm, 10 um); mobile phase: [Neu-EtOH]; B %: 25%-25%, 5.2 min; 920 min) to get peak 1 (34.5 g) and peak 2 (35.0 g). Compound 69 (34.5 g, 109 mmol, 49.3% yield) (Peak 1) was obtained as a white solid Compound 70 (35.0 g, 111 mmol, 50.0% yield) (Peak 2) was obtained as a white solid.

Step 5: To a solution of compound 69 (17.0 g, 53.9 mmol, 1.00 eq) in HCl (3.00 M, 898 mL, 50.0 eq) was added HOAc (323 g, 5.39 mol, 308 mL, 100 eq). The mixture was stirred at 125° C. for 60 hrs. LC-MS showed compound 69 was completely consumed, and one main peak with the desired mass was detected. The mixture was concentrated under reduced pressure to give a white solid, and the residue was washed with DCM (300 mL*2). Compound 71 (27.5 g, crude, HCl, 2 batches) was obtained as a white solid.

Step 6: To a solution of compound 71 (15.5 g, 66.3 mmol, 1.00 eq, HCl) in $H_2SO_4$ (101 g, 1.03 mol, 55.0 mL, 15.6 eq) was added $HNO_3$ (7.56 g, 81.6 mmol, 5.40 mL, 68.0% purity, 1.23 eq) at −20° C., and the mixture was stirred at 0° C. for 0.5 hr. HPLC indicated compound 71 was completely consumed. The mixture was added to crushed ice (500 mL), and solid $Na_2CO_3$ was added until the pH=8. Compounds 72 and 73 (16.1 g, crude) in $H_2O$ (500 mL) were obtained as a yellow suspension which was used directly in the next step.

Step 7: To compounds 72 and 73 (48.0 g, 198 mmol, 1.50 L $H_2O$, 1.00 eq) in THF (1.50 L) was added $Boc_2O$ (86.5 g, 396 mmol, 91.1 mL, 2.00 eq). The mixture was degassed and purged with $N_2$ for 3 times and then stirred at 25° C. for 1 hrs under $N_2$ atmosphere. LCMS showed compounds 72 and 73 were consumed completely, and one main peak with desired mass was detected. The mixture was extracted with ethyl acetate (700 mL*2), and the aqueous layer was discarded. The organic layers were washed with $H_2O$ (300 mL*3) to provide an aqueous extract which was adjusted to pH 5 by the addition of 1M HCl, and extracted with ethyl acetate to provide crude compounds 74 and 75. The combined organic layers were washed with $H_2O$ (500 mL*2), brine (500 mL), and dried over $Na_2SO_4$, filtered, and concentrated under reduced pressure to give a residue. The residue was purified by SFC (column: REGIS (s,s) WHELK-01 (250 mm*50 mm, 10 um); mobile phase: [0.1% $NH_3H_2O$-MeOH]; B %: 20%-20%, 2.5 min; 1025 min) to provide peak 1 and peak 2. Peak 1 was concentrated under reduced pressure to give a yellow solid (compound 74, 45 g). Peak 2 was concentrated under reduced pressure to give a residue (P1). The residue (P1) was dissolved in $H_2O$ (300 mL) and 0.05 M HCl was added until the pH=5, then extracted with ethyl acetate (300 mL*2). The combined organic layers were dried over $Na_2SO_4$ and concentrated under reduced pressure to give a residue. The residue was triturated with MTBE/PE (200 mL, V/V=1/1) at 25° C. for 1 hr and filtered to give a cake (10.2 g). The filtrate was concentrated under reduced pressure to give a yellow solid (compound 75, 7.00 g, crude). Compound 74 was obtained as a yellow solid. Compound 74 (45.0 g, 125 mmol, 63.2% yield, $NH_3$) (Peak 1) was obtained as a yellow solid.

Example 7: General Scheme—Synthesis of Compounds 218-220, 228-230, 234, 240-296, 389-390, 393-394, 397, 399, 404-405, and 418-419

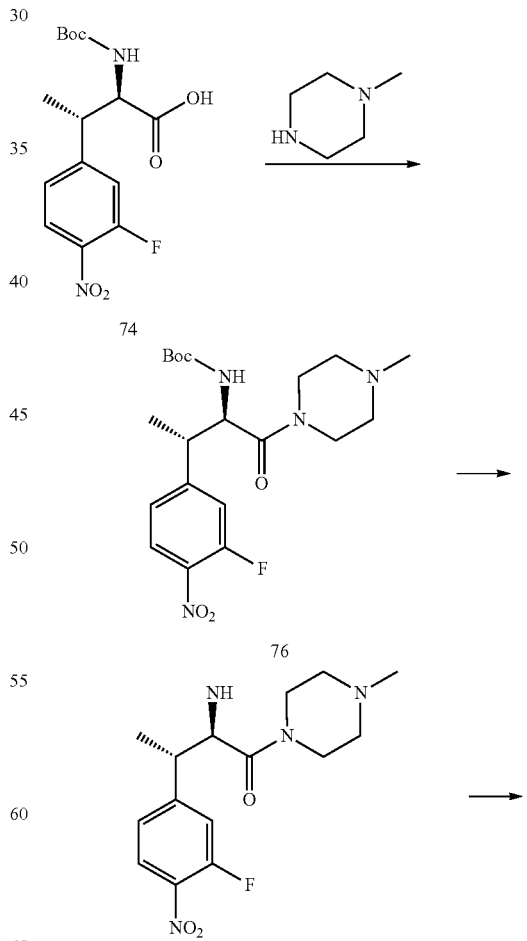

-continued

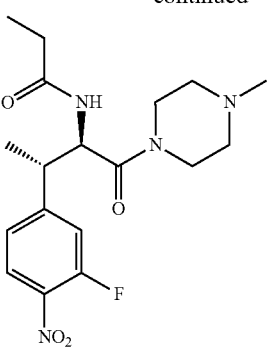

78

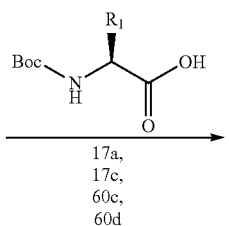

79

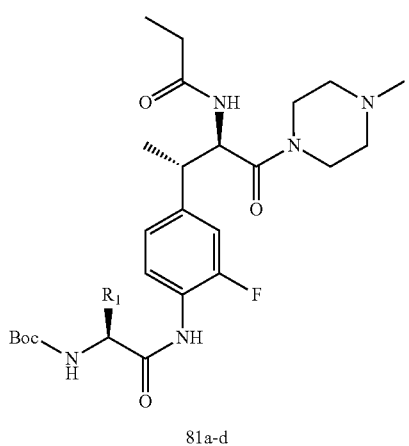

81a-d

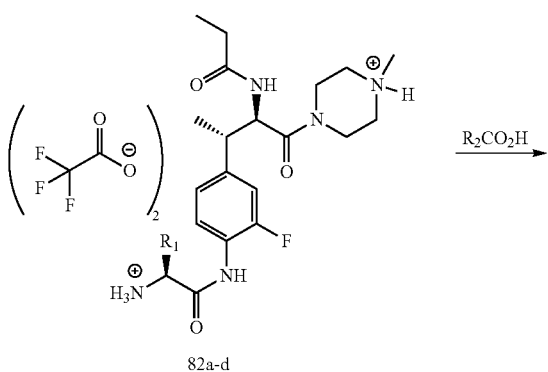

82a-d

-continued

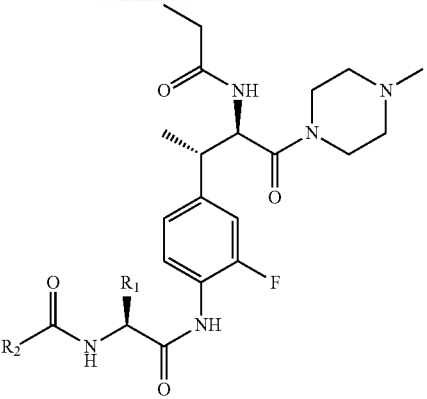

218-220, 228-230, 234, 240-296,
389, 390, 393, 394, 397, 399, 404,
405, 418 and 419.

Step 1: To a solution of 74 (1.13 g, 3.30 mmol, 1.0 eq.) in DMF (10 mL) was added N-methyl piperazine (0.44 mL, 3.96 mmol, 1.2 eq), DIPEA (2.9 mL, 16.5 mmol, 5.0 eq), and HATU (1.88 g, 4.95 mmol, 1.5 eq.), and the resulting mixture was stirred at RT under a $N_2$ atmosphere for 1 h. The mixture was diluted with aq. sat. $NaHCO_3$ solution (600 mL) and then extracted with DCM (150 mL). The organic layer was washed with brine (200 mL), dried over $Na_2SO_4$, and then concentrated to afford 76 as an off-white solid (1.15 g, 82% yield) which was used in the next step without further purification. UPLC-MS (basic 2 min): Rt=1.06 min; m/z=425.2 for $[M+H]^+$.

Step 2: To a solution of 76 (0.683 g, 1.61 mmol, 1.0 eq.) in DCM (6 mL) was added TFA (3 mL), and the resulting mixture was stirred at RT for 1 h. The reaction mixture was concentrated to dryness and the residue was dissolved in DCM (15 mL), stirred in aq. sat. $K_2CO_3$ solution (2.5 g in 15 mL $H_2O$), and then extracted with DCM to afford 77 as a brown oil (0.458 g, 88% yield), which was used in the next step without further purification. UPLC-MS (basic 2 min): Rt=0.85 min; m/z=325.2 for $[M+H]^+$.

Step 3: To a solution of 77 (0.458 g, 1.41 mmol, 1.0 eq.) in DMF (5.0 mL) was added propionic anhydride (0.22 mL, 1.69 mmol, 1.2 eq.) and DIPEA (0.74 mL, 4.24 mmol, 1.2 eq), and the resulting mixture was stirred at RT under a $N_2$ atmosphere for 1 h. The mixture was diluted with aq. sat. $NaHCO_3$ solution (100 mL) and then extracted with DCM (100 mL). The organic layers were washed with brine (100 mL), dried over $Na_2SO_4$, and then concentrated to afford 78 as a dark yellow oil (0.425 g, 70% yield), which was used in the next step without further purification. UPLC-MS (basic 2 min): Rt=0.90 min; m/z=381.2 for $[M+H]^+$.

Step 4: To a degassed solution of 78 (0.425 g, 1.12 mmol, 1.0 eq) in EtOH (10 mL) and THF (10 mL) was added Pd/C (0.050 g, 0.224 mmol, 0.20 eq). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness. The residue was triturated with DCM and iso-hexane to afford 79 as a light brown solid (0.354 g, 90% yield). UPLC-MS (basic 2 min): Rt=0.79 min; m/z=351.2 for $[M+H]^+$.

Example 8: General Scheme Synthesis of Intermediates 81a-d (Step 5)

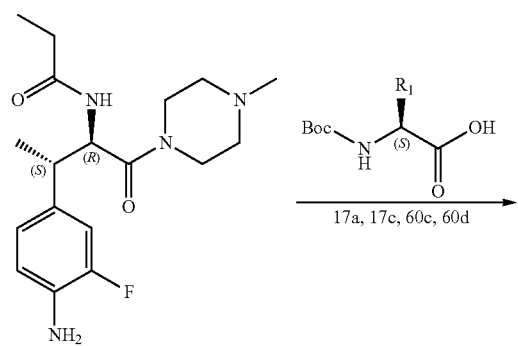

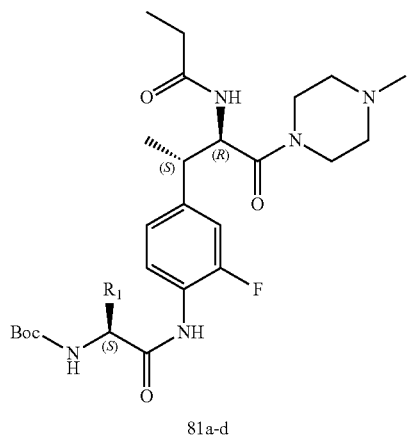

Reagents

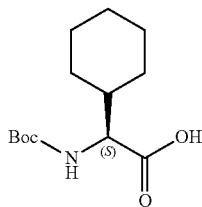

17a

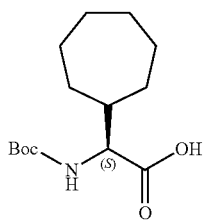

17c

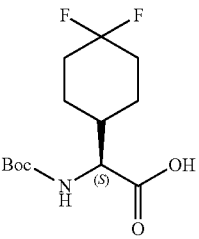

60c

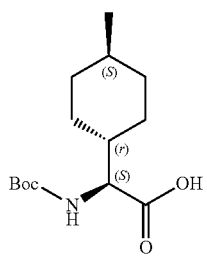

60d

To a solution of 79 (1.0 eq.) in DMF (0.1M) were added 17a, 17c, 60c, or 60d (1.2 eq.), DIPEA (4.0-8.0 eq.), and HATU (1.5-2.0 eq.), and the resulting mixture was stirred for 1 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM) to afford 81a-c.

Step 5a: Compound 79 (0.118 g, 0.337 mmol, 1.0 eq.) was reacted with (2S)-2-{[(tert-butoxy)carbonyl]amino}-2-cyclohexylacetic acid 17a (0.104 g, 0.404 mmol, 1.2 eq.), HATU (0.256 g, 0.673 mmol, 2.0 eq.), and DIPEA (0.47 mL, 2.69 mmol, 8.0 eq.) in DMF (5 mL) to afford, after flash column chromatography, 81a (0.136 g, 51% yield) as a brown solid. UPLC-MS (basic 2 min): rt=1.10 min; m/z=590.3 for [M+H]$^+$.

Step 5b: Compound 79 (0.118 g, 0.337 mmol, 1.0 eq.) was reacted with (2S)-2-{[(tert-butoxy)carbonyl]amino}-2-cycloheptylacetic acid) 17c (0.110 g, 0.404 mmol, 1.2 eq.), HATU (0.256 g, 0.673 mmol, 2.0 eq.), and DIPEA (0.47 mL, 2.69 mmol, 8.0 eq.) in DMF (5 mL) to afford, after flash column chromatography, 81b (0.124 g, 61% yield) as a brown solid. UPLC-MS (basic 2 min): rt=1.15 min; m/z=604.4 for [M+H]$^+$.

Step 5c: Compound 79 (0.118 g, 0.337 mmol, 1.0 eq.) was reacted with (2S)-2-{[(tert-butoxy)carbonyl]amino}-2-(4,4-difluorocyclohexyl)acetic acid) 60c (0.119 g, 0.404 mmol, 1.2 eq.), HATU (0.256 g, 0.673 mmol, 2.0 eq.), and DIPEA (0.47 mL, 2.69 mmol, 8.0 eq.) in DMF (5 mL) to afford, after flash column chromatography, 81c (0.104 g, 49% yield) as a brown solid. UPLC-MS (basic 2 min): rt=1.06 min; m/z=626.3 for [M+H]$^+$.

Step 5d: Compound 79 (0.300 g, 0.856 mmol, 1.0 eq) in DMF (3 mL) was reacted with (2S)-2-{[(tert-butoxy)carbonyl]amino}-2-[(1r,4S)-4-methylcyclohexyl]acetic acid) 60d (0.279 g, 1.03 mmol, 1.2 eq.), DIPEA, (1.2 mL, 6.85 mmol, 8.0 eq.) and then HATU (0.488 g, 1.28 mmol, 1.5 eq.), and the resulting mixture was stirred at RT for 18 h. The combined organic phase was washed with brine, dried over sodium sulfate then concentrated to afford 81d which was used in the next step without further purification. UPLC-MS (2 min basic run) Rt=1.15 min. m z=604.4 for [M+H]$^+$

Example 9: General Scheme Synthesis of Intermediates 82a-d (Step 6)

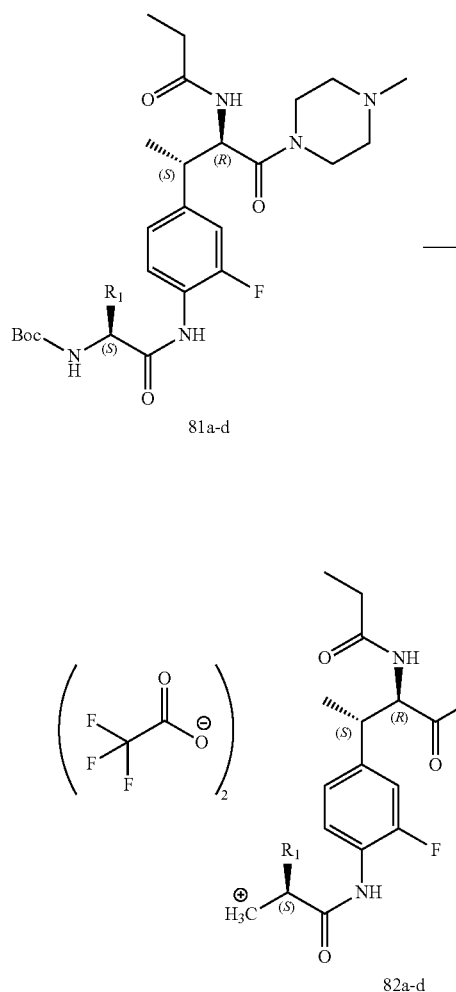

To a solution of 81a-d (1.0 eq.) in DCM was added TFA (10 eq.), and the resulting mixture was stirred at RT for 0.5 h. The reaction mixture was concentrated to dryness to afford 82a-d which was used in the next step without further purification.

Step 6a: Compound 81a (0.103 g, 0.175 mmol, 1.0 eq.) was reacted with TFA (2 mL) in DCM (2 mL) to afford, after concentration to dryness, 82a (0.106 g, 99% yield) as a brown oil which was used in the next step without further purification. UPLC-MS (basic 2 min): rt=0.96 min; m/z=490.3 for [M+H]$^+$.

Step 6b: Compound 81b (0.140 g, 0.237 mmol, 1.0 eq.) was reacted with TFA (2 mL) in DCM (2 mL) to afford, after concentration to dryness, 82b (0.127 g, 99% yield) as a brown oil which was used in the next step without further purification. UPLC-MS (basic 2 min): rt=1.01 min; m/z=504.3 for [M+H]$^+$.

Step 6c: Compound 81c (0.104 g, 0.166 mmol, 1.0 eq.) was reacted with TFA (1 mL) in DCM (1 mL) to afford, after aqueous work-up, 82c (0.106 g, 99% yield) as a brown oil which was used in the next step without further purification. UPLC-MS (basic 2 min): rt=0.91 min; m/z=526.3 for [M+H]$^+$.

Step 6d: Compound 81d (0.280 g, 0.464 mmol, 1.0 eq.) in DCM (3 mL) was reacted with TFA (0.36 mL, 4.64 mmol, 10 eq.) and the resulting mixture was stirred at RT for 0.5 h. The reaction mixture was concentrated to dryness to afford 82d (0.340 g, 100%) as a brown gummy solid which was used in the next step without further purification.

Example 10: General Scheme Synthesis of Compounds 218-220, 228-230, 234, 240-296, 389-390, 393-394, 397, 399, 404-405, and 418-419 from Intermediates 82a-d

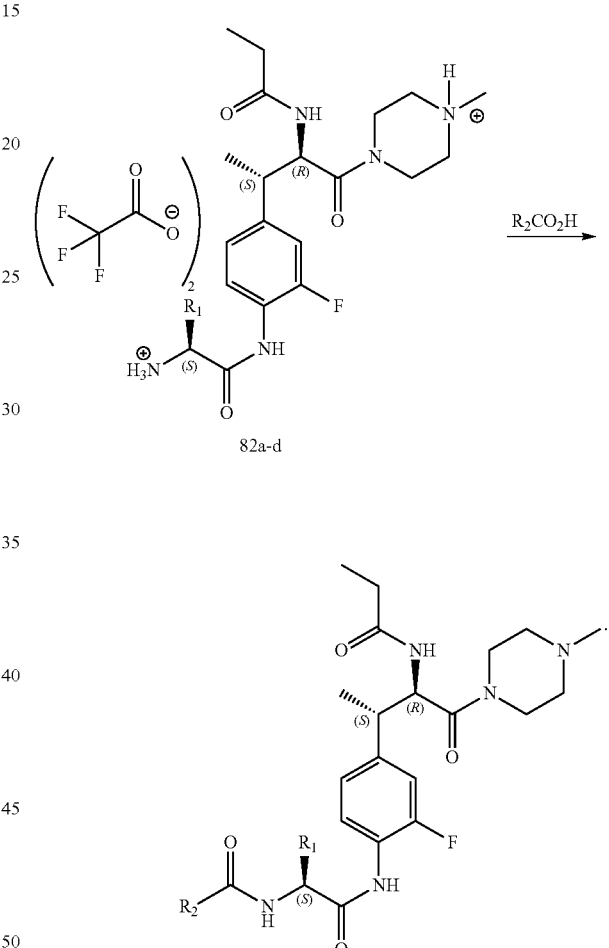

218-220, 228-230, 234, 240-296, 389, 390, 393, 394, 397, 399, 404, 405, 418 and 419

To a solution of 82a-d thereof (1.0 eq) in DMF were added the required carboxylic acid, DIPEA (8.0 eq.), and HATU (1.5 eq.), and the resulting mixture was stirred at RT for 1 h. The mixture was concentrated to dryness, and the residue was purified via reverse phase column chromatography on a 120 g C18 cartridge eluting with a 5-95% H$_2$O:MeCN eluent (0.1% ammonia) to afford 218-220, 228-230, 234, 240-296, 389, 390, 393, 394, 397, 399, 404, 405, 418 and 419.

The following compounds were made following a procedure analogous to Example 10 starting from 82a-d and reacting with the appropriate carboxylic acid.

218
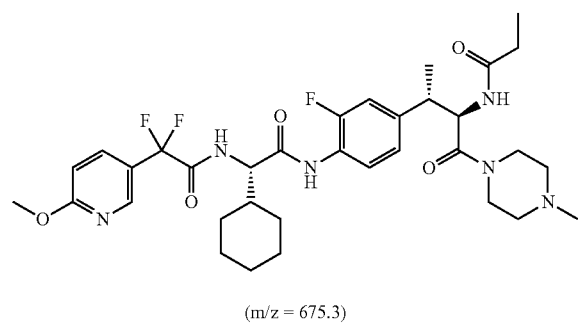
(m/z = 675.3)
219
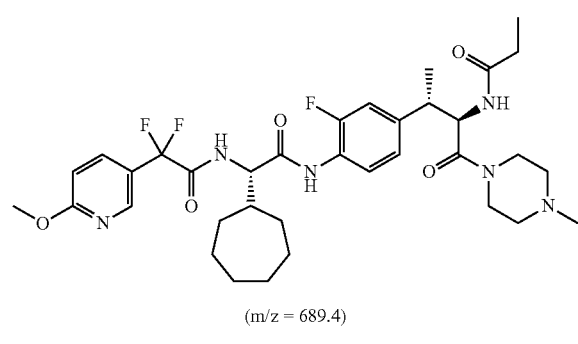
(m/z = 689.4)
220
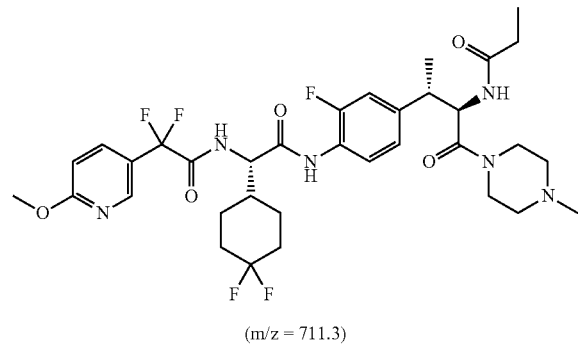
(m/z = 711.3)
228
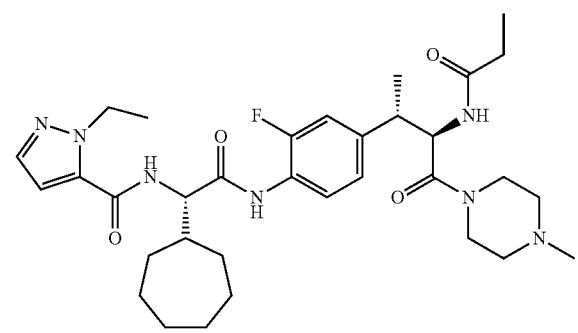
(m/z = 626.4)
229
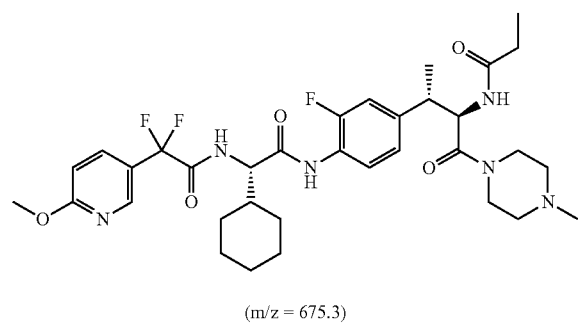
(m/z = 612.4)
230
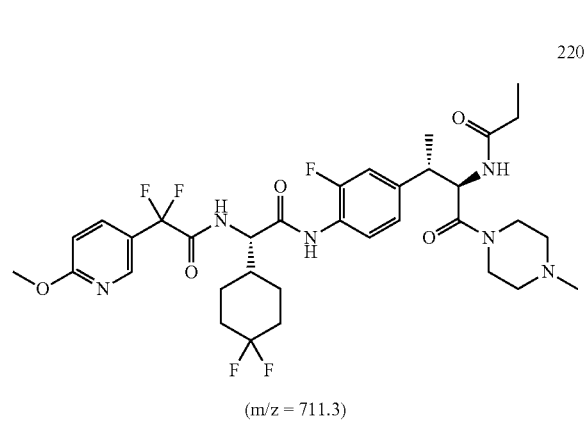
(m/z = 669.4)
234
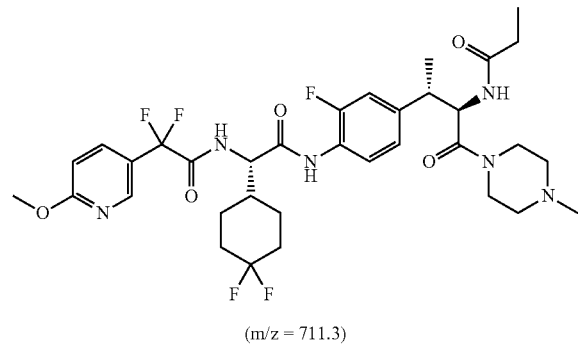
(m/z = 626.4)
240
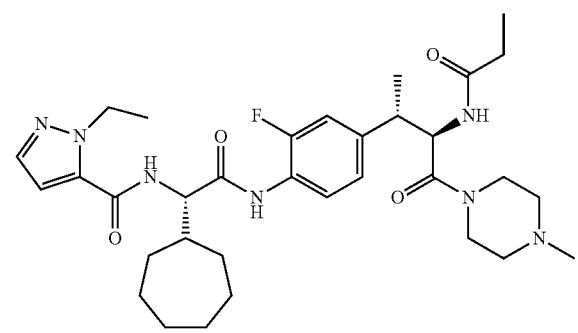
(m/z = 648.4)

-continued
241
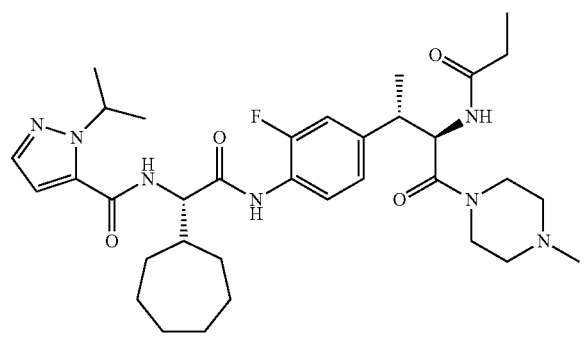
(m/z = 640.5)
242
(m/z = 608.3)
243
(m/z = 674.4)
244
(m/z = 688.4)
-continued
245
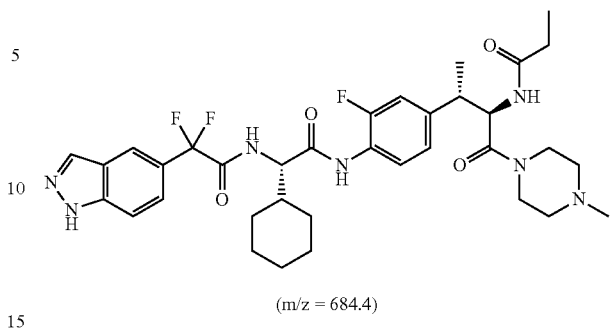
(m/z = 684.4)
246
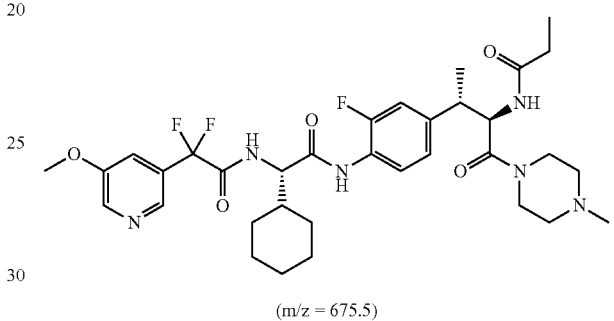
(m/z = 675.5)
247
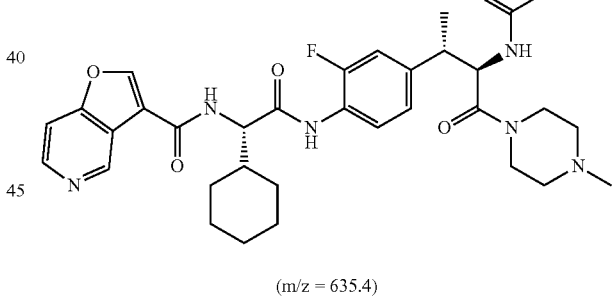
(m/z = 635.4)
248
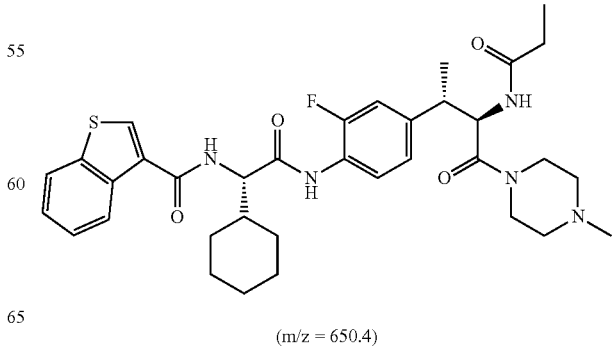
(m/z = 650.4)

249
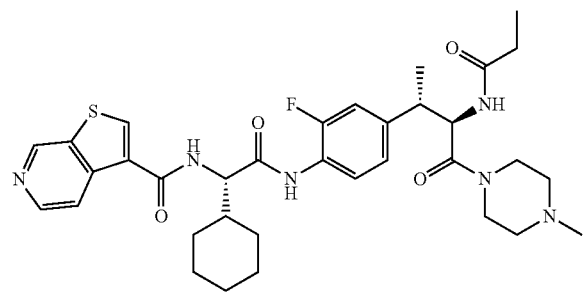
(m/z = 651.4)
250
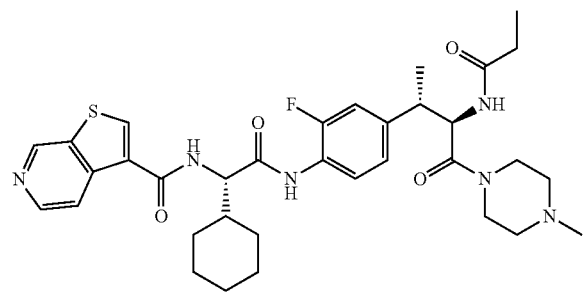
(m/z = 651.4)
251
(m/z = 737.3)
252
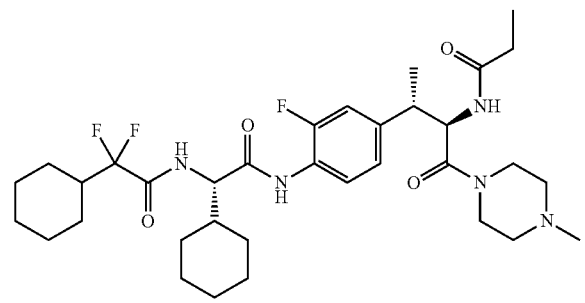
(m/z = 650.4)
253
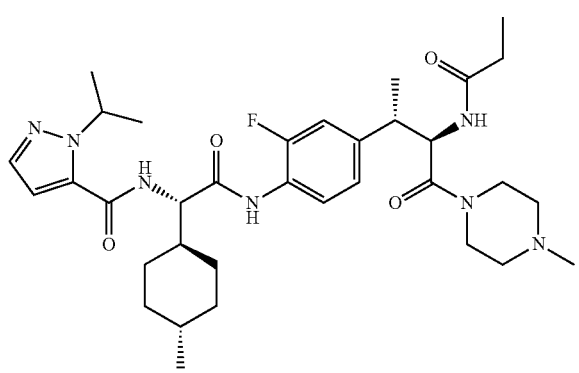
(m/z = 640.4)
254
(m/z = 611.4)
255
(m/z = 664.4)
256
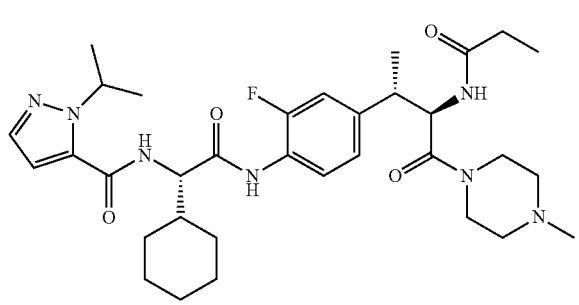
(m/z = 626.4)

257
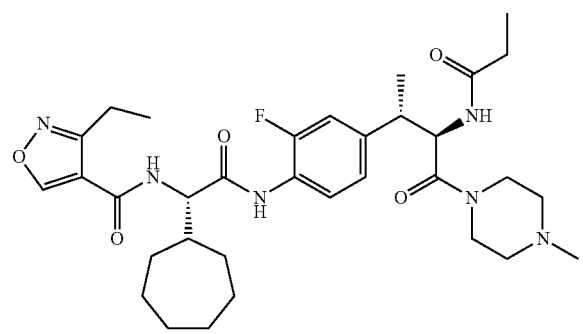
(m/z = 627.3)
258
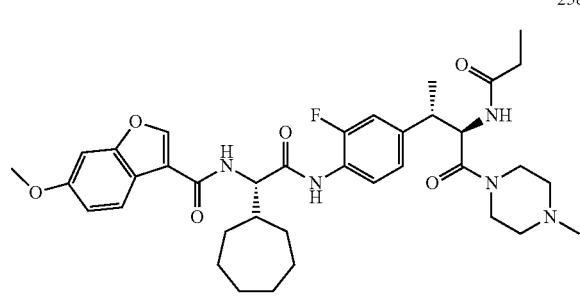
(m/z = 678.3)
259
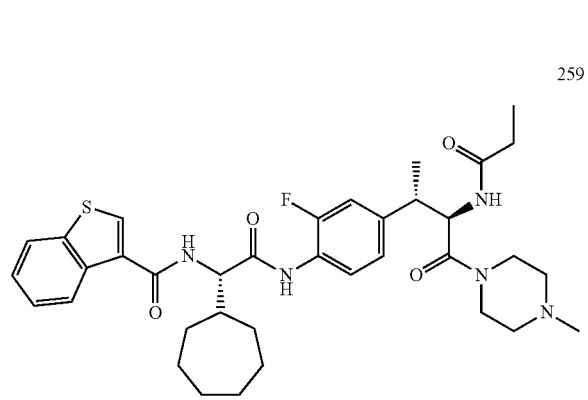
(m/z = 664.3)
260
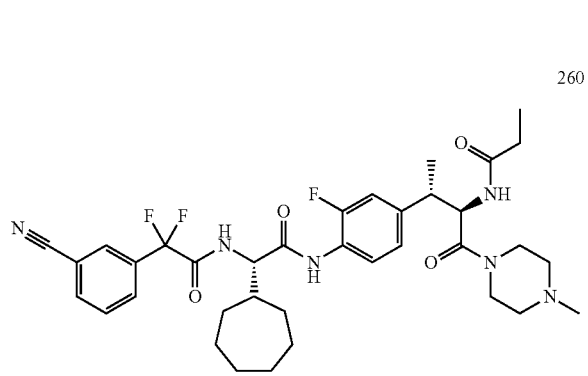
(m/z = 683.3)
261
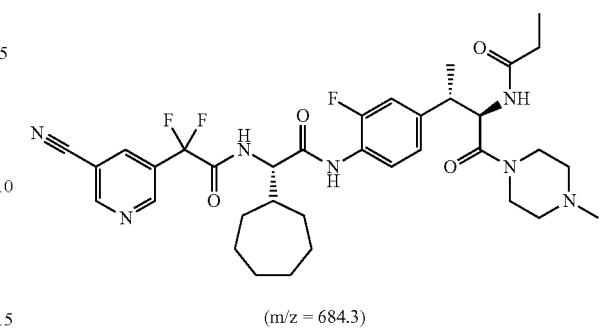
(m/z = 684.3)
262
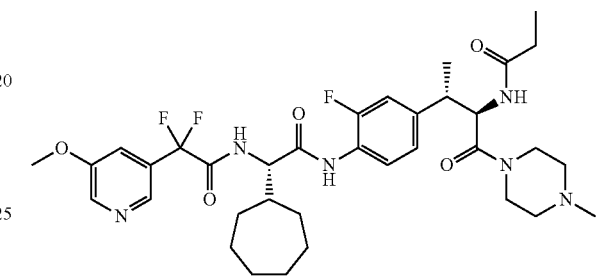
(m/z = 689.4)
263
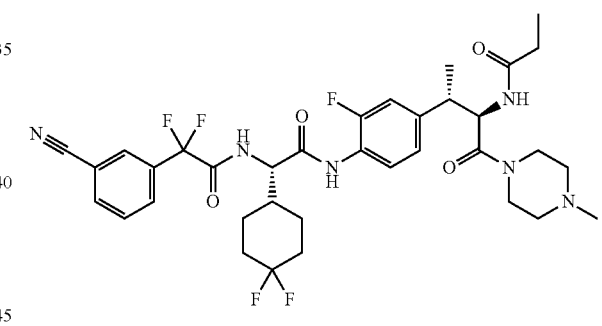
(m/z = 705.3)
264
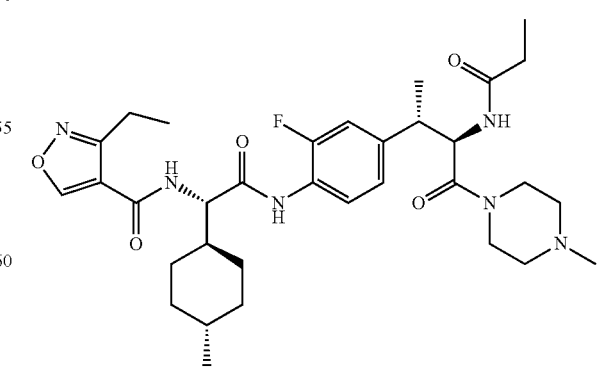
(m/z = 627.4)

265
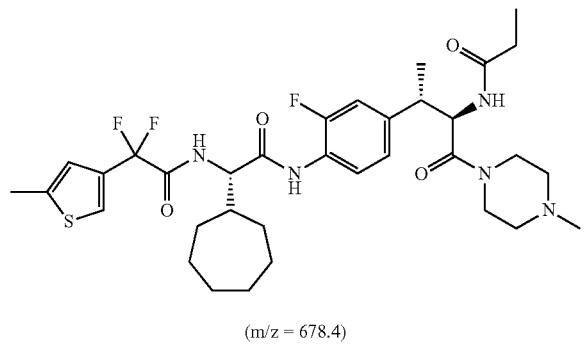
(m/z = 678.4)
266
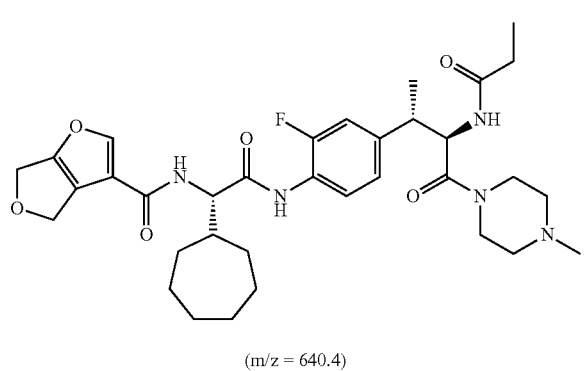
(m/z = 640.4)
267
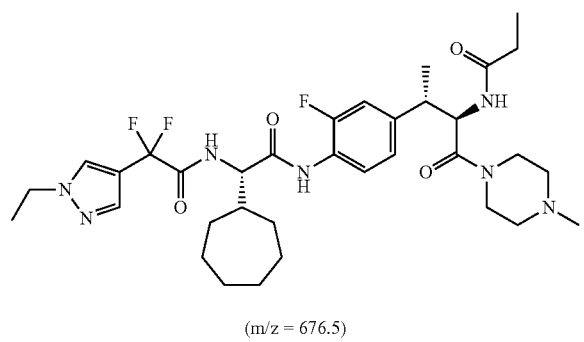
(m/z = 676.5)
268
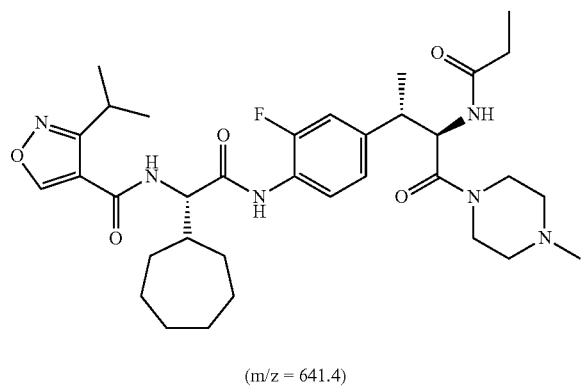
(m/z = 641.4)
269
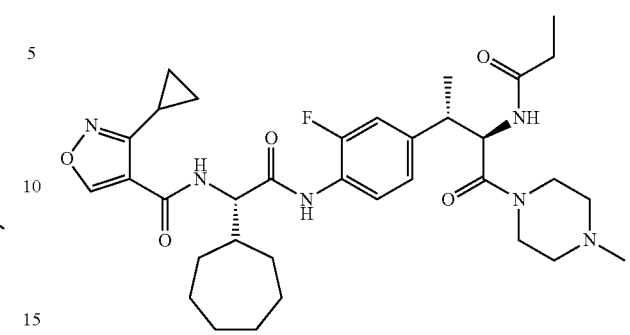
(m/z = 639.4)
270
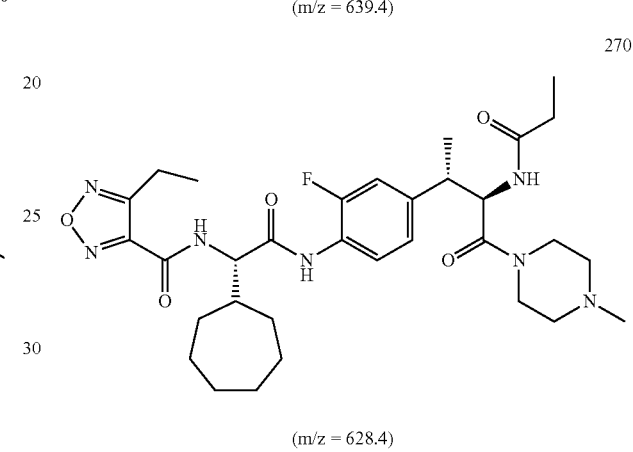
(m/z = 628.4)
271
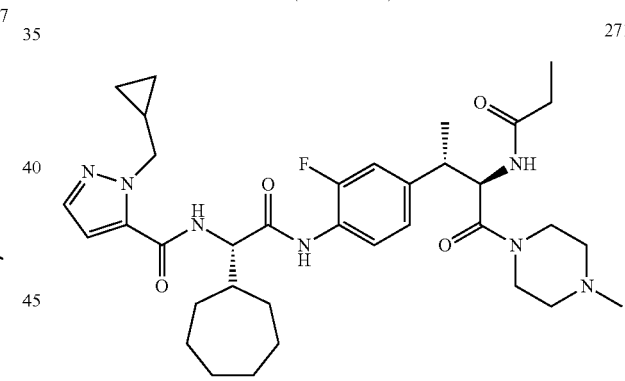
(m/z = 652.3)
272
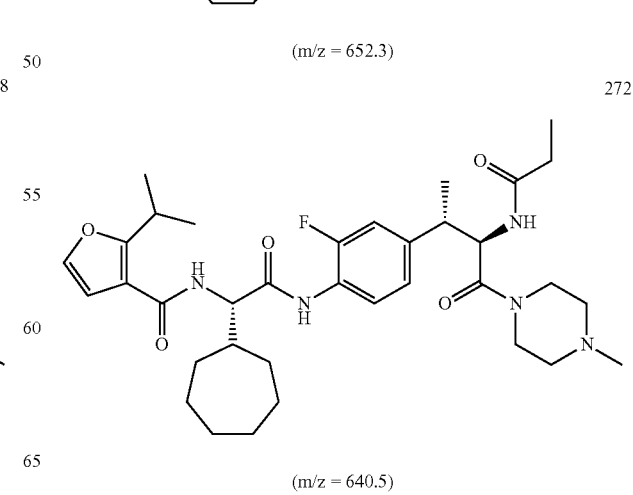
(m/z = 640.5)

273
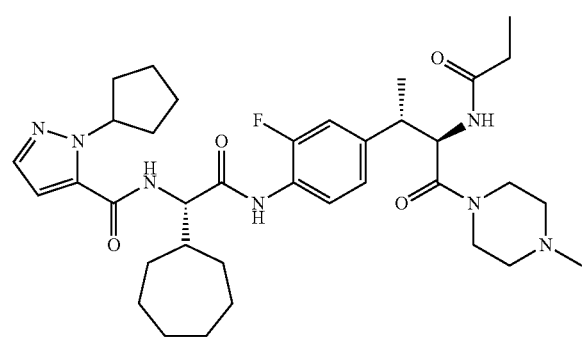
(m/z = 666.5)
274
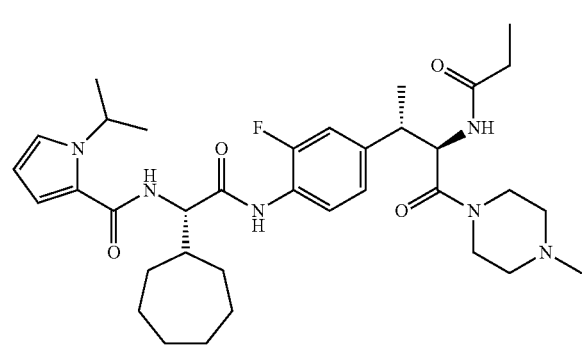
(m/z = 639.4)
275
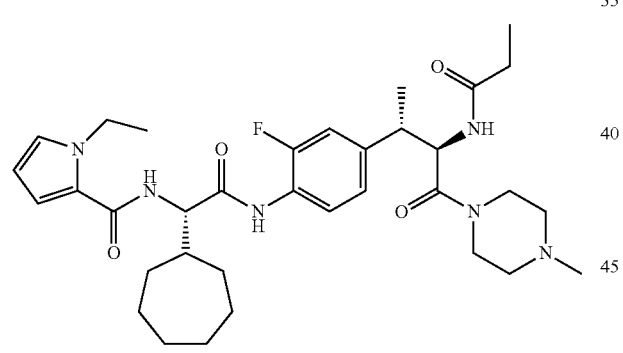
(m/z = 625.4)
276
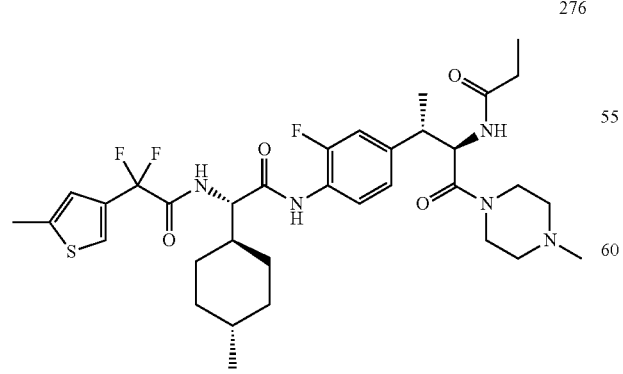
(m/z = 678.3)
277
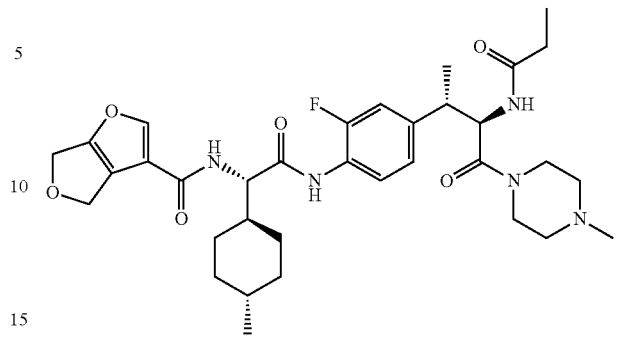
(m/z = 640.3)
278
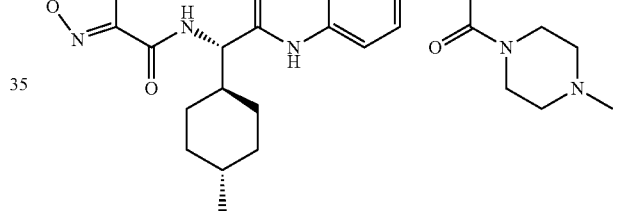
(m/z = 628.3)
279
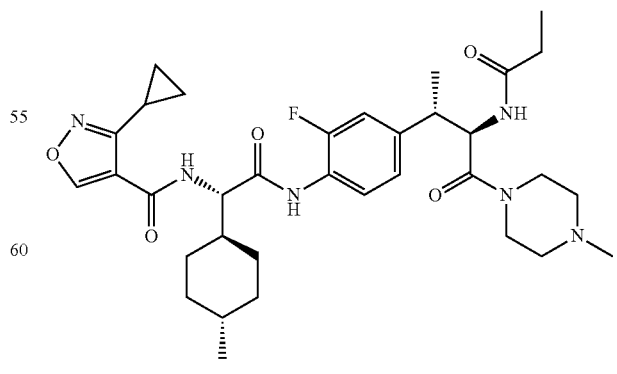
(m/z = 639.3)

280
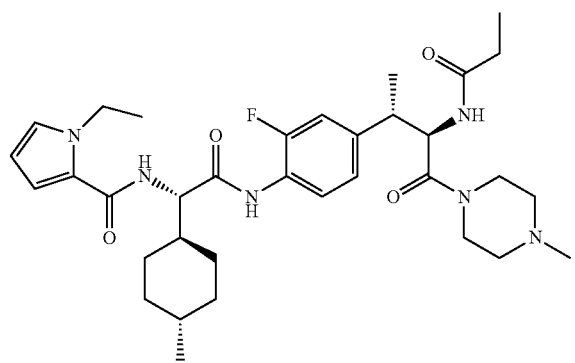
(m/z = 625.3)
284
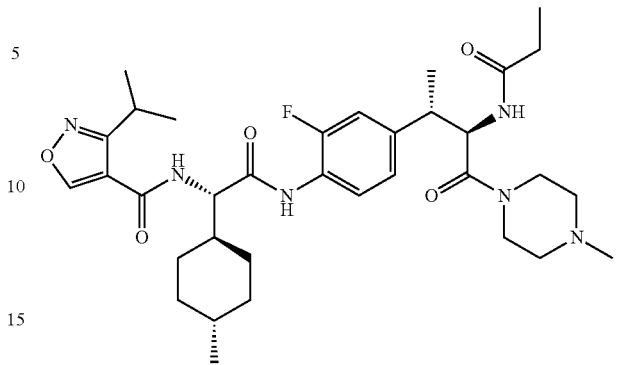
(m/z = 641.3)
281
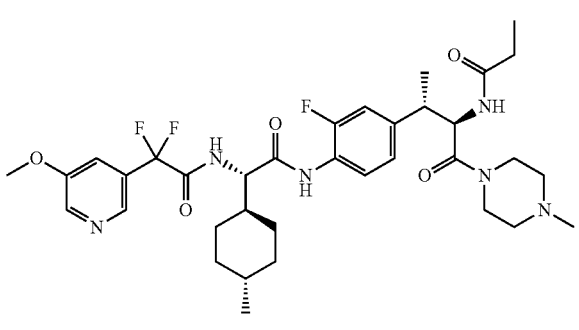
(m/z = 689.4)
285
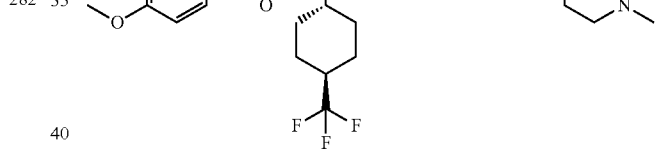
(m/z = 743.3)
282
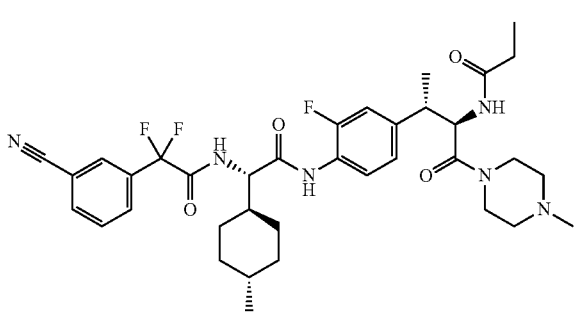
(m/z = 683.4)
283
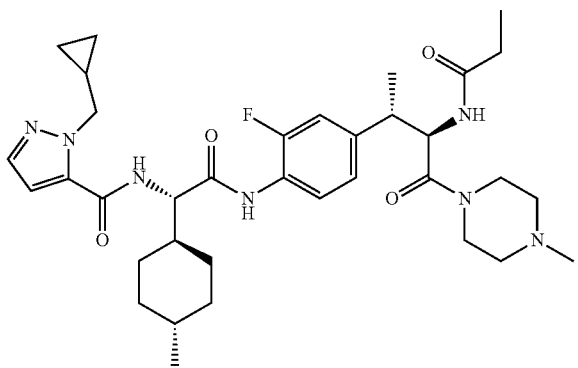
(m/z = 652.3)
286
(m/z = 737.3)

287
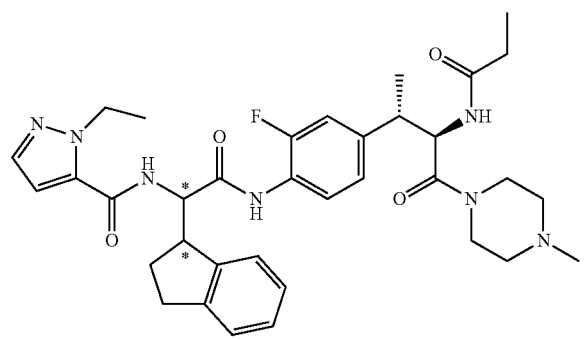
Single diastereomer with undetermined absolute
stereochemistry at *
(m/z = 646.4)
288
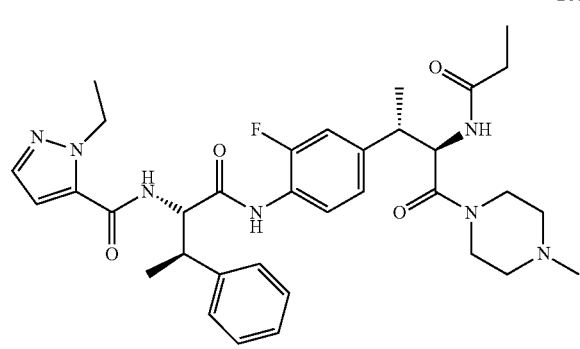
(m/z = 634.3)
289
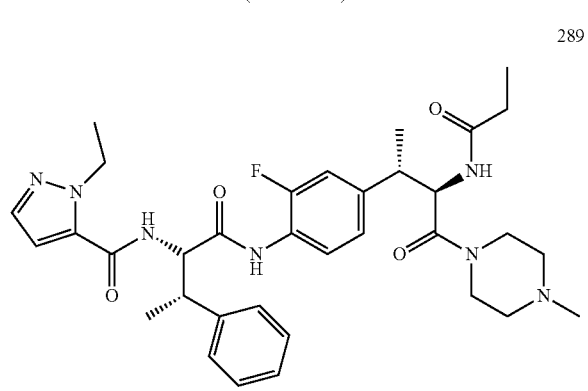
(m/z = 634.4)
290
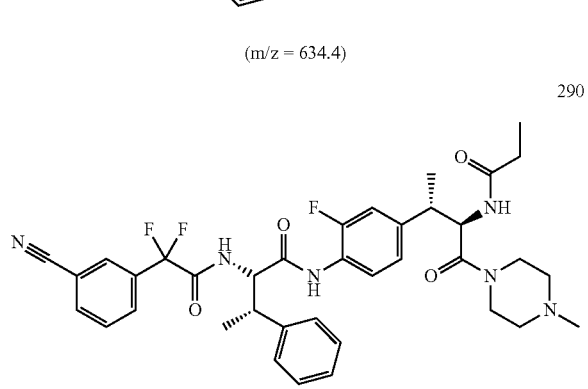
(m/z = 691.3)
291
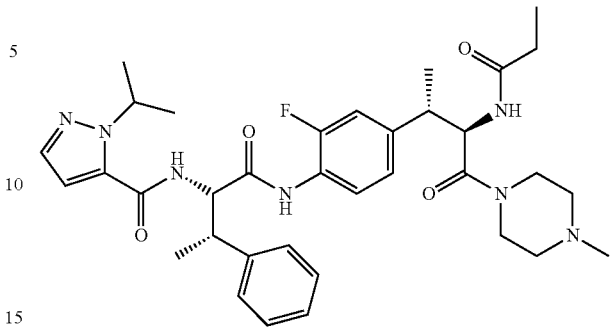
(m/z = 648.4)
292
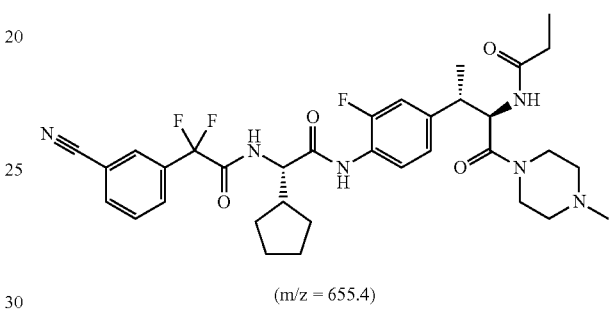
(m/z = 655.4)
293
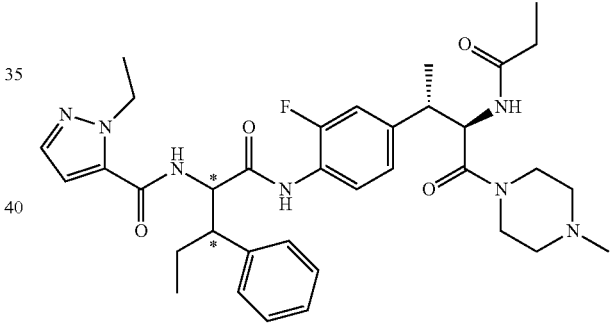
Single diastereomer with undetermined absolute
stereochemistry at *
(m/z = 648.4)
294
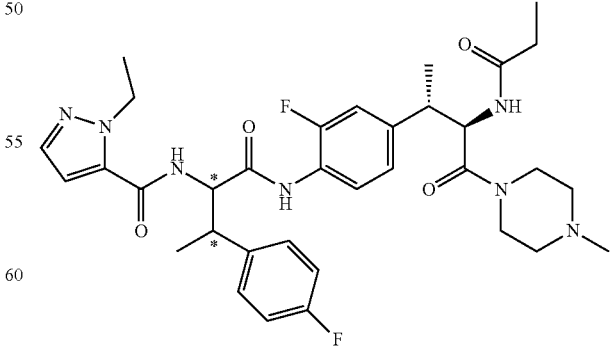
Single diastereomer with undetermined absolute
stereochemistry at *
(m/z = 653.4)

295
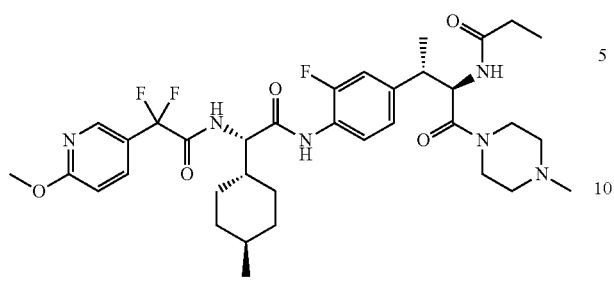
(m/z = 689.3)
296
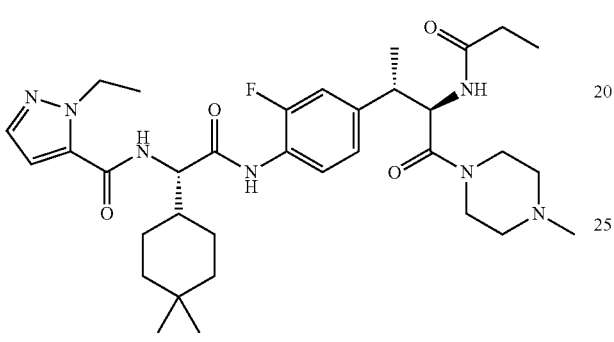
(m/z = 640.5)
389
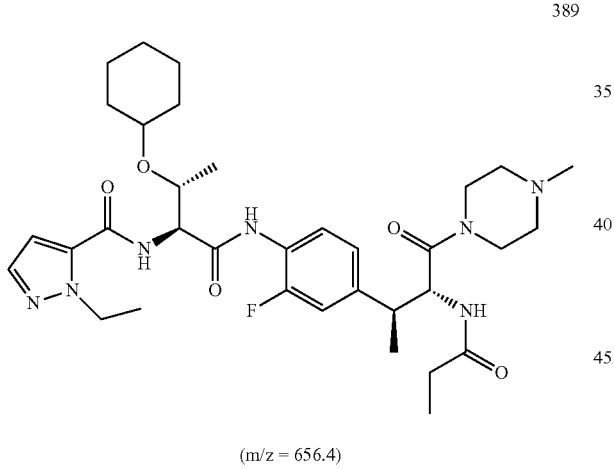
(m/z = 656.4)
390
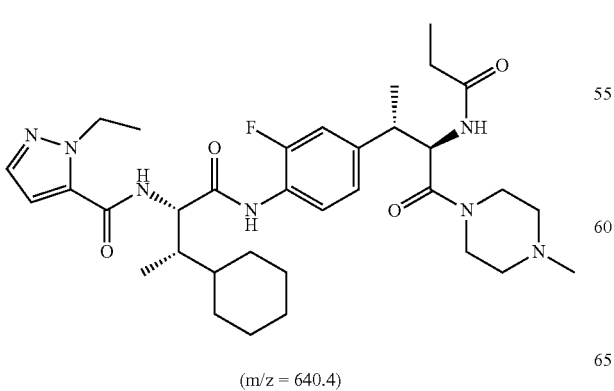
(m/z = 640.4)
393
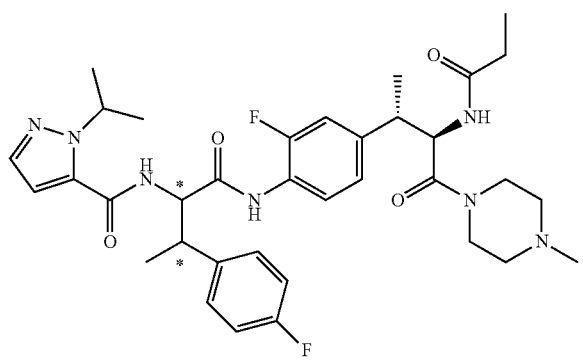
Single diastereomer with undetermined absolute stereochemistry at *
(m/z = 666.4)
394
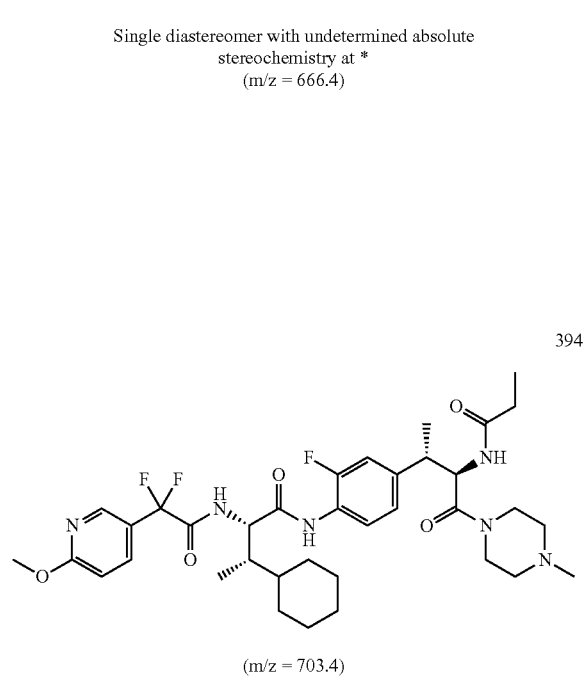
(m/z = 703.4)
397
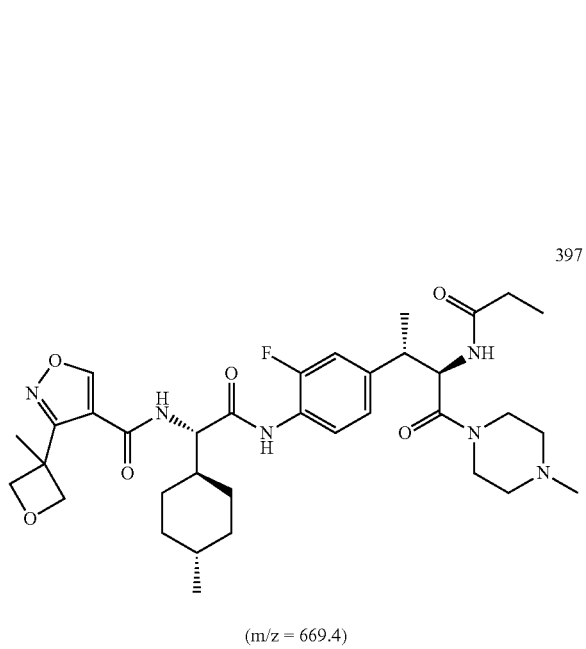
(m/z = 669.4)

399
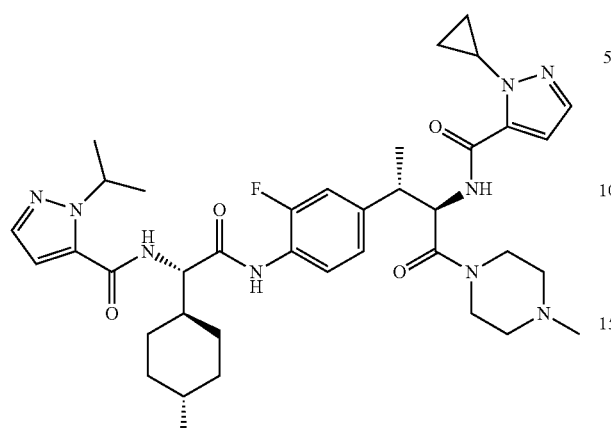
(m/z = 718.5)
404
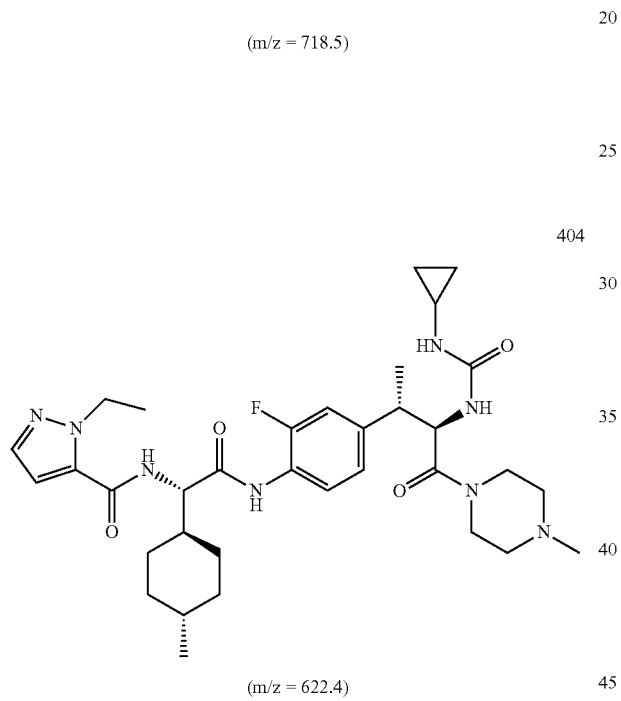
(m/z = 622.4)
405
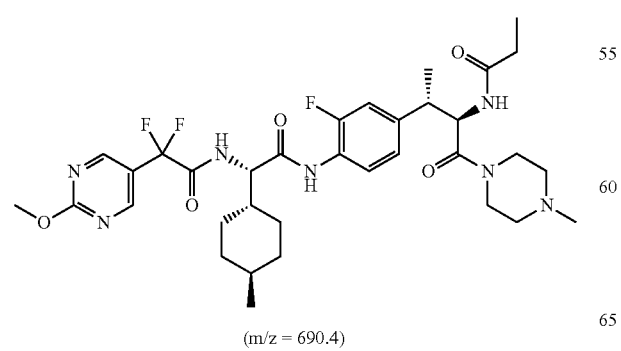
(m/z = 690.4)
418
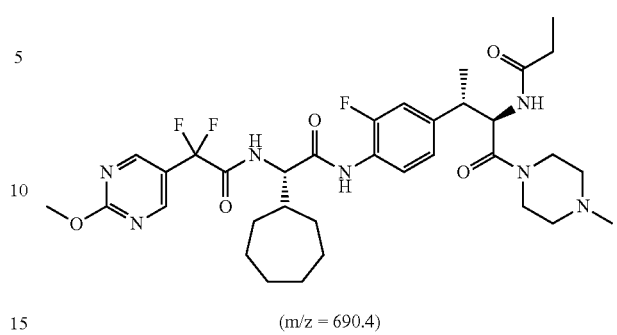
(m/z = 690.4)
419
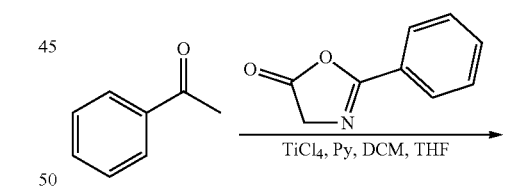
(m/z = 664.4)
Example 11: Exemplary Scheme—Synthesis of Intermediate Compound 91
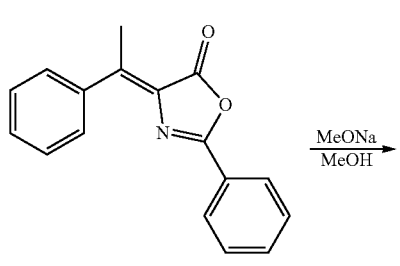

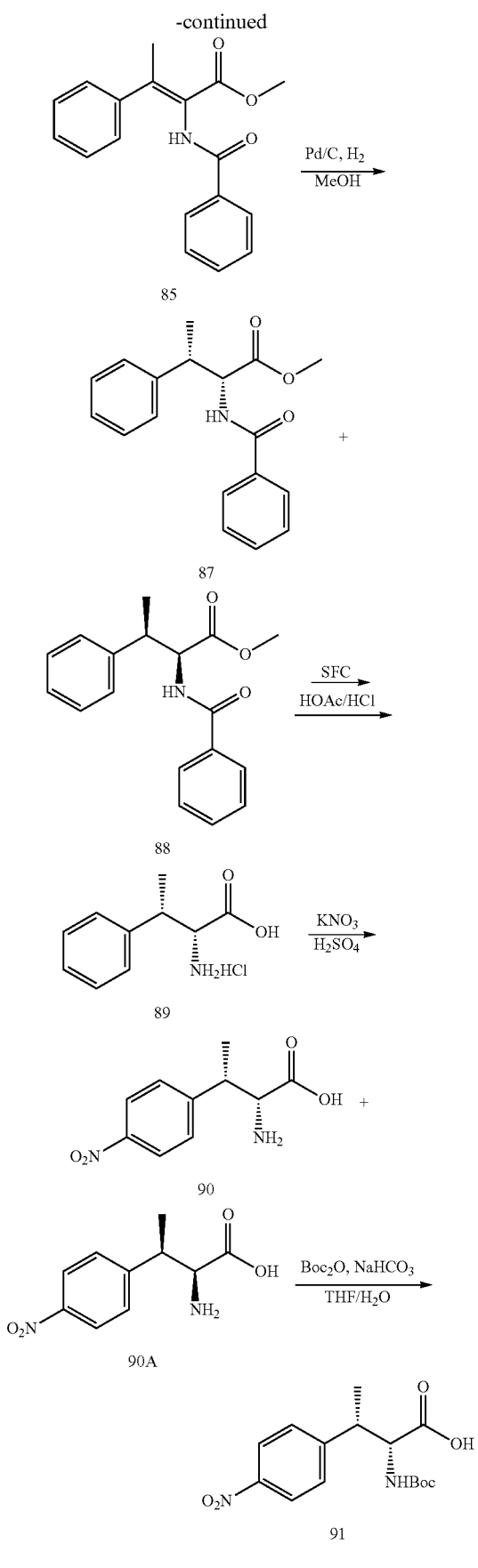

Step 1: THF (150 mL) was chilled under N$_2$ to −10° C. A solution of TiCl$_4$ (23.7 g, 124 mmol, 13.7 mL, 1.50 eq) in DCM (30.0 mL) was added and stirred for 20 mins. To the stirring solution, compound 83 (10.0 g, 83.2 mmol, 9.71 mL, 1.00 eq) was added, then the mixture was stirred for 10 mins, then the substituted benzene derivative compound (14.8 g, 91.6 mmol, 1.10 eq) was added, and the reaction was stirred for a further 30 mins. To this mixture, pyridine (13.2 g, 166 mmol, 13.4 mL, 2.00 eq) was added dropwise. The mixture was stirred for a further 5 hrs at 25° C. TLC (Petroleum ether:Ethyl acetate=10:1, plate 1, R$_f$ (R1)=0.70, R$_f$ (P1)=0.75) showed compound 83 was completely consumed, and a major new spot was generated. The mixture was added to saturated NH$_4$Cl (400 mL), and the aqueous layer was extracted with ethyl acetate (300 mL*2). The combined organic phases were washed with brine (200 mL*2), dried over Na$_2$SO$_4$, and concentrated under reduced pressure to give a residue. The residue was slurried with MeOH (50.0 mL). Compound 84 (7.80 g, 28.9 mmol, 34.7% yield, 97.6% purity) was obtained as a yellow solid, confirmed by LCMS: Rt=1.06 mins, (M+H)$^+$: 264.2.

Step 2: To a solution of CH$_3$ONa (365 mg, 6.76 mmol, 0.100 eq) in MeOH (350 mL) at 25° C. was added compound 84 (17.8 g, 67.6 mmol, 1.00 eq), and then the mixture was stirred at 25° C. for 1 hr. TLC (Petroleum ether:Ethyl acetate=5:1, plate 1, R$_f$ (R1)=0.85, R$_f$ (P1)=0.15) showed compound 84 was completely consumed, and a major new spot was generated. MeOH was removed in vacuo to give a residue. Cold water (50.0 mL) was added dropwise to the residue, which was then filtered, and the filter cake was collected as a white solid. Compound 85 (19.2 g, 65.0 mmol, 96.2% yield, 100% purity) was obtained as a white solid, confirmed by LCMS: Rt=0.894 mins, (M+H)$^+$: 296.1

Step 3: To a solution of compound 85 (19.2 g, 65.0 mmol, 990 uL, 1.00 eq) in MeOH (500 mL) was added Pd/C (4.00 g, 10.0% purity), and the reaction was stirred at 35° C. under H$_2$ (50 psi) for 12 hrs. TLC (Petroleum ether:Ethyl acetate=3:1, plate 1, R$_f$ (R1)=0.20, R$_f$ (P1)=0.25) showed compound 85 was consumed completely, and a major new spot was generated. The mixture was filtered, and the filtrate was concentrated in vacuum to give a residue. A mixture of compounds 87 and 88 (19.3 g, 64.9 mmol, 99.8% yield, 100% purity) was obtained as a white solid, confirmed by LCMS: Rt=0.915 min, (M+H)$^+$: 298.1.

Step 4: The mixture of compounds 87 and 88 was resolved by SFC (column: DAICEL CHIRALPAK AD (250 mm*30 mm, 10 um); mobile phase: [0.1% NH$_3$H$_2$O ETOH]; B %: 20%-20%, 3.4 min, 780 min) to get 2 products: compound 87 (9.45 g, 31.8 mmol, 49.0% yield, 100% purity) (LCMS (Rt=0.909 min, (M+1)$^+$: 298.1)) as a white solid and compound 88 (9.57 g, 32.2 mmol, 49.6% yield, 100% purity) (LCMS (Rt=0.920 min, (M+1)$^+$: 298.1)) as a white solid.

Step 5: To a solution of compound 87 (9.40 g, 31.6 mmol, 1.00 eq) in HCl (3 M, 527 mL, 50.0 eq) was added AcOH (190 g, 3.16 mol, 181 mL, 100 eq), and then the mixture was stirred at 125° C. for 60 hrs. LCMS showed compound 87 was consumed. The solvent was removed in vacuo to provide a residue which was purified by slurrying with DCM (50.0 mL) to get the desired product compound 89 (6.21 g, 28.3 mmol, 89.7% yield, 98.4% purity, HCl) as a white solid, confirmed by LCMS: Rt=0.360 min, (M+1)$^+$: 180.1.

Step 6: To a solution of compound 89 (5.21 g, 23.8 mmol, 1.00 eq, HCl) in H$_2$SO$_4$ (30.0 mL) was added KNO$_3$ (2.65 g, 26.2 mmol, 1.10 eq) at 0° C., and then the mixture was warmed to 25° C. and stirred for 0.5 hr. LCMS showed the desired product was formed. HPLC showed there was one major peak formed. The reaction mixture was quenched with ice water (250 mL), then the solution was adjusted to pH 9 with solid $Na_2CO_3$ to give the desired product compounds 90 and 90A (5.33 g, 23.8 mmol, 100% yield), which was stored in water and used in the next step directly. LCMS: Rt=0.533 min, (M+1)$^+$: 225.0.

Step 7: To a mixture of compounds 90 and 90A (not shown) (5.33 g, 23.8 mmol, 1.00 eq) in water (250 mL) was added THF (40.0 mL), and then $Boc_2O$ (7.78 g, 35.7 mmol, 8.19 mL, 1.50 eq) was added at 0° C., and the solution was warmed to 25° C. and stirred for 2 hrs. LCMS indicated the desired product was formed. The reaction mixture was diluted with petroleum ether (100 mL), then the pH of the solution was adjusted to 3 with 1 N HCl at 0° C., and then extracted with ethyl acetate (100 mL*4). The combined organic layers were dried over $Na_2SO_4$ and concentrated under reduced pressure to give a residue. The residue was purified by SFC (column: DAICEL CHIRALPAK AD-H (250 mm*30 mm, 5 um); mobile phase: [0.1% $NH_3H_2O$ MEOH]; B %: 30%-30%, 3.2 min; 400 min) to give the desired product 91 (4.70 g, 14.5 mmol, 61.0% yield, 100% purity) (LCMS: Rt=0.876 min, (M-99)$^+$: 225.2) as a light yellow solid.

Example 12: General Scheme—Synthesis of Compounds 221, 222, 232, and 297-301

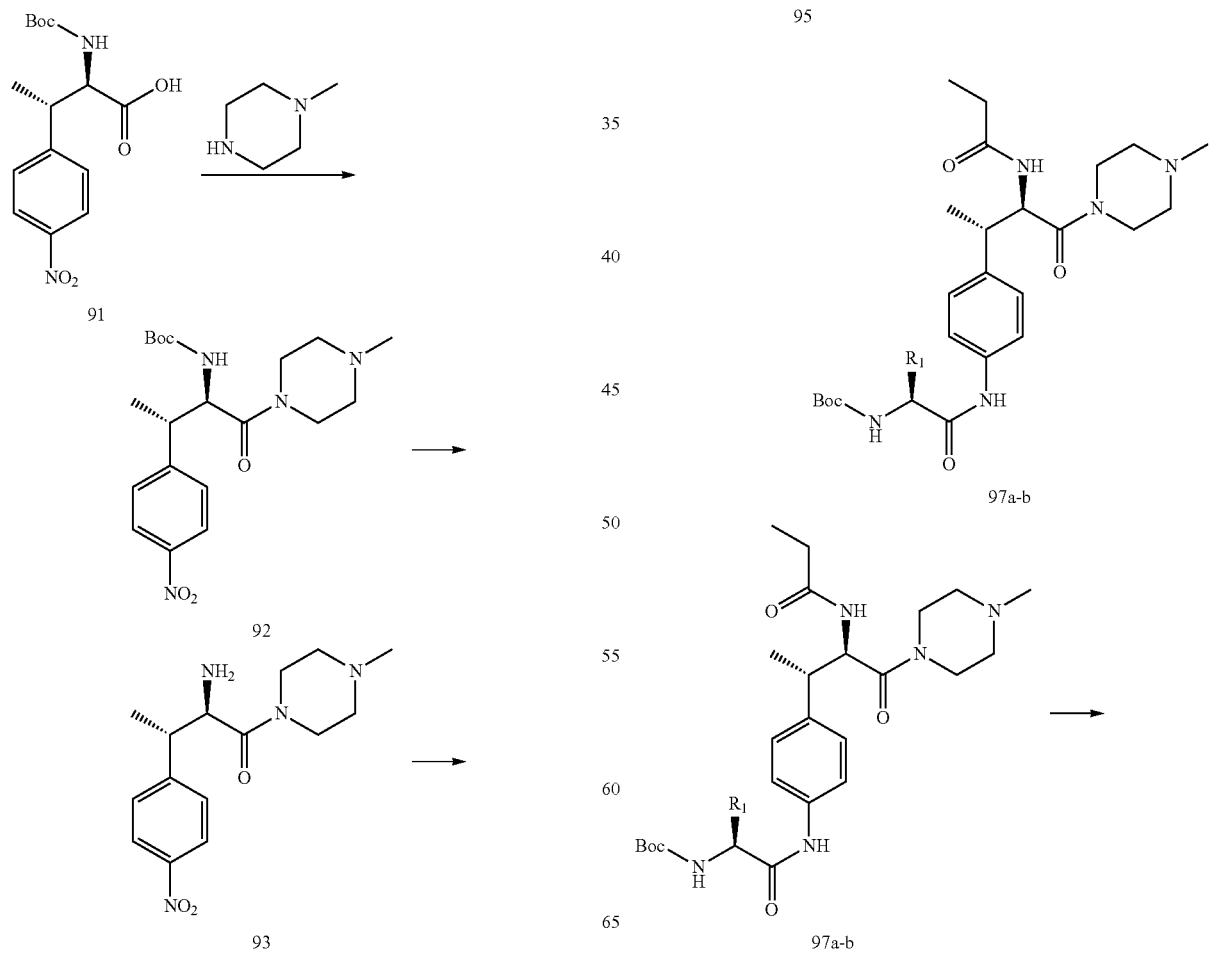

-continued

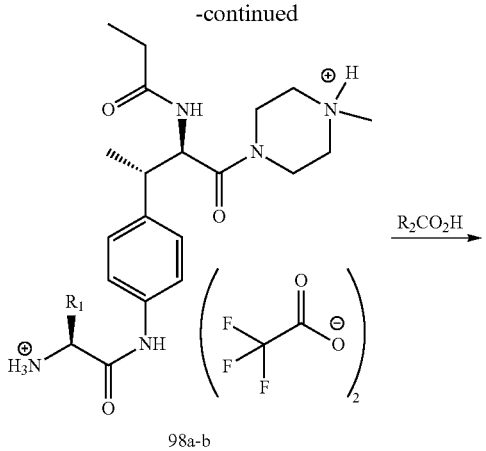

98a-b

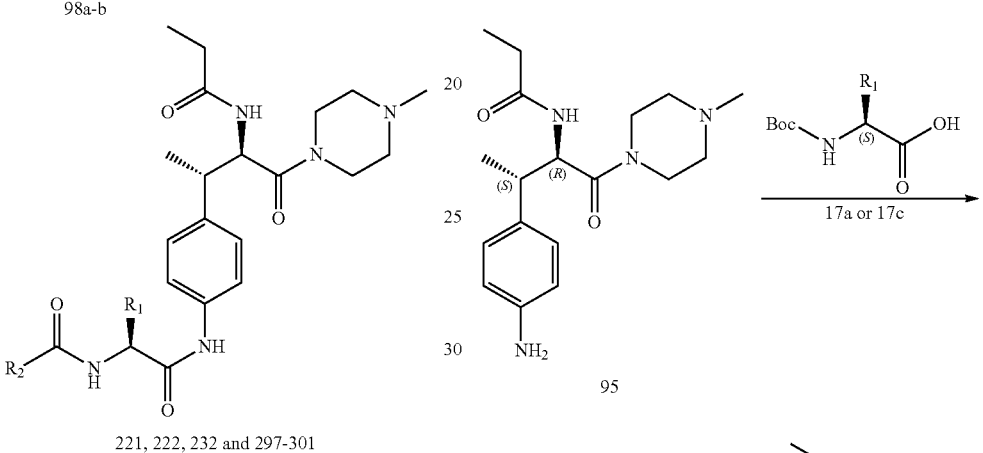

221, 222, 232 and 297-301

Step 1: To a solution of 91 (0.600 g, 1.85 mmol, 1.0 eq.) in DMF (6 mL) was added N-methyl piperazine (0.25 mL, 2.22 mmol, 1.2 eq), DIPEA (0.97 mL, 5.55 mmol, 3.0 eq), and HATU (1.06 g, 2.78 mmol, 1.5 eq.), and the resulting mixture was stirred at RT under a $N_2$ atmosphere for 1 h. The mixture was diluted with aq. sat. $NaHCO_3$ solution (20 mL) and then extracted with EtOAc (2×20 mL). The organic layers were washed with brine (50 mL), dried over $Na_2SO_4$, and then concentrated to afford 92 as a yellow oil (0.684 g, 91%). UPLC-MS (basic 2 min): Rt=1.06 min; m/z=407.2 for $[M+H]^+$.

Step 2: To a solution of 92 (0.684 g, 1.68 mmol, 1.0 eq.) in DCM (10 mL) was added TFA (5 mL), and the resulting mixture was stirred at RT for 1 h. The reaction mixture was concentrated to dryness, and the residue was dissolved in DCM (10 mL), stirred in aq. sat. $K_2CO_3$ solution (1 g in 10 mL $H_2O$), and then extracted with DCM to afford 93 as a yellow gummy solid (0.316 g, 61% yield). UPLC-MS (basic 2 min): Rt=0.83 min; m/z=307.2 for $[M+H]^+$.

Step 3: To a solution of 93 (0.310 g, 1.01 mmol, 1.0 eq.) in DMF (3.0 mL) was added propionic anhydride (0.16 mL, 1.21 mmol, 1.2 eq.) and DIPEA (0.53 mL, 3.04 mmol, 3.0 eq), and the resulting mixture was stirred at RT under a $N_2$ atmosphere for 1 h. The mixture was diluted with aq. sat. $NaHCO_3$ solution (20 mL) and then extracted with EtOAc (2×20 mL). The organic layer was washed with brine (50 mL), dried over $Na_2SO_4$, and concentrated to afford 94 as a yellow oil (0.350 g, 95% yield) which was used in the next step without further purification. UPLC-MS (basic 2 min): Rt=0.88 min; m/z=363.2 for $[M+H]^+$.

Step 4: To a degassed solution of 94 (0.362 g, 1.00 mmol, 1.0 eq) in EtOH (10 mL) and THF (10 mL) was added Pd/C (0.020 g, 0.200 mmol, 0.20 eq). The mixture was degassed for another 20 minutes and then evacuated under vacuum before introducing a hydrogen balloon. The resulting mixture was stirred at RT for 6 h. The mixture was filtered through a pad of celite which was washed with EtOH (50 mL) and concentrated to dryness. The residue was triturated with DCM and iso-hexane to afford 95 as a yellow gummy solid (0.200 g, 60% yield) which was used in the next step without further purification. UPLC-MS (basic 2 min): Rt=0.75 min; m/z=333.2 for $[M+H]^+$.

Example 13: General Scheme—Synthesis of Intermediates 97a and 97b (Step 5)

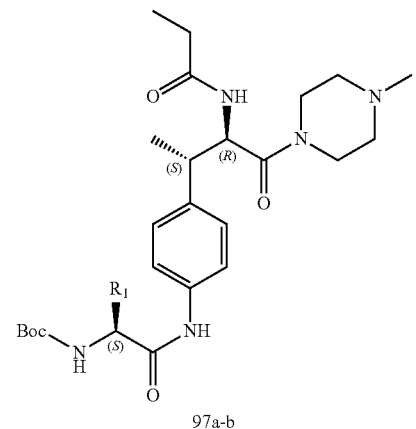

95

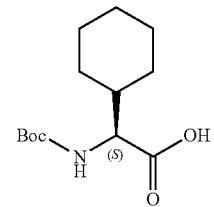

97a-b

Reagents

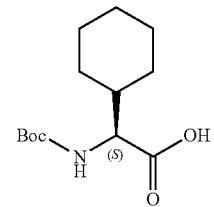

17a

-continued

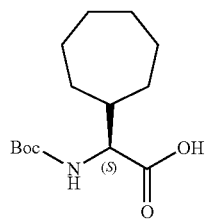

17c

To a solution of 95 (1.0 eq.) in DMF (0.1M) was added 17a or 17c (1.2 eq.), DIPEA (4.0-8.0 eq.), and HATU (1.5-2.0 eq.), and the resulting mixture was stirred for 1 h. Aqueous saturated sodium bicarbonate solution was added, and then the product was extracted with EtOAc. The combined organic phases were washed with brine, dried over sodium sulfate, and then concentrated to dryness to afford 97a-b which was used in the next step without further purification.

Step 5a: Compound 95 (0.100 g, 0.301 mmol, 1.0 eq.) was reacted with (2S)-2-{[(tert-butoxy)carbonyl]amino}-2-cyclohexylacetic acid 17a (0.093 g, 0.361 mmol, 1.2 eq.), HATU (0.172 g, 0.451 mmol, 1.5 eq.), and DIPEA (0.16 mL, 0.902 mmol, 3.0 eq.) in DMF (1 mL) to afford, after aqueous work-up, 97a (0.065 g, 38% yield) as a yellow gummy solid which was used in the next step without further purification. UPLC-MS (basic 2 min): rt=1.08 min; m z=572.3 for [M+H]$^+$.

Step 5b: Compound 95 (0.100 g, 0.301 mmol, 1.0 eq.) was reacted with (2S)-2-{[(tert-butoxy)carbonyl]amino}-2-cycloheptylacetic acid) 17c (0.098 g, 0.361 mmol, 1.2 eq.), HATU (0.172 g, 0.451 mmol, 1.5 eq.), and DIPEA (0.16 mL, 0.902 mmol, 3.0 eq.) in DMF (1 mL) to afford, after aqueous work-up, 97b (0.058 g, 33% yield) as a yellow gummy solid which was used in the next step without further purification. UPLC-MS (basic 2 min): rt=1.12 min; m z=586.3 for [M+H]$^+$.

Example 14: General Scheme—Synthesis of Intermediates 98a-b (Step 6)

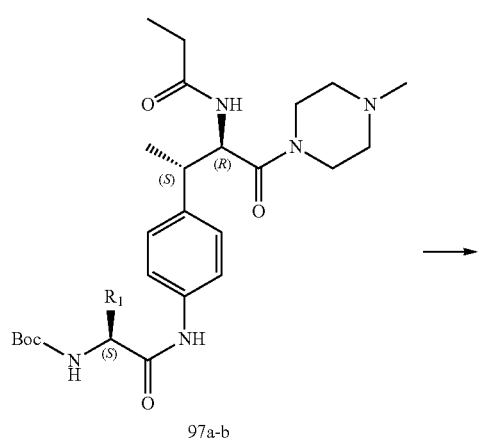

97a-b

-continued

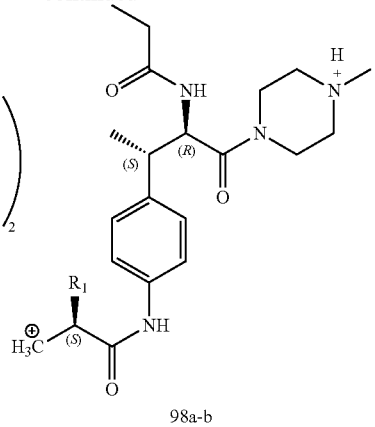

98a-b

To a solution of 97a-b (1.0 eq.) in DCM was added TFA, and the resulting mixture was stirred at RT for 0.5 h. The reaction mixture was concentrated to dryness to afford 98a-b which was used in the next step without further purification.

Step 6a: Compound 97a (0.065 g, 0.114 mmol, 1.0 eq.) was reacted with TFA (0.5 mL) in DCM (1 mL) to afford, after concentration to dryness, 98a (0.066 g, 99% yield) as a brown oil which was used in the next step without further purification. UPLC-MS (basic 2 min): rt=0.91 min; m/z=472.3 for [M+H]$^+$.

Step 6b: Compound 97b (0.058 g, 0.099 mmol, 1.0 eq.) was reacted with TFA (0.5 mL) in DCM (1 mL) to afford, after concentration to dryness, 98b (0.066 g, 99% yield) as a brown oil which was used in the next step without further purification. UPLC-MS (basic 2 min): rt=285; m z=486.3 for [M+H]$^+$.

Example 15: General Scheme—Synthesis of Compounds 221, 222, 232, 297, 298, and 300

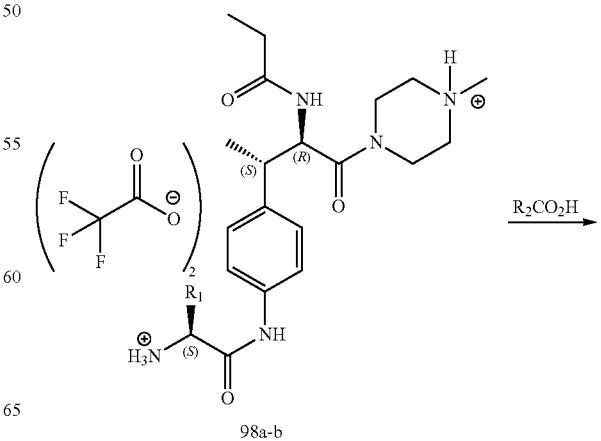

98a-b

129
-continued
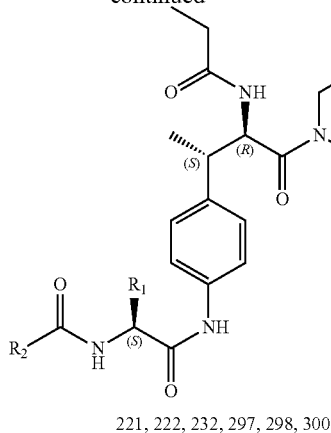
221, 222, 232, 297, 298, 300
The following compounds were made following a procedure analogous to Example 15 starting from 98a-b and reacting with the appropriate carboxylic acid.
130
-continued
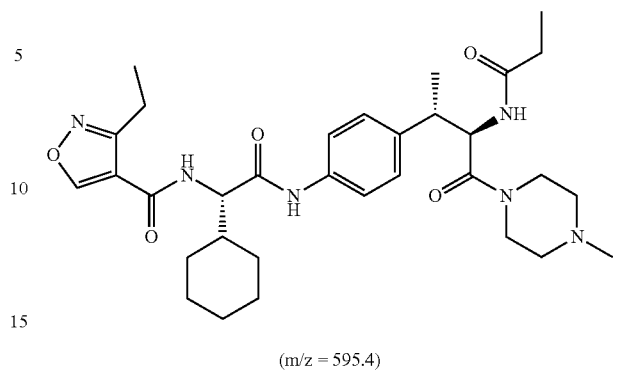
298
(m/z = 595.4)
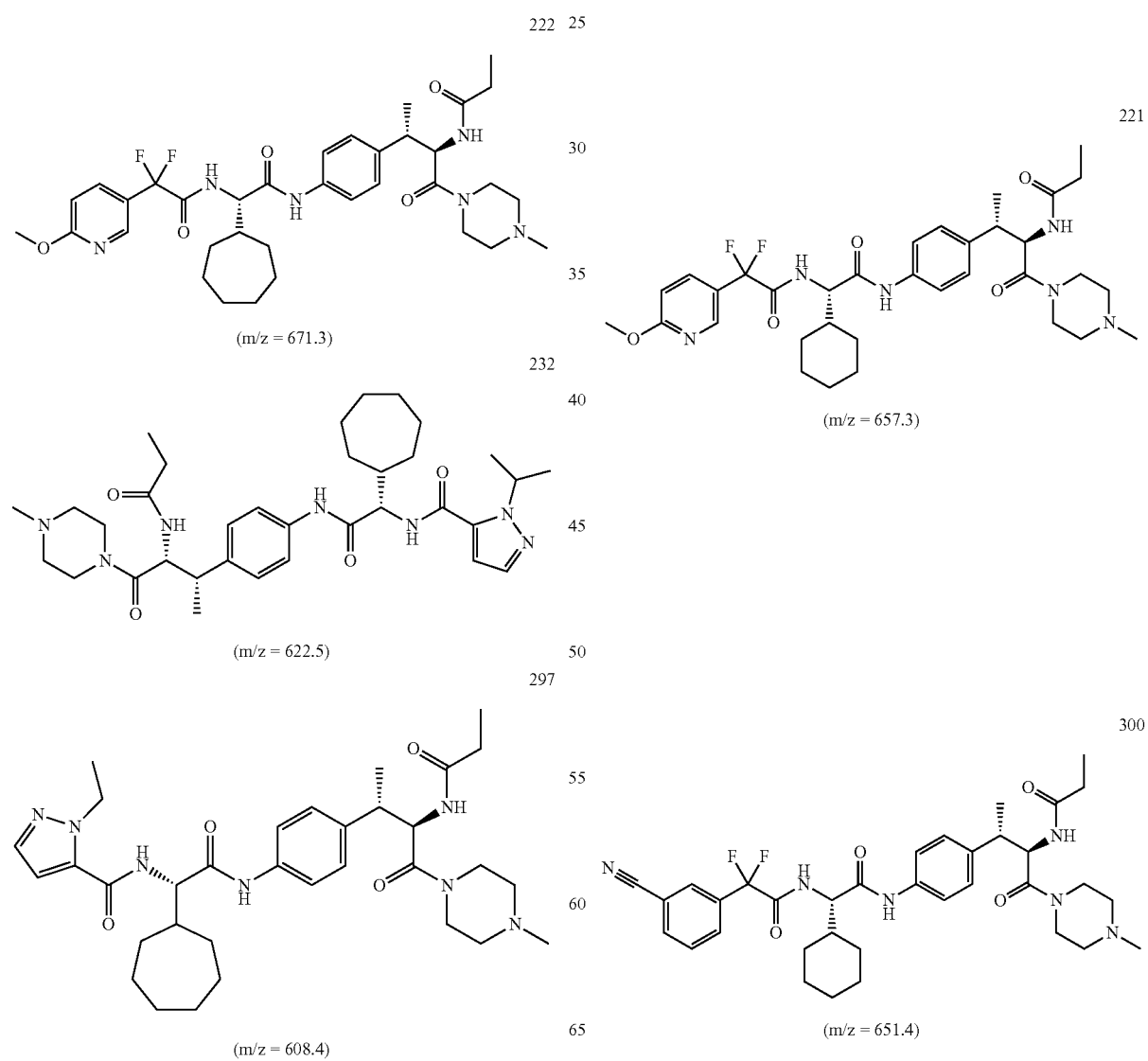

Example 16: General Scheme—Synthesis of Compounds 224, 303-318

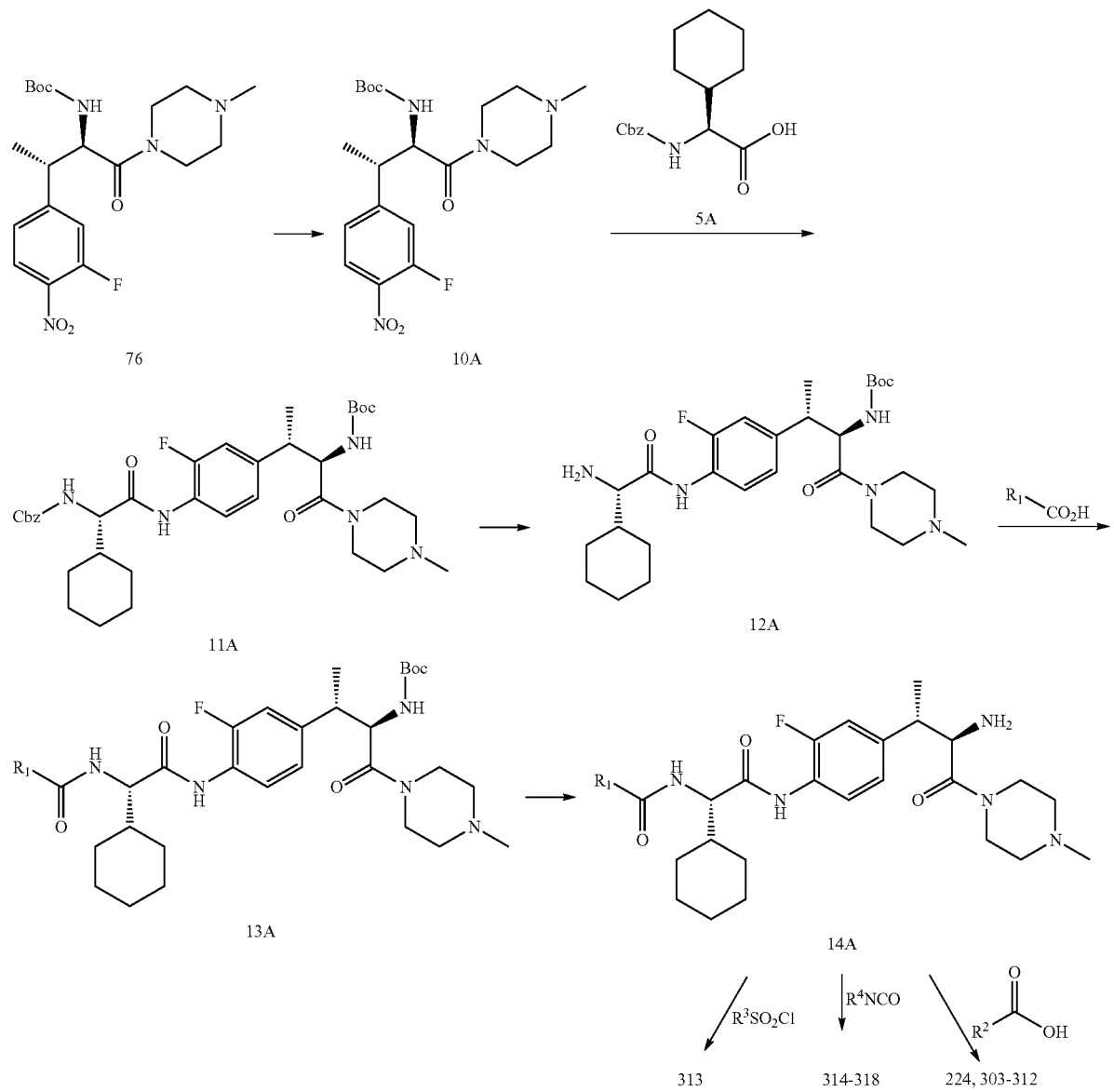

Step 1: To a degassed solution of 76 (0.457 g, 1.08 mmol, 1.0 eq) in THF (10 mL) was added Pd(OH)$_2$/C (0.150 g, 1.08 mmol, 1.0 eq.). The mixture was degassed for another 20 minutes and then evacuated under vacuum before introducing a hydrogen balloon. The resulting mixture was stirred at RT for 18 h, filtered through a pad of celite, and concentrated to dryness to afford 10A as a light brown solid (0.414 g, 98% yield), which was used in the next step without further purification. UPLC-MS (basic 2 min): Rt=0.96 min; m/z=395.3 for [M+H]$^+$.

Step 2: To a solution of 10A (0.200 g, 0.507 mmol, 1.0 eq.) in DMF (2 mL) were added 5A (0.177 g, 0.291 mmol, 1.2 eq.), DIPEA (0.5 mL, 2.87 mmol, 5.7 eq.) and HATU (0.739 g, 1.94 mmol, 3.8 eq.), and the resulting mixture was stirred for 18 h. More 5A (0.250 g, 0.858 mmol, 1.7 eq.) and COMU (0.217 g, 0.507 mmol, 1.0 eq.) were added, and the reaction mixture stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM with 0.1% ammonia additive) to afford 11A as a yellow-orange solid (0.187 g, 55% yield). UPLC-MS (basic 2 min): Rt=1.23 min; m/z=668.5 for [M+H]$^+$.

Step 3: To a degassed solution of 11A (0.187 g, 0.280 mmol, 1.0 eq) in THF (10 mL) was added Pd(OH)$_2$/C (0.050 g, 0.356 mmol, 1.27 eq.). The mixture was degassed for another 20 minutes and then evacuated under vacuum before introducing a hydrogen balloon. The resulting mixture was stirred at RT for 2 h. The mixture was filtered through a pad of celite, and the filtrate was concentrated to dryness to afford 12A as a brown oil (0.149 g, 100% yield), which was used in the next step without further purification. UPLC-MS (basic 2 min): Rt=1.11 min; m/z=534.4 for [M+H]$^+$.

Step 4: To a solution of 12A (0.158 g, 0.296 mmol, 1.0 eq) in DMF (4 mL) was added 2-difluoro-2-(6-methoxypyridin-3-yl)acetic acid (1.2 eq.), DIPEA (0.21 mL, 1.18 mmol, 4.0 eq.), and then HATU (0.220 g, 0.185 mmol, 1.5 eq.), and the resulting mixture was stirred at RT for 1 h. Aqueous saturated sodium bicarbonate solution was added, and then the product was extracted with EtOAc. The combined organic phases were washed with brine, dried over sodium sulfate, and then concentrated to dryness to afford 13A as a white solid (0.158 g, 74%), which was used in the next step without further purification. UPLC-MS (basic 2 min): Rt=1.23 min; m/z=719.3 for [M+H]⁺.

Step 5: To a solution of 13A (0.158 g, 0.220 mmol, 1.0 eq.) in DCM (2 mL) was added TFA (2 mL), and the resulting mixture was stirred at RT for 2 h. The reaction mixture was concentrated to dryness, and the residue was dissolved in DCM (10 mL), stirred in aq. sat. K₂CO₃ solution (1 g in 10 mL H₂O), and then extracted with DCM to afford 14A as an off-white solid (0.136 g, 100% yield), which was used in the next step without further purification. UPLC-MS (basic 2 min): rt=1.06 min; m/z=619.3 for [M+H]⁺.

Example 17: General Scheme—Synthesis of Compounds 224, 303-318 from Intermediates 11A-14A The following compounds were made following a procedure analogous to Example 16 starting from amine 11A, 12A, 13A or 14A and reacting with the appropriate carboxylic acid, sulfonyl chloride, or isocyanate.

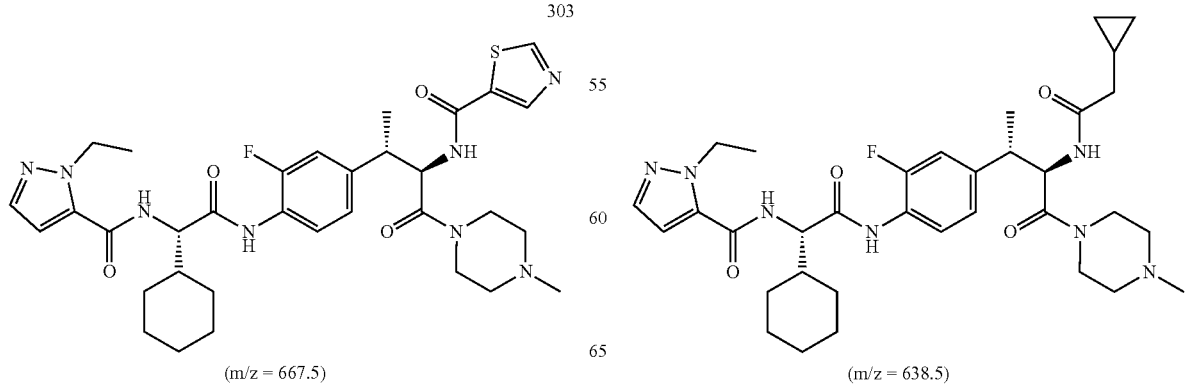

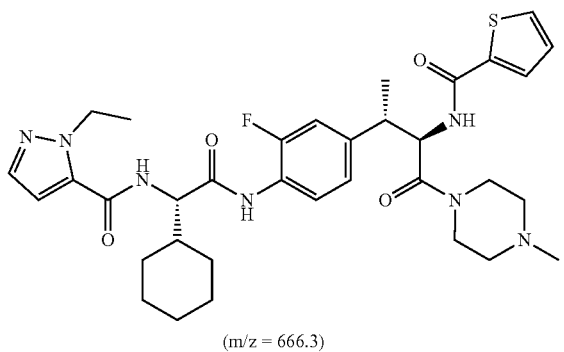

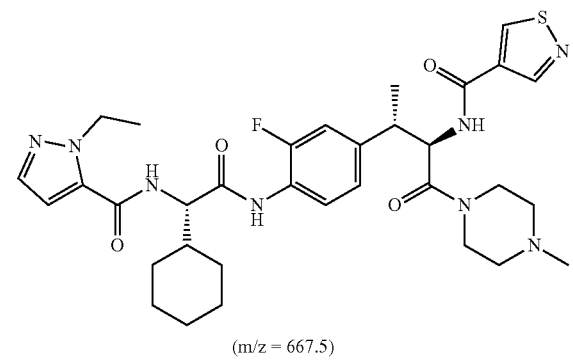

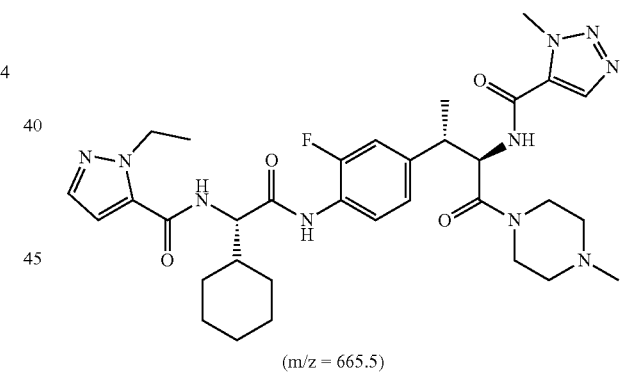

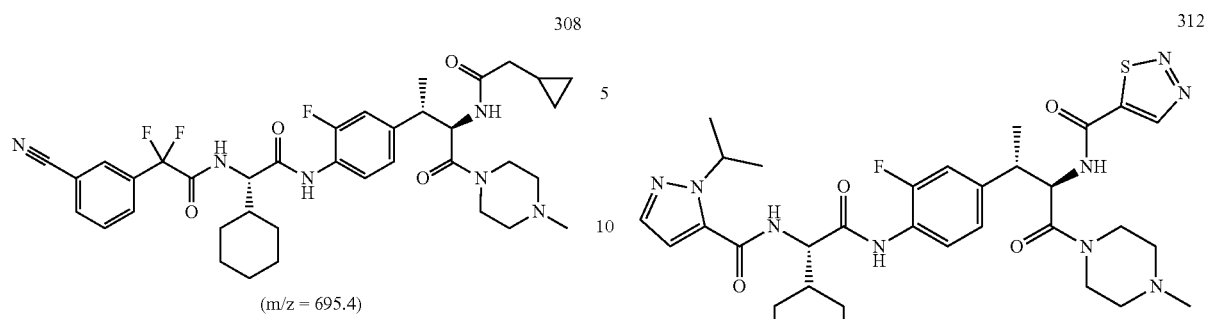
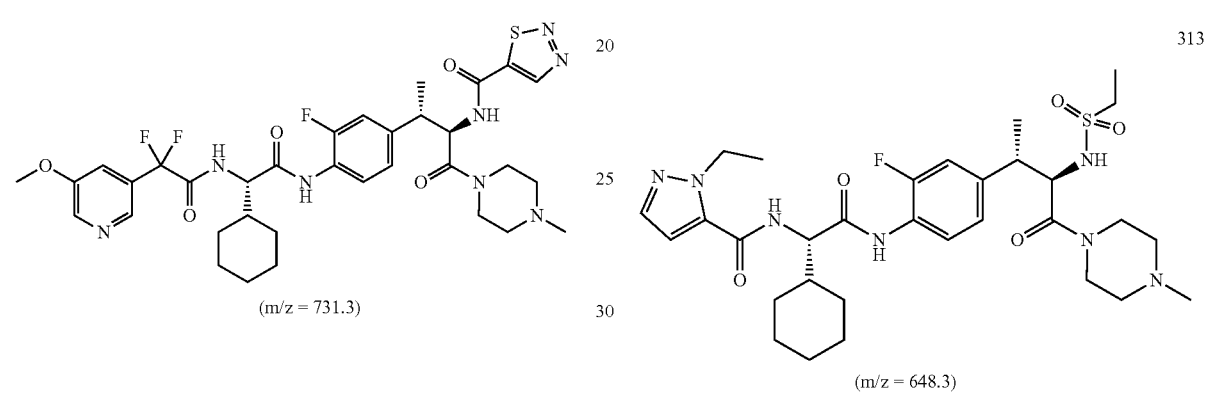
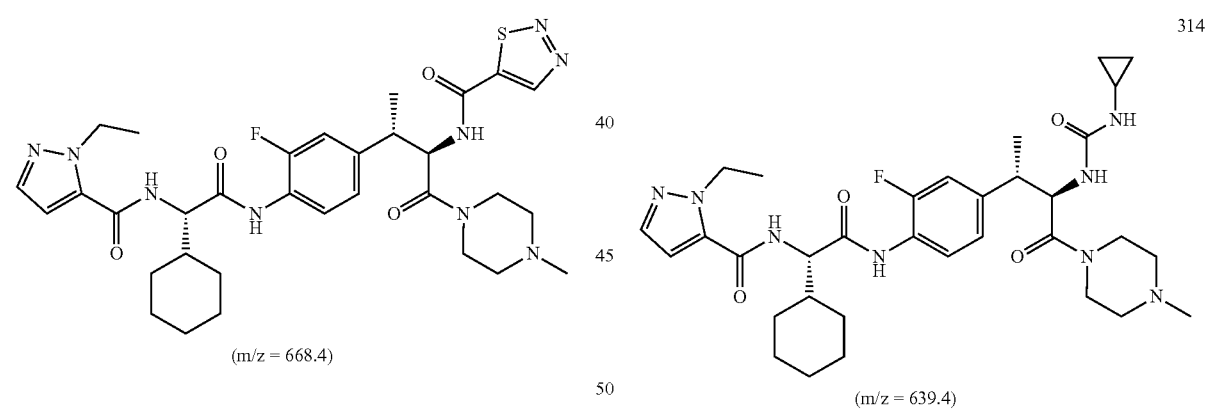
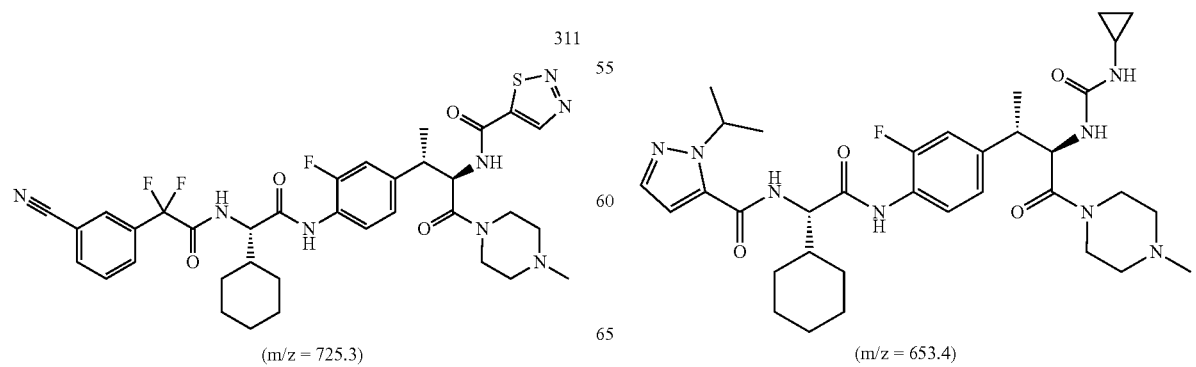

316
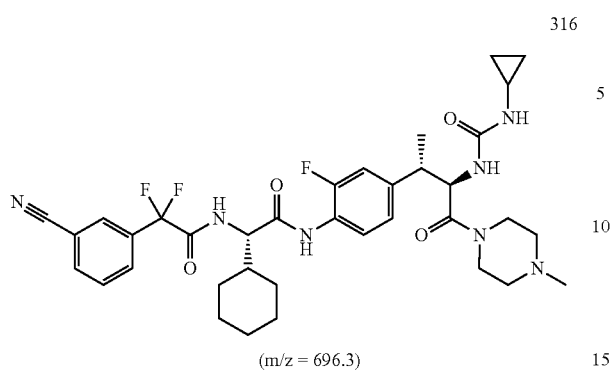
(m/z = 696.3)
317
(m/z = 670.3)
318
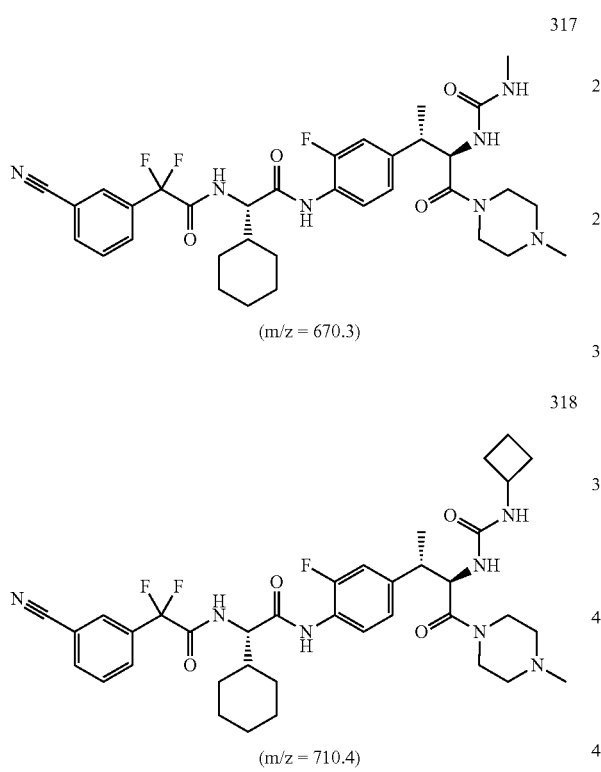
(m/z = 710.4)
Example 18: General Scheme—Synthesis of Compound 231
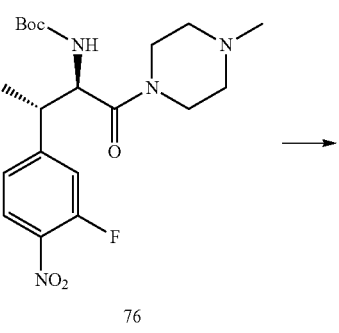
76
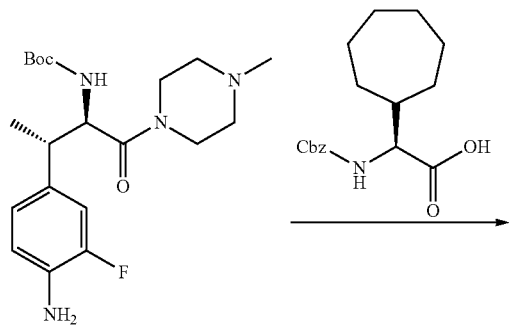
74B
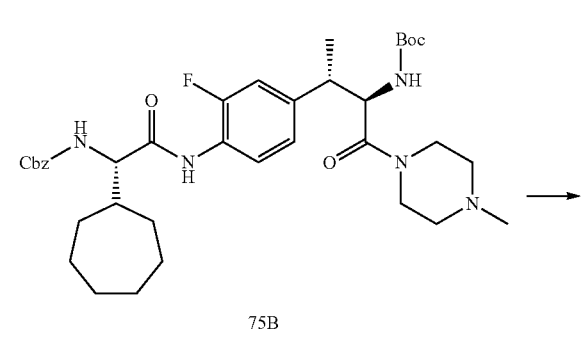
75B
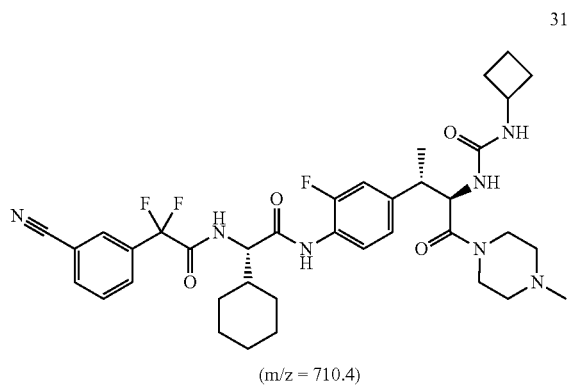
76B
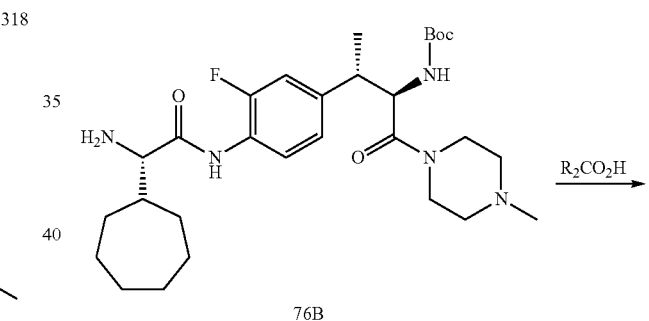
77B
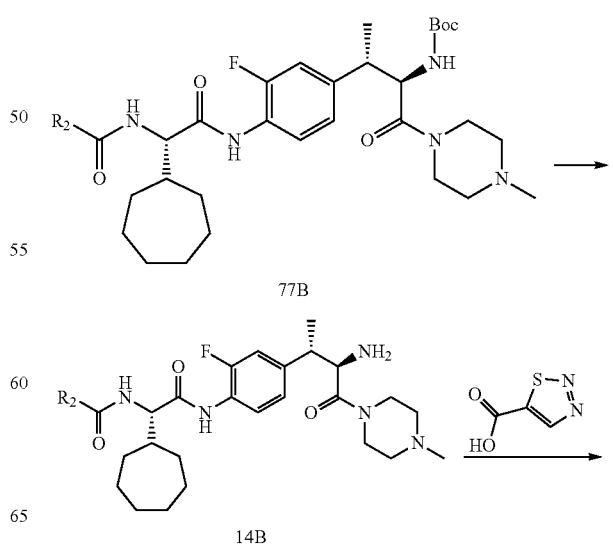
14B

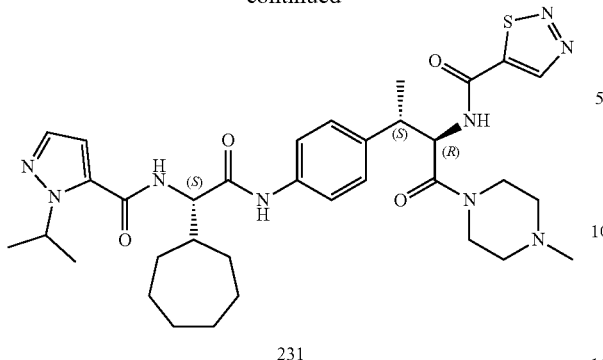

231

Steps 1 and 2: To a solution of 74B (0.811 g, 2.06 mmol, 1.0 eq.) prepared by hydrogenation of 76 in DMF (3.0 mL) was added (2R)-2-{[(benzyloxy)carbonyl]amino}-2-cycloheptylacetic acid) (1.13 g, 3.69 mmol, 1.7 eq.), DIPEA (1.1 mL, 6.17 mmol, 3.0 eq.), and then HATU (1.56 g, 4.11 mmol, 2.0 eq.), and the resulting mixture was stirred at RT for 24 h. The mixture was directly purified via reverse phase column chromatography on a 120 g C18 cartridge eluting with a 5-95% H$_2$O:MeCN eluent (0.1% ammonia) to afford 75B (0.824 g, 59%) as a white solid. UPLC-MS (basic 2 min): rt=1.27 min; m/z=682.4 for [M+H]$^+$.

Step 3: To a degassed solution of 75B (0.824 g, 1.21 mmol, 1.0 eq) in EtOH (4 mL) and THF (4 mL) was added Pd/C (0.257 g, 0.242 mmol, 0.2 eq.). The mixture was degassed for another 20 minutes and then evacuated under vacuum before introducing a hydrogen balloon. The resulting mixture was stirred at RT for 1 h. The mixture was filtered through a pad of celite which was washed with EtOH (50 mL). The solution was concentrated to dryness to afford 76B as a yellow solid (0.656 g, 99%) which was used in the next step without further purification. UPLC-MS (basic 2 min): rt=1.16 min; m/z=548.3 for [M+H]$^+$.

Step 3: To a solution of 76B (1.0 eq.) in DMF (0.1 M) were added required carboxylic acid (1.2 eq.), DIPEA (3.0-8.0 eq.) and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified via reverse phase column chromatography on a 120 g C18 cartridge eluting with a 5-95% H$_2$O:MeCN eluent (0.1% ammonia) to afford 77B.

Step 4: To a solution of 77B (1.0 eq.) in DCM was added TFA, and the resulting mixture was stirred at RT for 0.5 h. The reaction mixture was concentrated to dryness, and the residue was stirred in aq. sat. K$_2$CO$_3$ solution and then extracted with DCM to afford 14B which was used in the next step without further purification.

Step 5: Synthesis of Compound 231 To a solution of 14B (0.101 g, 0.179 mmol, 1.0 eq.) in DMF (1.0 mL), was added 1,2,3-thiadiazole-5-carboxylic acid (0.026 g, 0.197 mmol, 1.2 eq.), DIPEA (0.25 mL, 1.44 mmol, 8.0 eq.), and HATU (0.102 g, 0.268 mmol, 1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by reverse phase column chromatography on a 120 g C18 cartridge eluting with a 5-95% H$_2$O:MeCN eluent (0.1% ammonia) to afford 231 as a white solid (54.0 mg). m/z=677.86 for [M+H]$^+$.

Example 19: Exemplified Scheme—Synthesis of Intermediate Compound 19A

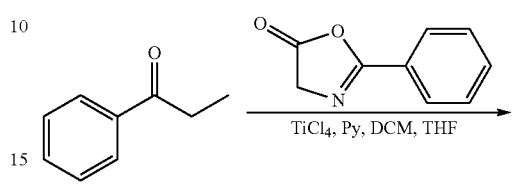

35A

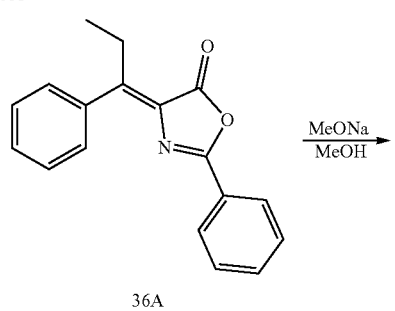

36A

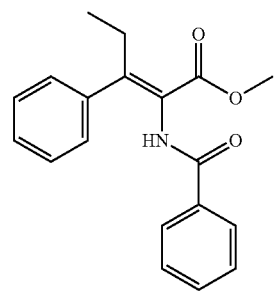

37A

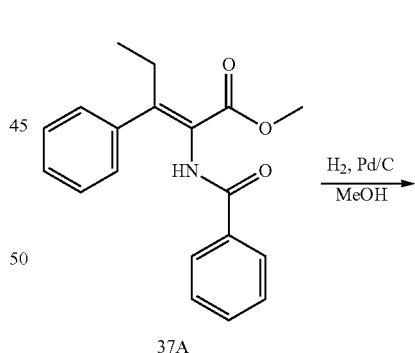

37A

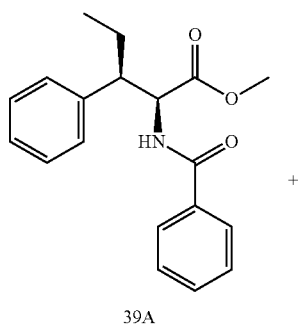

39A

-continued

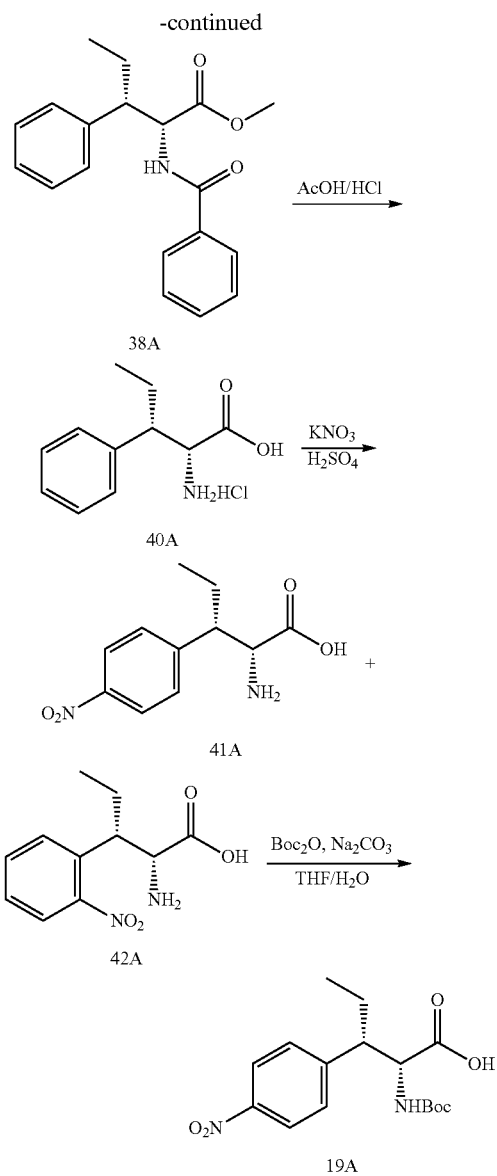

Step 1: THF (150 mL) was chilled under $N_2$ to −10° C. A solution of $TiCl_4$ (21.2 g, 112 mmol, 1.50 eq) in DCM (30.0 mL) was added and stirred for 20 min. A solution of compound 35A (10.0 g, 74.5 mmol, 9.90 mL, 1.00 eq) in THF (30.0 mL) was added to this stirring solution, and the mixture was stirred for 10 min, then the imino lactone depicted above (18.0 g, 112 mmol, 1.50 eq) was added, and the reaction was stirred for a further 30 min. Pyridine (11.8 g, 149 mmol, 12.0 mL, 2.00 eq) was then added dropwise to this mixture. The mixture was stirred for a further 5 hrs at 0° C. TLC (petroleum ether:ethyl acetate=10:1, plate 1, $R_f$ $(R_1)$=0.80, $R_f$ $(P_1)$=0.75) showed compound 35A was consumed completely, and a major new spot was generated. Saturated $NH_4Cl$ (400 mL) was added to the solution, and the aqueous layer was extracted with EtOAc (300 mL*2). The combined organic phases were washed with brine (200 mL*2), dried over $Na_2SO_4$, and concentrated under reduced pressure to give a residue. The residue was purified by column with petroleum ether:ethyl acetate=50:1 ($SiO_2$, petroleum ether:ethyl acetate=10:1, plate 2, $R_f$ $(P_1)$=0.75).

Compound 36A (16.6 g, 59.9 mmol, 80.3% yield) was obtained as a light yellow oil, confirmed by LCMS: $(M+H)^+$: 278.2

Step 2: To a solution of $CH_3ONa$ (323 mg, 5.99 mmol, 0.100 eq) in MeOH (150 mL) at 25° C. was added compound 36A (16.6 g, 59.8 mmol, 1.00 eq), and then the mixture was stirred at 25° C. for 2 hrs. TLC (petroleum ether:ethyl acetate=5:1, plate 1, $R_f$ $(R_1)$=0.75, $R_f$ $(P_1)$=0.20) showed compound 36A was consumed completely, and a major new spot was generated. MeOH was removed in vacuo to give a residue. The residue was purified by column with petroleum ether:methyl tert-butyl ether=3:1 ($SiO_2$, petroleum ether:ethyl acetate=5:1, plate 2, $R_f$ $(P_1)$=0.20). Compound 37A (9.60 g, 30.3 mmol, 50.7% yield, 97.8% purity) was obtained as a white solid, confirmed by LCMS: $(M+H)^+$: 310.2

Step 3: To a solution of compound 37A (9.60 g, 31.0 mmol, 990 uL, 1.00 eq) in MeOH (150 mL) was added Pd/C (2.00 g, 10.0% purity), and the reaction was stirred at 40° C. under $H_2$ (50 psi) for 12 hrs. TLC (petroleum ether:ethyl acetate=5:1, plate 1, $R_f$ $(R_1)$=0.20, $R_f$ $(P_1)$=0.25) showed compound 37A was consumed completely, and a major new spot was generated. The mixture was filtered, and the filtrate was concentrated in vacuum to give a residue, which was a mixture of stereoisomers 38A and 39A. It was directly used for the next step without further purification. Compound 38A was purified by Prep-SFC (column: DAICEL CHIRAL-PAK AD-H (250 mm*30 mm, 5 um); mobile phase: [0.1% $NH_3H_2O$ MeOH]; B %: 25%-25%, 4 min; 520 min). Compound 38A (4.50 g, 14.4 mmol, 95.7% yield, 100% purity) was obtained as a white solid, confirmed by LCMS: $(M+H)^+$: 312.2;

Step 4: A solution of compound 38A (4.50 g, 14.4 mmol, 1.00 eq) in HCl (3 M, 240 mL, 50.0 eq) and AcOH (86.8 g, 1.45 mol, 82.6 mL, 100 eq) was stirred at 125° C. for 60 hrs. TLC (dichloromethane:methanol=10:1, plate 1, $R_f$ $(R_1)$=0.95, $R_f$ $(P_1)$=0.00) showed compound 38A was consumed completely, and a major new spot was generated. The mixture was evaporated under reduced pressure to give a residue. The residue was slurried with DCM (100 mL). Compound 40A (3.22 g, 14.0 mmol, 97.0% yield, 100% purity, HCl) was obtained as a white solid, confirmed by LCMS: $(M+H)^+$: 194.1

Step 5: To a solution of compound 40A (1.60 g, 6.97 mmol, 1.00 eq, HCl) in $H_2SO_4$ (27.3 g, 278 mmol, 14.9 mL, 40.0 eq) was added $KNO_3$ (774 mg, 7.66 mmol, 1.10 eq) in portions at 0° C., and then the mixture was stirred at 25° C. for 2 hrs. LCMS (EW17597-90-P1D1) showed compound 40A was consumed completely, and the desired MS was detected. The mixture was slowly added to ice water (200 mL), and $Na_2CO_3$ (31.8 g, 300 mmol) was added to this mixture to adjust the pH to 7~8. The solution was directly used for the next step. Compounds 41A and 42A (1.66 g, crude) was obtained as a light yellow solution.

Step 6: To a solution of compounds 41A and 42A (1.66 g, 6.97 mmol, 1.00 eq) in $H_2O$ (200 mL) was added THF (150 mL), $Na_2CO_3$ (2.22 g, 20.9 mmol, 3.00 eq), and $Boc_2O$ (2.28 g, 10.4 mmol, 2.40 mL, 1.50 eq), and then the mixture was stirred at 25° C. for 4 hrs. LCMS showed that compounds 41A and 42A were consumed completely, and the desired MS was detected. THF was evaporated in vacuo, and $H_2O$ (100 mL) was added. The aqueous phase was acidified with 1 N HCl to adjust the pH to 5~6, and then the product was extracted with EtOAc (150 mL*2). The combined organic phases were washed with brine (100 mL*2), dried over $Na_2SO_4$, filtered, and concentrated under reduced pressure to give a residue. The residue was purified by Prep-SFC (column: DAICEL CHIRALPAK AD-H (250 mm*30 mm, 5 um); mobile phase: [0.1% NH₃H₂O MeOH]; B %: 25%-25%, 3.7 min; 740 min). Compound 19A (1.22 g, 3.58 mmol, 51.4% yield, 99.3% purity) was obtained as a light yellow solid, confirmed by LCMS: (M-99)⁺: 239.1

Example 20: General Scheme—Synthesis of Intermediate 26A

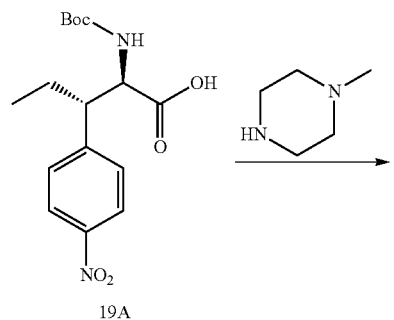

19A

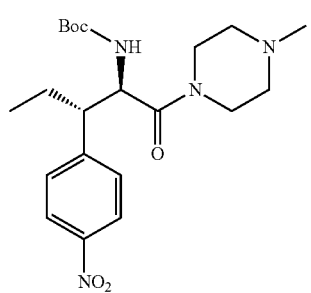

20A

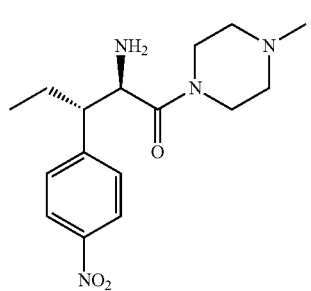

21A

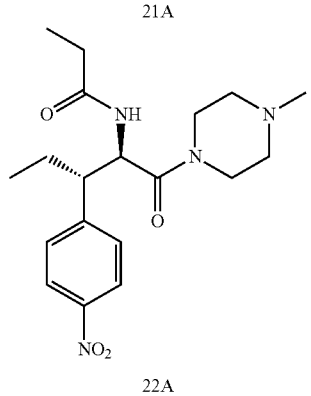

22A

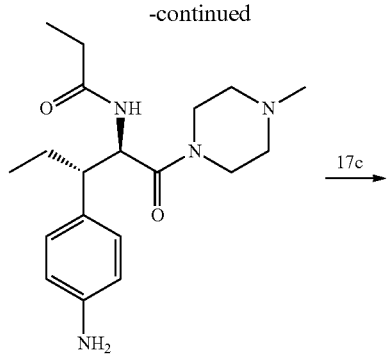

23A

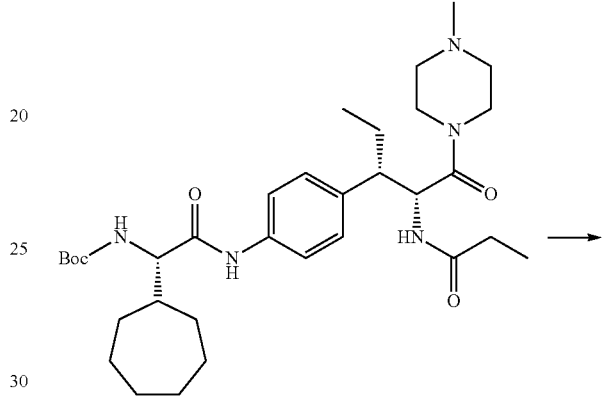

25A

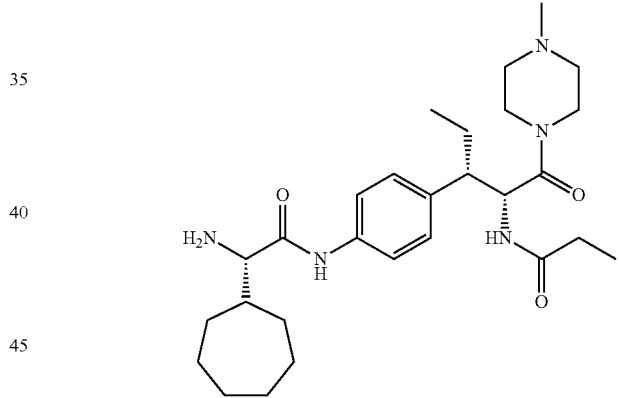

26A

Step 1: To a solution of 19A (0.843 g, 2.49 mmol, 1.0 eq.) in DMF (7 mL) was added N-methyl piperazine (0.33 mL, 2.99 mmol, 1.2 eq), DIPEA, (2.2 mL, 12.5 mmol, 5.0 eq) and HATU (1.42 g, 3.74 mmol, 1.5 eq.), and the resulting mixture was stirred at RT under a N₂ atmosphere for 1 h. The mixture was diluted with aq. sat. NaHCO₃ solution (50 mL) and then extracted with DCM (50 mL). The organic layers were washed with brine (200 mL), dried over Na₂SO₄, and then concentrated. The residue was purified by flash column chromatography (Silica, 0-10% MeOH, DCM) to afford 20A as a yellow solid (0.932 g, 89% yield). UPLC-MS (basic 2 min): Rt=1.12 min; m/z=421.3 for [M+H]⁺

Step 2: To a solution of 20A (0.932 g, 2.22 mmol, 1.0 eq.) in DCM (8 mL) was added TFA (4 mL), and the resulting mixture was stirred at RT for 20 min. The reaction mixture was concentrated to dryness, and the residue was dissolved in DCM (25 mL), stirred in aq. sat. K$_2$CO$_3$ solution (4 g in 25 mL H$_2$O), and then extracted with DCM to afford 21A as an off-white solid (0.579 g, 82% yield), which was used in the next step without further purification. UPLC-MS (basic 2 min): Rt=0.88 min; m/z=320.2 for [M+H]$^+$.

Step 3: To a solution of 21A (0.579 g, 1.81 mmol, 1.0 eq.) in DMF (5.0 mL) was added propionic anhydride (0.28 mL, 2.17 mmol, 1.2 eq.) and DIPEA (0.94 mL, 5.42 mmol, 3.0 eq), and the resulting mixture was stirred at RT under a N$_2$ atmosphere for 1 h. The mixture was diluted with aq. sat. NaHCO$_3$ solution (100 mL), and then the product was extracted with DCM (100 mL). The organic layer was washed with brine (100 mL), dried over Na$_2$SO$_4$, and then concentrated to afford 22A as a yellow solid (0.612 g, 90% yield), which was used in the next step without further purification. UPLC-MS (basic 2 min): Rt=0.94 min; m/z=377.2 for [M+H]$^+$.

Step 4: To a degassed solution of 22A (0.612 g, 1.63 mmol, 1.0 eq) in EtOH (15 mL) and THF (15 mL) was added Pd/C (0.061 g, 0.573 mmol, 0.35 eq). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness. The residue was purified by reverse phase column chromatography 48 g C18 cartridge eluting with a 5-95% H$_2$O:MeCN eluent to afford 23A as an off-white solid (0.338 g, 60% yield). UPLC-MS (basic 2 min): Rt=0.80 min; m/z=347.3 for [M+H]$^+$.

Step 5: To a solution of 23A (0.224 g, 0.647 mmol, 1.0 eq.) in DMF (5.0 mL) was added 17c (0.211 g, 0.776 mmol, 1.2 eq.), DIPEA (0.9 mL, 5.17 mmol, 8.0 eq.), and HATU (0.492 g, 1.29 mmol, 1.5 eq.), and the resulting mixture was stirred for 2 h. Aqueous saturated sodium bicarbonate solution (100 mL) was added, and then the product was extracted with DCM (50 mL). The combined organic phases were washed with brine (100 mL), dried over sodium sulfate, and then concentrated to dryness to afford 25A as a pale brown solid (0.223 g, 58% yield), which was used in the next step without further purification. UPLC-MS (basic 2 min): Rt=1.16 min; m/z=598.3 for [M+H]$^+$.

Step 6: To a solution of 25A (0.225 g, 0.375 mmol, 1.0 eq.) in DCM (3 mL) was added TFA (3 mL), and the resulting mixture was stirred at RT for 30 min. The reaction mixture was concentrated to dryness, and the residue was dissolved in DCM (15 mL), stirred in aq. sat. K$_2$CO$_3$ solution (1 g in 15 mL H$_2$O), and then the product was extracted with DCM to afford 26A as an off-white solid (0.356 g, 95% yield), which was used in the next step without further purification. UPLC-MS (basic 2 min): Rt=1.00 min; m/z=500.3 for [M+H]$^+$.

Example 21: Synthesis of Compound 227 and 319

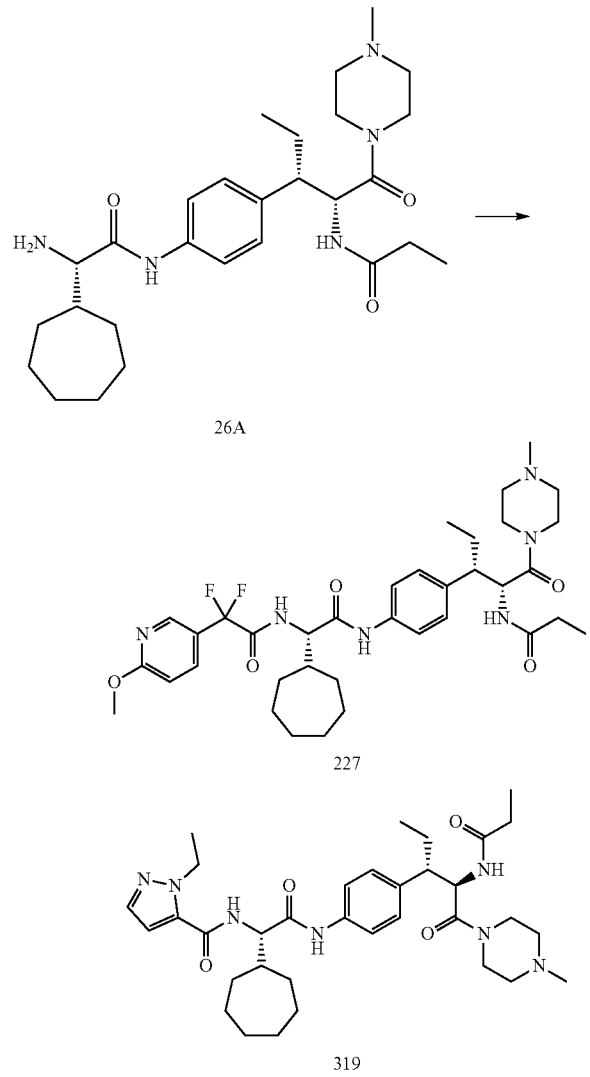

Synthesis of Compound 227: To a solution of 26A (0.089 g, 0.178 mmol, 1.0 eq.) in DMF (1.0 mL) was added 2,2-difluoro-2-(6-methoxypyridin-3-yl)acetic acid (0.043 g, 0.212 mmol, 1.2 eq.), DIPEA (0.25 mL, 1.43 mmol, 8.0 eq.), and then HATU (0.102 g, 0.267 mmol, 1.5 eq.), and the resulting mixture was stirred at RT for 4 h. The mixture was concentrated to dryness, and the residue was purified via reverse phase column chromatography on a 120 g C18 cartridge eluting with a 5-95% H$_2$O:MeCN eluent (0.1% ammonia) to afford 227 (43.0 mg) as a white solid. UPLC-MS (basic 2 min): Rt=1.94 min; m/z=685.4 for [M+H]$^+$. Synthesis of Compound 319: To a solution of 26A (0.089 g, 0.178 mmol, 1.0 eq.) in DMF (1.0 mL) was added pyrazolic acid (0.043 g, 0.212 mmol, 1.2 eq.), DIPEA (0.25 mL, 1.43 mmol, 8.0 eq.), and then HATU (0.102 g, 0.267 mmol, 1.5 eq.), and the resulting mixture was stirred at RT for 4 h. The mixture was concentrated to dryness, and the residue was purified via reverse phase column chromatography on a 120 g C18 cartridge eluting with a 5-95% H$_2$O:MeCN eluent (0.1% ammonia) to afford 319. UPLC-MS (basic 2 min): rt=1.08 min; m/z=622.4 for [M+H]$^+$.

Example 22: Exemplary Scheme—Synthesis of Compounds 320 and 321-324

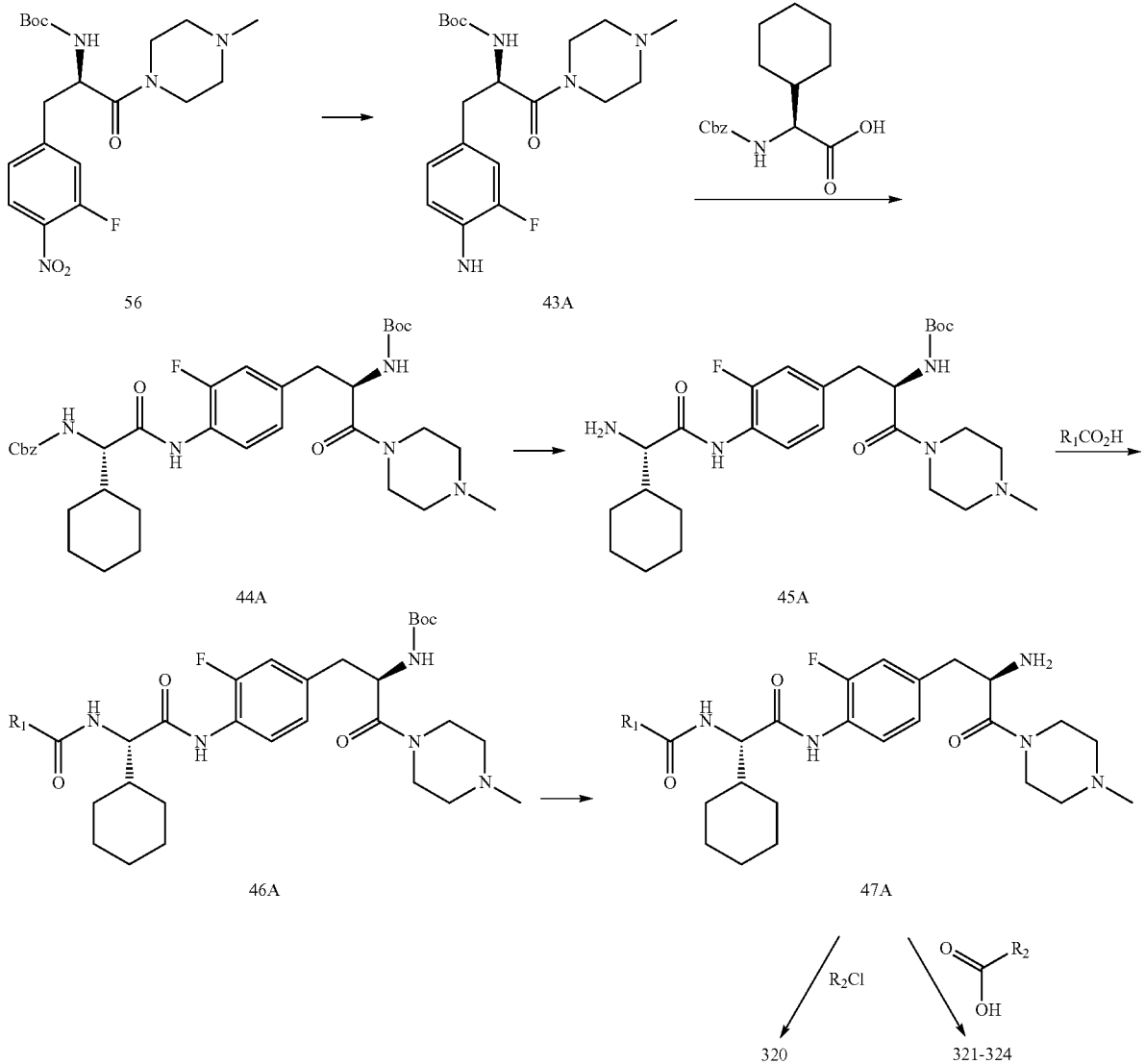

Step 1: To a degassed solution of 56 (5.30 g, 12.9 mmol, 1.0 eq) in EtOH (50 mL) was added Pd/C (0.5 g). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness to afford 43A as a yellow oil (4.50 g, 91%). UPLC-MS (basic 4 min): Rt=1.35 min; m/z=381.3 for [M+H]$^+$.

Step 2: To a solution of 43A (1.0 g, 2.63 mmol, 1.0 eq.) in DMF (10 mL) were added Z-Chg-OH (0.919 g, 3.15 mmol, 1.2 eq.), DIPEA (1.8 mL, 10.5 mmol, 4.0 eq.), and HATU (1.50 g, 3.94 mmol, 1.5 eq.), and the resulting mixture was stirred for 18 h. Aqueous saturated sodium bicarbonate solution was added, and then the product was extracted with EtOAc. The combined organic phase was washed with brine, dried over sodium sulfate, and then concentrated to dryness. The residue was purified by flash column chromatography (Silica, 0-10% MeOH, DCM with 5% aq. NH$_3$) to afford 44A as a white solid (1.12 g, 65%). UPLC-MS (basic 4 min): Rt=2.05 min; m/z=654.3 for [M+H]$^+$.

Step 3: To a degassed solution of 44A (0.280 g, 0.428 mmol, 1.0 eq) in EtOH (50 mL) was added Pd(OH)$_2$ (0.150 g, 0.214 mmol, 0.5 eq.). The mixture was degassed for another 20 minutes and then evacuated under vacuum before introducing a hydrogen balloon. The resulting mixture was stirred at RT for 1 h. The mixture was filtered through a pad of celite which was washed with EtOH (50 mL). The solution was concentrated to dryness to afford 45A as a yellow oil (0.217 g, 78%). UPLC-MS (basic 2 min): Rt=1.08 min; m/z=520.3 for [M+H]$^+$.

Step 4: To a solution of 45A (1.0 eq.) in DMF 0.10 mL) was added required carboxylic acid (1.2 eq.), DIPEA (3.0-8.0 eq.), and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM) to afford 46A.

Step 5: To a solution of 46A (1.0 eq.) in DCM was added TFA, and the resulting mixture was stirred at RT for 0.5 h. The reaction mixture was concentrated to dryness, and the residue was stirred in aq. sat. $K_2CO_3$ solution and then extracted with DCM to afford 47A which was used in the next step without further purification.

Example 23: Synthesis of Compounds 320-324

A suspension of 47A (1.0 eq.), the required aryl chloride (1.0 eq.), and potassium fluoride (5.0 eq.) in $H_2O$ (0.1 M) was heated at 100° C. via microwave irradiation for 5 minutes. The reaction mixture was cooled to RT and then directly purified via reverse phase column chromatography on a 120 g C18 cartridge eluting with a 5-95% $H_2O$:MeCN eluent (0.1% ammonia) to afford 320

To a solution of 47A (1.0 eq.) in DMF (0.1 M) was added the required carboxylic acid (1.2 eq.), DIPEA (3.0-8.0 eq.), and then HATU (1.5-2.0 eq.), and the resulting mixture was stirred at RT for 1 h. The mixture was concentrated to dryness, and the residue was purified via reverse phase column chromatography on a 120 g C18 cartridge eluting with a 5-95% $H_2O$:MeCN eluent (0.1% ammonia) to afford 321-324.

The following compounds were made following a procedure analogous to Example 22 starting from 47A and reacting with the appropriate carboxylic acid or aryl chloride.

320

(m/z = 671.5)

321

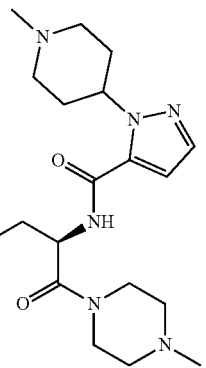

(m/z = 733.4)

322

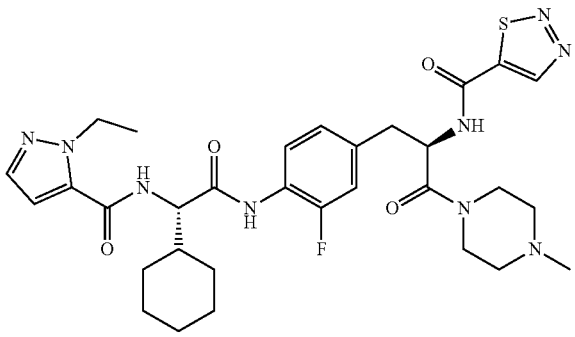

(m/z = 654.3)

323

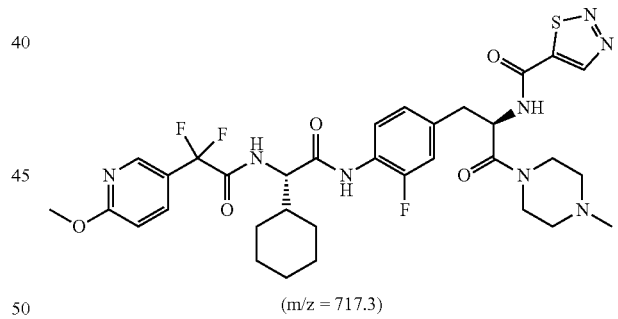

(m/z = 717.3)

324

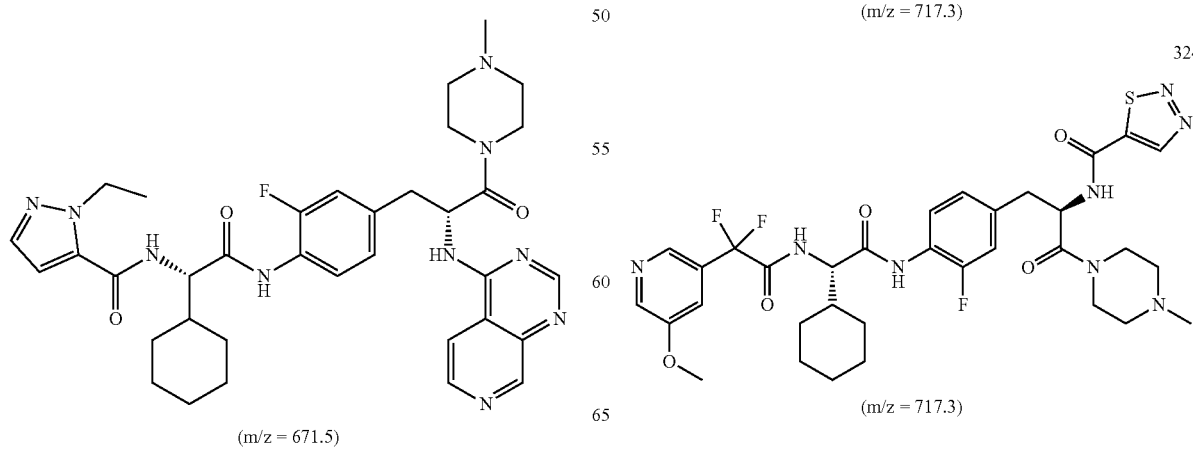

(m/z = 717.3)

Example 24: General Scheme—Synthesis of Compounds 325 and 382

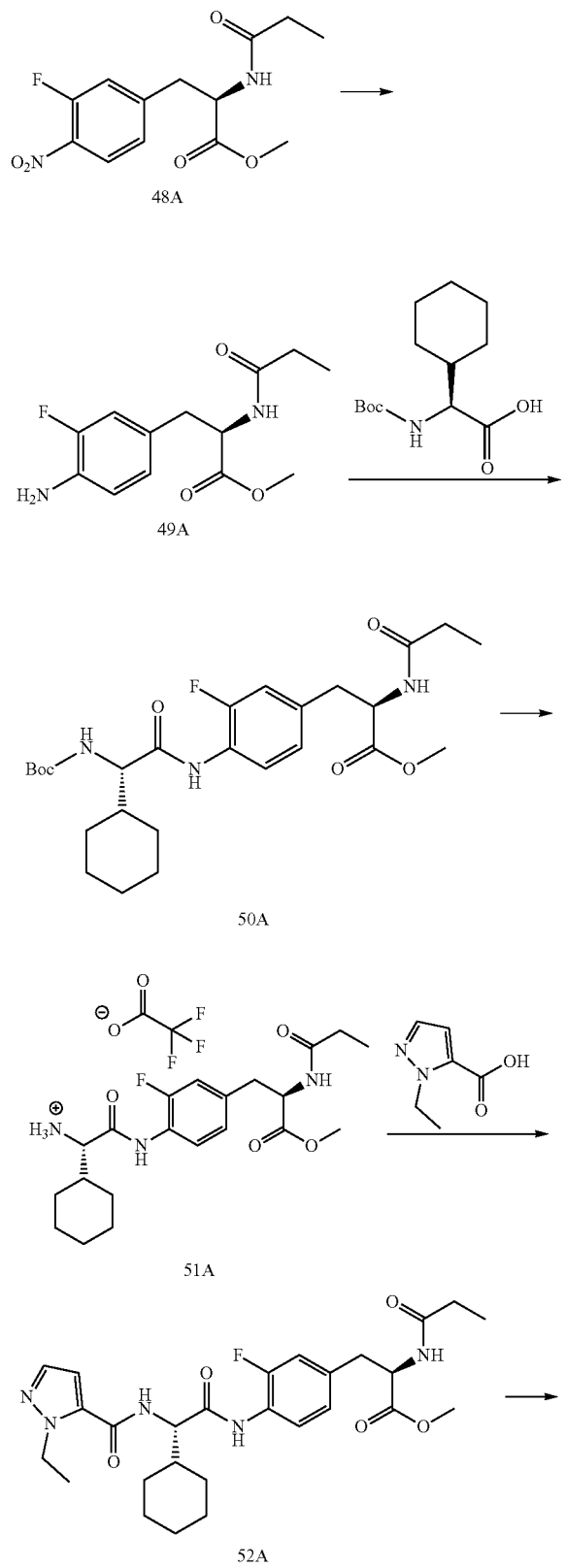

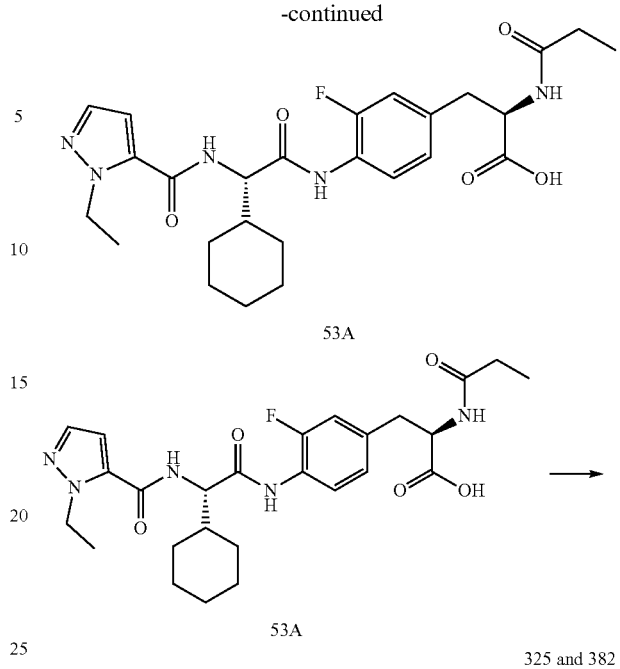

Step 1: To a degassed solution of 48A prepared from by conventional methods (1.70 g, 5.70 mmol, 1.0 eq) in EtOH (30 mL) was added Pd/C (0.5 g). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness to afford 49A as a brown solid (1.33 g, 87%). UPLC-MS (basic 2 min): Rt=0.80 min; m/z=269.1 for [M+H]$^+$.

Step 2: To a solution of 49A (1.33 g, 4.96 mmol, 1.0 eq.) in DMF (25 mL) was added (2S)-2-{[(tert-butoxy)carbonyl]amino}-2-cyclohexylacetic acid) (1.30 g, 5.05 mmol, 1.02 eq.), DIPEA (7.0 mL, 40.2 mmol, 8.0 eq.), and HATU (3.20 g, 8.42 mmol, 1.7 eq.), and the resulting mixture was stirred for 18 h. Aqueous saturated sodium bicarbonate solution was added, and then the product was extracted with EtOAc. The combined organic phase was washed with brine, dried over sodium sulfate, and then concentrated to dryness. The residue was purified by flash column chromatography (Silica, 0-10% MeOH, DCM) to afford 50A as a white solid (1.99 g, 79%). UPLC-MS (basic 2 min): Rt=1.17 min; m/z=508.4 for [M+H]$^+$.

Step 3: To a solution of 50A (1.99 g, 3.92 mmol, 1.0 eq.) in DCM (24.0 mL) was added TFA (6.0 mL), and the resulting mixture was stirred at RT for 1 h. The reaction mixture was concentrated to dryness to afford 51A (1.43 g, 70%), which was used in the next step without further purification. UPLC-MS (basic 2 min): rt=0.85 min; m/z=408.3 for [M+H]$^+$.

Step 4: To a solution of 51A (1.43 g, 2.74 mmol, 1.0 eq.) in DMF (25 mL) was added 1-ethyl-1H-pyrazole-5-carboxylic acid (0.388 g, 2.77 mmol, 1.01 eq.), DIPEA (4.0 mL, 23.0 mmol, 8.0 eq), and HATU (1.70 g, 4.47 mmol, 1.6 eq.), and the resulting mixture was stirred at RT for 1 h. The mixture was diluted with aq. sat. NaHCO$_3$ solution (30 mL), and then the product was extracted with DCM (30 mL). The organic layer was washed with brine (30 mL), dried over Na$_2$SO$_4$, and then concentrated to afford 52A as an off-white solid (1.00 g, 69% yield), which was used in the next step without further purification. UPLC-MS (basic 2 min): rt=1.07 min; m/z=530.3 for [M+H]$^+$.

Step 5: To a solution of 52A (1.00 g, 1.88 mmol, 1.0 eq.) in THF (20 mL) was added a solution of LiOH.H$_2$O (1.6 g, 38.1 mmol, 20.0 eq.) in H$_2$O (20 mL). The resulting mixture was stirred at RT for 1 h and then acidified with 1M aq. HCl solution. The resulting precipitate was filtered to afford 53A as a white solid (0.632 g, 65%). UPLC-MS (basic 2 min): rt=1.00 min; m/z=514.3 for [M−H]$^+$.

Example 25: Synthesis of Compounds 325 and 382 from Intermediate 53A

To a solution of 53A (1.0 eq.) in DMF (0.1 M) was added the required amine (1.2 eq.), DIPEA (3.0-8.0 eq.), and then HATU (1.5 eq.), and the resulting mixture was stirred at RT for 1 h. The mixture was concentrated to dryness, and the residue was purified via reverse phase column chromatography on a 120 g C18 cartridge eluting with a 5-95% H$_2$O:MeCN eluent (0.1% ammonia) to afford 325 and 382.

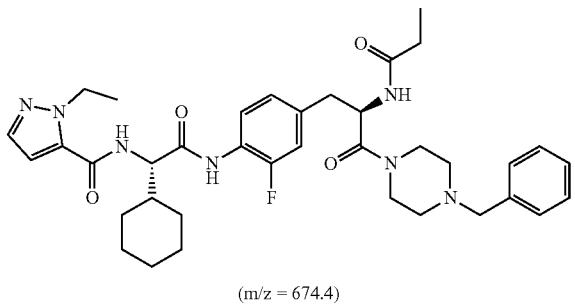

325

(m/z = 674.4)

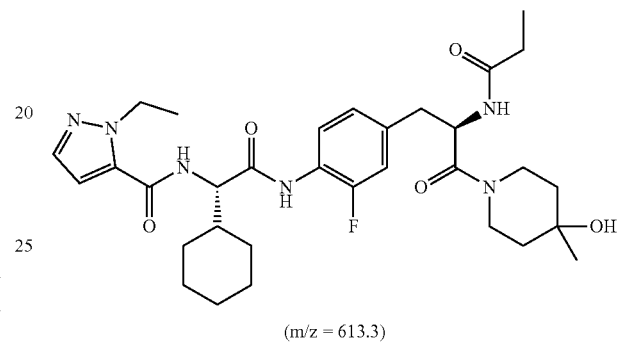

382

(m/z = 613.3)

Example 26. General Scheme—Synthesis of Compounds 326, 327, 328, 329-337, 338, 339 340, 388, 391, 396, 398, 400, 402, 406-410, and 414

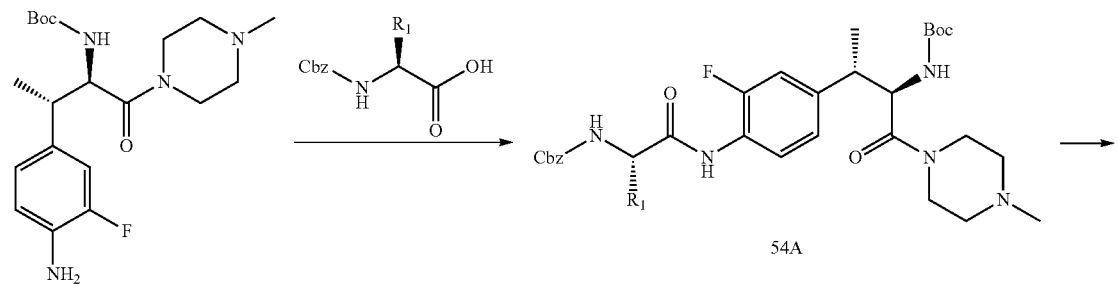

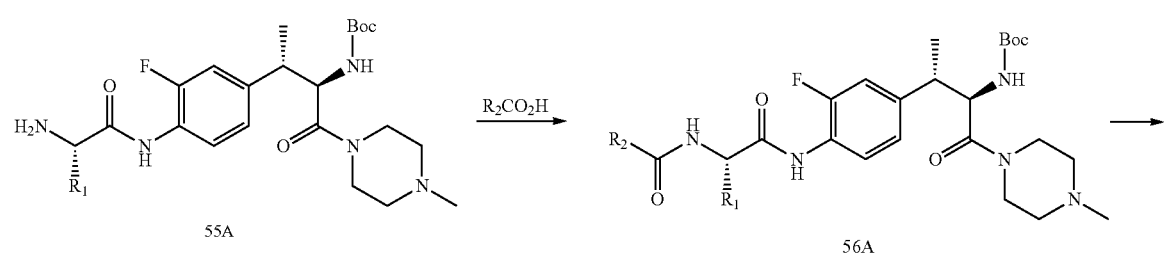

-continued

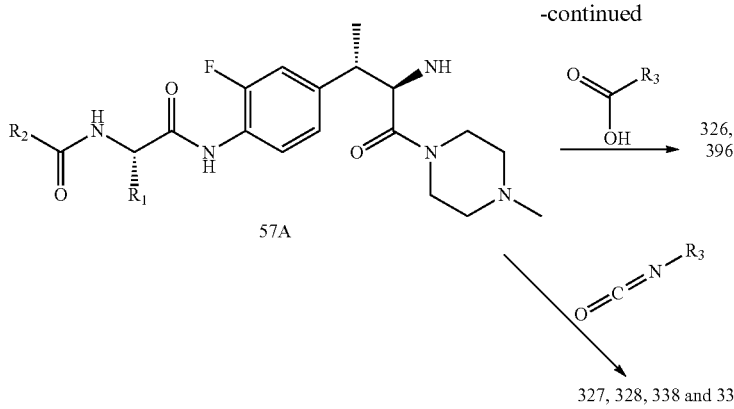

57A

→ 326, 329-337, 340, 388, 391, 396, 398, 400, 406-410 and 414

↘ 327, 328, 338 and 339

Step 1: To a solution of 10A (1.0 eq.) in DMF was added the Cbz protected glycine derivative (1.2 eq.), DIPEA (4.0 eq.), and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM with 5% aq. $NH_3$) to afford 54A.

Step 2: To a degassed solution of 54A (1.0 eq) in EtOH was added $Pd(OH)_2$ (0.5 eq.). The mixture was degassed for another 20 minutes and then evacuated under vacuum before introducing a hydrogen balloon. The resulting mixture was stirred at RT for 1 h. The mixture was filtered through a pad of celite which was washed with EtOH. The solution was concentrated to dryness to afford 55A.

Step 3: To a solution of 55A (1.0 eq.) in DMF 0.10 mL) was added required carboxylic acid (1.2 eq.), DIPEA (3.0-8.0 eq.), and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM) to afford 56A.

Step 4: To a solution of 56A (1.0 eq.) in DCM was added TFA, and the resulting mixture was stirred at RT for 0.5 h. The reaction mixture was concentrated to dryness, and the residue was stirred in aq. sat. $K_2CO_3$ solution and then extracted with DCM to afford 57A, which was used in the next step without further purification.

Example 27: Synthesis of Compounds 326, 329-337, 340, 388, 391, 396, 398, 400, 406-410, and 414; and Compounds 327, 328, 338, 339

To a solution of 57A (1.0 eq.) in DMF (0.1 M) was added the required carboxylic acid (1.2 eq.), DIPEA (3.0-8.0 eq.), and then HATU (1.5 eq.), and the resulting mixture was stirred at RT for 1 h. The mixture was concentrated to dryness, and the residue was purified via reverse phase column chromatography on a 120 g C18 cartridge eluting with a 5-95% $H_2O$:MeCN eluent (0.1% ammonia) to afford 326, 329-337, 340, 388, 391, 396, 398, 400, 406-410 and 414.

To a solution of 57A (1.0 eq.) in DMF (0.1 M) was added the required isocyanate (1.2 eq.) and DIPEA (3.0-8.0 eq.), and the resulting mixture was stirred at RT for 1 h. The mixture was concentrated to dryness, and the residue was purified via reverse phase column chromatography on a 120 g C18 cartridge eluting with a 5-95% $H_2O$:MeCN eluent (0.1% ammonia) to afford 327, 328, 338 and 339.

The following compounds were made following a procedure analogous to Example 26 starting from 57A and reacting with the appropriate carboxylic acid or isocyanate.

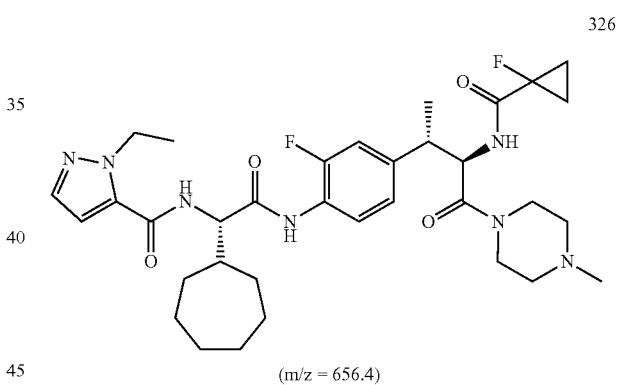

326

(m/z = 656.4)

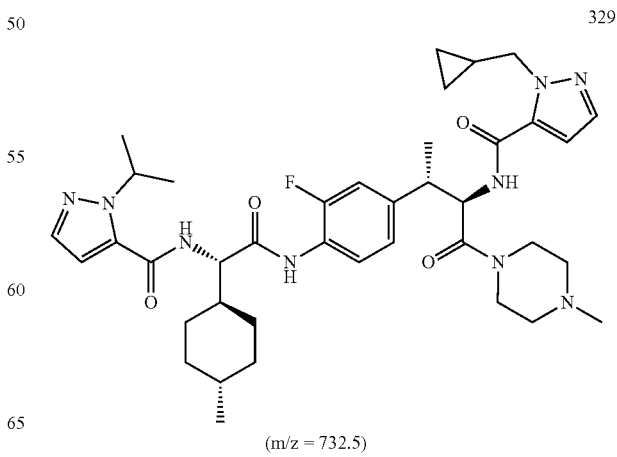

329

(m/z = 732.5)

330
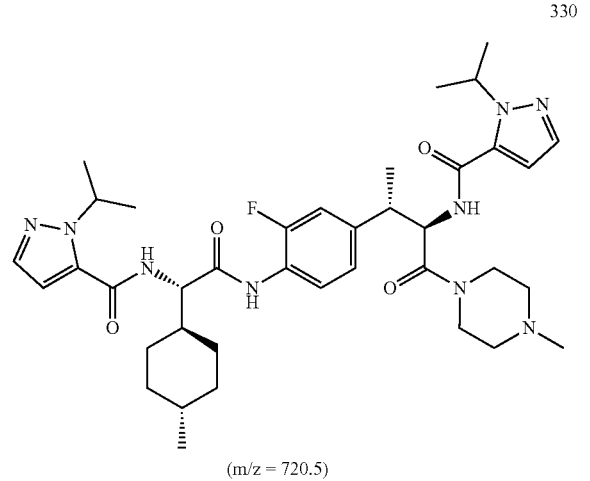
(m/z = 720.5)
331
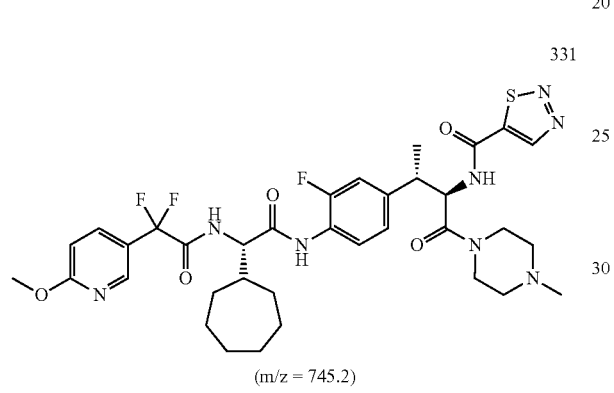
(m/z = 745.2)
332
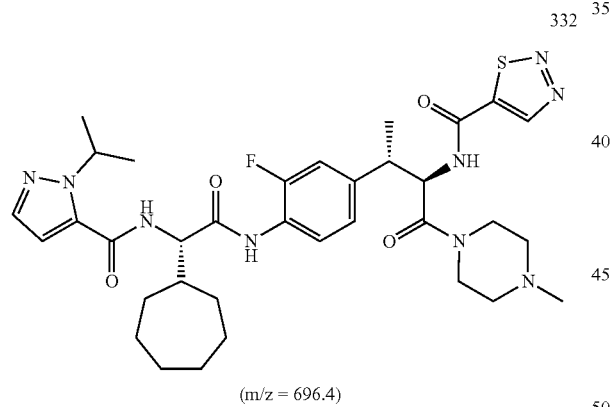
(m/z = 696.4)
333
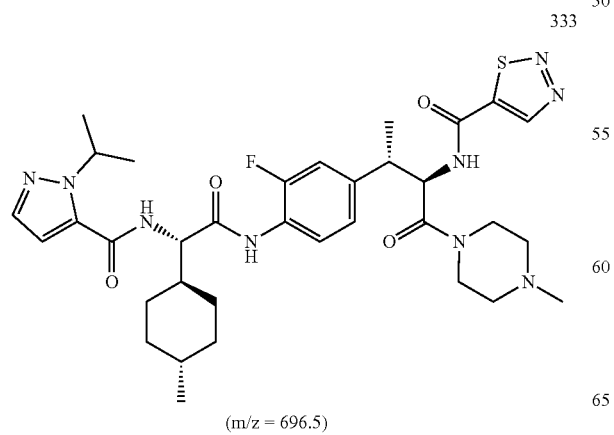
(m/z = 696.5)
334
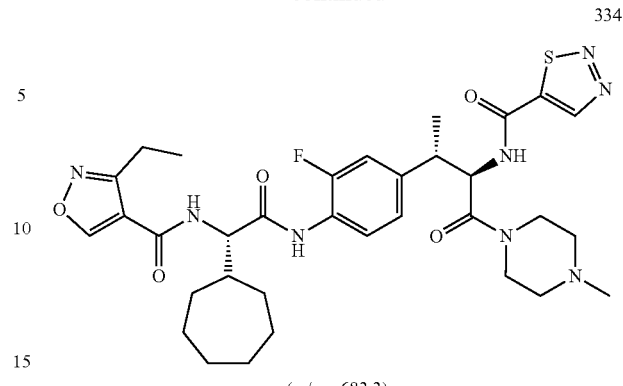
(m/z = 683.3)
335
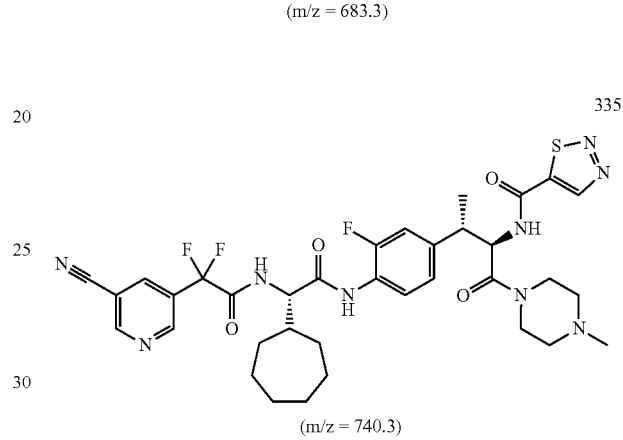
(m/z = 740.3)
336
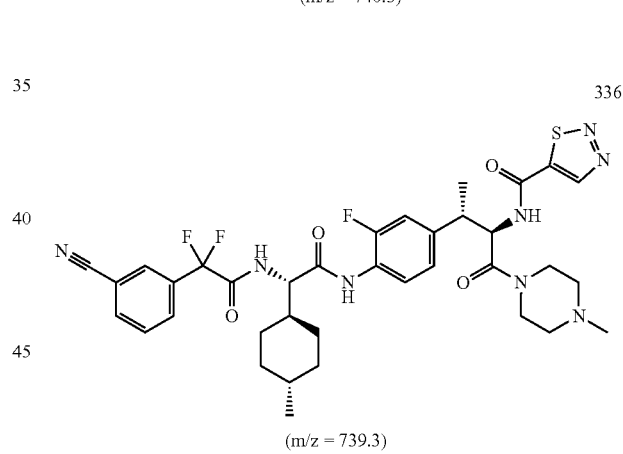
(m/z = 739.3)
337
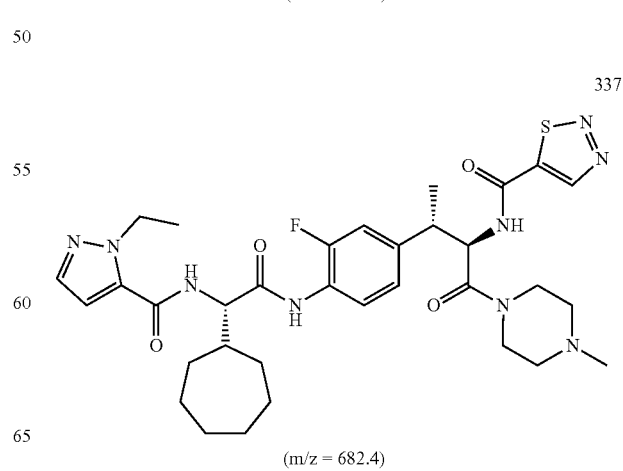
(m/z = 682.4)

340
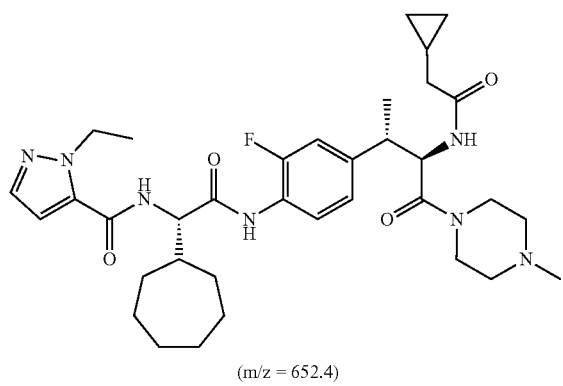
(m/z = 652.4)
388
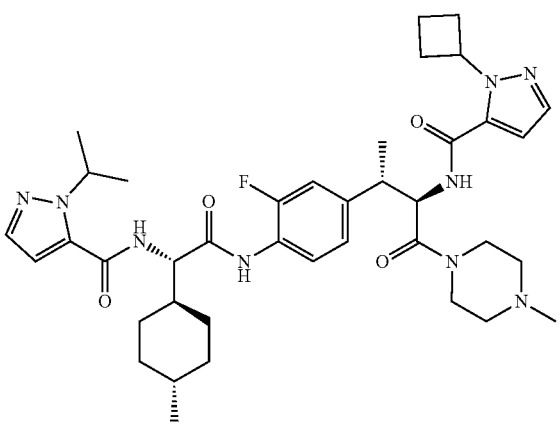
(m/z = 682.5)
391
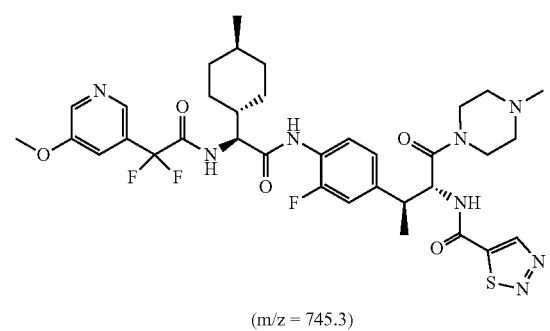
(m/z = 739.2)
396
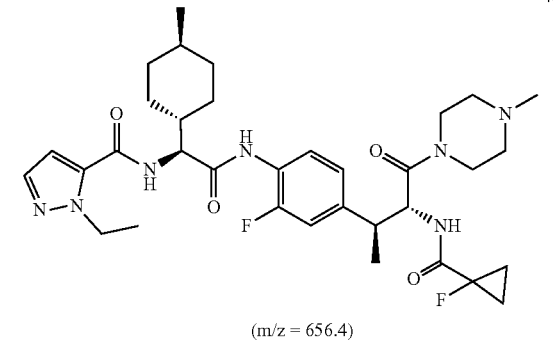
(m/z = 652.4)
398
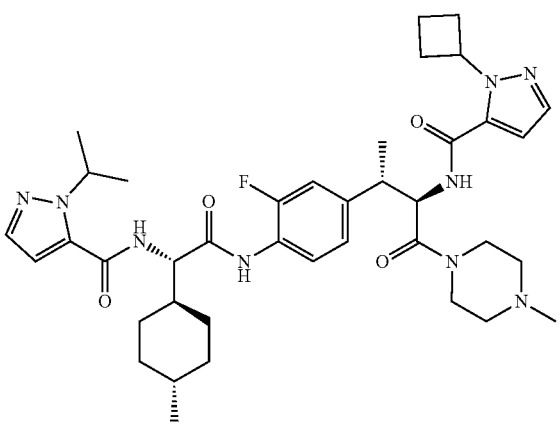
(m/z = 732.5)
400
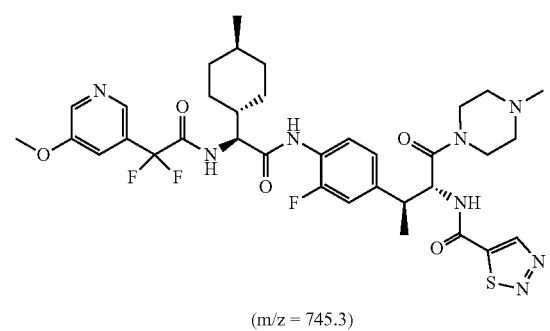
(m/z = 745.3)
406
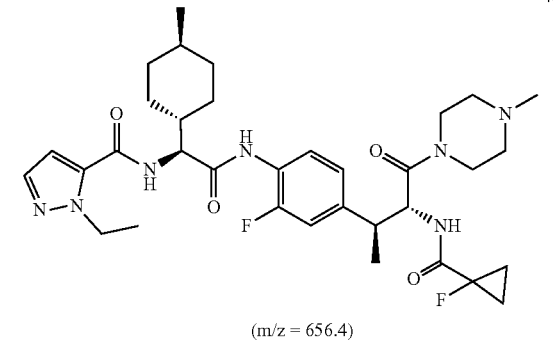
(m/z = 656.4)
407
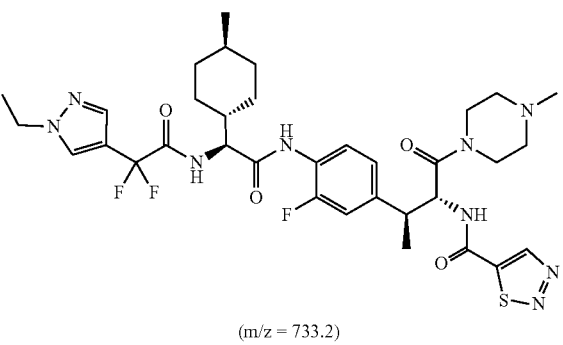
(m/z = 733.2)

408
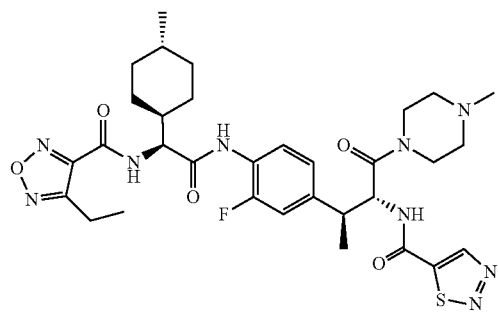
(m/z = 684.3)
409
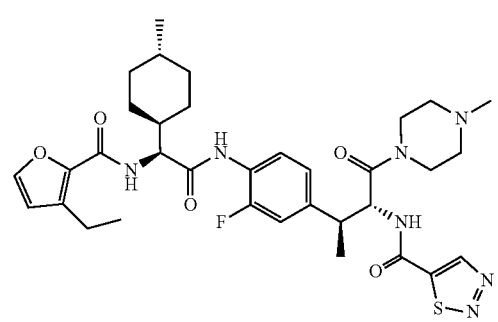
(m/z = 682.3)
410
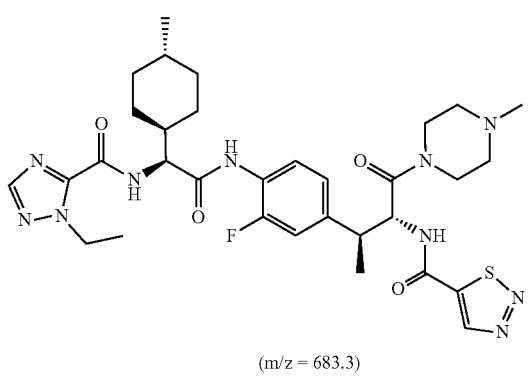
(m/z = 683.3)
414
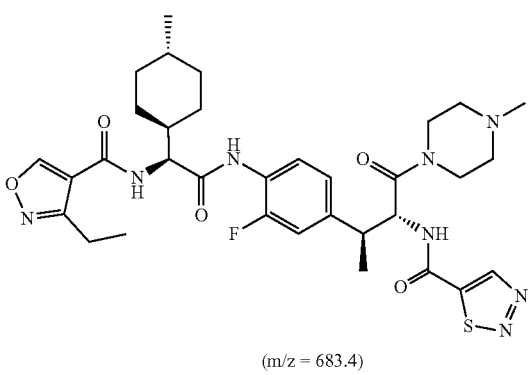
(m/z = 683.4)
327
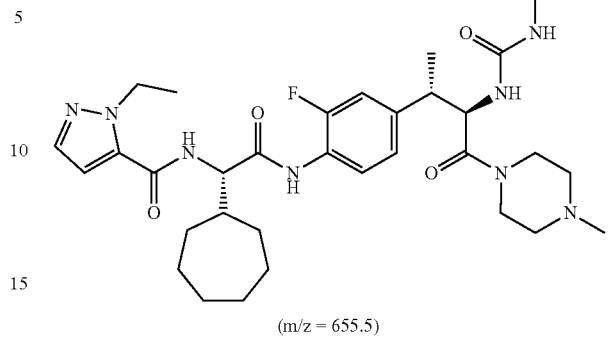
(m/z = 655.5)
328
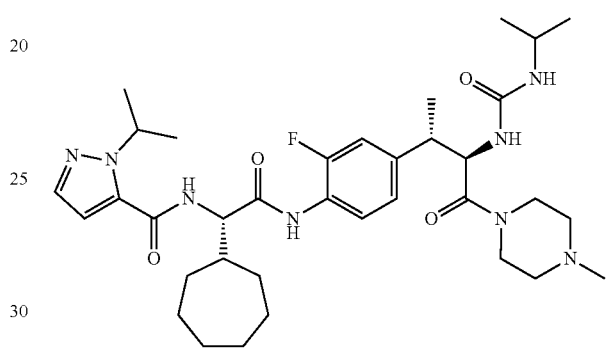
(m/z = 669.5)
338
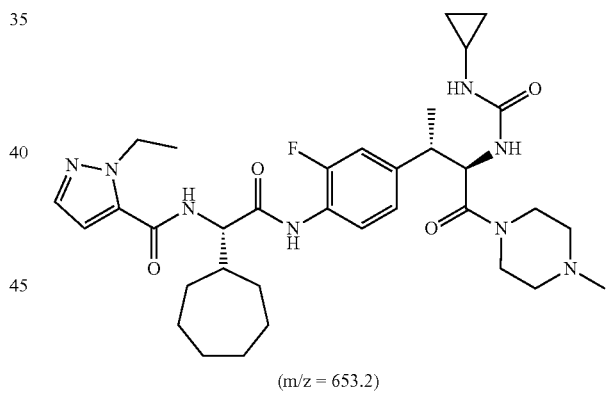
(m/z = 653.2)
339
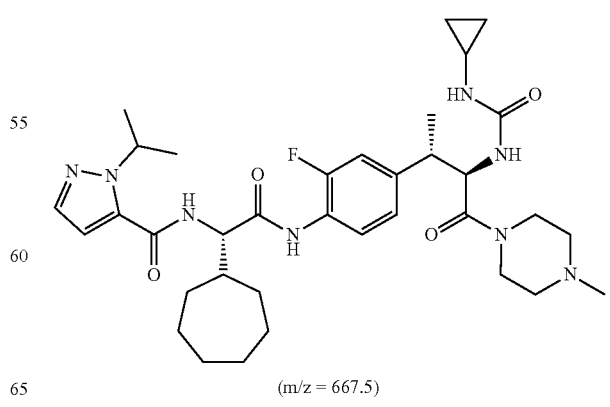
(m/z = 667.5)

Example 28: General Scheme—Synthesis of Compounds 341-346, 348-375, and 392

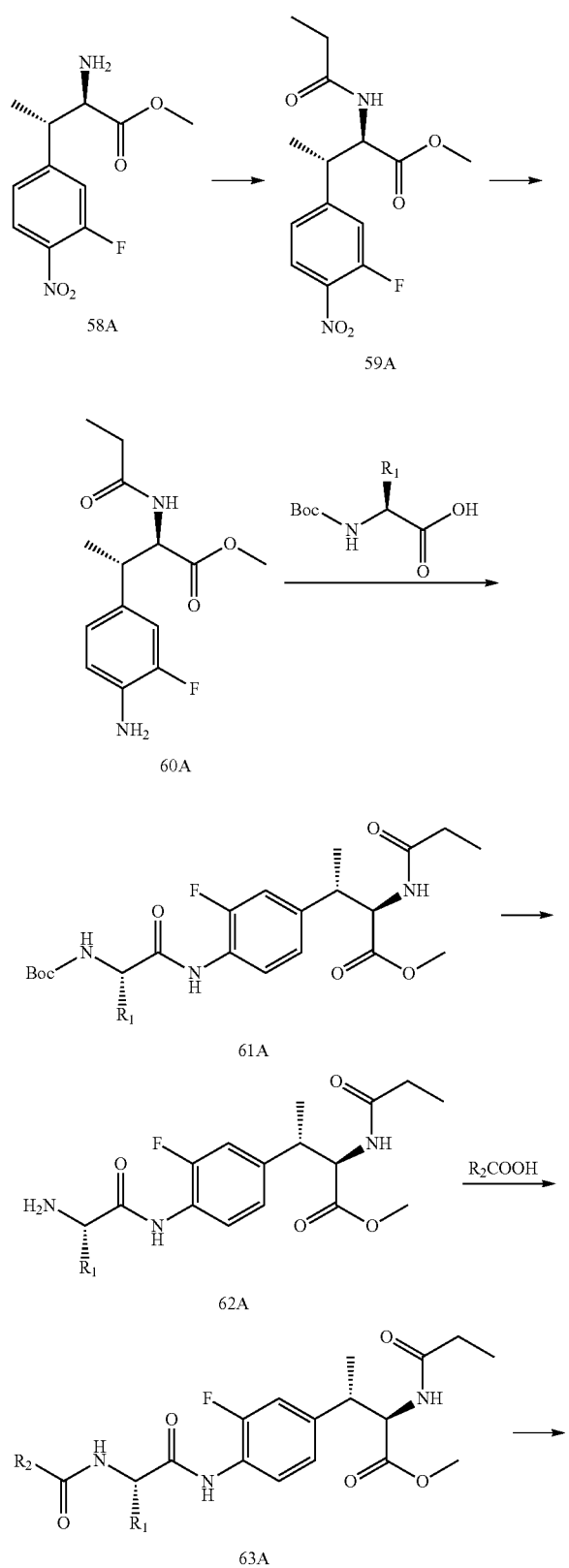

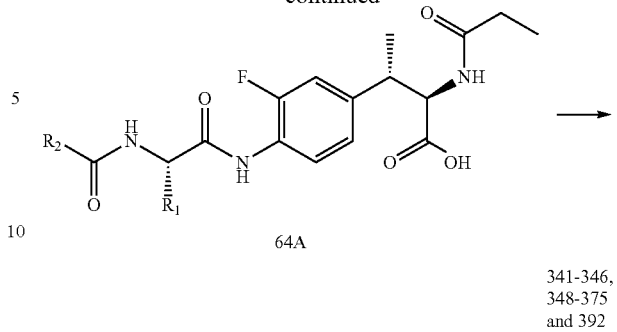

341-346,
348-375
and 392

Step 1: To a solution of 58A (0.970 g, 3.31 mmol, 1.0 eq.) in DMF (10 mL), which can be readily prepared from compound 74 by those of skill in the art, was added DIPEA (2.9 mL, 16.6 mmol, 5.0 eq.) and propionyl chloride (0.4 mL, 4.56 mmol, 1.4 eq.), and the resulting mixture was stirred at RT for 1 h. The mixture was concentrated to dryness, and the residue was taken up in an aqueous NaHCO$_3$ solution, and then the product was extracted with EtOAc. The combined organic phases were washed with brine, dried over sodium sulfate, and then concentrated to dryness to afford 59A as a red solid. UPLC-MS (basic 2 min): Rt=0.97 min; m/z=313.1 for [M+H]$^+$.

Step 2: To a degassed solution of 59A (0.930 g, 2.98 mmol, 1.0 eq) in EtOH (10 mL) was added Pd(OH)$_2$/C (0.209 g 1.5 mmol, 0.5 eq.). The mixture was degassed for another 20 minutes and then evacuated under vacuum before introducing a hydrogen balloon. The resulting mixture was stirred at RT for 3 h. The mixture was filtered through a pad of celite which was washed with EtOH (50 mL). The solution was concentrated to dryness to afford 60A as a yellow solid (0.989 g, 99%). UPLC-MS (basic 2 min): Rt=0.86 min; m/z=283.1 for [M+H]$^+$.

Step 3: To a solution of 60A (1.0 eq.) in DMF was added the required Boc protected glycine derivative (1.2 eq.), DIPEA (4.0 eq.), and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM with 5% aq. NH$_3$) to afford 61A.

Step 4: To a solution of 61A (1.0 eq.) in DCM was added TFA, and the resulting mixture was stirred at RT for 0.5 h. The reaction mixture was concentrated to dryness, and the residue was stirred in aq. sat. K$_2$CO$_3$ solution and then extracted with DCM to afford 62A, which was used in the next step without further purification.

Step 5: To a solution of 62A (1.0 eq.) in DMF (0.10 mL) was added the required carboxylic acid (1.2 eq.), DIPEA (3.0-8.0 eq.), and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM) to afford 63A.

Step 6: To a solution of 63A (1.0 eq.) in MeOH and THF was added a solution of 1M LiOH in H$_2$O (1.3 eq.), and the resulting mixture was stirred at RT for 0.5 h. The reaction mixture was concentrated to dryness and the residue was stirred in aq. sat. NaHCO$_3$ solution, and then extracted with EtOAc. The aqueous layer was acidified with conc. HCl, and the precipitate was filtered to afford 64A, which was used in the next step without further purification.

Example 29: General Scheme—Synthesis of Compounds 341-346, 348-375, and 392 from Intermediate 64A To a solution of 64A (1.0 eq.) in DMF (0.1 M) was added the required amine (1.2 eq.), DIPEA (3.0-8.0 eq.), and then HATU (1.5 eq.), and the resulting mixture was stirred at RT for 1 h. The mixture was concentrated to dryness, and the residue was purified via reverse phase column chromatography on a 120 g C18 cartridge eluting with a 5-95% H₂O:MeCN eluent (0.1% ammonia) to afford 341-346, 348-375 and 392.

The following compounds were made following a procedure analogous to Example 28 starting from 64A and reacting with the appropriate amine.

341

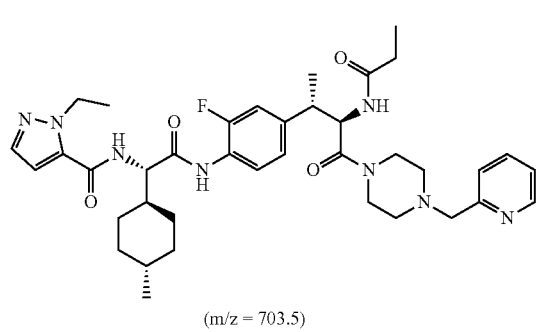

(m/z = 703.5)

342

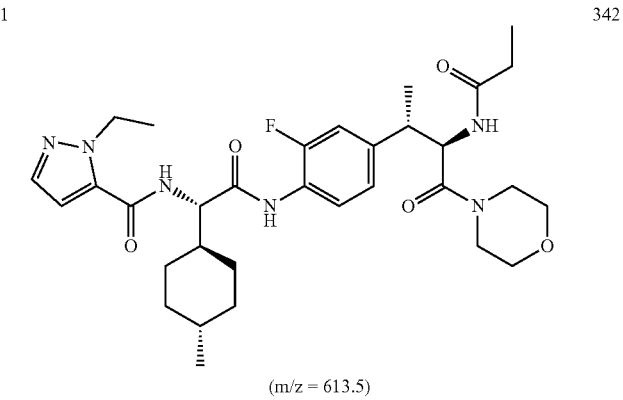

(m/z = 613.5)

343

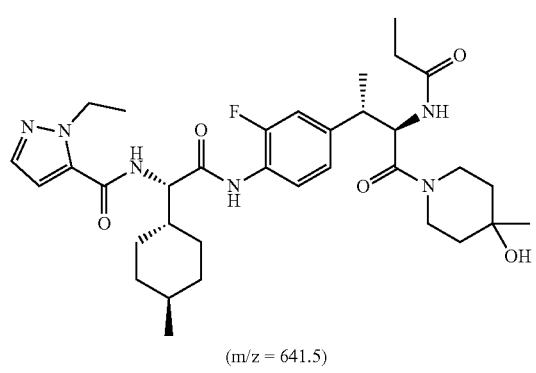

(m/z = 641.5)

344

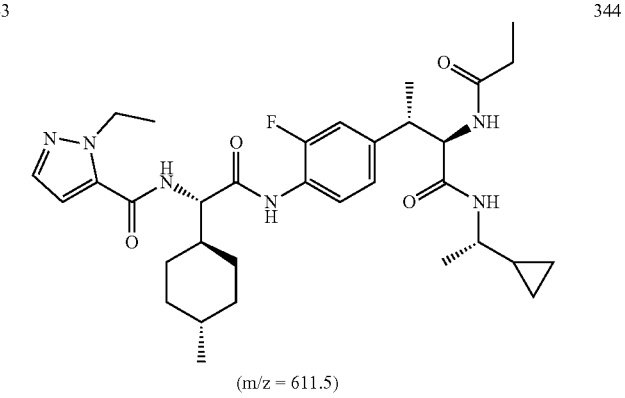

(m/z = 611.5)

345

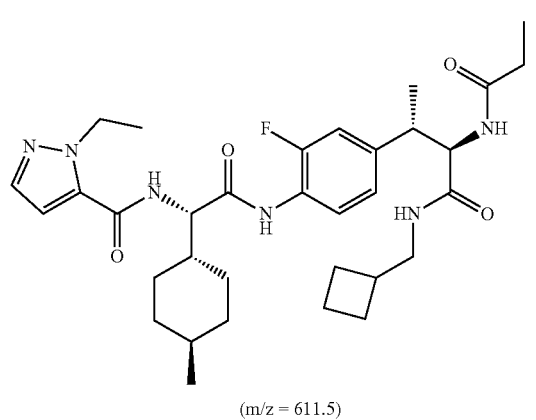

(m/z = 611.5)

346

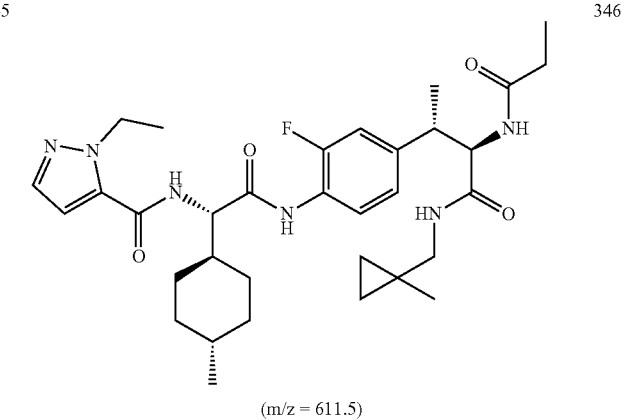

(m/z = 611.5)

-continued
348
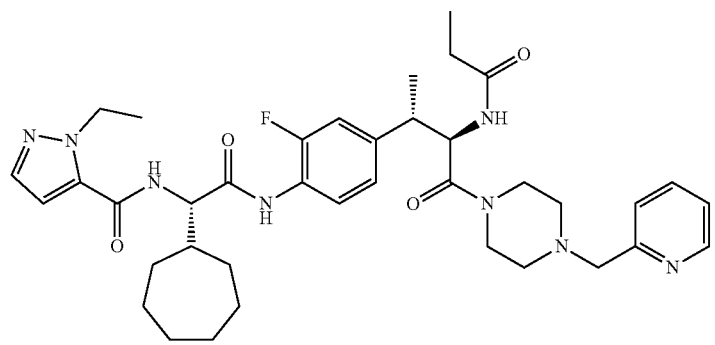
(m/z = 703.4)
349
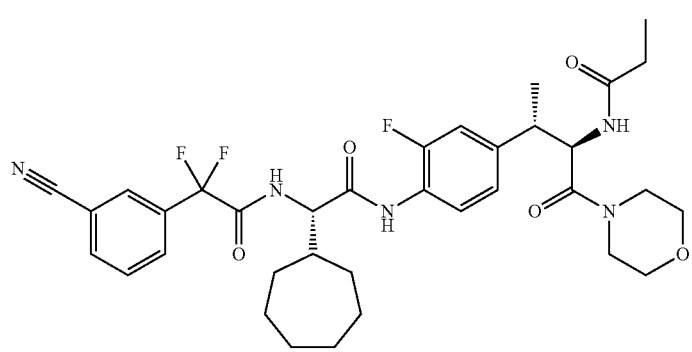
(m/z = 670.3)
350
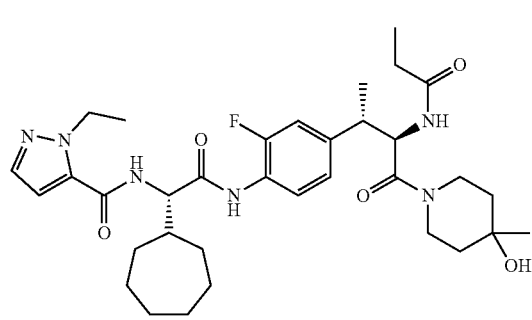
(m/z = 641.4)
351
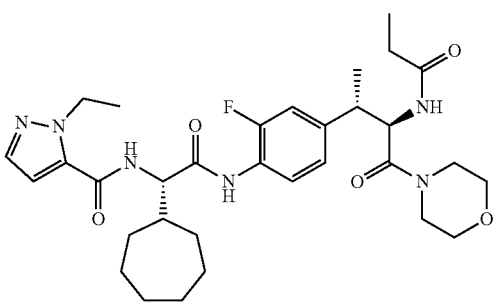
(m/z = 613.4)
352
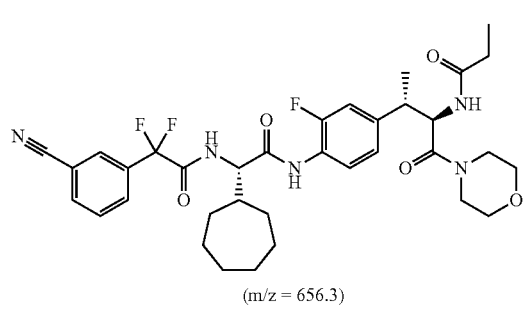
(m/z = 656.3)
353
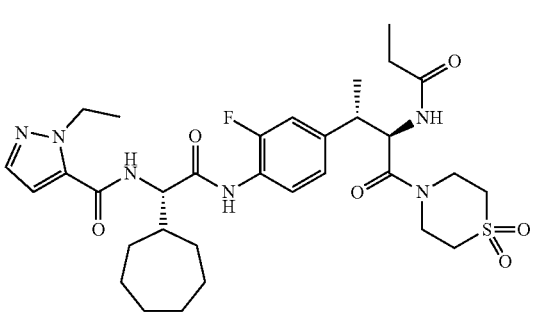
(m/z = 661.3)

-continued
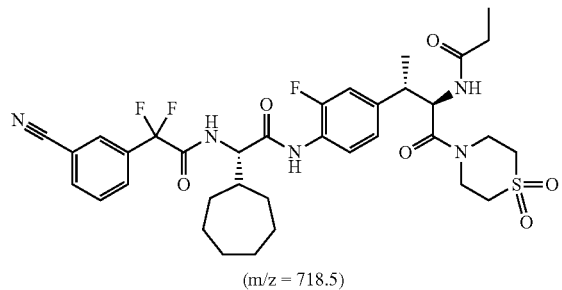
354
(m/z = 718.5)
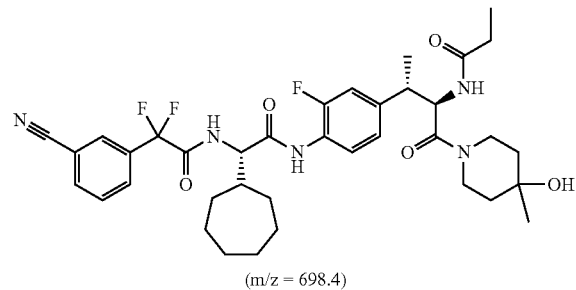
355
(m/z = 698.4)
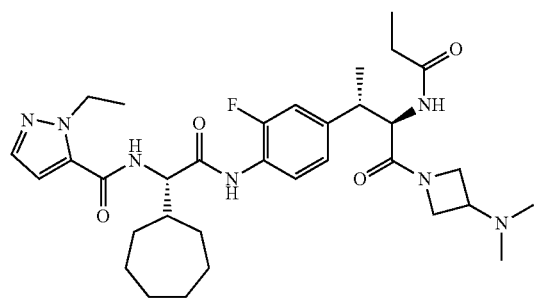
356
(m/z = 626.4)
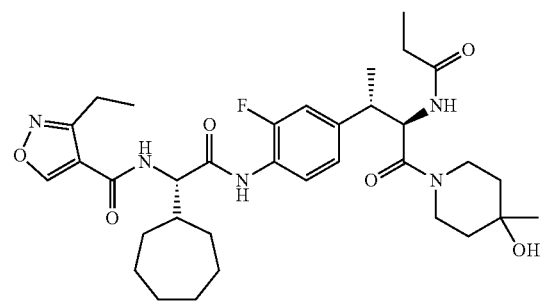
357
(m/z = 642.4)
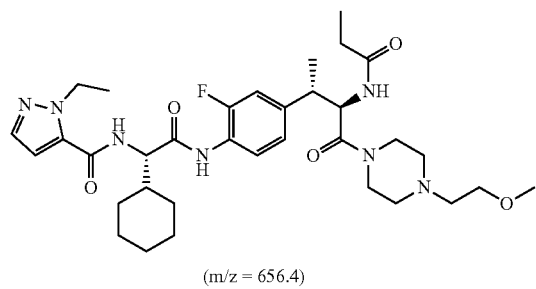
358
(m/z = 656.4)
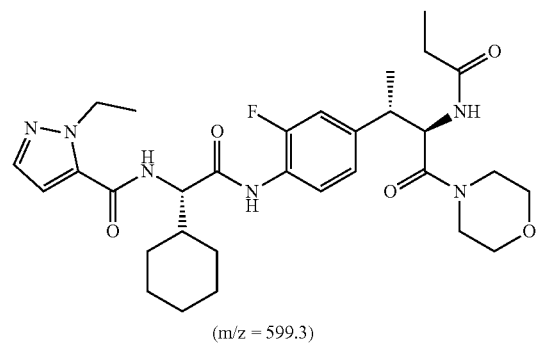
359
(m/z = 599.3)
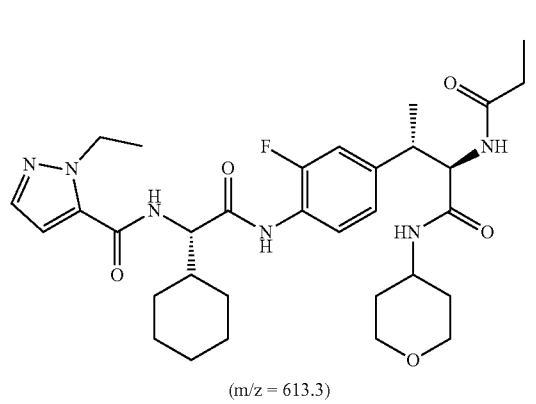
360
(m/z = 613.3)
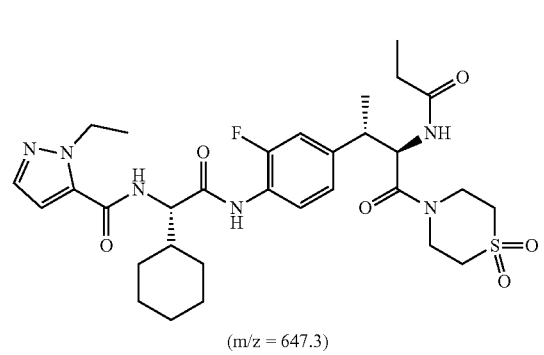
361
(m/z = 647.3)

-continued
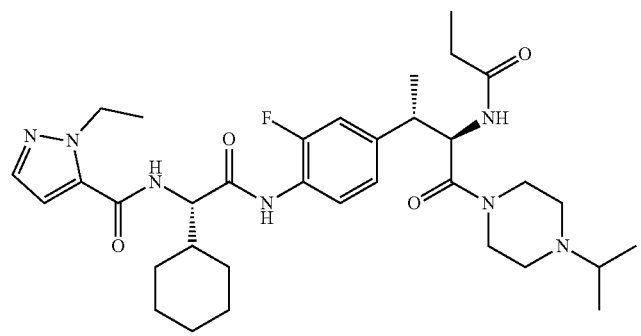
362
(m/z = 640.4)
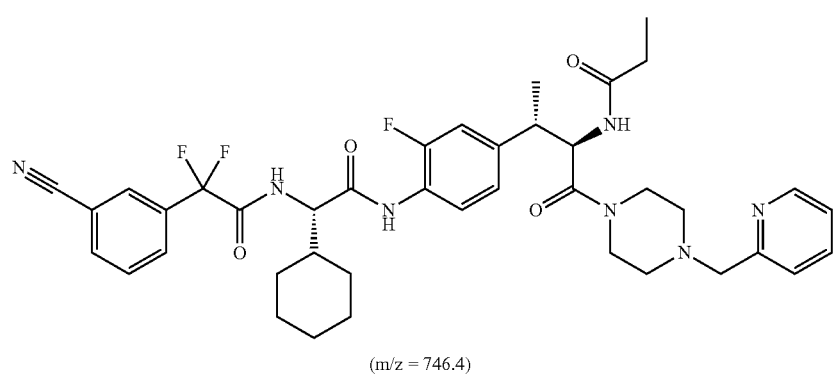
363
(m/z = 746.4)
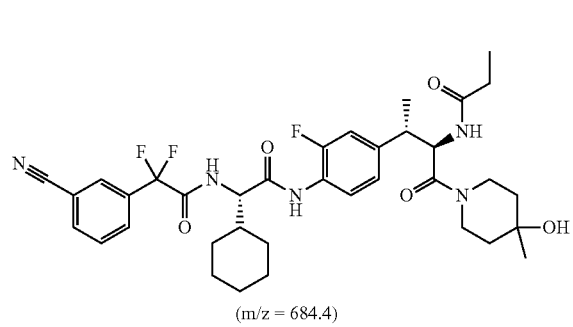
364
(m/z = 684.4)
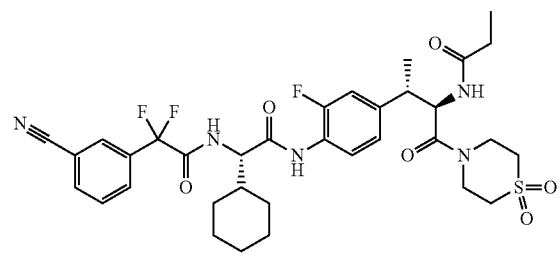
365
(m/z =704.3)
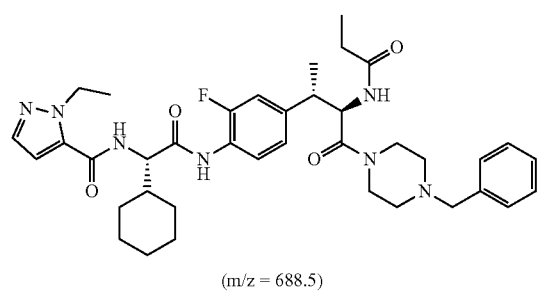
366
(m/z = 688.5)
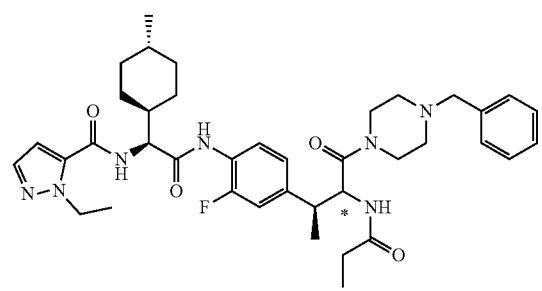
367
Single diastereomer with undetermined absolute stereochemistry at *
(m/z = 702.4)

368
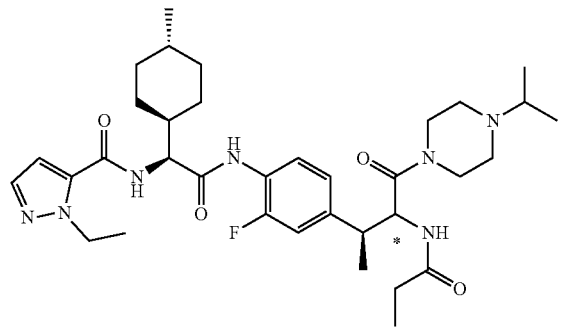
Single diastereomer with undetermined absolute stereochemistry at *
(m/z = 654.5)
369
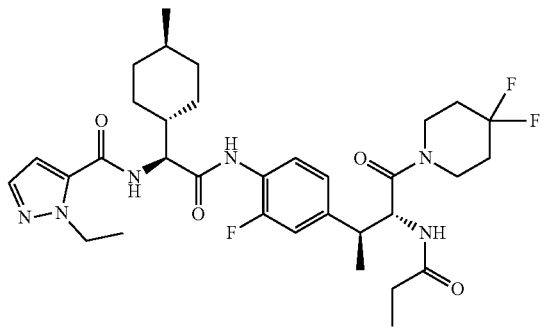
(m/z = 647.3)
370
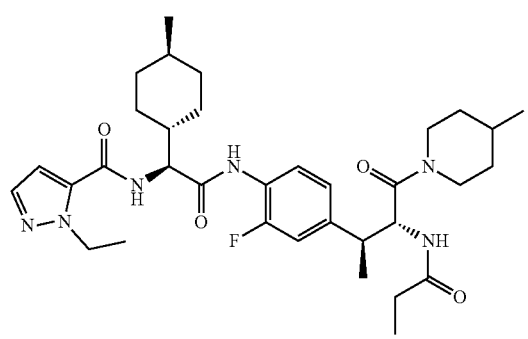
(m/z = 625.4)
371
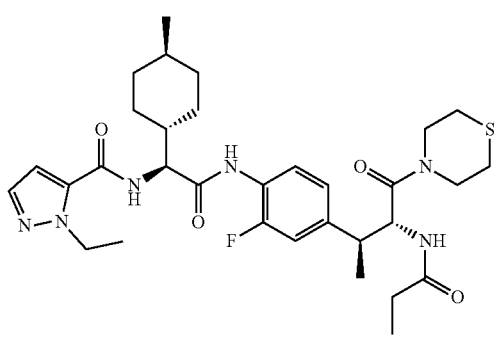
(m/z = 629.4)
372
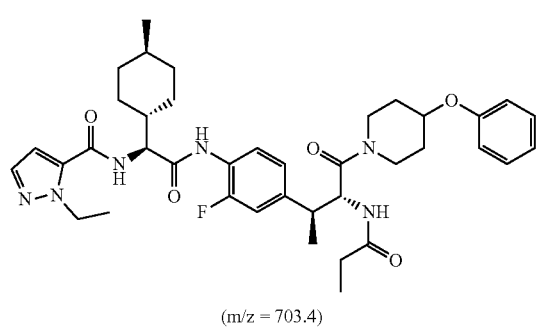
(m/z = 703.4)
373
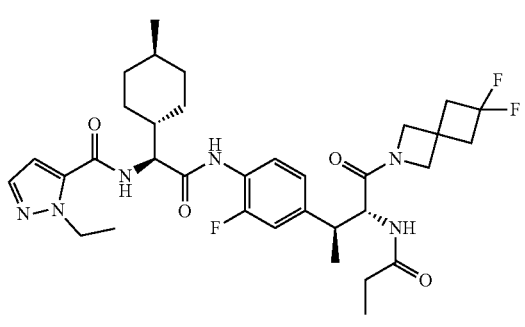
(m/z = 659.4)
374
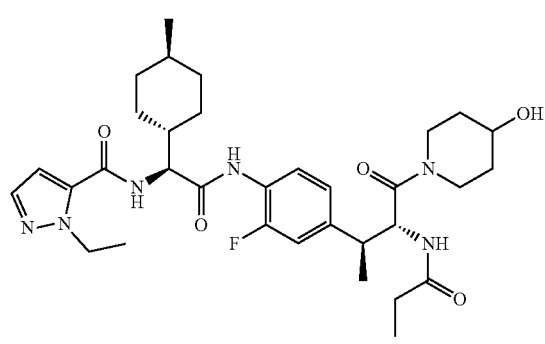
(m/z = 627.3)
375
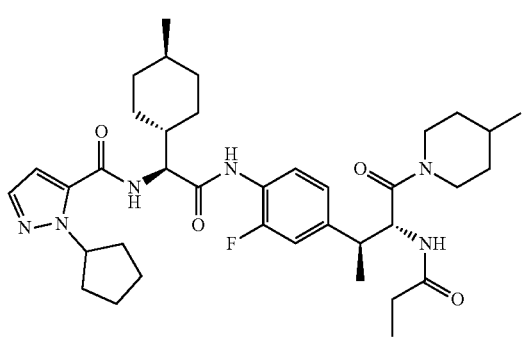
(m/z = 665.5)

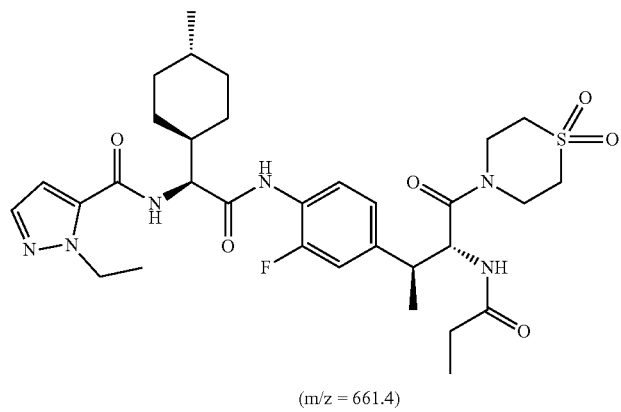

(m/z = 661.4)

Example 30: General Scheme—Synthesis of Compounds 347, 376-378, 531-534

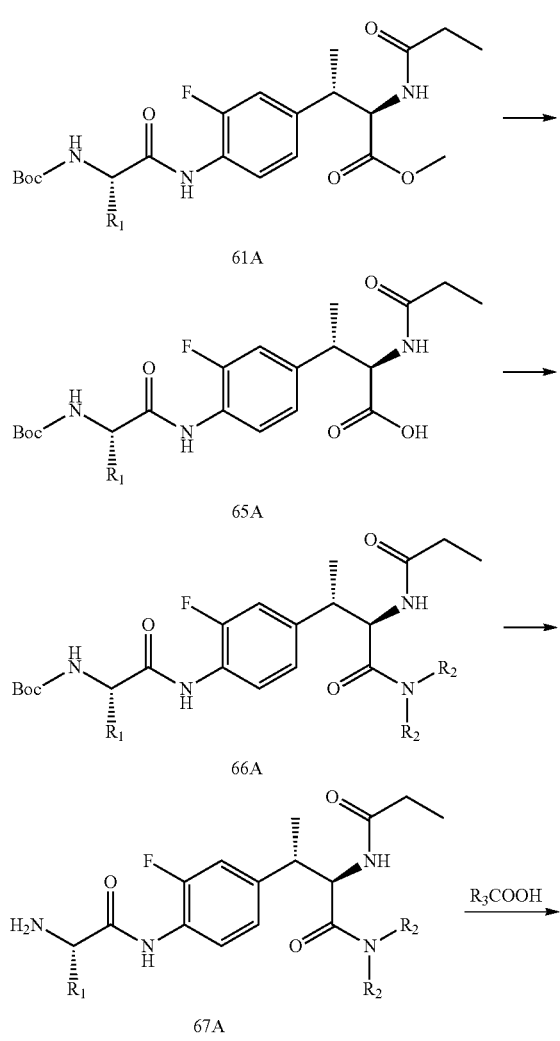

347, 376-378, 531-534

Step 1: To a solution of 61A (1.0 eq.) in MeOH and THF was added a solution of 1M LiOH in $H_2O$ (1.3 eq.), and the resulting mixture was stirred at RT for 0.5 h. The reaction mixture was concentrated to dryness, and the residue was stirred in aq. sat. $NaHCO_3$ solution and then extracted with EtOAc. The aqueous layer was acidified with conc. HCl, and the precipitate was filtered to afford 65A which was used in the next step without further purification.

Step 2: To a solution of 65A (1.0 eq.) in DMF (0.10 mL) was added the required amine (1.2 eq.), DIPEA (3.0-8.0 eq.), and HATU (1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness. The residue was purified by flash column chromatography (Silica, 0-10% MeOH, DCM) to afford 66A.

Step 3: To a solution of 66A (1.0 eq.) in DCM was added TFA, and the resulting mixture was stirred at RT for 0.5 h. The reaction mixture was concentrated to dryness, and the residue was stirred in aq. sat. $K_2CO_3$ solution and then extracted with DCM to afford 67A, which was used in the next step without further purification.

Example 31: General Scheme—Synthesis of Compounds 347, 376-378, and 531-534 from Intermediate 67A To a solution of 67A (1.0 eq.) in DMF (0.1 M) was added the required acid (1.2 eq.), DIPEA (3.0-8.0 eq.), and then HATU (1.5 eq.), and the resulting mixture was stirred at RT for 1 h. The mixture was concentrated to dryness, and the residue was purified via reverse phase column chromatography on a 120 g C18 cartridge eluting with a 5-95% $H_2O$:MeCN eluent (0.1% ammonia) to afford 376-378, 392, and 531-534.

The following compounds were made following a procedure analogous to Example 30 starting from 67A and reacting with the appropriate acid.

177
376
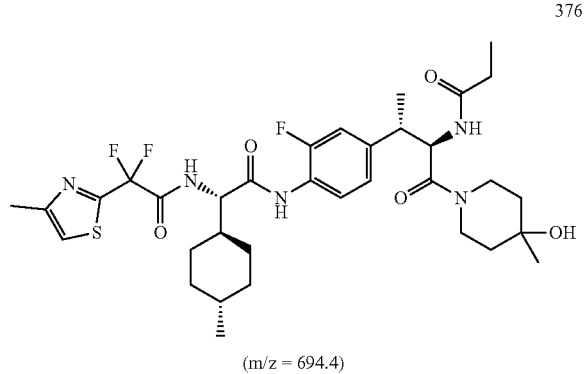
(m/z = 694.4)
377
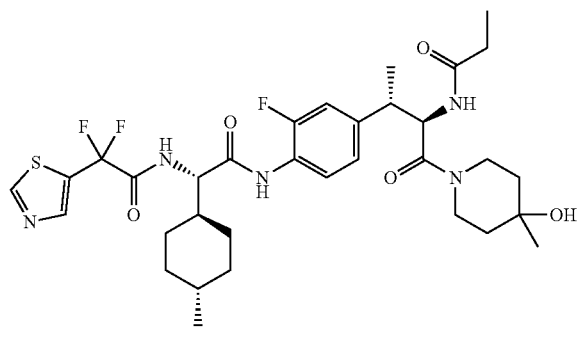
(m/z = 655.4)
378
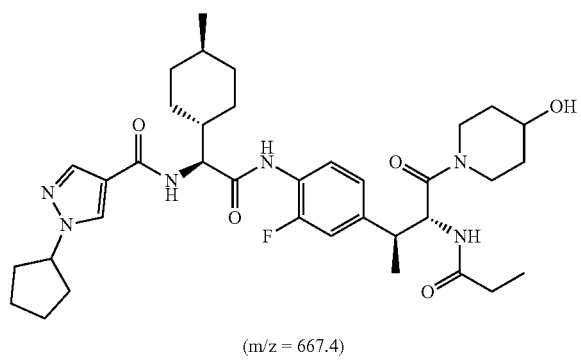
(m/z = 680.3)
531
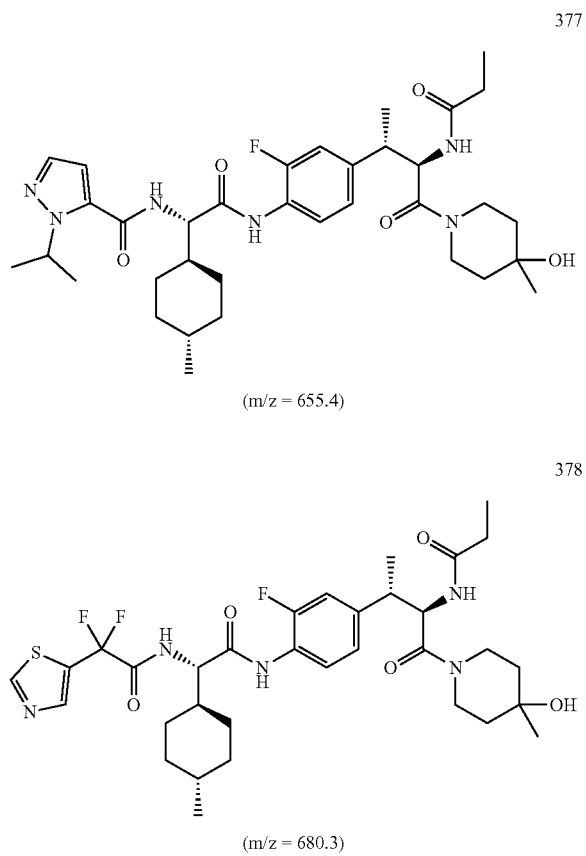
(m/z = 667.4)
178
-continued
532
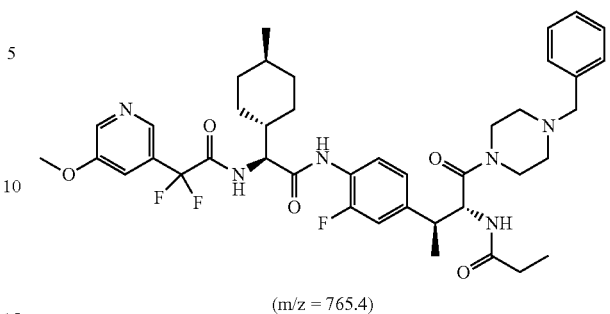
(m/z = 765.4)
533
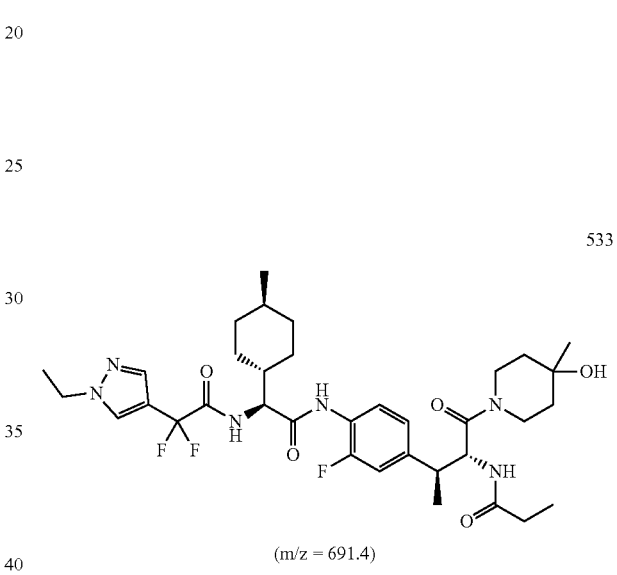
(m/z = 691.4)
534
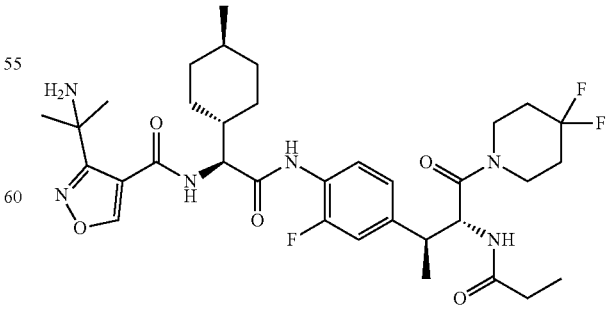
(m/z = 677.4)

Example 32: Exemplified Scheme—Synthesis of Intermediate 83B
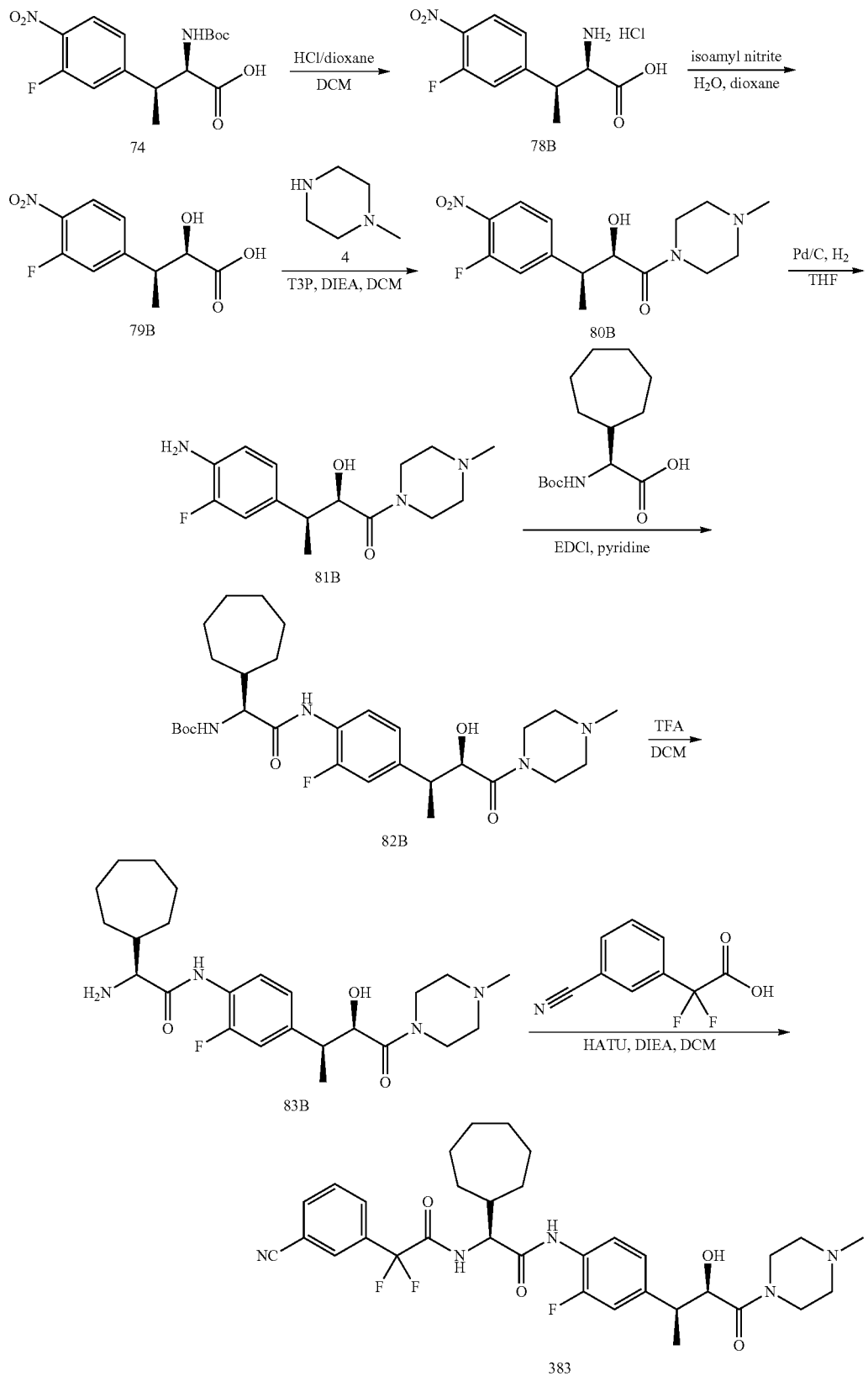

Step 1: To a solution of 74 (500 mg, 1.46 mmol, 1.00 eq) in DCM (5.00 mL) was added HCl/dioxane (4 M, 5.00 mL, 13.6 eq) at 0° C. The mixture was stirred at 25° C. for 1 hr. LC-MS showed 74 was consumed completely, and the desired mass was detected. The reaction mixture was concentrated under reduced pressure to give a residue. Compound 78B (400 mg, 1.44 mmol, 98.2% yield, HCl) was obtained as white solid. LC-MS: (2M+1): 483.1.

Step 2: To a solution of compound 78B (400 mg, 1.44 mmol, 1.00 eq, HCl) in $H_2O$ (10.0 mL) and dioxane (10.0 mL) was added isoamyl nitrite (252 mg, 2.15 mmol, 289 uL, 1.50 eq) at 0° C. The mixture was stirred at 25° C. for 3 hrs. LC-MS showed that the desired mass was detected. EtOAc (20.0 mL) and $H_2O$ (20.0 mL) were added to the reaction mixture. The organic phase was separated, and the water phase was extracted with EtOAc (50.0 mL*2). The combined organic phases were dried over $Na_2SO_4$, filtered, and concentrated under reduced pressure to give a residue. The residue was purified by Prep-HPLC (FA condition; column: Waters Atlantis T3 150*30 mm*5 um; mobile phase: [water (0.225% formic acid)-MeCN]; B %: 18%-48%, 10 min). Compound 79B (180 mg, 740 umol, 51.5% yield) was obtained as yellow solid.

Step 3: To a solution of compound 79B (160 mg, 657 umol, 1.00 eq) and compound 4 (98.8 mg, 986 umol, 109 uL, 1.50 eq) in DCM (5.00 mL) was added DIEA (425 mg, 3.29 mmol, 572 uL, 5.00 eq) and T3P (1.26 g, 1.97 mmol, 1.17 mL, 50.0% purity, 3.00 eq) at 0° C. The mixture was stirred at 25° C. for 12 hrs. TLC indicated compound 79B was consumed completely, and many new spots formed. EtOAc (20.0 mL) and $H_2O$ (20.0 mL) were added to the reaction mixture. The organic phase was separated, and the water phase was extracted with EtOAc (50.0 mL*2). The combined organic phases were dried over $Na_2SO_4$, filtered, and concentrated under reduced pressure to give a residue. The residue was purified by Prep-TLC ($SiO_2$, DCM:MeOH=10:1, Plate 1: DCM:MeOH=10:1). Compound 80B (90.0 mg, 276 umol, 42.0% yield) was obtained as yellow oil. LC-MS: m/z=326.1, $[M+H]^+$.

Step 4: To a solution of compound 80B (80.0 mg, 245 umol, 1.00 eq) in THF (10.0 mL) was added Pd/C (5.00 mg, 10% purity) under $N_2$. The suspension was degassed under vacuum and purged with $H_2$ several times. The mixture was stirred under $H_2$ (15 psi) at 25° C. for 1 hr. LC-MS showed that the desired mass was detected. The reaction mixture was filtered and concentrated under reduced pressure to give a residue. Compound 81B (60.0 mg, crude) was obtained as yellow oil. LC-MS: m/z=296.2, $[M+H]^+$.

Step 5: To a solution of compound 81B (60.0 mg, 203 umol, 1.00 eq) and the protected cycloheptylglycine (82.6 mg, 304 umol, 1.50 eq) in pyridine (10.0 mL) was added EDCI (77.8 mg, 406 umol, 2.00 eq). The mixture was stirred at 25° C. for 12 hrs. LC-MS showed the desired mass was detected. $H_2O$ (10.0 mL) was added to the reaction mixture, and the product was extracted with DCM (20.0 mL*2). The combined organic layers were washed with sat. aq $NaHCO_3$ (40.0 mL), dried over $Na_2SO_4$, filtered, and concentrated under reduced pressure to give a residue. The residue was purified by Prep-TLC ($SiO_2$, DCM:MeOH=10:1, $R_f$=0.430). Compound 82B (35.0 mg, 63.7 umol, 31.4% yield) was obtained as a white solid. LC-MS: m/z=549.5, $[M+H]^+$.

Step 6: To a solution of compound 82B (30.0 mg, 54.6 umol, 1.00 eq) in DCM (4.00 mL) was added TFA (3.08 g, 27.0 mmol, 2.00 mL, 494 eq) at 0° C. The mixture was stirred at 25° C. for 2 hrs. LC-MS showed detection of the desired mass. The reaction mixture was diluted with $H_2O$ (10.0 mL), and sat.aq $NaHCO_3$ was added to adjust pH to 9. The mixture was extracted with DCM (20.0 mL*2). The combined organic layers were dried over $Na_2SO_4$, filtered, and concentrated under reduced pressure to give a residue. Compound 83B (20.0 mg, 44.5 umol, 81.5% yield) was obtained as yellow oil. LC-MS: m/z=449.4, $[M+H]^+$.

Step 7: Synthesis of Compound 383 from Intermediate 83B To a solution of compound 83B (13.1 mg, 66.8 umol, 1.50 eq) and HATU (50.8 mg, 133 umol, 3.00 eq) in DCM (5.00 mL) was added DIEA (28.8 mg, 222 umol, 38.8 uL, 5.00 eq). The mixture was stirred at 25° C. for 30 min. The carboxylic acid (20.0 mg, 44.5 umol, 1.00 eq) was added to the mixture and stirred at 25° C. for 12 hrs. LC-MS showed the desired mass was detected. The reaction mixture was diluted with $H_2O$ (10.0 mL), and sat.aq $NaHCO_3$ was added to adjust pH to 9. The mixture was extracted with DCM (20.0 mL*2). The combined organic layers were dried over $Na_2SO_4$, filtered, and concentrated under reduced pressure to give a residue. The residue was purified by Prep-HPLC (basic condition, column: Waters Xbridge 150*25 mm*5 um; mobile phase: [water (0.05% ammonia hydroxide v/v)-MeCN]; B %: 40%-70%, 10 min). Compound 383 (4.00 mg, 5.79 umol, 12.9% yield, 90.8% purity) was obtained as white solid. LC-MS: m/z=628.5, $[M+H]^+$.

Example 33: General Scheme—Synthesis of Compound 402

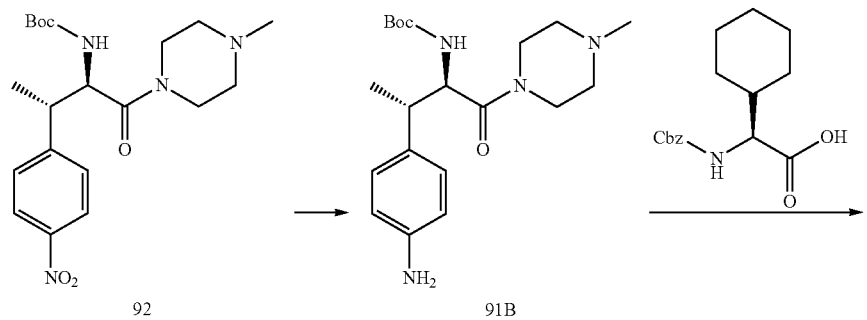

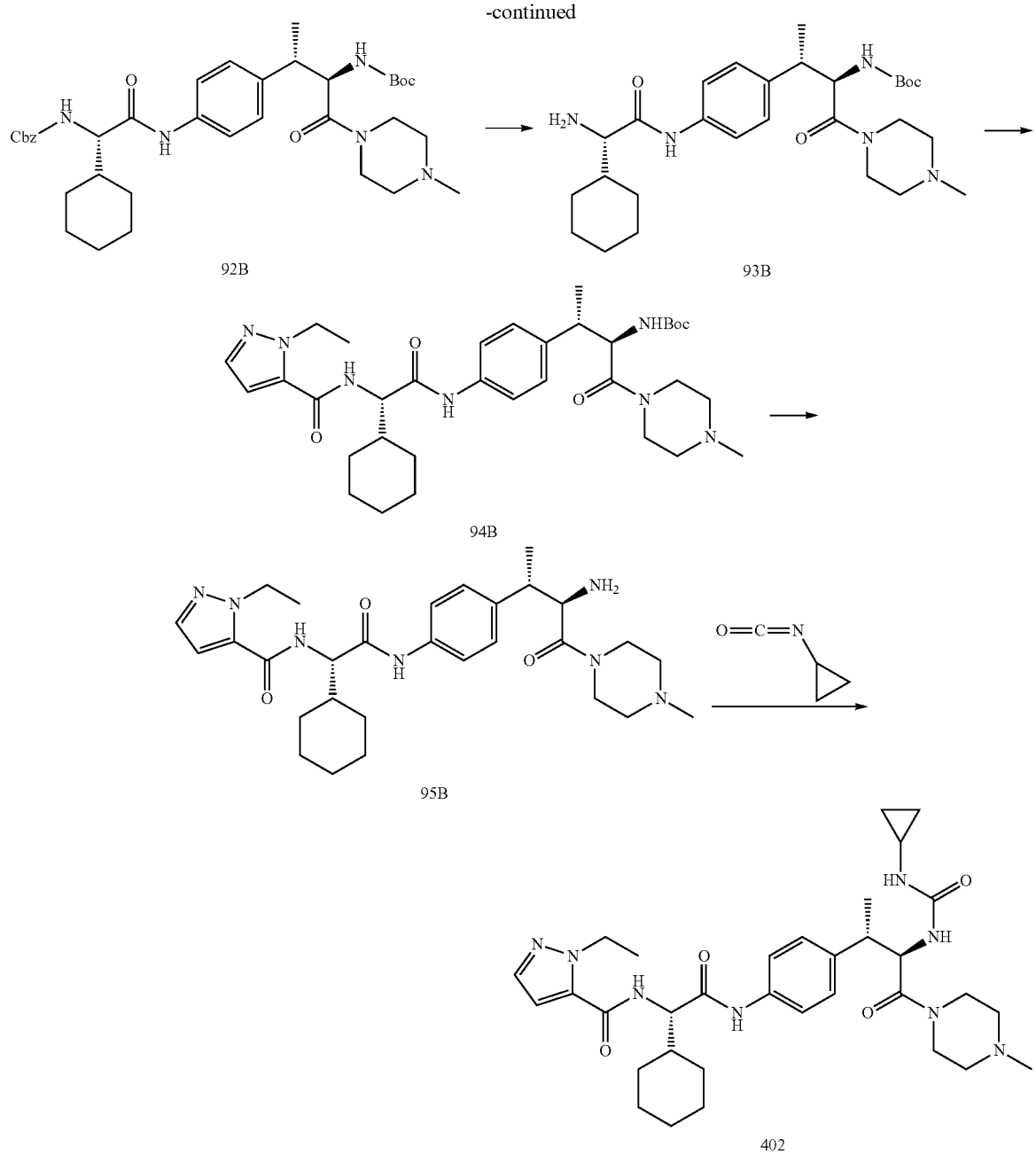

Step 1: To a degassed solution of 92 (0.680 g, 1.67 mmol, 1.0 eq) in EtOH (7 mL) and THF (7 mL) was added Pd/C (0.7 g). The mixture was degassed for another 20 minutes and then evacuated under vacuum before introducing a hydrogen balloon. The resulting mixture was stirred at RT for 6 h. The mixture was filtered through a pad of celite which was washed with EtOH (50 mL). The solution was concentrated to dryness to afford 91B as an off-white solid (0.525 g, 83%) which was used in the next step without further purification. UPLC-MS (basic 2 min): Rt=0.94 min; m/z=377.3 for [M+H]+

Step 2: To a solution of 91B (0.125 g, 0.332 mmol, 1.0 eq.) in DMF (1 mL) was added Z-Chg-OH (0.106 g, 0.364 mmol, 1.1 eq.), DIPEA (0.17 mL, 0.996 mmol, 3.0 eq.), and HATU (0.189 g, 0.498 mmol, 1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness to afford 92B as an orange solid (0.199 g, 92%) which was used in the next step without further purification. UPLC-MS (basic 2 min): Rt=1.21 min; m/z=650.3 for [M+H]+

Step 3: To a degassed solution of 92B (0.199 g, 0.306 mmol, 1.0 eq) in EtOH (8 mL) and THF (2 mL) was added Pd(OH)2 (0.020 g, 0.142 mmol, 0.5 eq.). The mixture was degassed for another 20 minutes and then evacuated under vacuum before introducing a hydrogen balloon. The resulting mixture was stirred at RT for 4 h. The mixture was filtered through a pad of celite which was washed with EtOH (50 mL). The solution was concentrated to dryness to afford 93B as an off-white solid (0.154 g, 98%) which was used in the next step without further purification. UPLC-MS (basic 2 min): Rt=1.06 min; m/z=516.3 for [M+H]$^+$ Step 4: To a solution of 93B (0.150 g, 0.291 mmol, 1.0 eq.) in DMF (1 mL) was added the required carboxylic acid (0.045 g, 0.320 mmol, 1.0 eq.), DIPEA (0.15 mmol, 0.873 mmol, 3.0 eq.), and HATU (0.166 g, 0.436 mmol, 1.5 eq.), and the resulting mixture was stirred for 18 h. Aqueous saturated sodium bicarbonate solution was added, and then the product was extracted with EtOAc. The combined organic phases were washed with brine, dried over sodium sulfate, and then concentrated to dryness to afford 94B (0.143 g, 77% yield) as a yellow solid which was used in the next step without further purification. UPLC-MS (basic 2 min): Rt=1.13 min; m z=638.4 for [M+H]$^+$.

Step 5: To a solution of 94B (0.142 g, 0.223 mmol, 1.0 eq.) in DCM (0.5 mL) was added TFA (0.5 mL), and the resulting mixture was stirred at RT for 0.5 h. The reaction mixture was concentrated to dryness, and the residue was stirred in aq. sat. K$_2$CO$_3$ solution and then extracted with DCM to afford 95B (0.062 g, 51% yield), which was used in the next step without further purification. UPLC-MS (basic 2 min): Rt=0.94 min; m/z=538.2 for [M+H]$^+$.

Step 6: Synthesis of Compound 402 To a solution of 95B (0.062 g, 0.115 mmol, 1.0 eq.) in DMF (0.4 mL) was added cyclopropyl isocyanate (0.011 g, 0.138 mmol, 1.2 eq.) and DIPEA (0.06 mL, 0.346 mmol, 3.0 eq.), and the resulting mixture was stirred at RT for 1 h. The mixture was concentrated to dryness, and the residue was purified via reverse phase column chromatography on a 120 g C18 cartridge eluting with a 5-95% H$_2$O:MeCN eluent (0.1% ammonia) to afford 402. UPLC-MS (basic 4 min): rt=1.59 min; m/z=621.3 for [M+H]$^+$.

Example 34: General Scheme—Synthesis of Compound 417

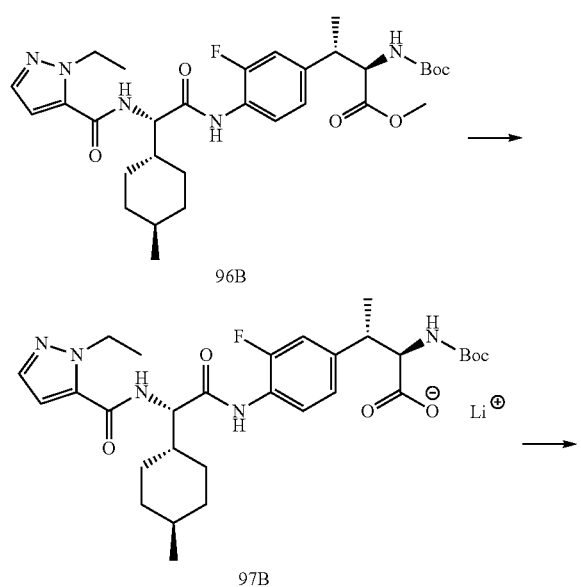

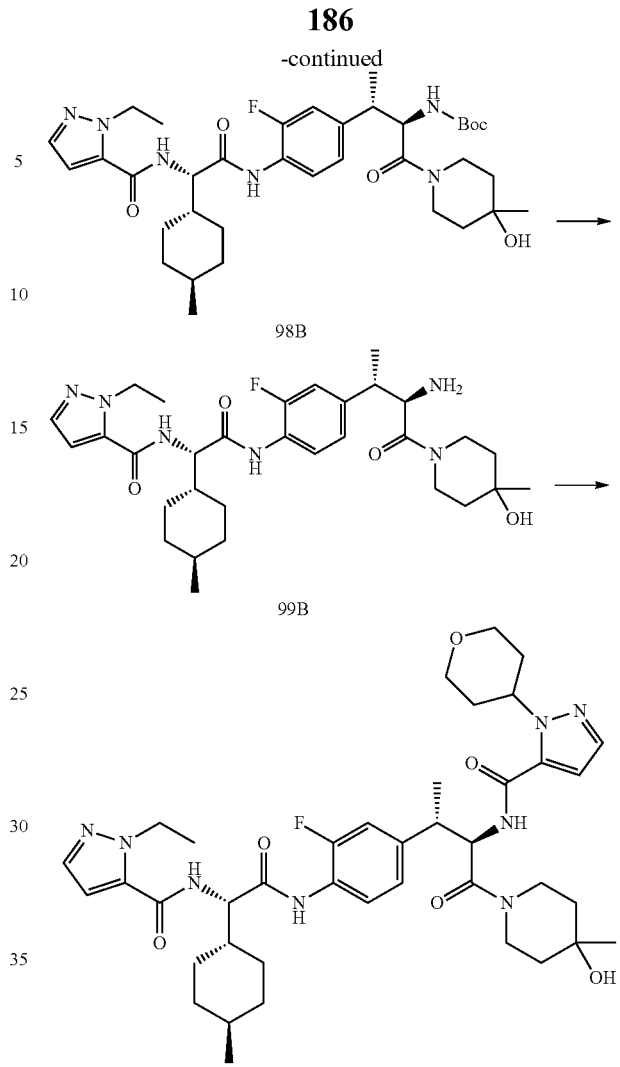

Step 1: To a solution of 96B (0.284 g, 0.472 mmol, 1.0 eq.) in THF (5 mL) was added a solution of LiOH (0.022 g, 0.519 mmol, 1.1 eq.) in H$_2$O (5 mL), and the resulting mixture was stirred at RT for 0.5 h. The reaction mixture was concentrated to dryness to afford 97B (0.280 g, 99%) as a white solid which was used in the next step without further purification. UPLC-MS (acidic 4 min): rt=1.99 min; m/z=586.4 for [M+H]$^+$.

Step 2: To a solution of 97B (0.350 g, 0.472 mmol, 1.0 eq.) in DMF (5 mL) was added 4-methylpiperidin-4-ol (0.060 g, 0.519 mmol, 1.1 eq.), DIPEA (0.41 mL, 2.36 mmol, 5.0 eq.), and then HATU (0.215 g, 0.566 mmol, 1.2 eq.), and the resulting mixture was stirred at RT for 1 h. The mixture was concentrated to dryness, and the residue was purified via reverse phase column chromatography on a 40 g C18 cartridge eluting with a 5-95% H$_2$O:MeCN eluent (0.1% ammonia) to afford 98B (0.140 g, 43%) as an orange solid. UPLC-MS (basic 4 min): rt=2.04 min; m/z=685.5 for [M+H]$^+$.

Step 3: To a solution of 98B (0.140 g, 0.204 mmol, 1.0 eq.) in DCM (1.4 mL) was added TFA (0.6 mL), and the resulting mixture was stirred at RT for 0.5 h. The reaction mixture was concentrated to dryness, and the residue was stirred in aq. sat. K$_2$CO$_3$ solution and then extracted with DCM to afford 99B (0.090 g, 75%) as a white solid which was used in the next step without further purification. UPLC-MS (basic 4 min): rt=1.67 min; m/z=585.5 for [M+H]$^+$.

Step 4: Synthesis of Compound 417 To a solution of 99B (0.045 g, 0.077 mmol, 1.0 eq.) in DMF (1 mL) was added the required carboxylic acid (0.017 g, 0.0785 mmol, 1.1 eq.), DIPEA (0.067 mL, 0.385 mmol, 5.0 eq.), and then HATU (0.035 g, 0.092 mmol, 1.2 eq.), and the resulting mixture was stirred at RT for 1 h. The mixture was concentrated to dryness, and the residue was purified via reverse phase column chromatography on a 120 g C18 cartridge eluting with a 5-95% H$_2$O:MeCN eluent (0.1% ammonia) to afford 417 (0.031 g) as a white solid. UPLC-MS (basic 4 min): rt=1.87 min; m/z=763.5 for [M+H]$^+$.

Example 35: General Scheme—Synthesis of Compounds (vi or xii): 417, 420-431, 435-460, 462, 464, 466-474, 476-482, 486, 489-507, 510, (vii): 432-434, 465, 488, 508, 509, 513-516, (viii): 461, 463, 485, 518, (ix): 483, (x): 484, and (xi) 517

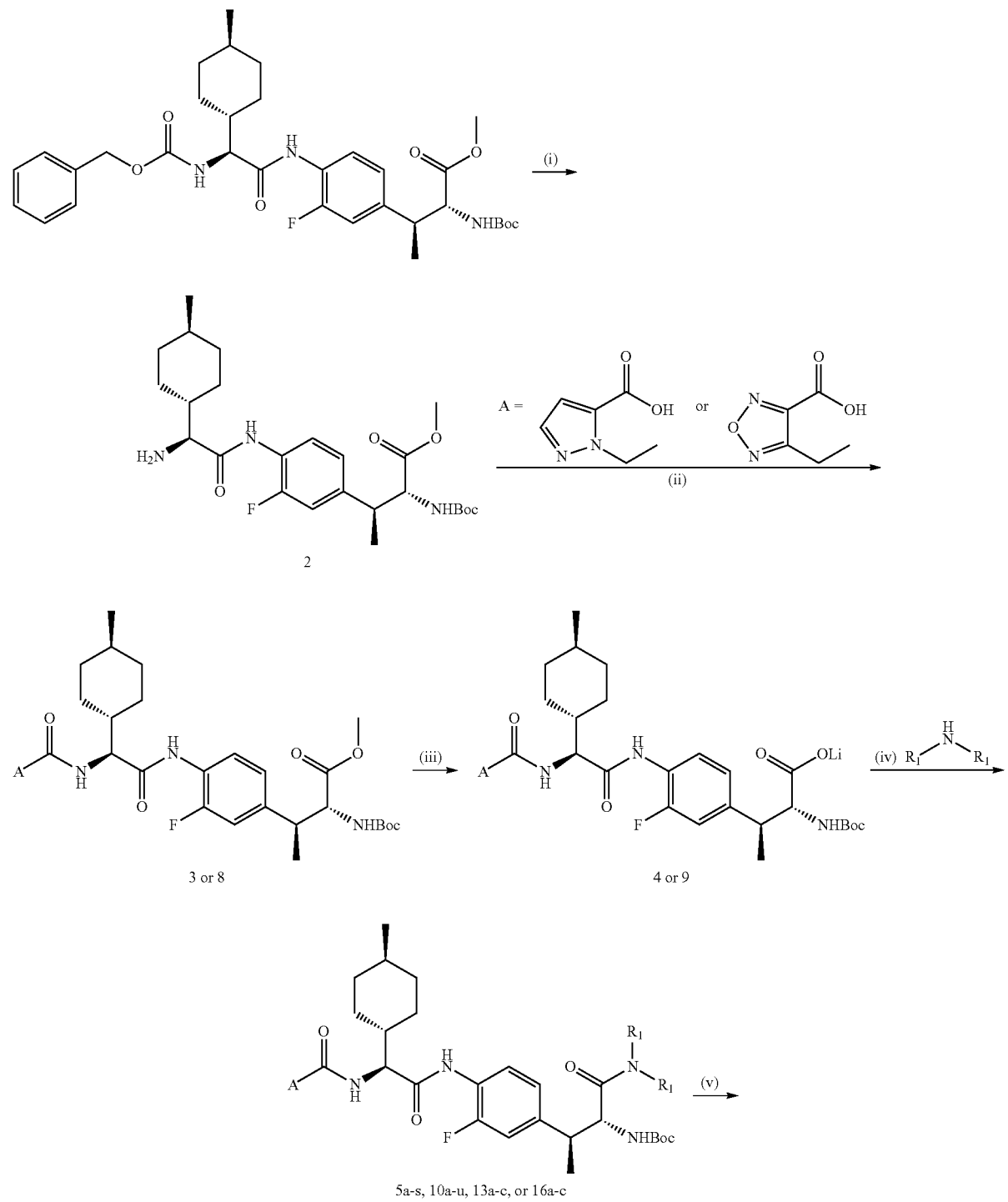

-continued

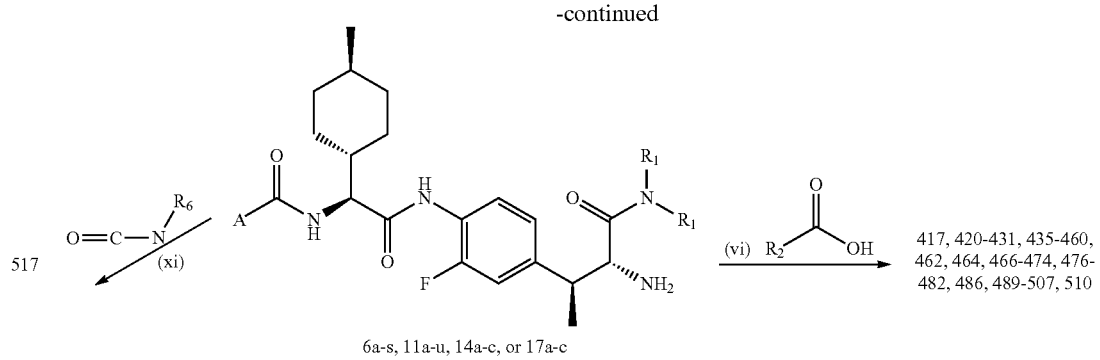

6a-s, 11a-u, 14a-c, or 17a-c

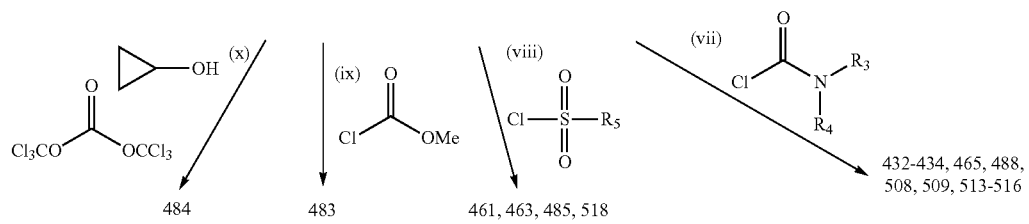

(i) H$_2$, Pd/C, EtOH, RT, 0.5 h. (ii) 2-ethyl-2H-pyrazole-5-carboxylic acid (1.2 eq.) or 4-ethyl-1,2,5-oxadiazole-3-carboxylic acid (1.2 eq.), HATU (1.5 eq), DIPEA (6.0 eq.), DMF, RT, 1 h. (iii) LiOH.H$_2$O (1.2 eq.), THF, H$_2$O, RT, 1 h. (iv) amine (1.2 eq.), HATU (1.5 eq), DIPEA (4.0 eq.), DMF, RT, 1 h. (v) TFA, DCM, RT, 1 h. (vi) propionic anhydride (1.2 eq.), DIPEA (4.0 eq.), RT, 1 h, DMF. (vii) amine (1.0 eq) in DMF, carbamoyl chloride (1.5 eq.) and DIPEA (3.0-8.0 eq.), RT, 18 h. (viii) amine (1.0 eq) in DCM, sulfonyl chloride (1.1 eq.) and DIPEA (3.0-8.0 eq.), RT, 1 h. (ix) amine (1.0 eq) in DMF, chloroformate (1.2 eq.) and DIPEA (3.0-8.0 eq.), RT, 1 h. (x) alcohol (1.0 eq), DCM, DIPEA (5 eq), ditrichloromethyl carbonate (0.33 eq), stir 10 min, add amine (0.51 eq), RT, 1 h. (xi) amine (1.0 eq) in DMF (0.1 M), isocyanate (1.2 eq.) and DIPEA (3.0-8.0 eq.), RT, 1 h. (xii) carboxylic acid (1.2 eq.), HATU (1.5 eq), DIPEA (6.0 eq.), DMF, RT, 1 h.

The following compounds were made following a procedure analogous to Example 35 starting from intermediates 6a-s, 11a-u, 14a-c, or 17a-c and reacting with the appropriate reagent.

-continued

421

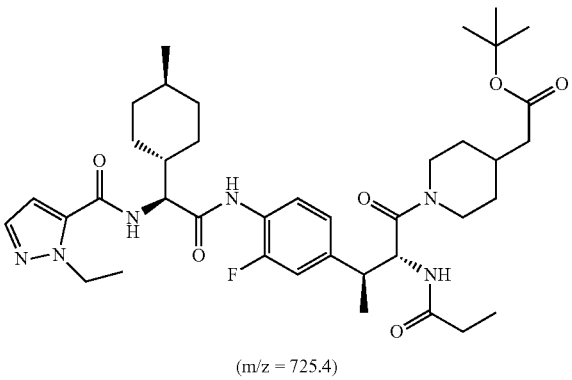

(m/z = 725.4)

420

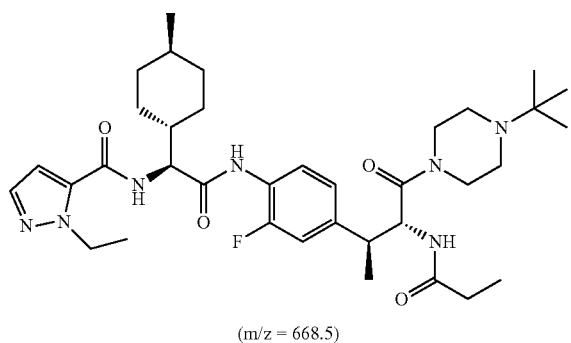

(m/z = 668.5)

422

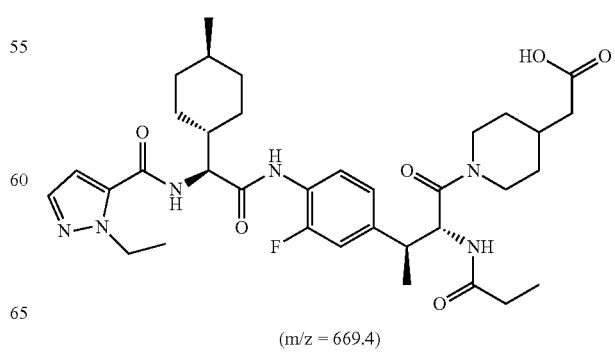

(m/z = 669.4)

191
-continued
423
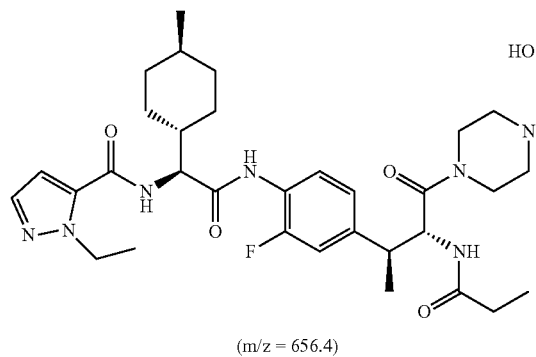
(m/z = 656.4)
424
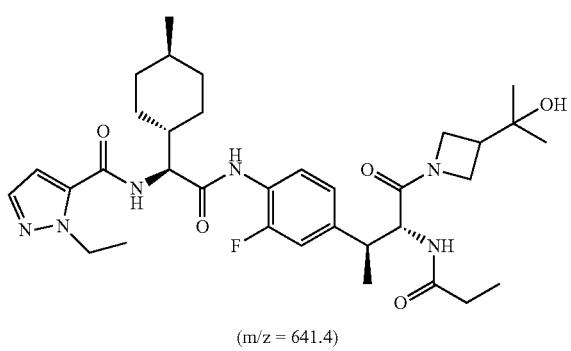
(m/z = 641.4)
425
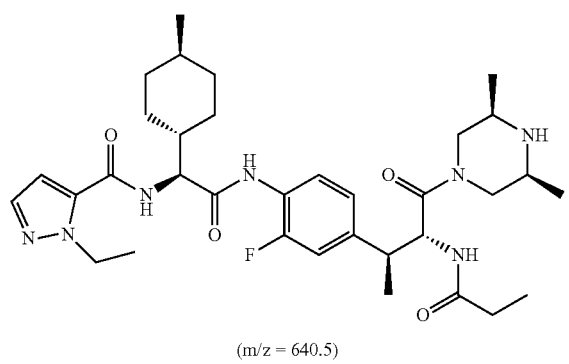
(m/z = 640.5)
426
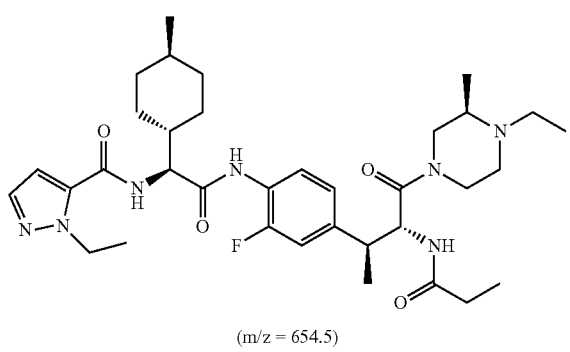
(m/z = 654.5)
192
-continued
427
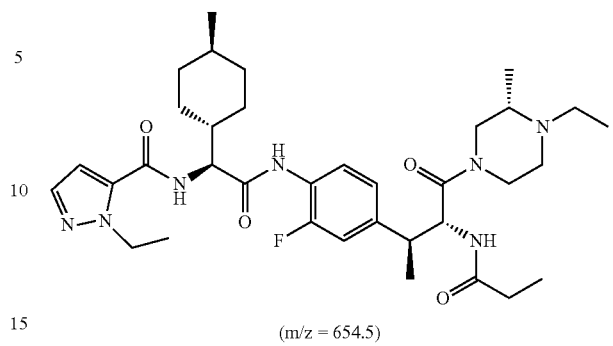
(m/z = 654.5)
428
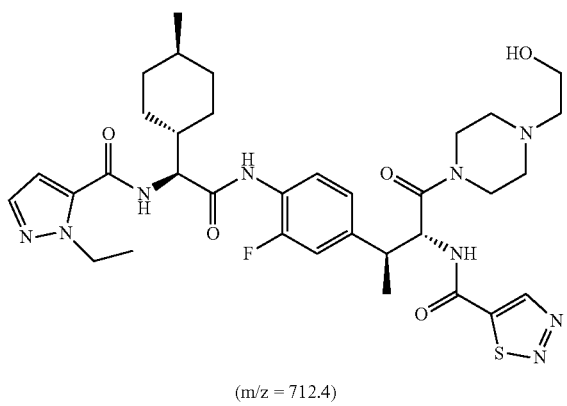
(m/z = 712.4)
429
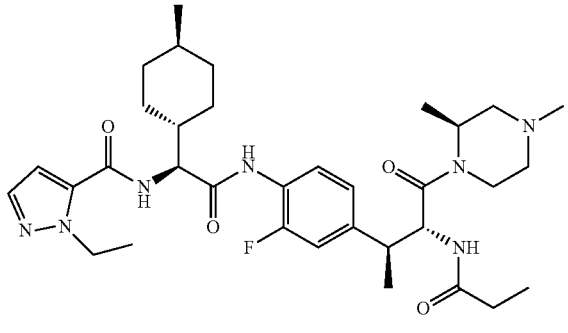
(m/z = 640.5)
430
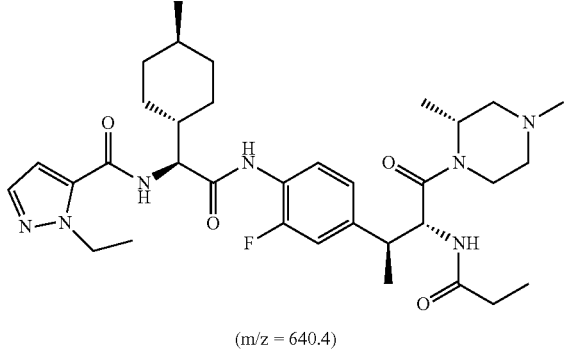
(m/z = 640.4)

193                                                    194
-continued                                             -continued
431
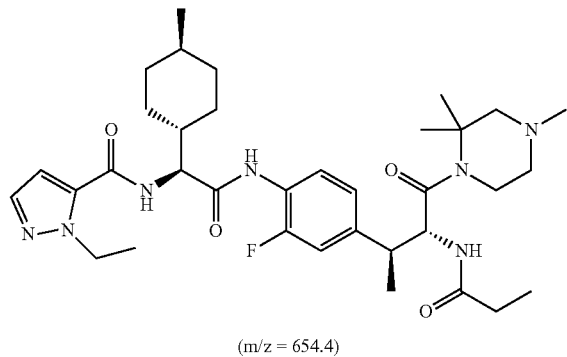
(m/z = 654.4)
435
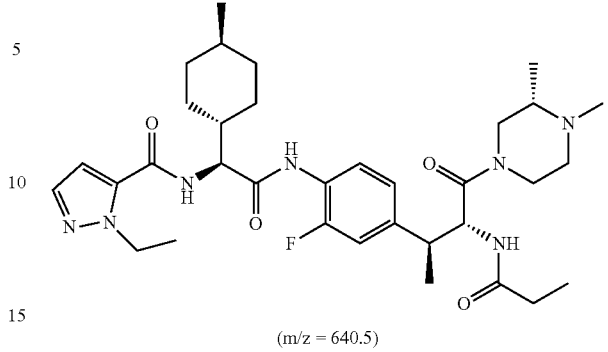
(m/z = 640.5)
432
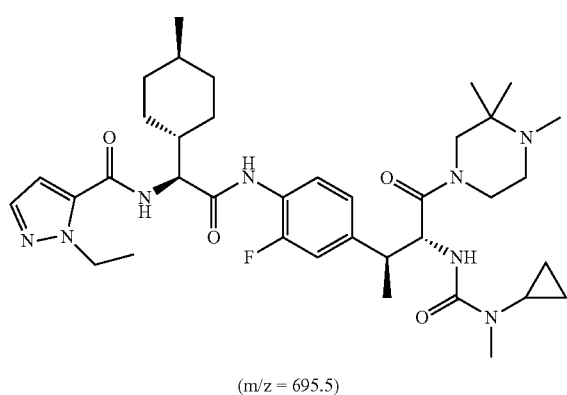
(m/z = 695.5)
436
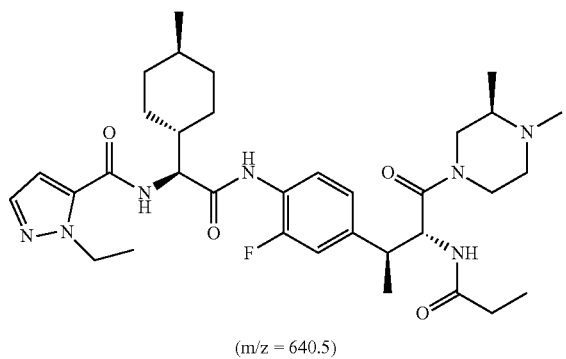
(m/z = 640.5)
433
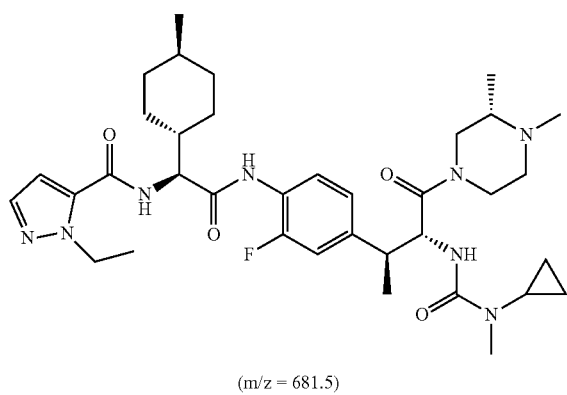
(m/z = 681.5)
437
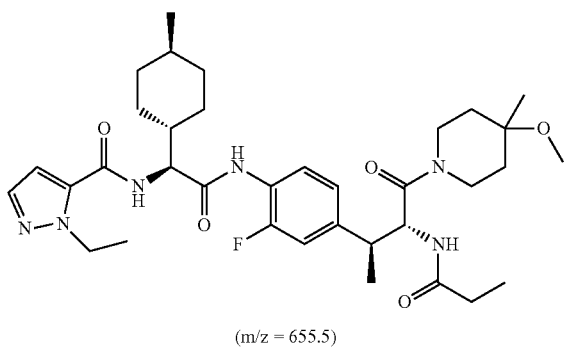
(m/z = 655.5)
434
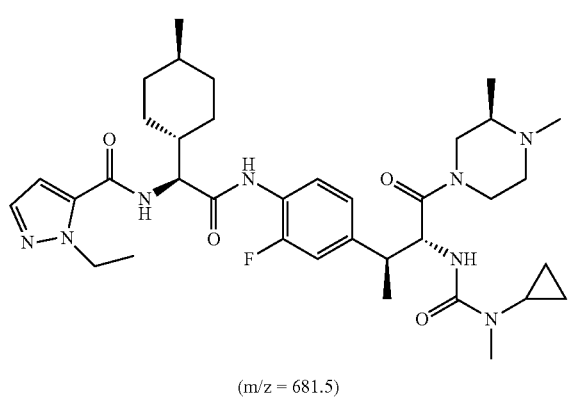
(m/z = 681.5)
438
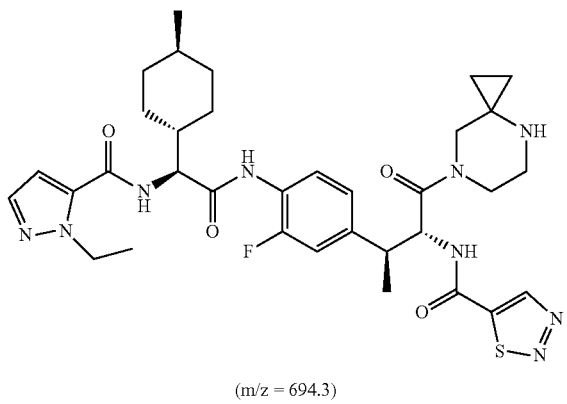
(m/z = 694.3)

439
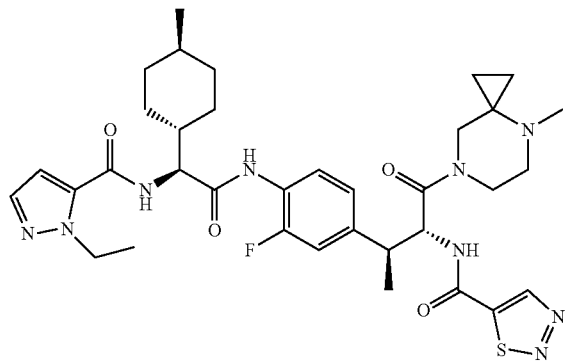
(m/z = 708.3)
440
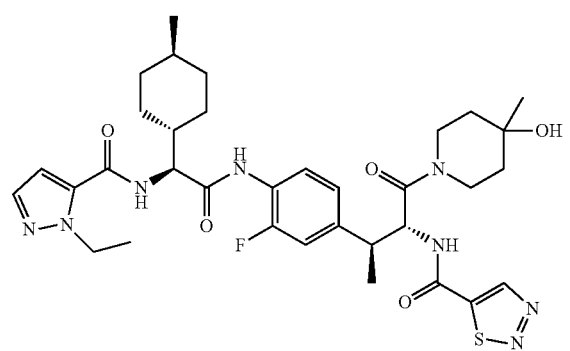
(m/z = 697.4)
441
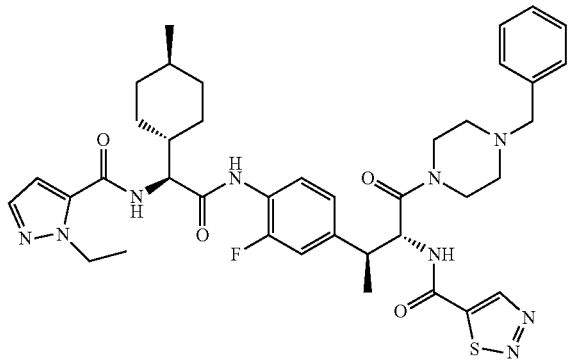
(m/z = 758.4)
442
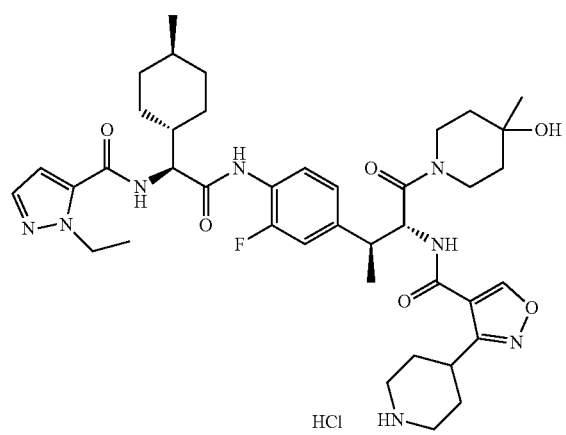
(m/z = 763.4)
443
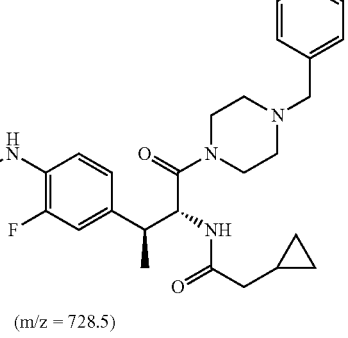
(m/z = 728.5)
444
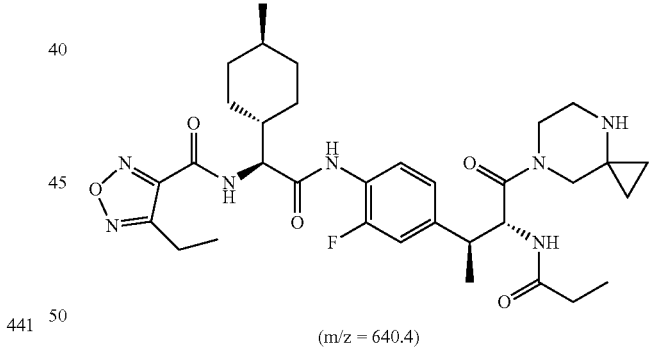
(m/z = 640.4)
445
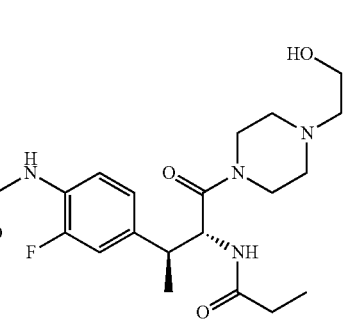
(m/z = 658.4)

197
-continued
446
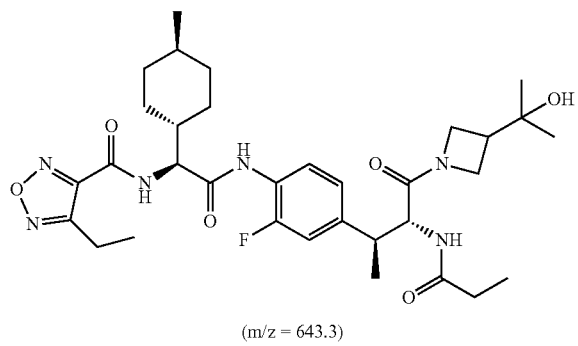
(m/z = 643.3)
447
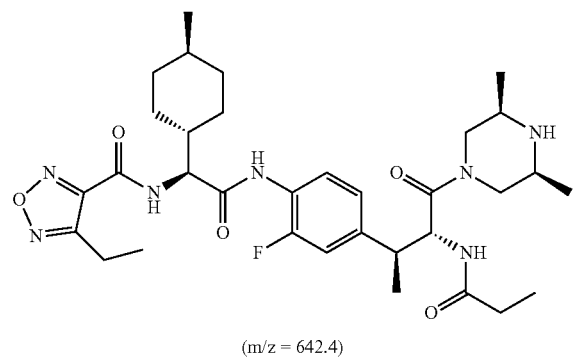
(m/z = 642.4)
448
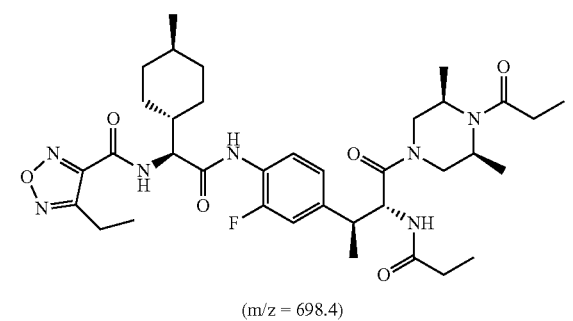
(m/z = 698.4)
449
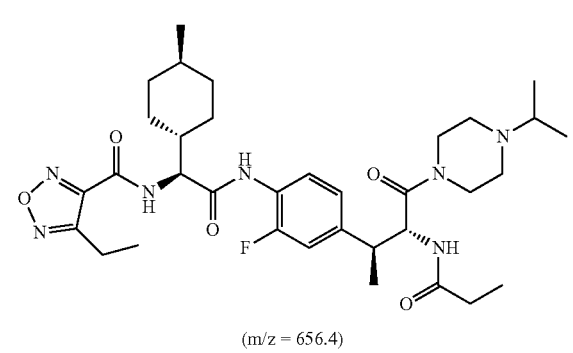
(m/z = 656.4)
198
-continued
450
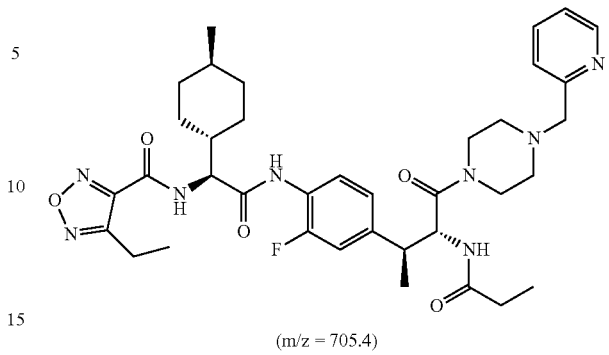
(m/z = 705.4)
451
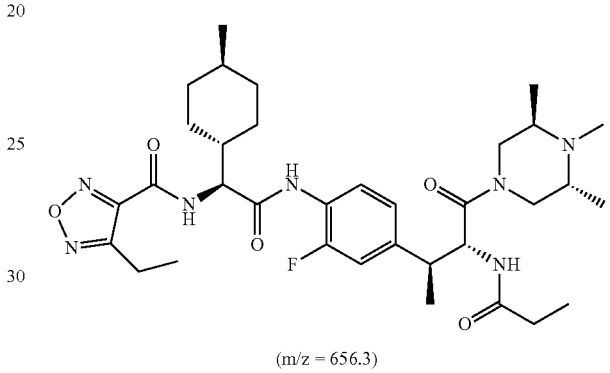
(m/z = 656.3)
452
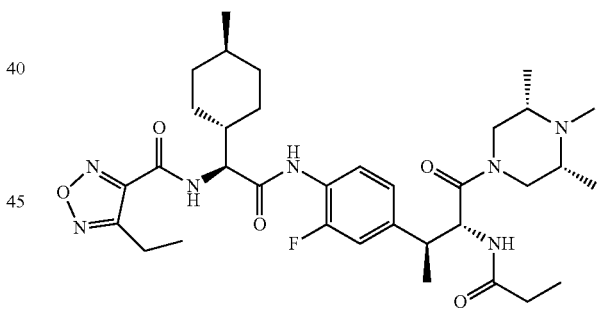
(m/z = 656.3)
453
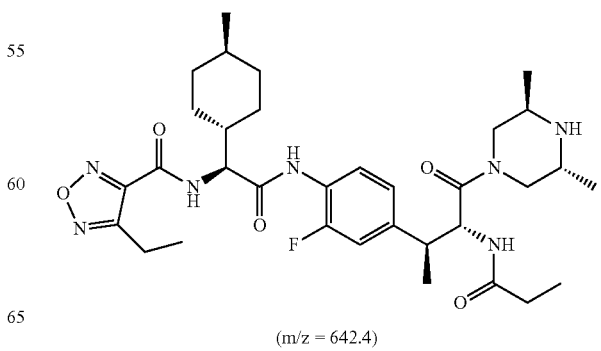
(m/z = 642.4)

199
454
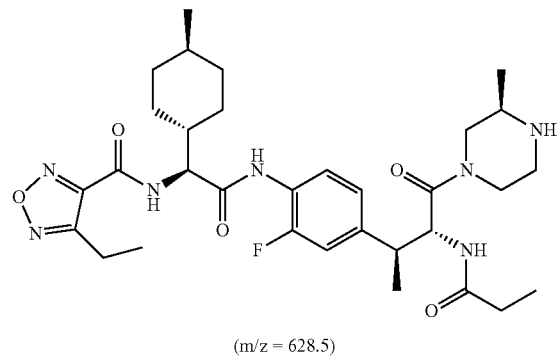
(m/z = 628.5)
455
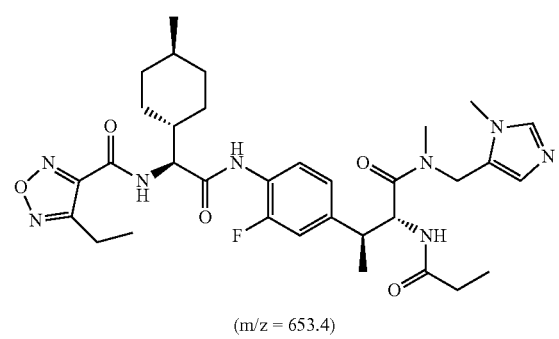
(m/z = 653.4)
456
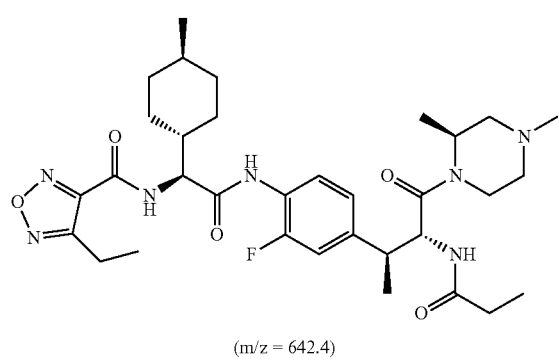
(m/z = 642.4)
457
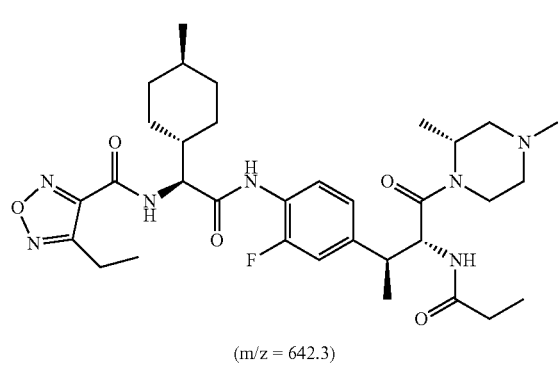
(m/z = 642.3)
200
458
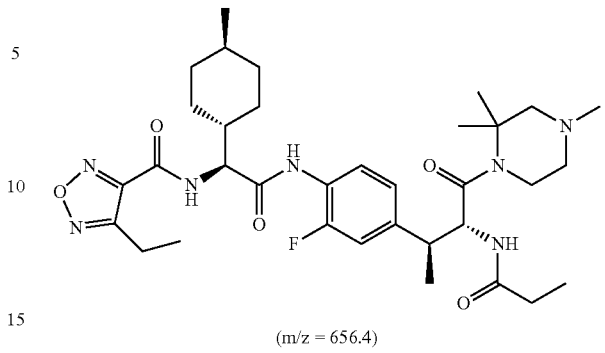
(m/z = 656.4)
459
(m/z = 698.5)
460
(m/z = 642.4)
461
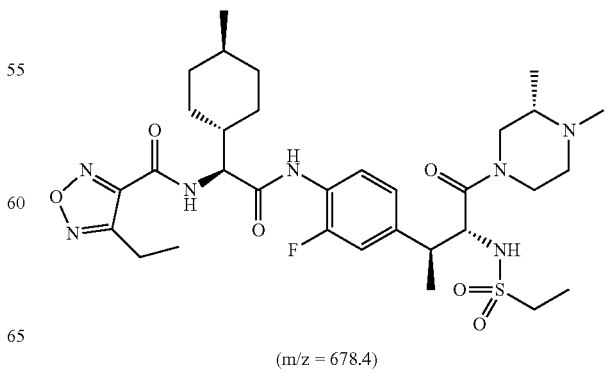
(m/z = 678.4)

201
-continued
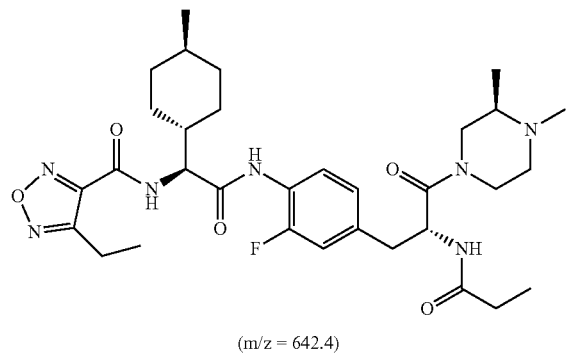
462
(m/z = 642.4)
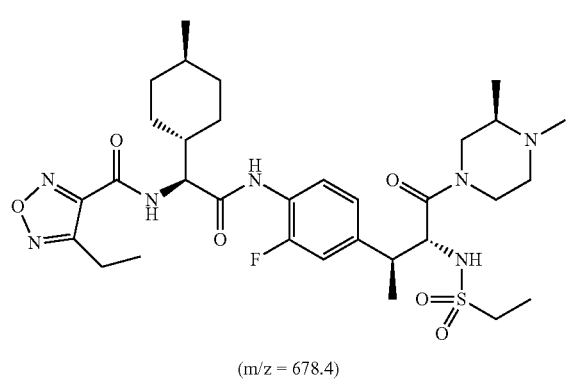
463
(m/z = 678.4)
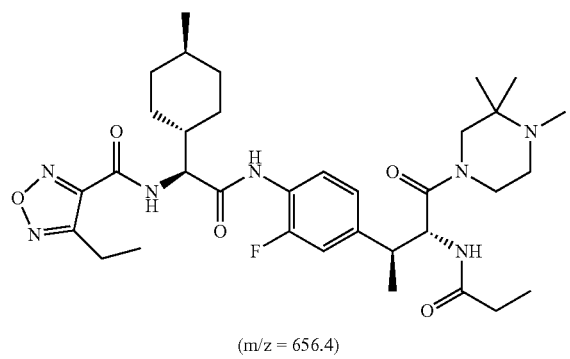
464
(m/z = 656.4)
465
(m/z = 697.6)
202
-continued
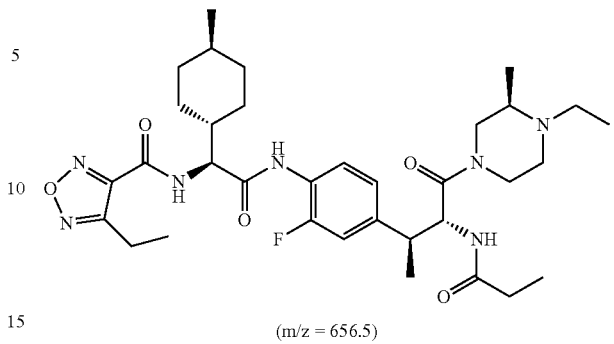
466
(m/z = 656.5)
467
(m/z = 656.4)
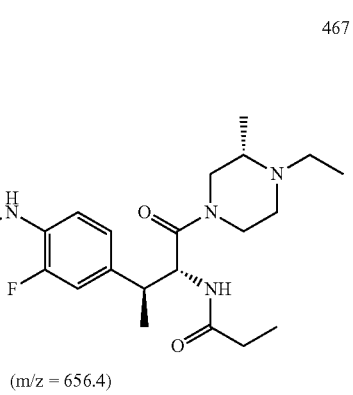
468
(m/z = 649.3)
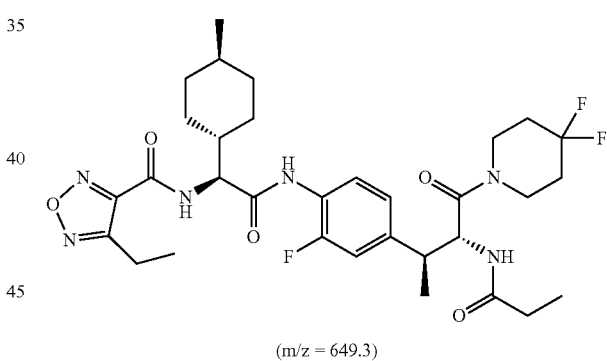
469
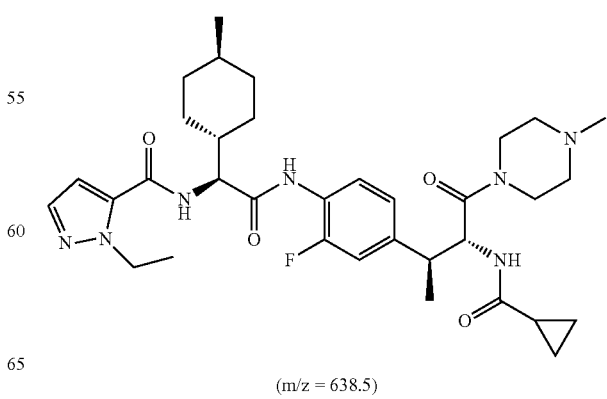
(m/z = 638.5)

470
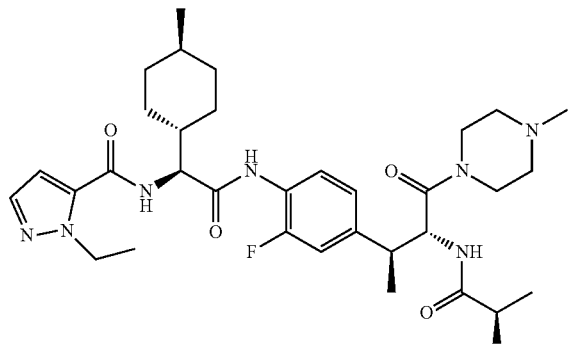
(m/z = 644.4)
471
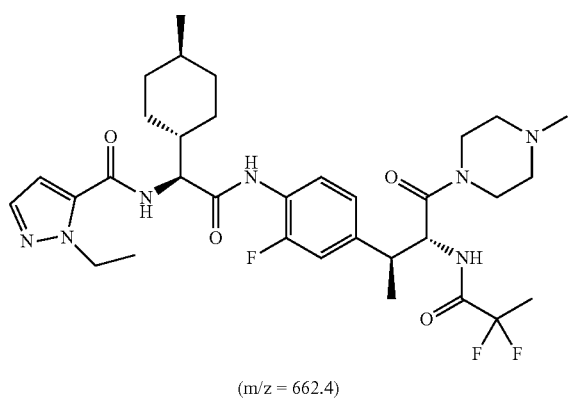
(m/z = 662.4)
472
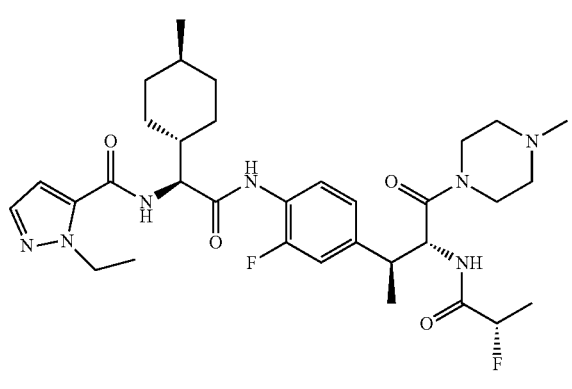
(m/z = 644.4)
473
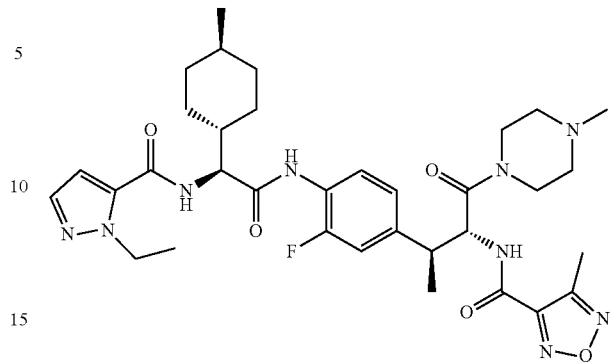
(m/z = 680.3)
474
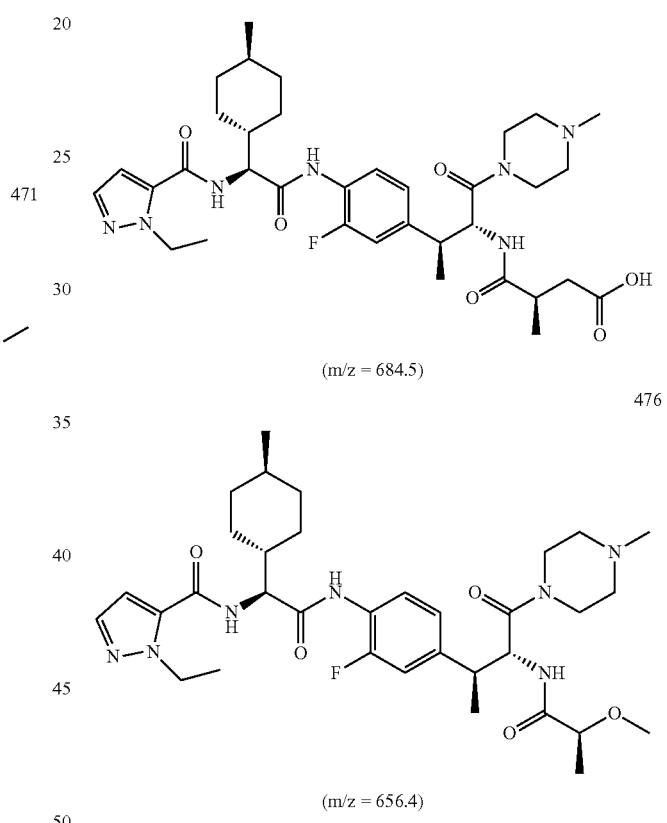
(m/z = 684.5)
476
(m/z = 656.4)
477
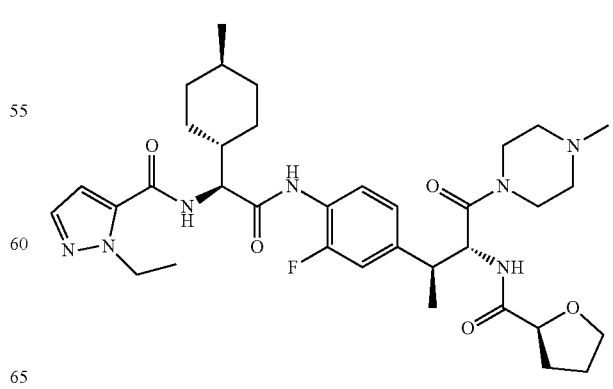
(m/z = 668.5)

205 / 206
-continued
478
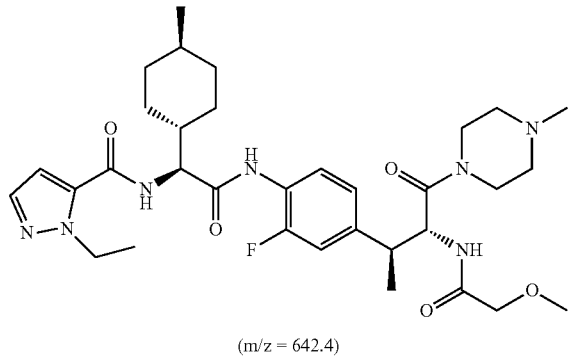
(m/z = 642.4)
482
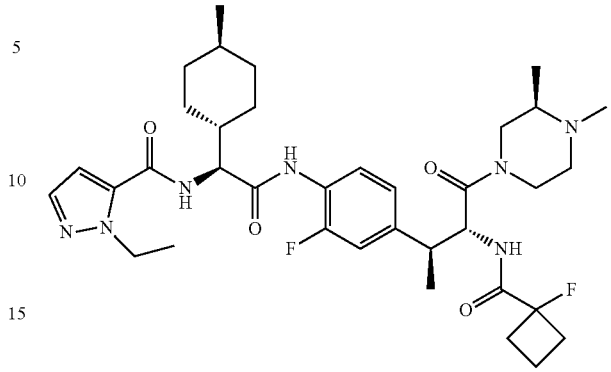
(m/z = 684.5)
479
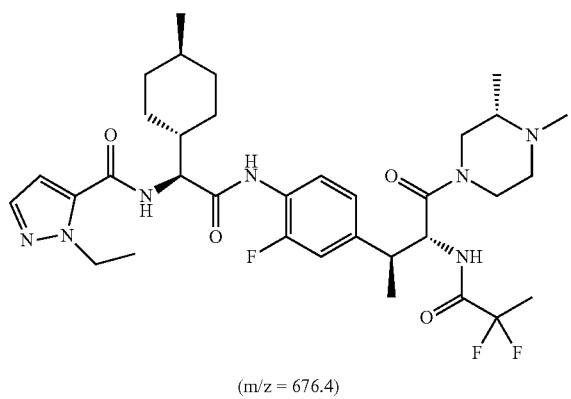
(m/z = 676.4)
483
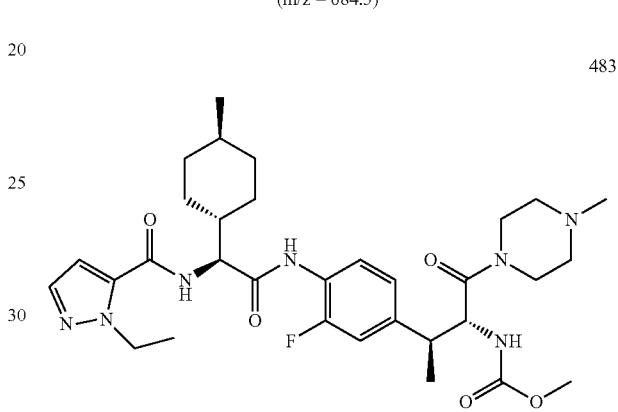
(m/z = 628.5)
480
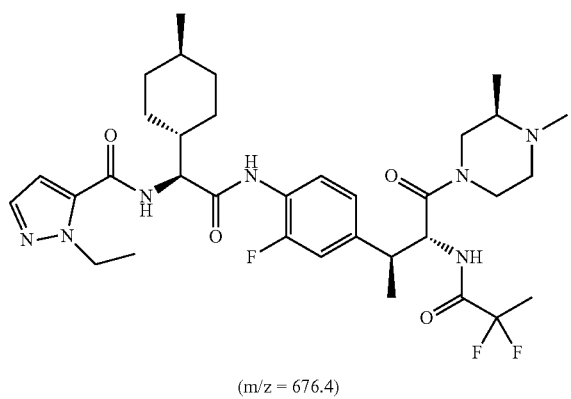
(m/z = 676.4)
484
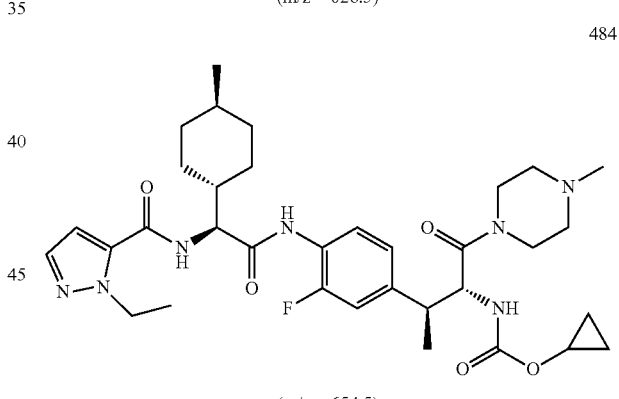
(m/z = 654.5)
481
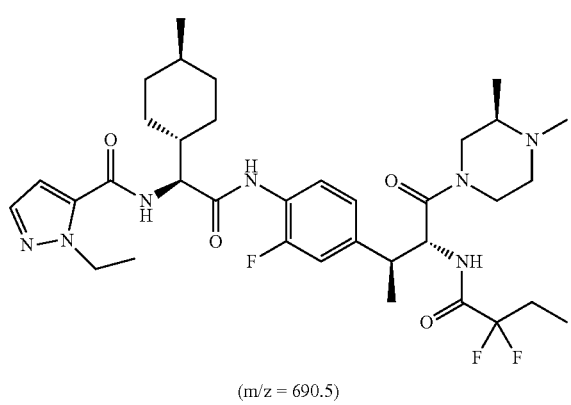
(m/z = 690.5)
485
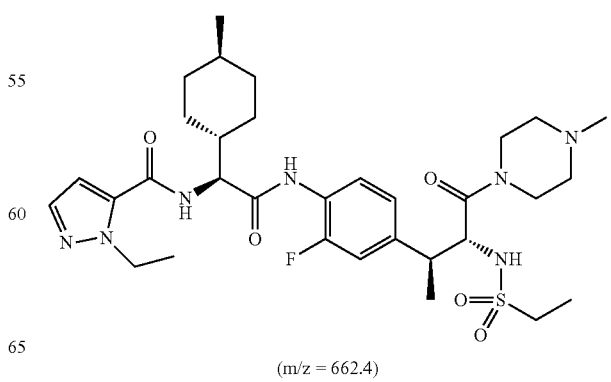
(m/z = 662.4)

486
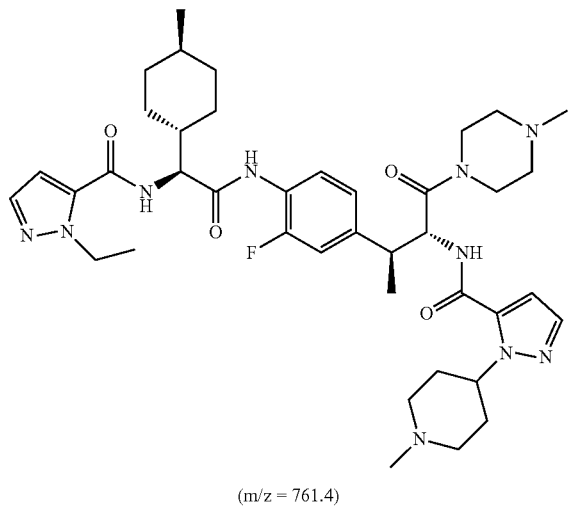
(m/z = 761.4)
487
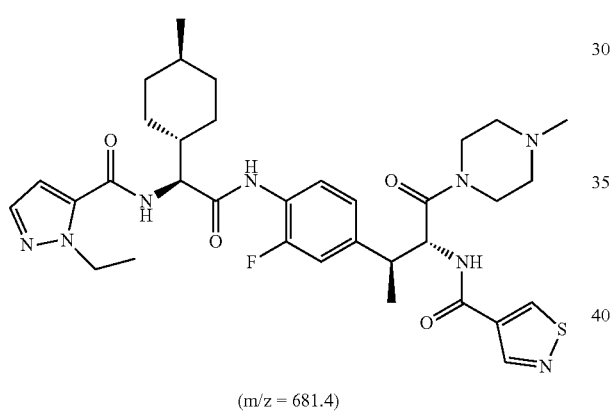
(m/z = 681.4)
488
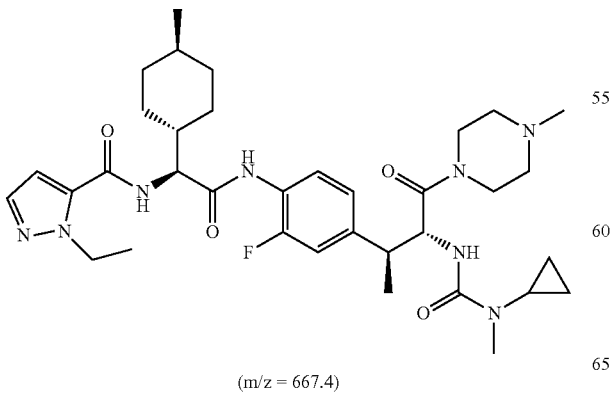
(m/z = 667.4)
489
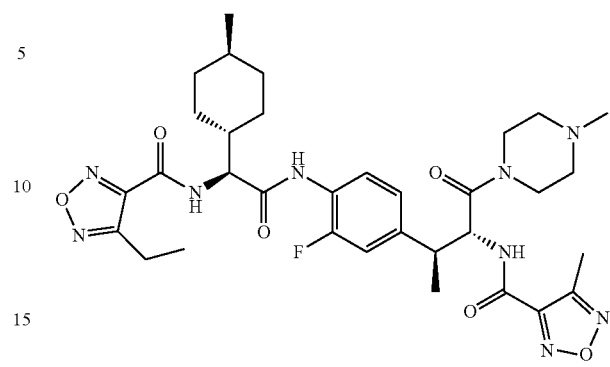
(m/z = 682.4)
490
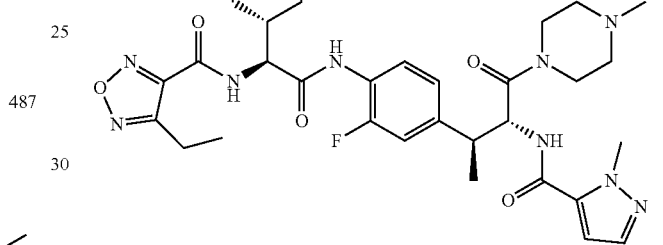
(m/z = 680.3)
491
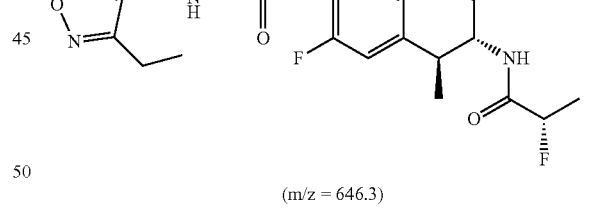
(m/z = 646.3)
492
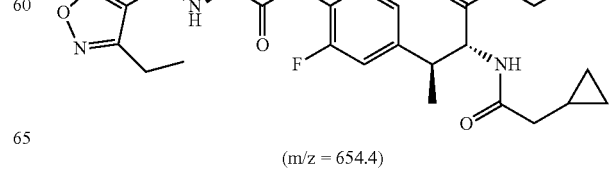
(m/z = 654.4)

209
-continued
493
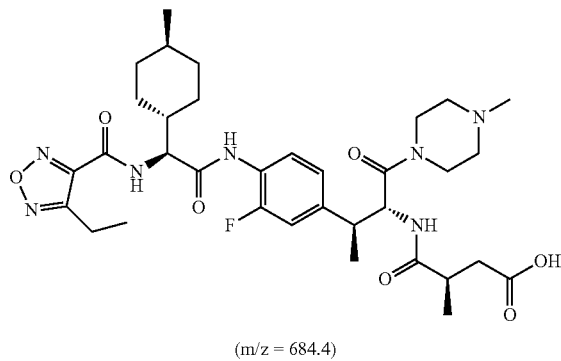
(m/z = 684.4)
494
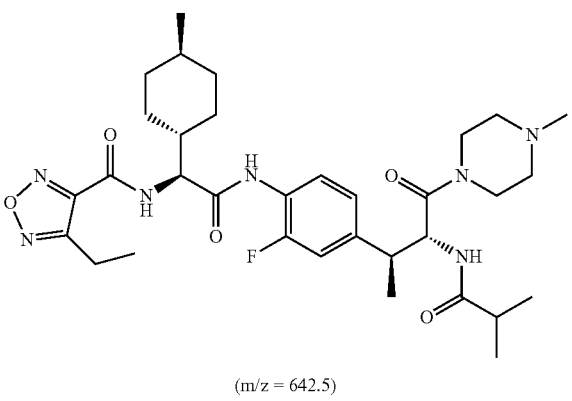
(m/z = 642.5)
495
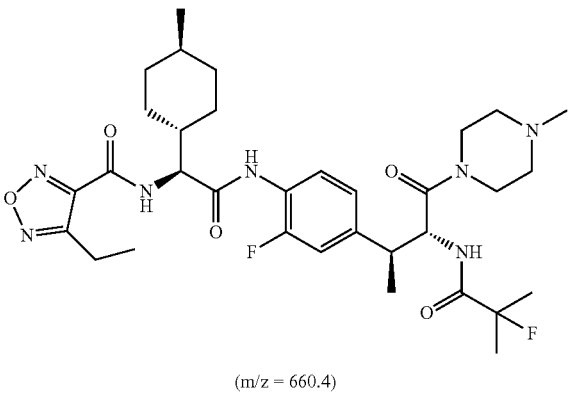
(m/z = 660.4)
496
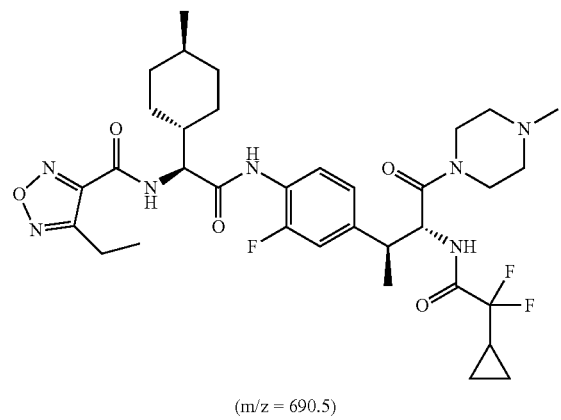
(m/z = 690.5)
210
-continued
497
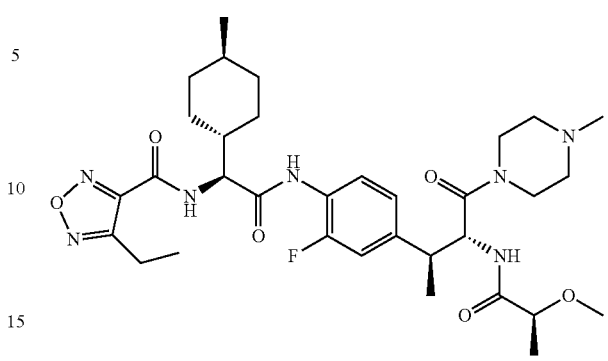
(m/z = 658.3)
498
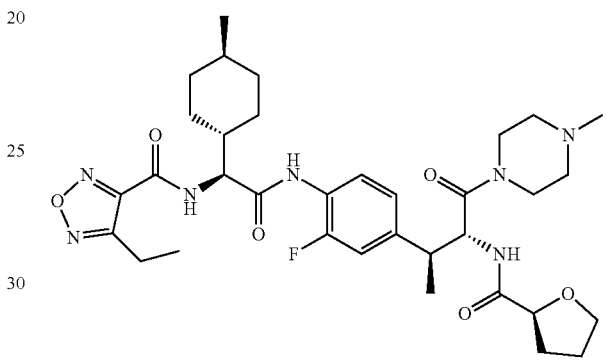
(m/z = 670.4)
499
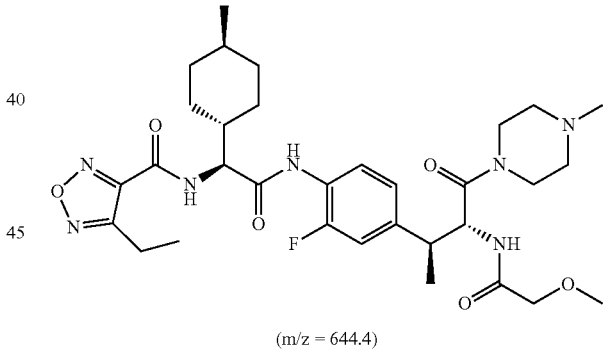
(m/z = 644.4)
500
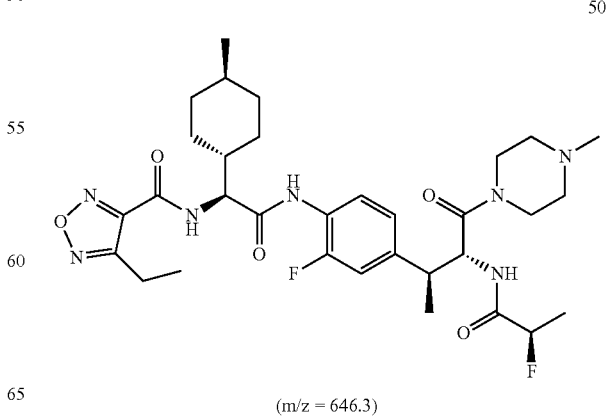
(m/z = 646.3)

211
-continued
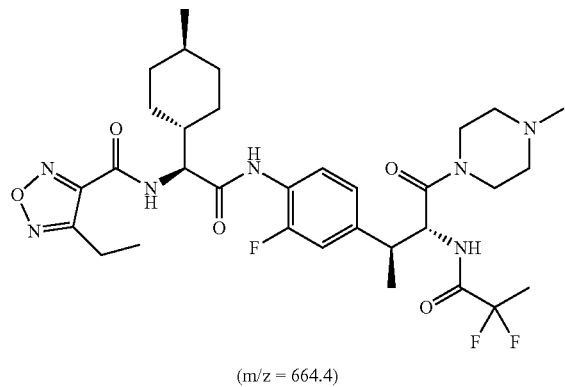
501
(m/z = 664.4)
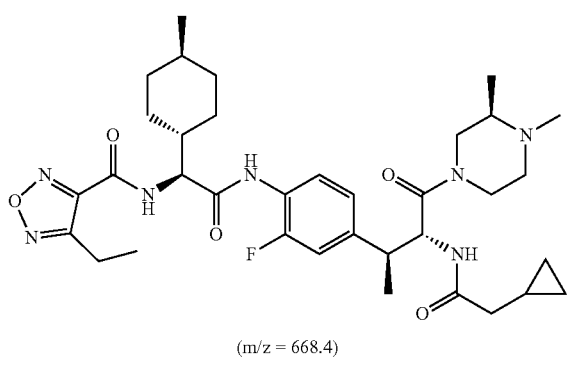
502
(m/z = 668.4)
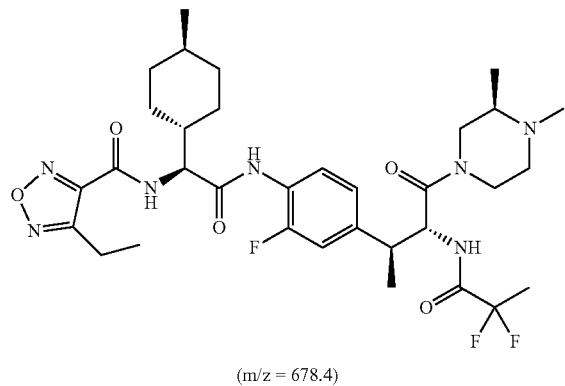
503
(m/z = 678.4)
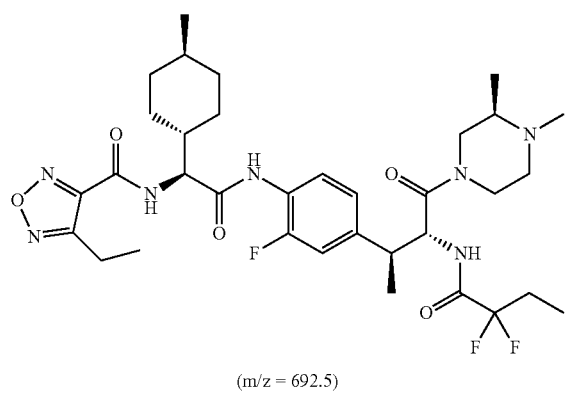
504
(m/z = 692.5)
212
-continued
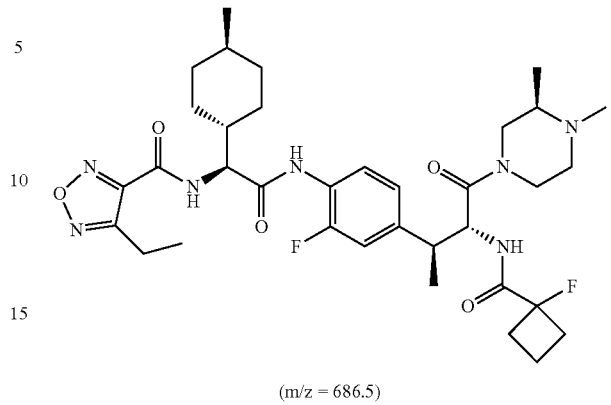
505
(m/z = 686.5)
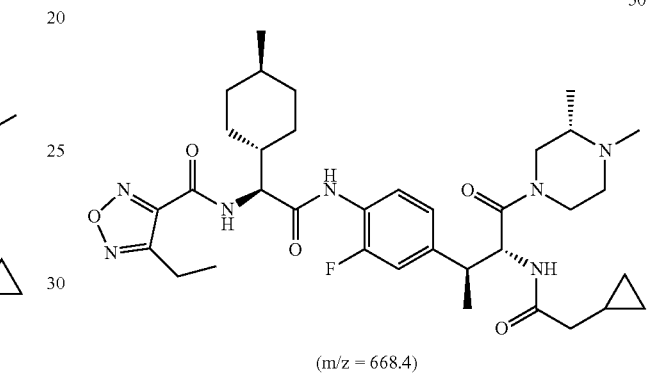
506
(m/z = 668.4)
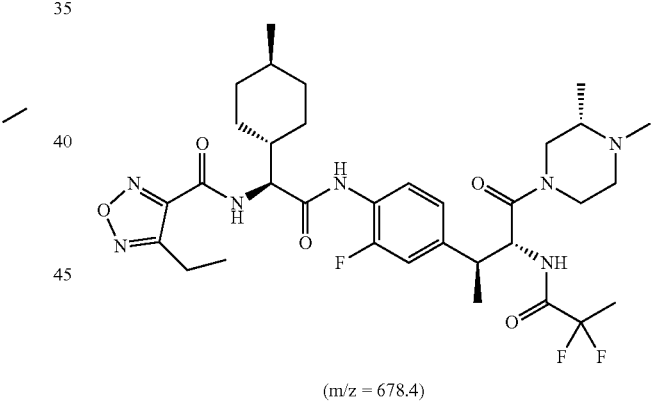
507
(m/z = 678.4)
508
(m/z = 683.4)

509
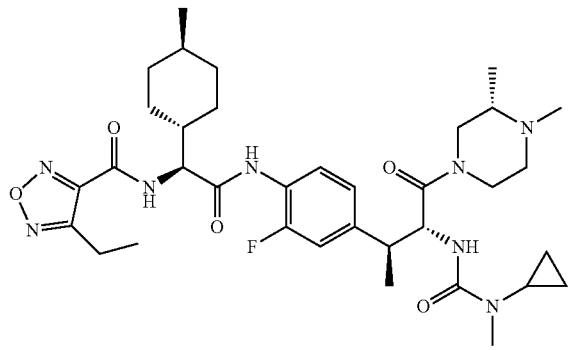
(m/z = 683.4)
510
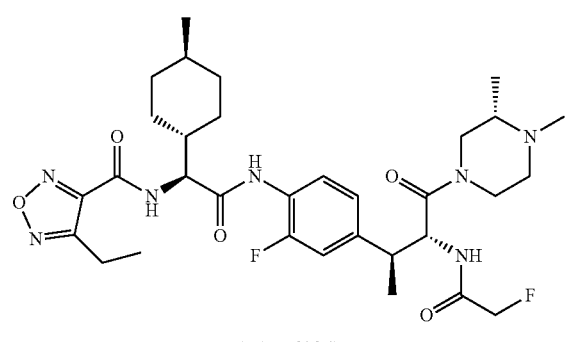
(m/z = 646.4)
511
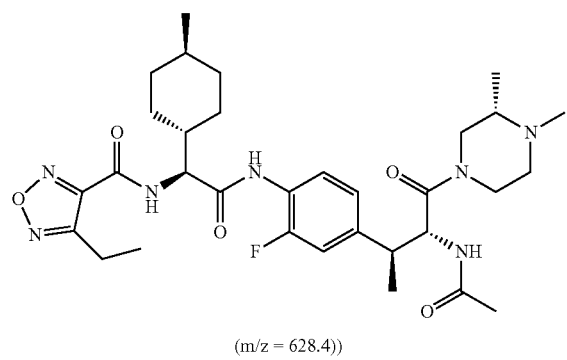
(m/z = 628.4))
512
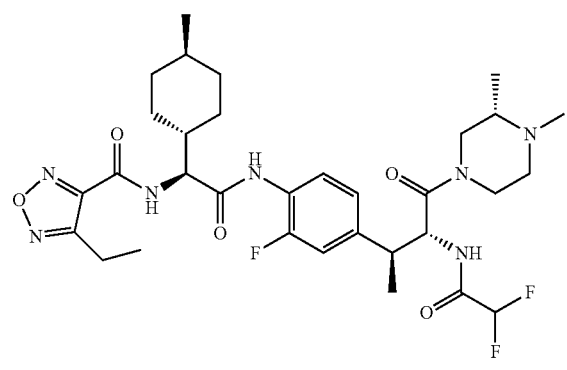
(m/z = 664.4)
513
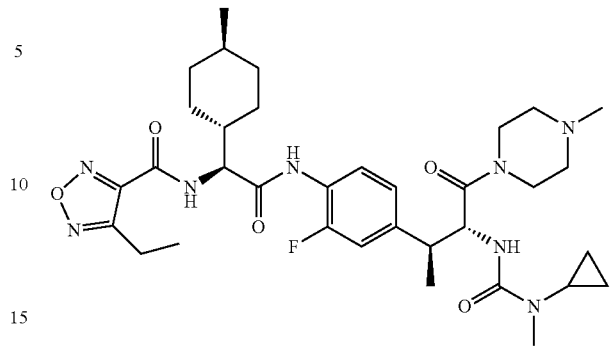
(m/z = 669.4)
514
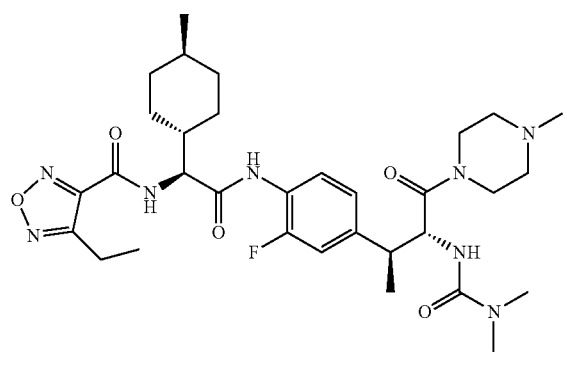
(m/z = 643.5)
515
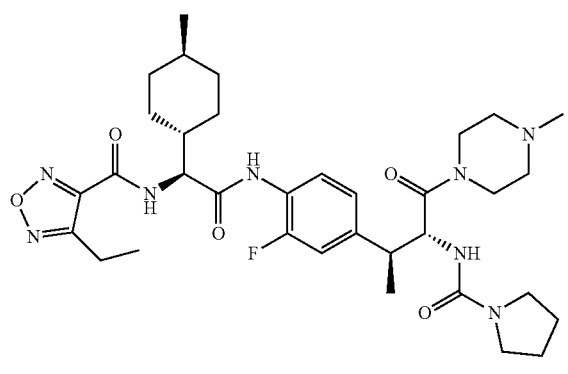
(m/z = 669.4)
516
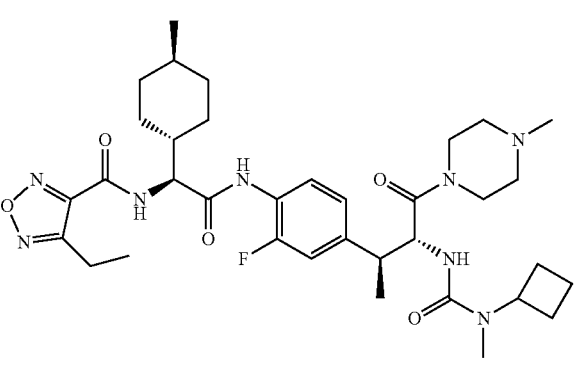
(m/z = 683.4)

215
-continued
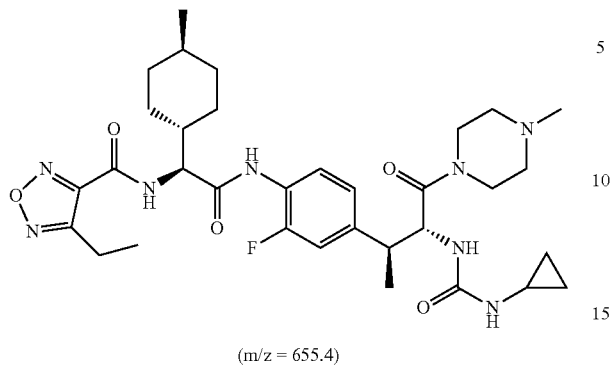
(m/z = 655.4)
517
(m/z = 664.3)
518
Example 36 General Scheme—Synthesis of Compounds 519-522
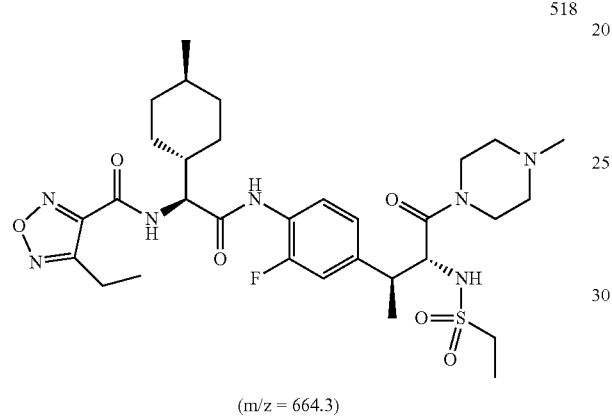
216
-continued
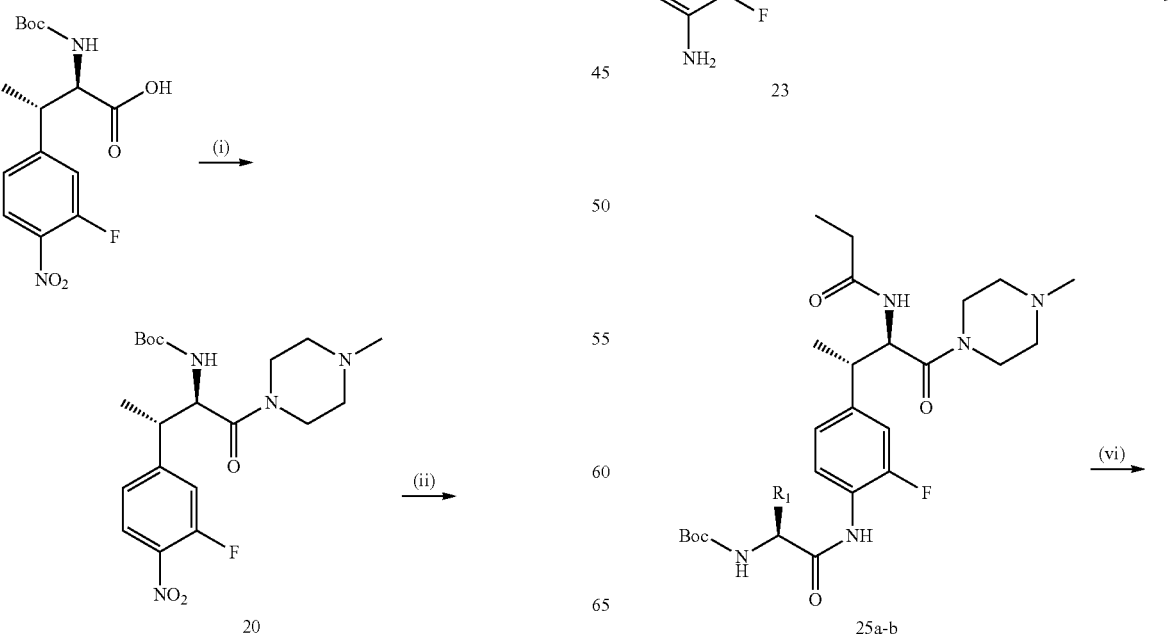

217
-continued

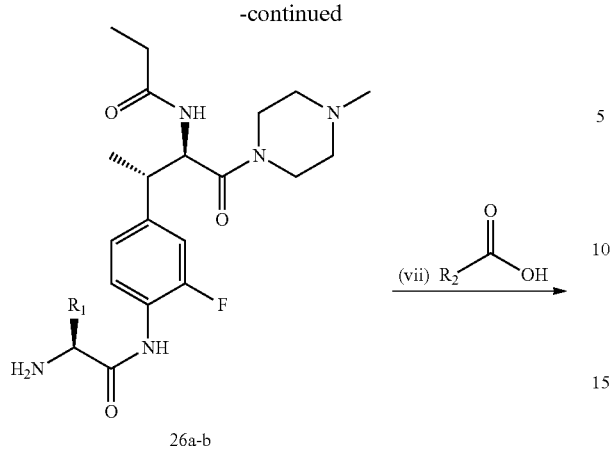

26a-b (vii) R$_2$ <image style="inline">COOH</image>
→

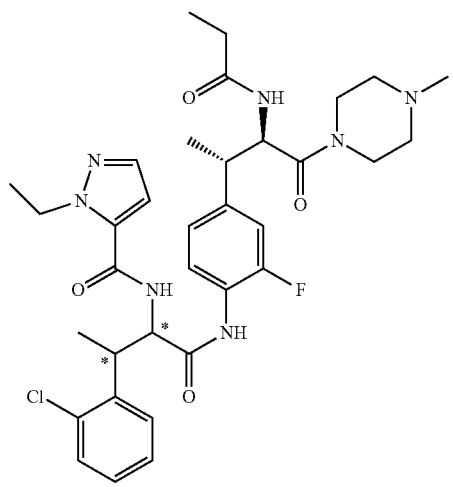

519 single diastereomer with undetermined
absolute stereochemistry at *, epimer is 520
(m/z = 668.3)

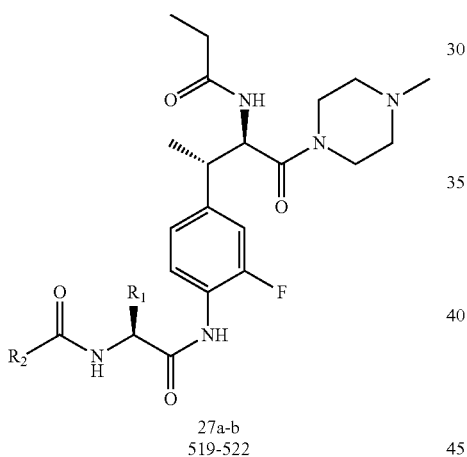

27a-b
519-522

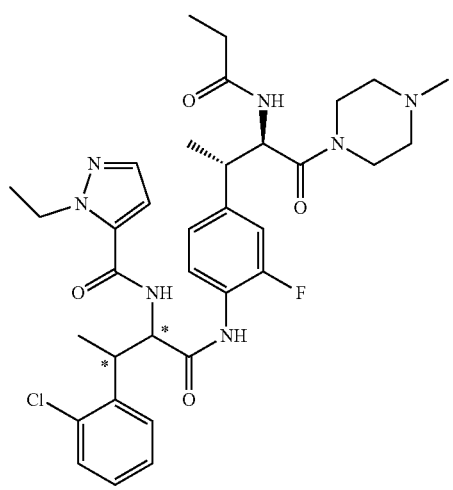

520 single diastereomer with undetermined
absolute stereochemistry at *, epimer is 519
(m/z = 668.3)

(i) N-methyl piperazine (1.2 eq.) HATU (1.5 eq.), DIPEA (5.0 eq.), DMF, RT, 1 h. (ii) TFA, DCM, RT, 1 h. (iii) propionic anhydride (1.2 eq.), DIPEA (1.2 eq.), DMF, RT, 1 h. (iv) H$_2$, Pd/C (20 mol %), EtOH, THF, RT, 18 h. (v) 24a-b (1.1 eq.), EDC (1.2 eq.), pyridine, RT, 18 h. (vi) TFA, DCM, RT, 0.5 h. (vii) carboxylic acid (1.2 eq.), HATU (1.5 eq.), DIPEA (3.0 eq.), DMF, RT, 1 h.

General Synthesis of Compounds 519-522

To a solution of 26a-b (1.0 eq.) in DMF were added the required carboxylic acid (1.2 eq.), DIPEA (4.0 eq.) and then HATU (1.5 eq.) and the resulting mixture was stirred at RT for 1 h. The reaction mixture was directly purified by Reverse Phase column chromatography on a 120 g C18 cartridge eluting with a 5-95% H$_2$O:MeCN eluent (0.1% ammonia) to afford 519-522.

219 -continued
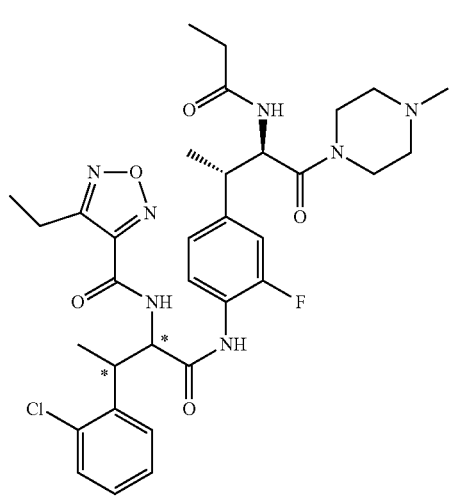
521
single diastereomer with undetermined
absolute stereochemistry at *, epimer is 522
(m/z = 670.3)
220 -continued
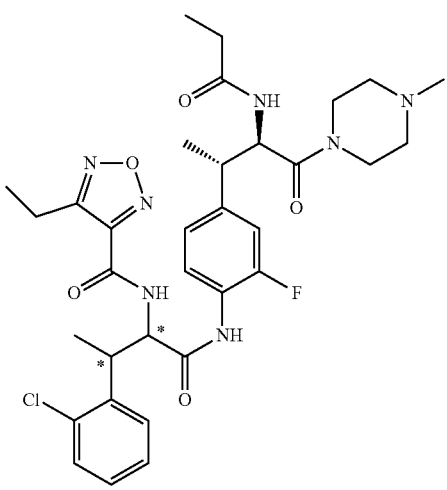
522
single diastereomer with undetermined
absolute stereochemistry at *, epimer is 521
(m/z = 670.3)
Example 37: General Scheme Synthesis of Compounds 523-526
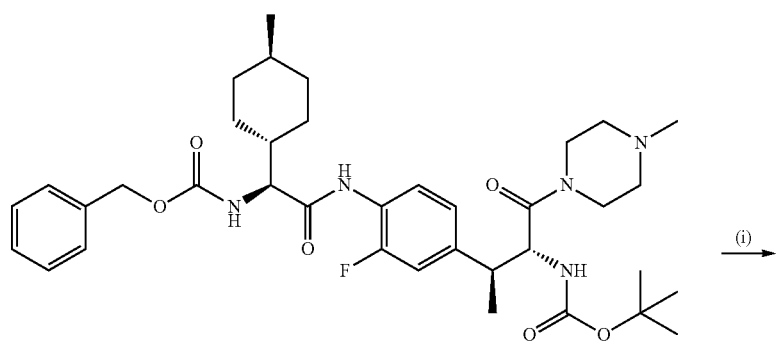
(i)
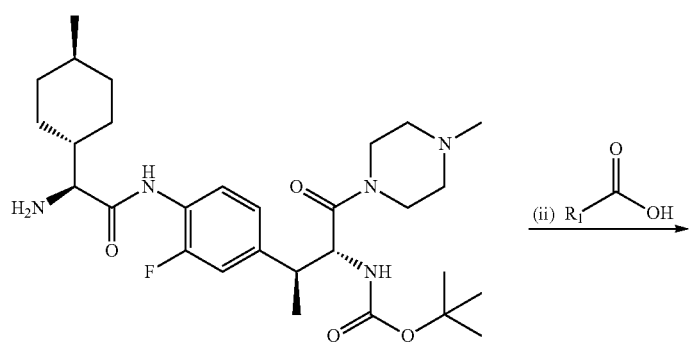
(ii) R₁—COOH
28

-continued

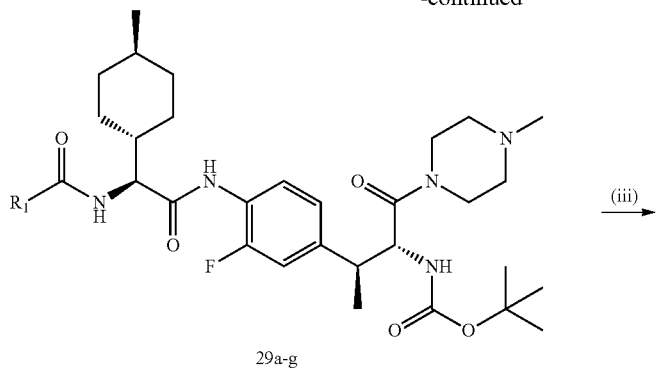
29a-g

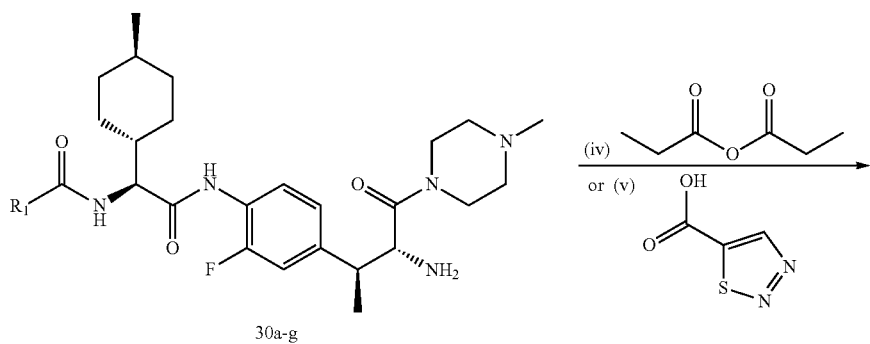
30a-g

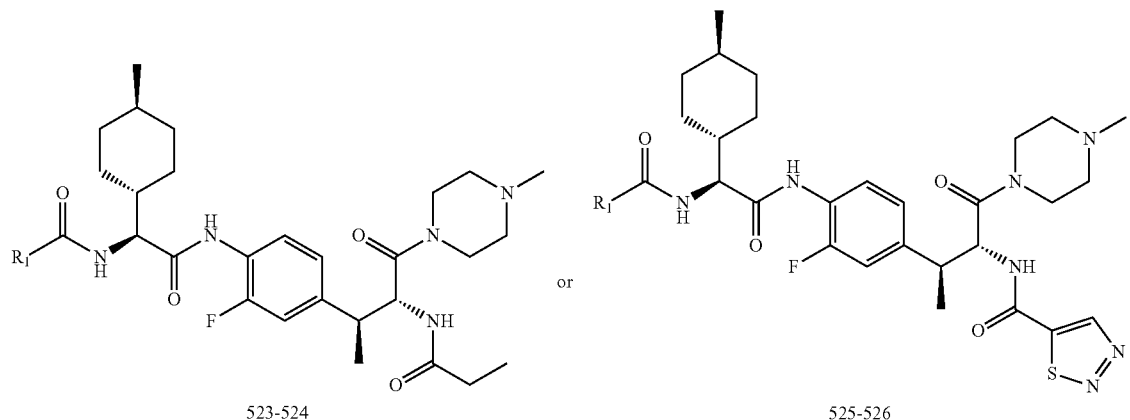
523-524 or 525-526

(i) H₂, Pd/C, EtOH, RT, 0.5 h. (ii) carboxylic acid (1.2 eq.), HATU (1.5 eq), DIPEA (6.0 eq.), DMF, RT, 1 h. (iii) TFA, DCM, RT, 1 h. (iv) propionic anhydride (1.2 eq.), DIPEA (4.0 eq.), RT, 1h, DMF. (v) DMF, 1,2,3-thiadiazole-5-carboxylic acid (1.2 eq.), DIPEA (4.0 eq.), and HATU (1.5 eq.)

(i) H₂, Pd/C, EtOH, RT, 0.5 h. (ii) carboxylic acid (1.2 eq.), HATU (1.5 eq), DIPEA (6.0 eq.), DMF, RT, 1 h. (iii) TFA, DCM, RT, 1 h. (iv) propionic anhydride (1.2 eq.), DIPEA (4.0 eq.), RT, 1 h, DMF. (v) DMF, 1,2,3-thiadiazole-5-carboxylic acid (1.2 eq.), DIPEA (4.0 eq.), and HATU (1.5 eq.)

523
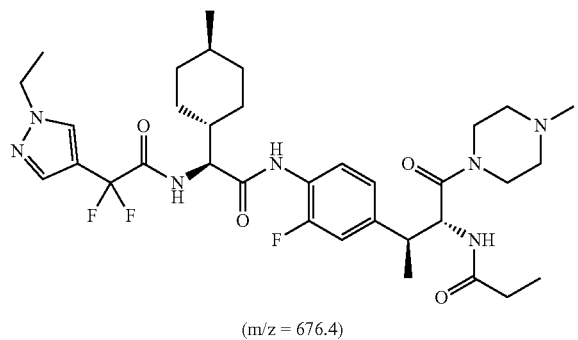
(m/z = 676.4)
524
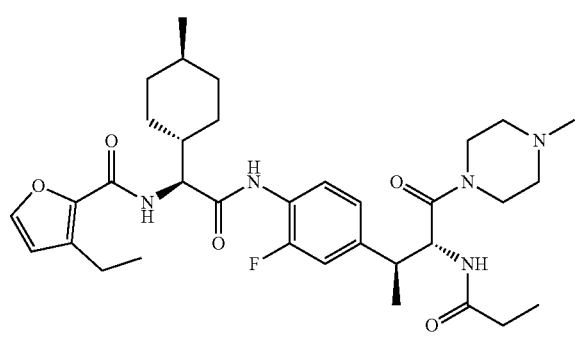
(m/z = 626.4)
-continued
525
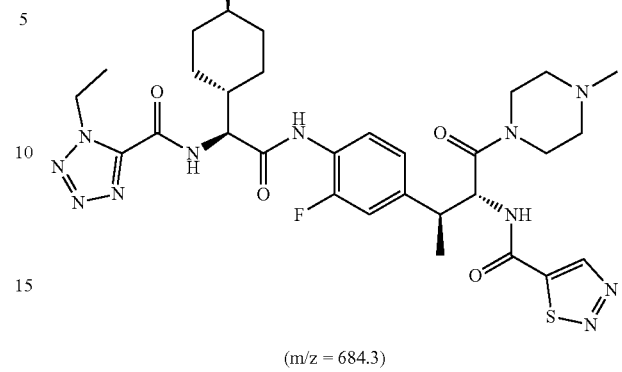
(m/z = 684.3)
526
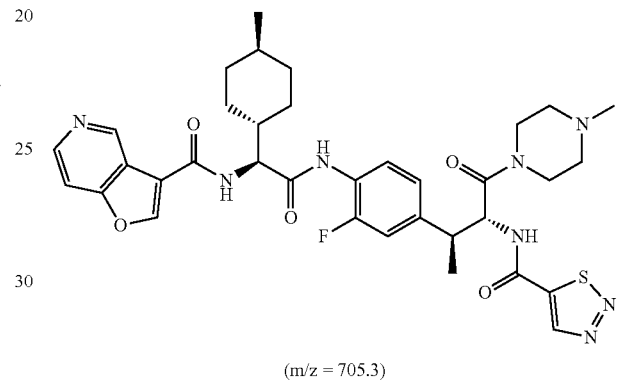
(m/z = 705.3)
Example 38: General Scheme Synthesis of Compounds 527-530
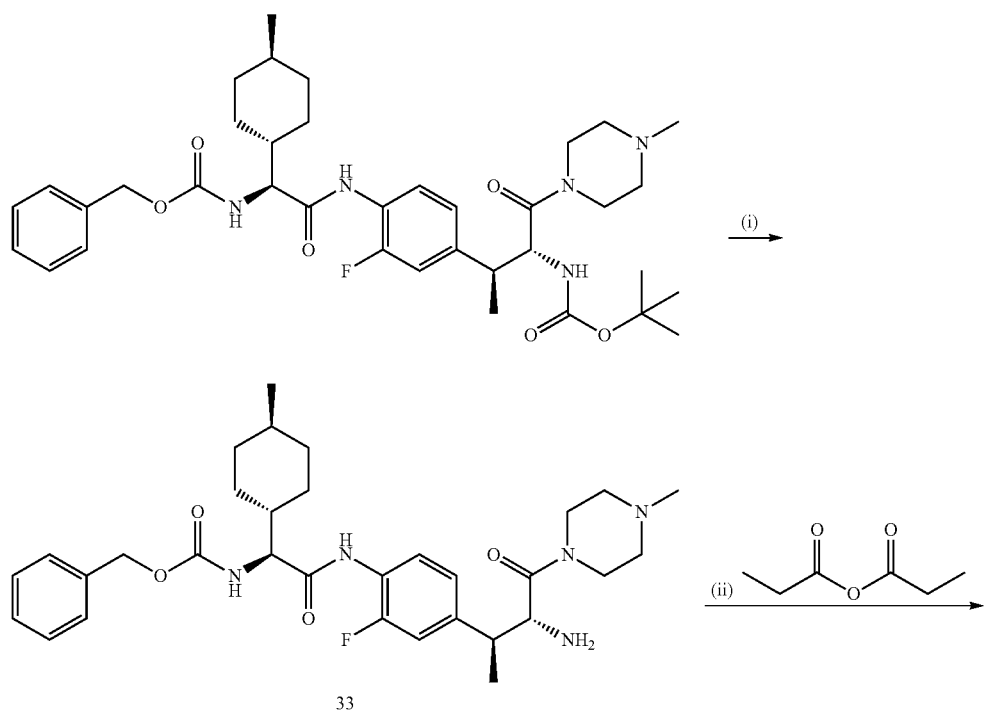

-continued
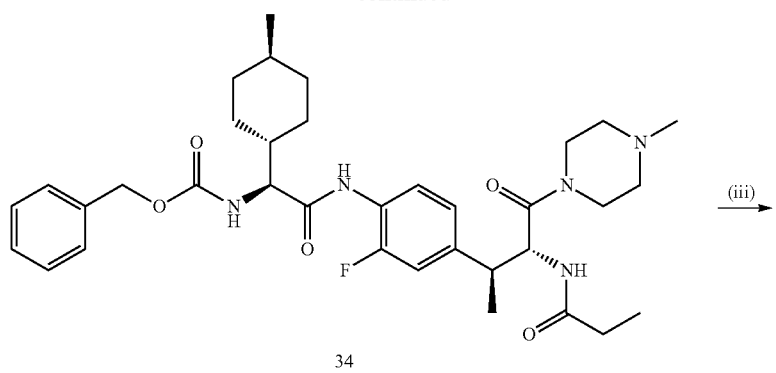
34
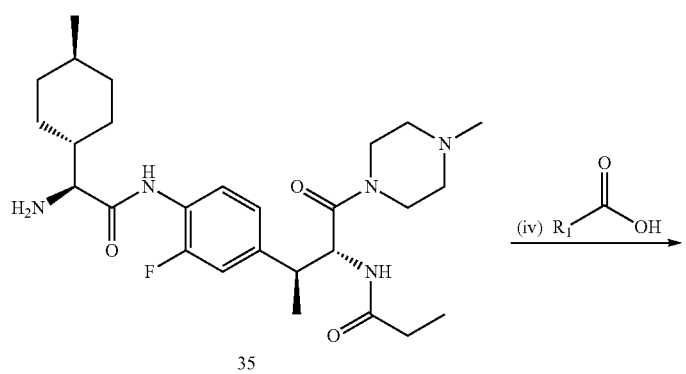
35
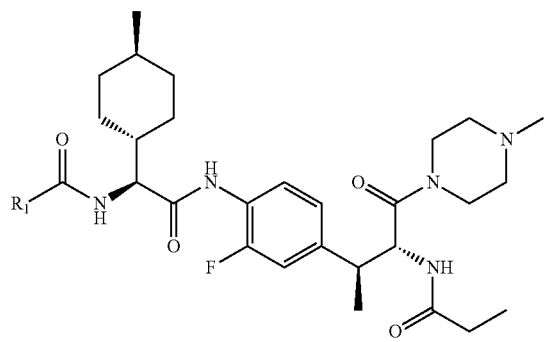
36a-d
527-530
(i) TFA, DCM, RT, 1 h. (ii) propionic anhydride (1.2 eq.), DIPEA (4.0 eq.), RT, 1 h, DMF. (iii) H₂, Pd/C, EtOH, RT, 0.5 h. (iv) carboxylic acid (1.2 eq.), HATU (1.5 eq), DIPEA (6.0 eq.), DMF, RT, 1 h.

227
528
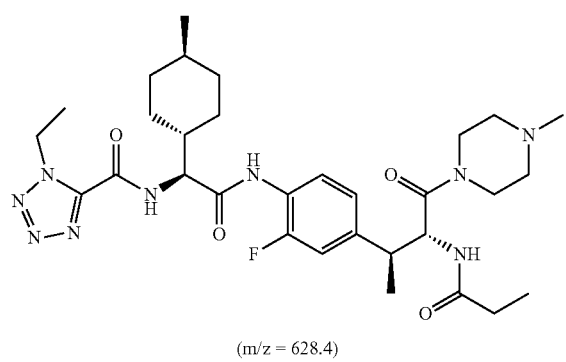
(m/z = 628.4)
529
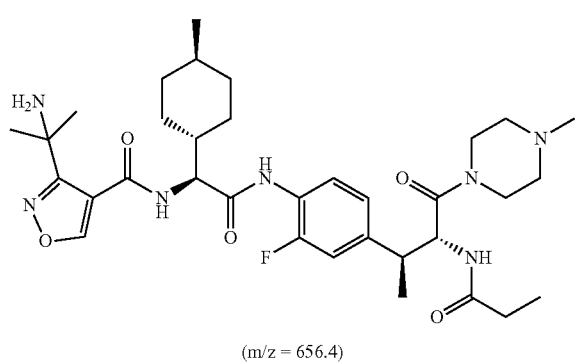
(m/z = 656.4)
299
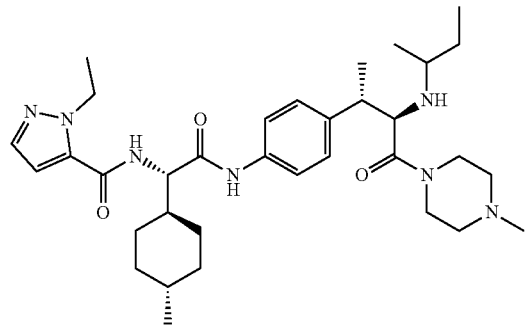
(m/z = 608.5)
347
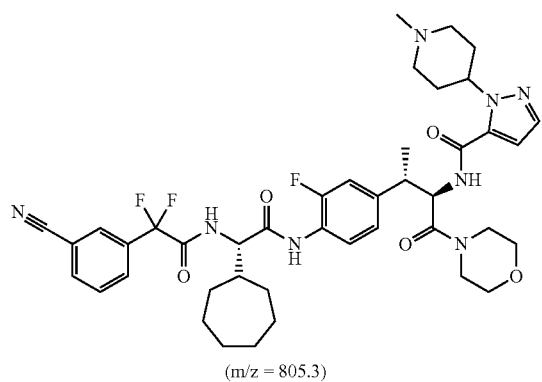
(m/z = 805.3)
228
-continued
530
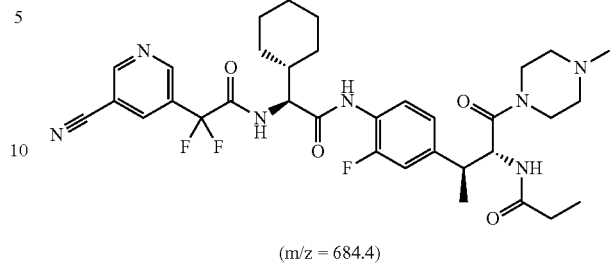
(m/z = 684.4)
Example 39: Synthesis of Compounds 299, 301, 347, 380, 381, 395, and 535-823
The compounds shown below were synthesized using analogous methods and procedures as previously described herein. * Denotes a stereocenter with an undetermined absolute stereochemistry of a single diastereomer.
301
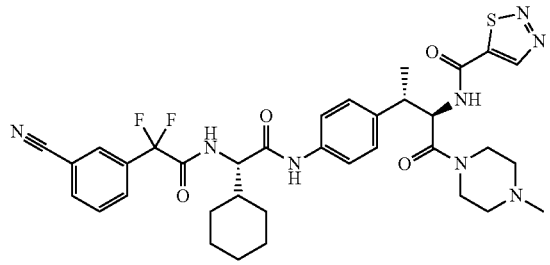
(m/z = 707.4)
380
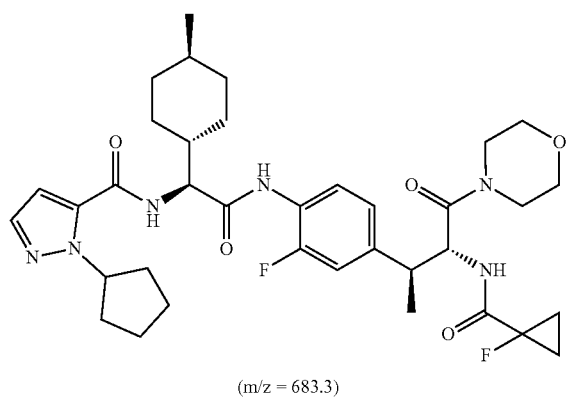
(m/z = 683.3)

-continued
381
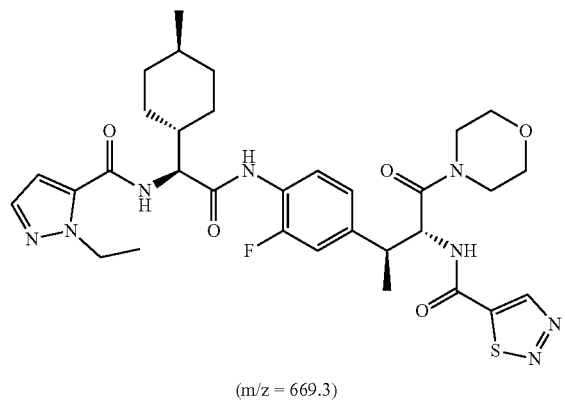
(m/z = 669.3)
535
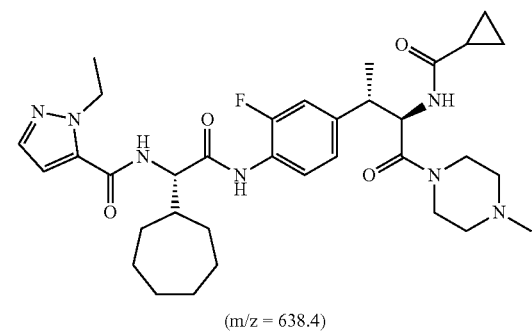
(m/z = 638.4)
536
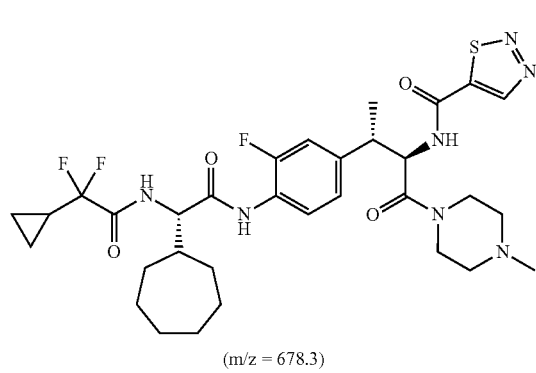
(m/z = 678.3)
537
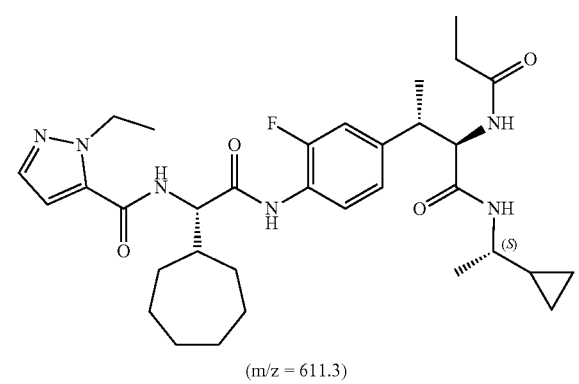
(m/z = 611.3)
538
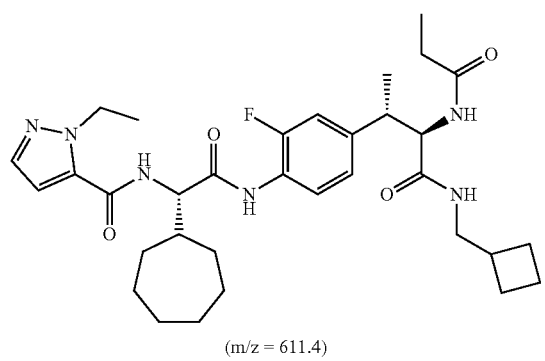
(m/z = 611.4)
539
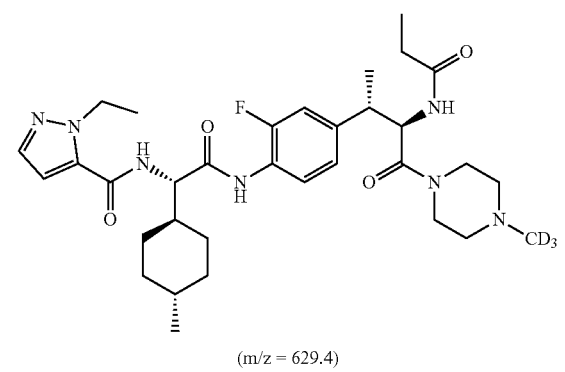
(m/z = 629.4)
540
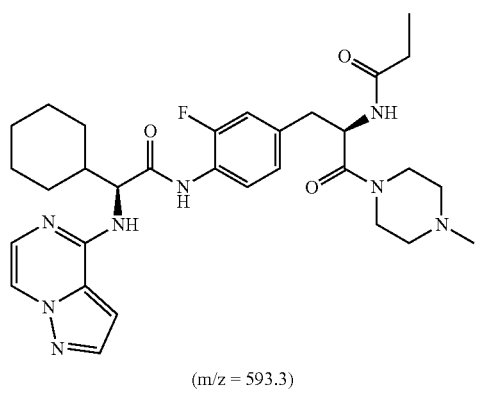
(m/z = 593.3)
541
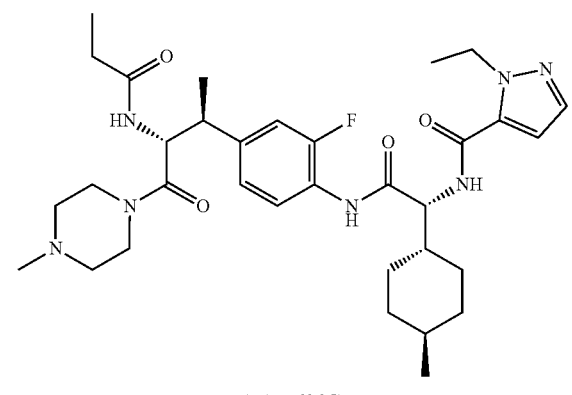
(m/z = 626.5)

-continued
542
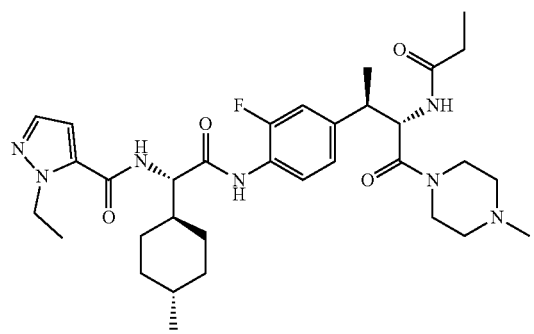
(m/z = 626.6)
543
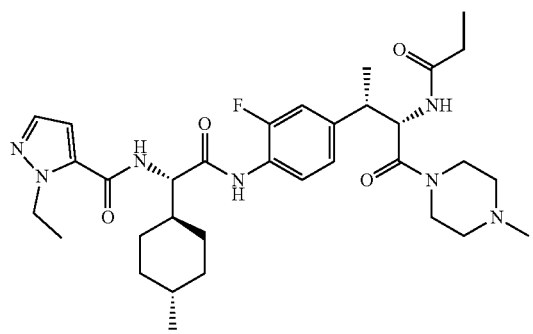
(m/z = 626.6)
544
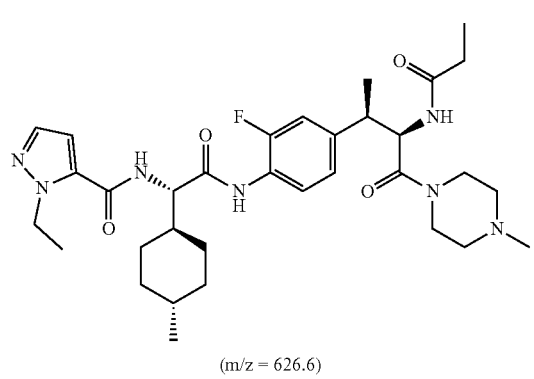
(m/z = 626.6)
545
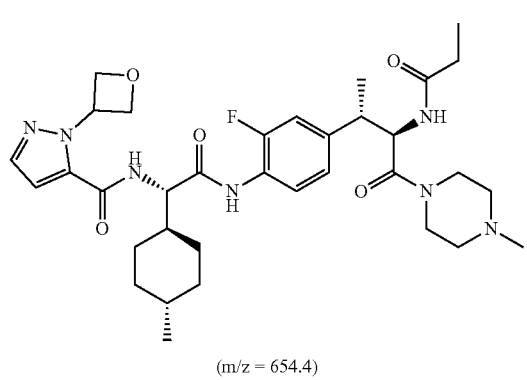
(m/z = 654.4)
546
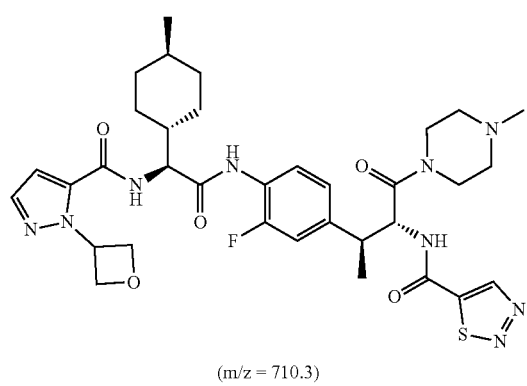
(m/z = 710.3)
547
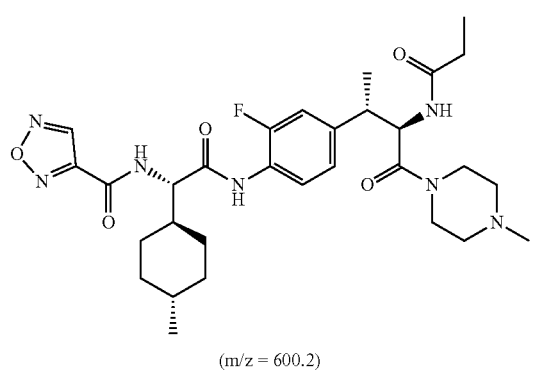
(m/z = 600.2)
548
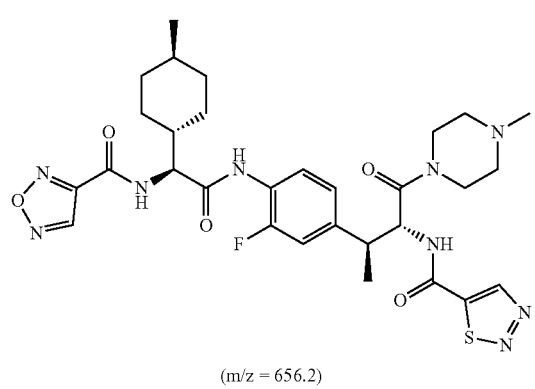
(m/z = 656.2)
549
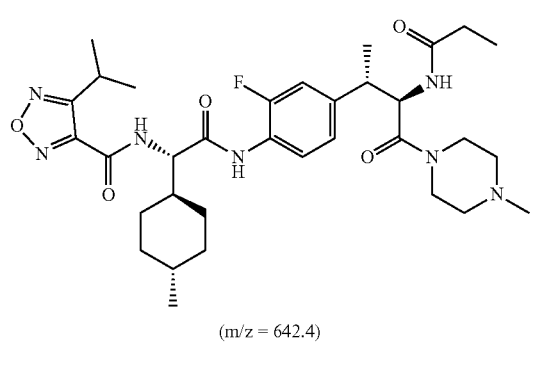
(m/z = 642.4)

-continued
550
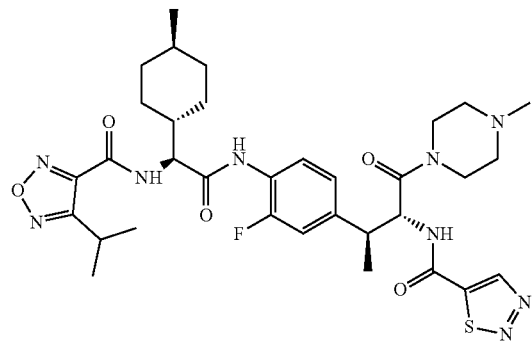
(m/z = 698.4)
551
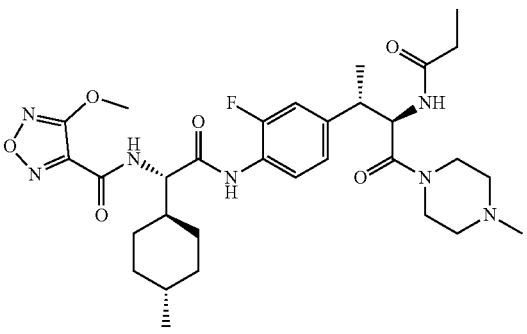
(m/z = 630.2)
552
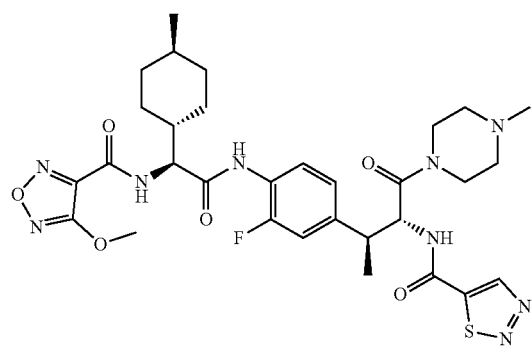
(m/z = 686.3)
553
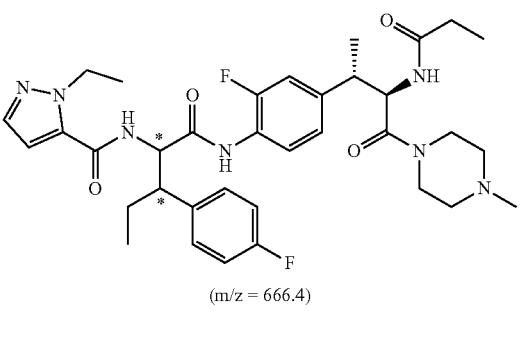
(m/z = 666.4)
554
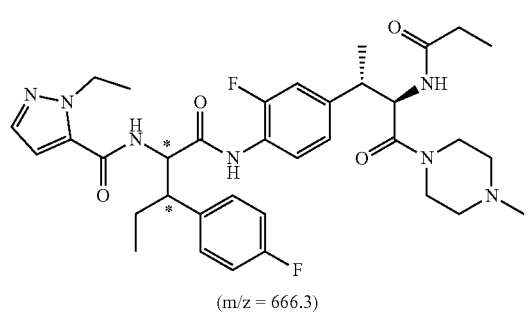
(m/z = 666.3)
555
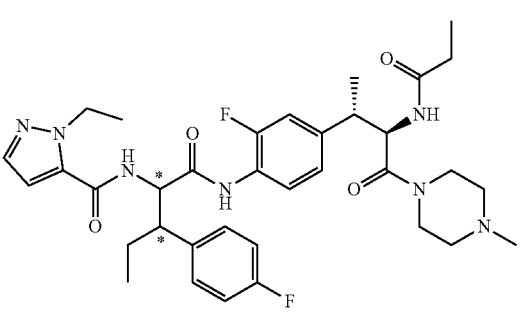
(m/z = 666.5)
556
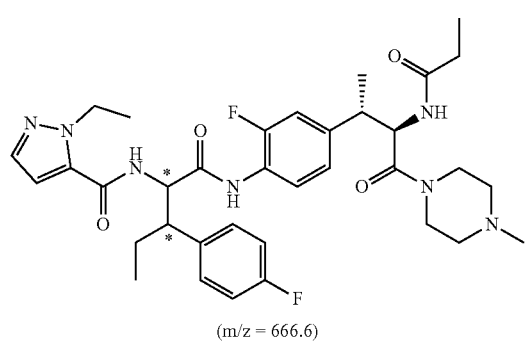
(m/z = 666.6)
557
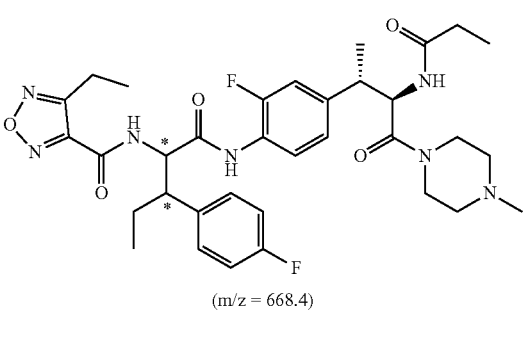
(m/z = 668.4)

-continued
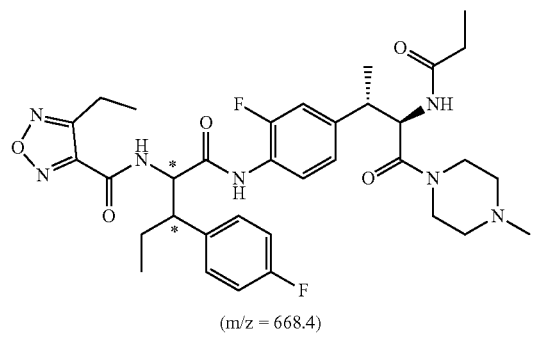
558
(m/z = 668.4)
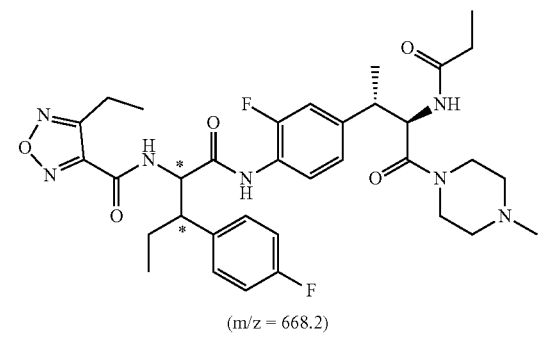
559
(m/z = 668.2)
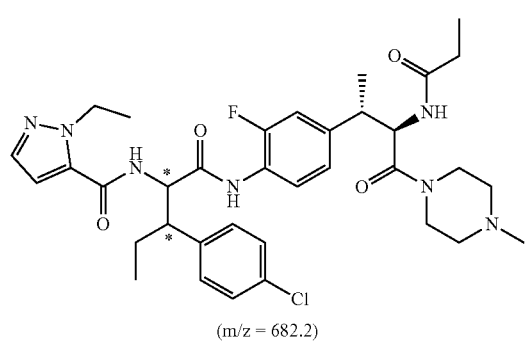
560
(m/z = 682.2)
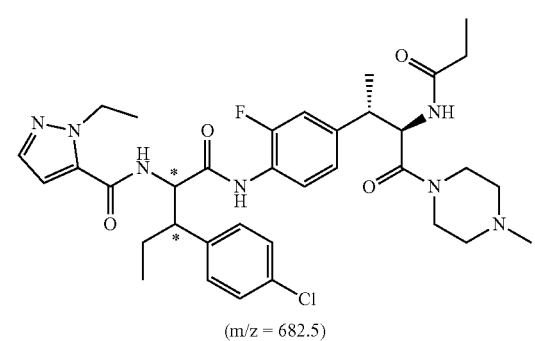
561
(m/z = 682.5)
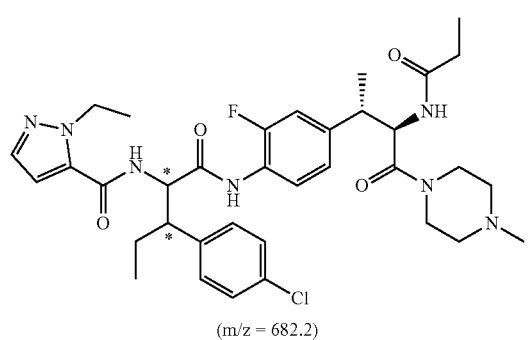
562
(m/z = 682.2)
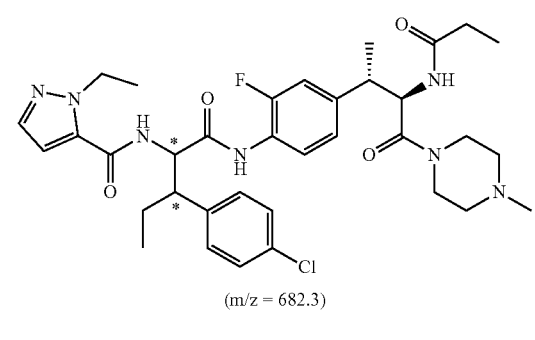
563
(m/z = 682.3)
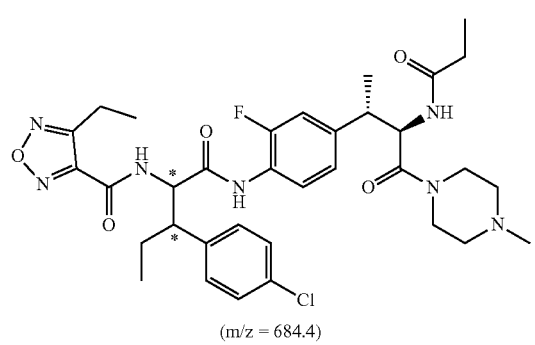
564
(m/z = 684.4)
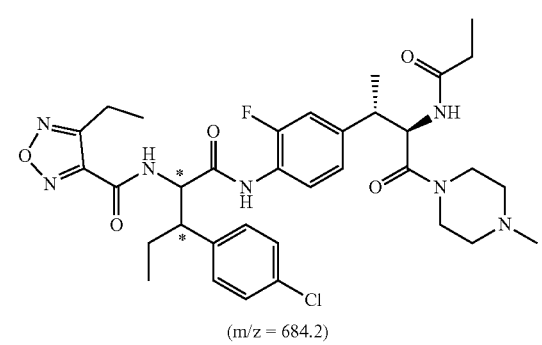
565
(m/z = 684.2)

-continued
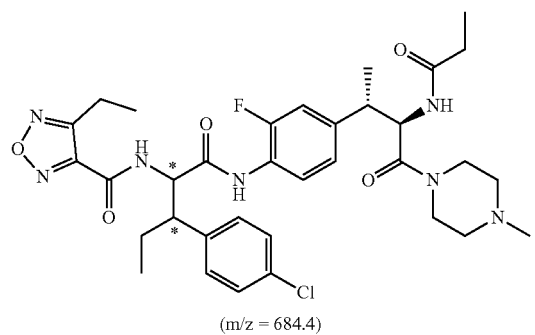
566
(m/z = 684.4)
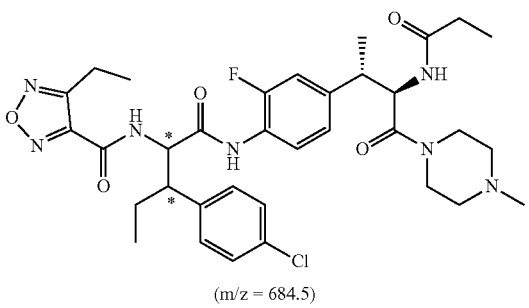
567
(m/z = 684.5)
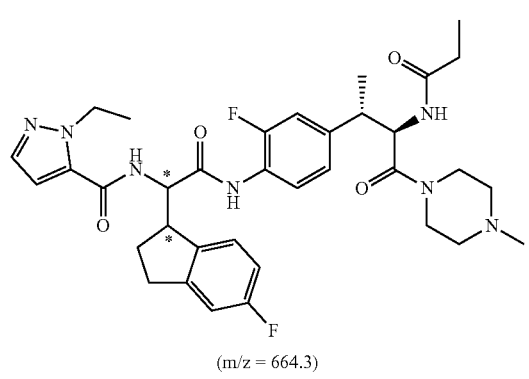
568
(m/z = 664.3)
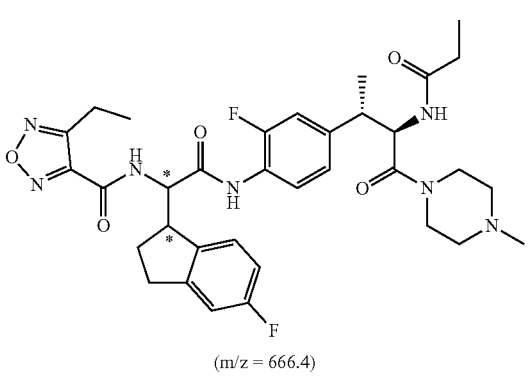
569
(m/z = 666.4)
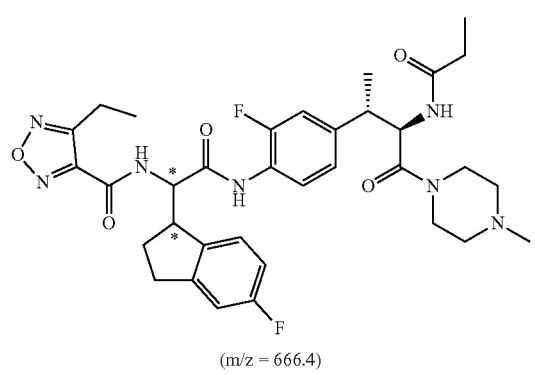
570
(m/z = 666.4)
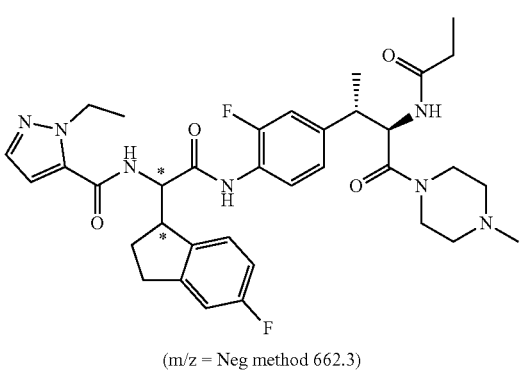
571
(m/z = Neg method 662.3)
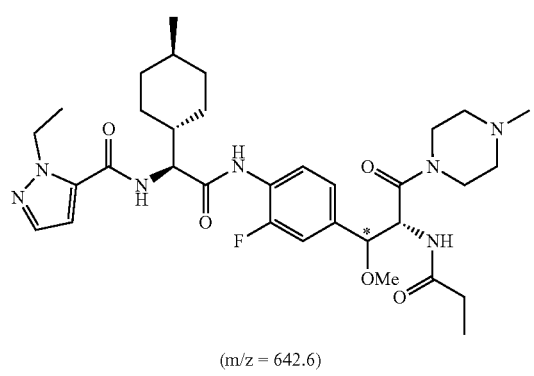
572
(m/z = 642.6)
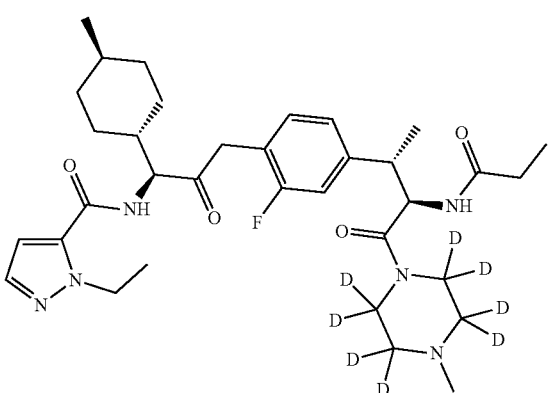
573
(m/z = 634.5)

574
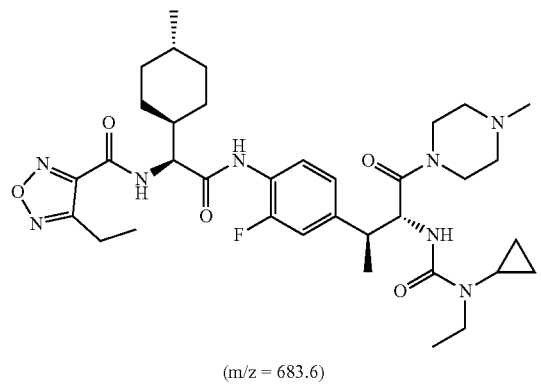
(m/z = 683.6)
575
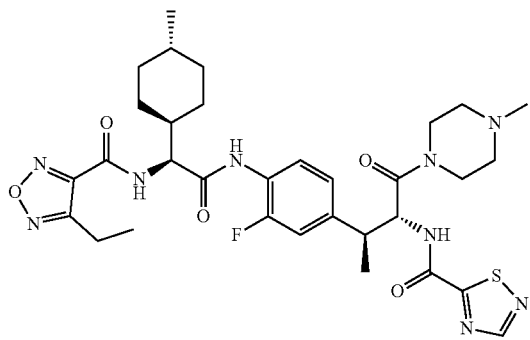
(m/z = 684.5)
576
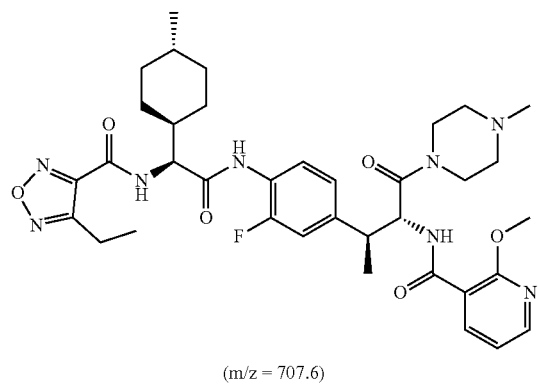
(m/z = 707.6)
577
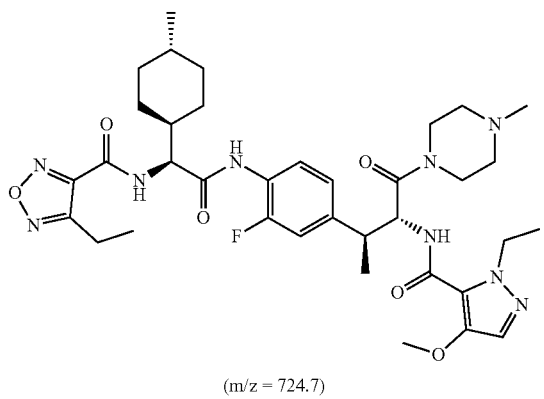
(m/z = 724.7)
578
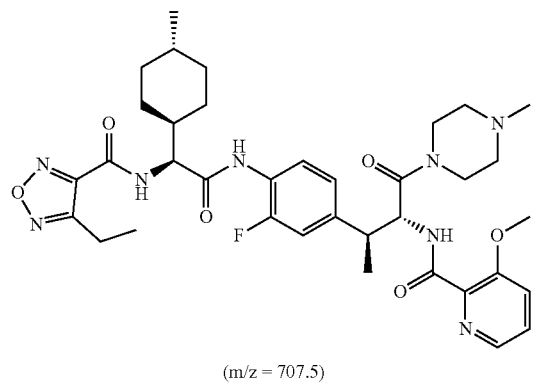
(m/z = 707.5)
579
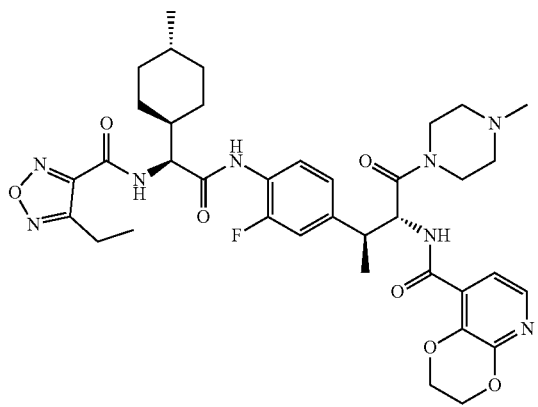
(m/z = 735.5)
580
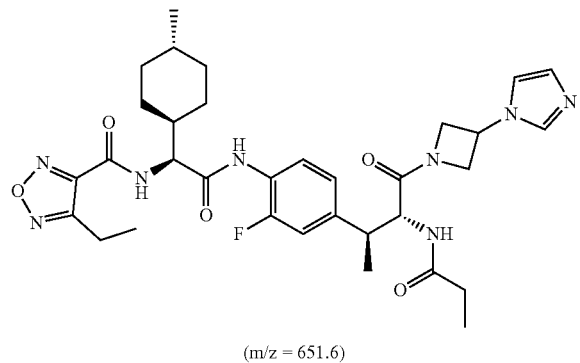
(m/z = 651.6)
581
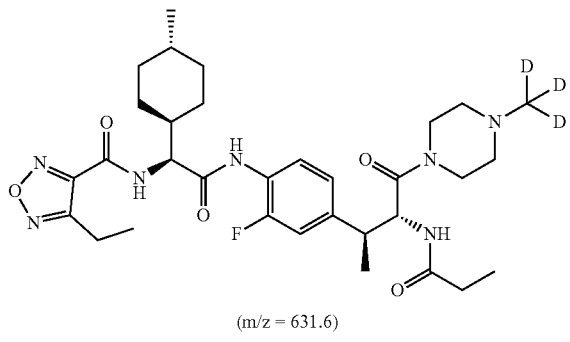
(m/z = 631.6)

582
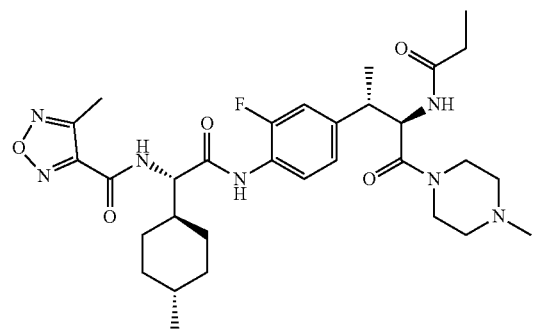
(m/z = 614.2)
583
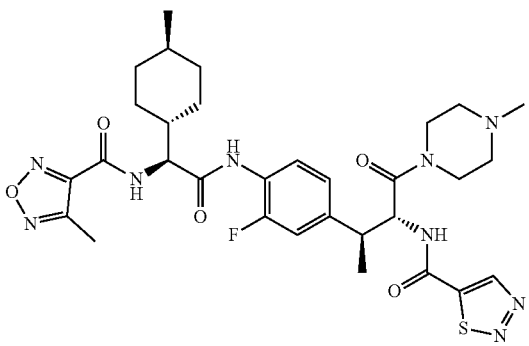
(M/Z = 670.3)
584
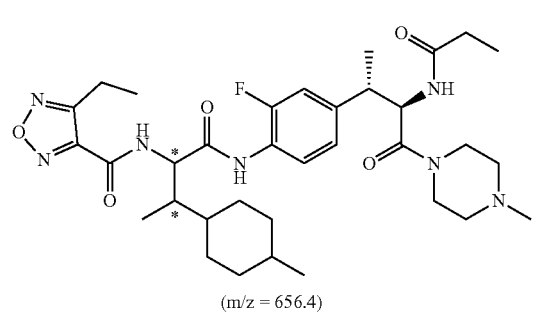
(m/z = 656.4)
585
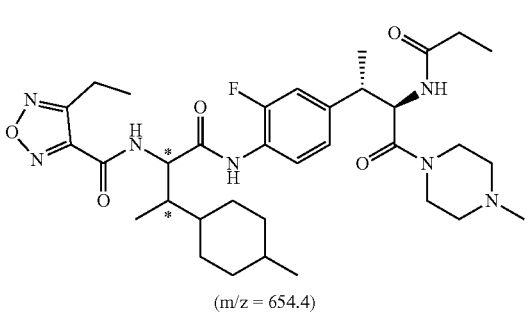
(m/z = 654.4)
586
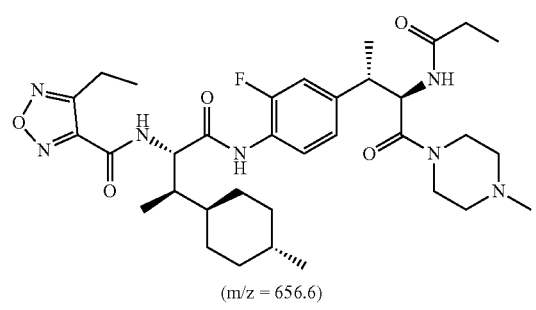
(m/z = 656.6)
587
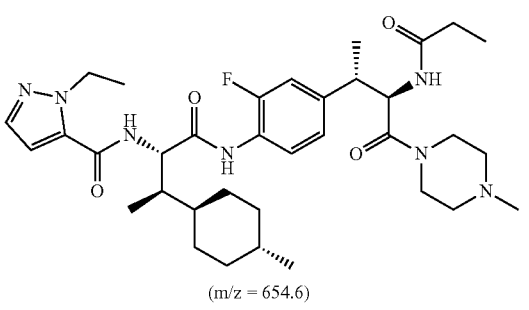
(m/z = 654.6)
588
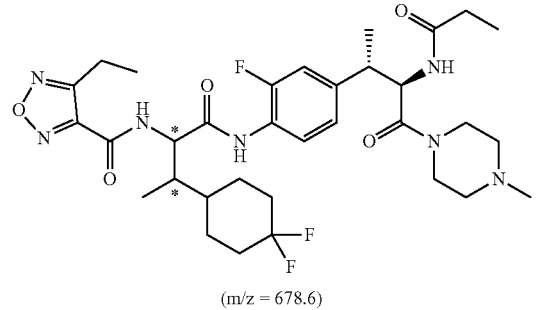
(m/z = 678.6)
589
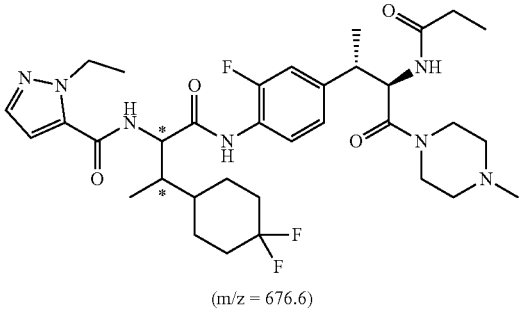
(m/z = 676.6)
590
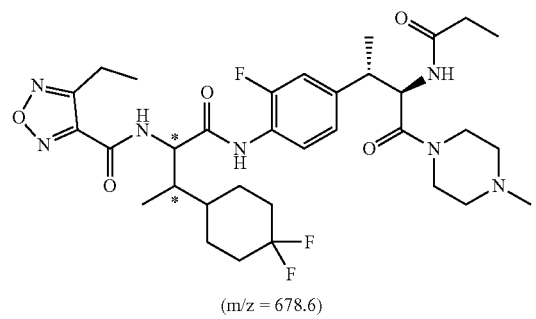
(m/z = 678.6)
591
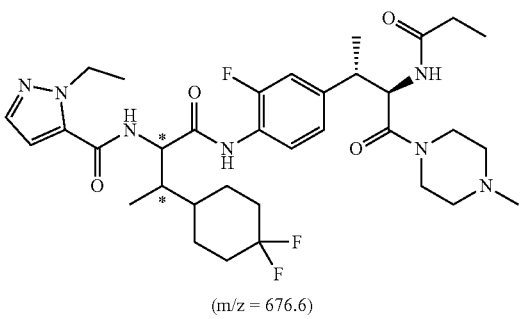
(m/z = 676.6)

-continued
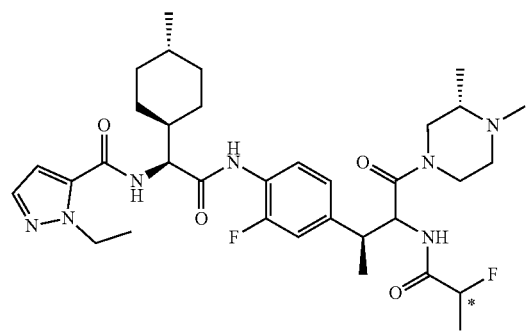
592
(m/z = 658.3)
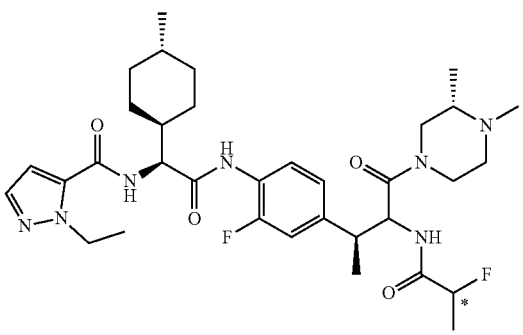
593
(m/z = 658.4)
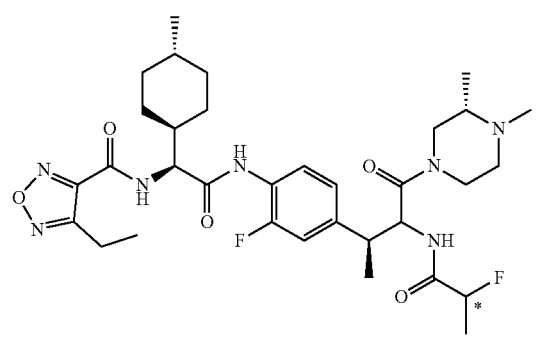
594
(m/z = 600.4)
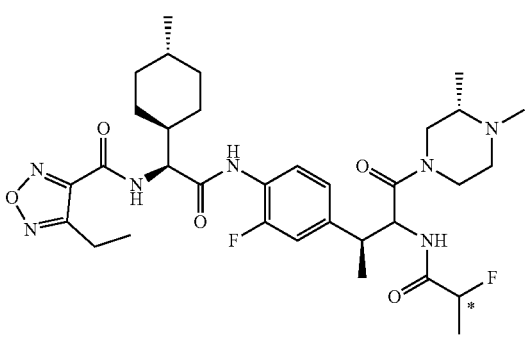
595
(m/z = 600.2)
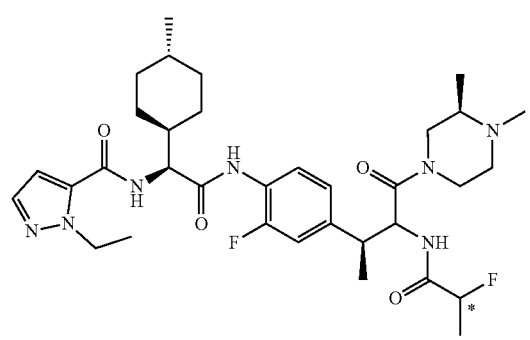
596
(m/z = 658.2)
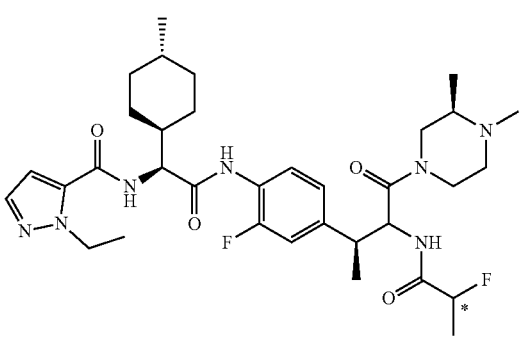
597
(m/z = 658.4)
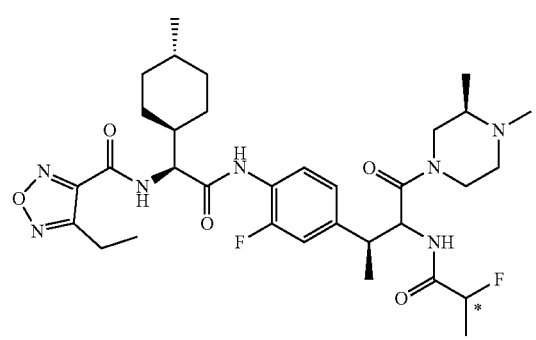
598
(m/z = 660.4)
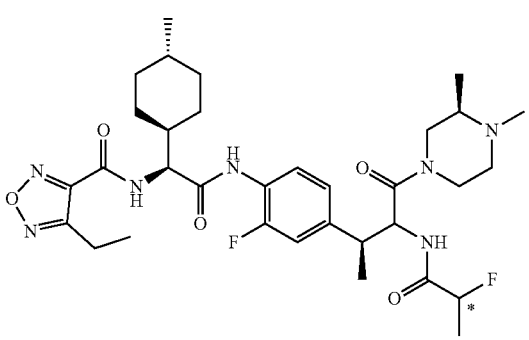
599
(m/z = 660.4)

600
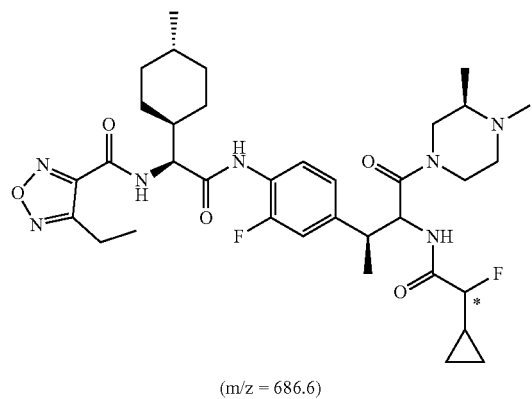
(m/z = 686.6)
601
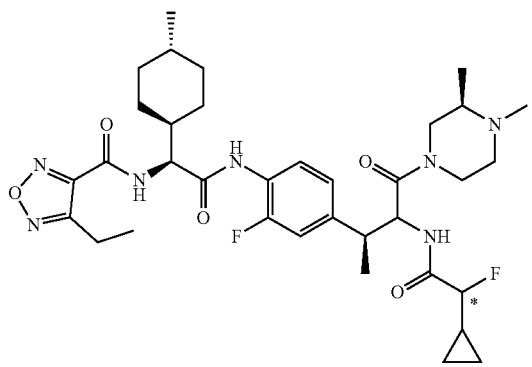
(m/z = 686.6)
602
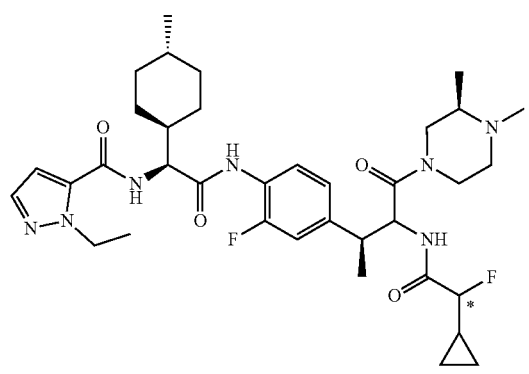
(m/z = 684.5)
603
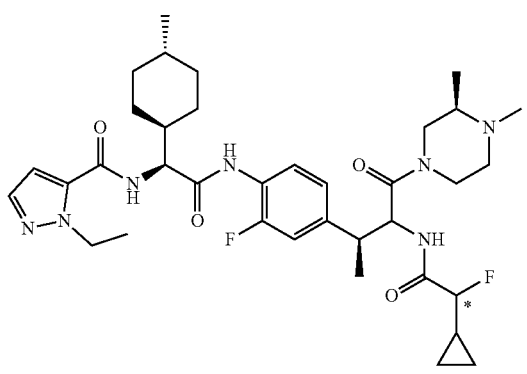
(m/z = 684.6)
604
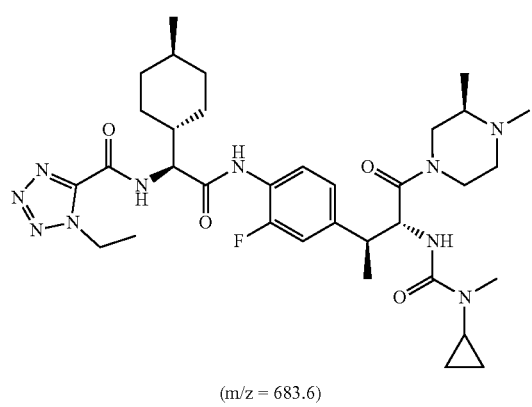
(m/z = 683.6)
605
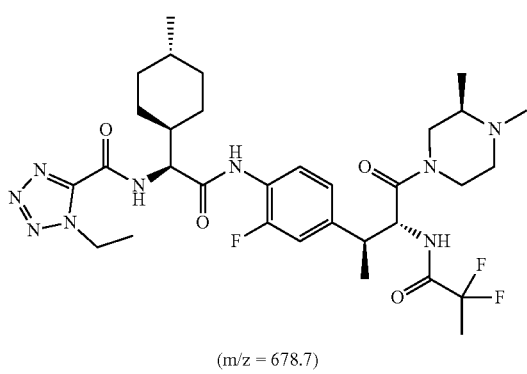
(m/z = 678.7)
606
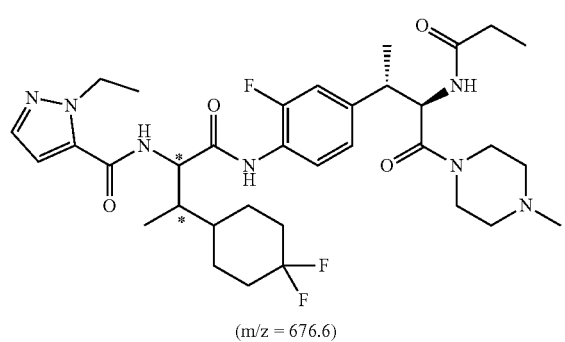
(m/z = 676.6)
607
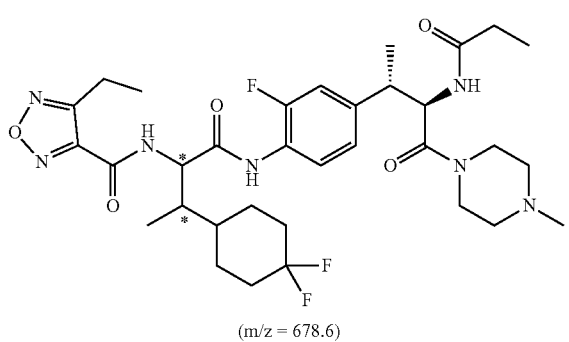
(m/z = 678.6)

-continued
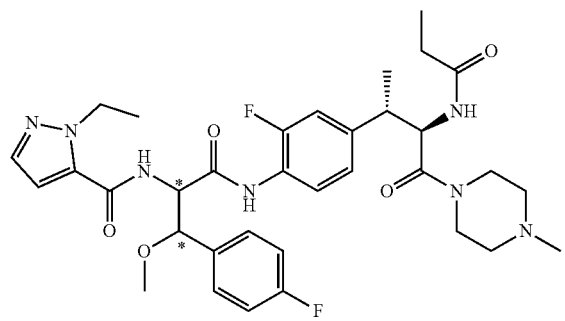
608
(m/z = 668.4)
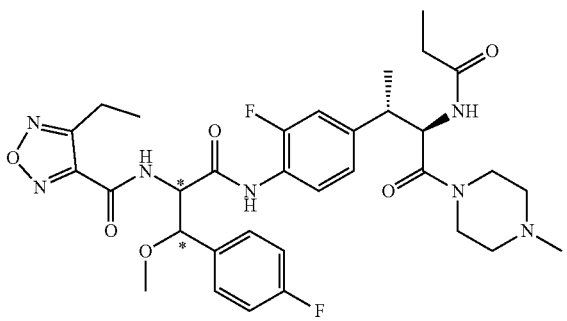
609
(m/z = 670.4)
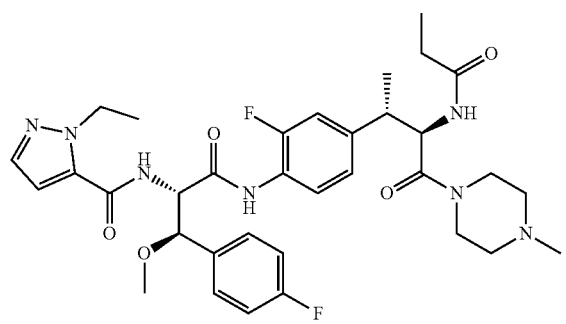
610
(m/z = 668.5)
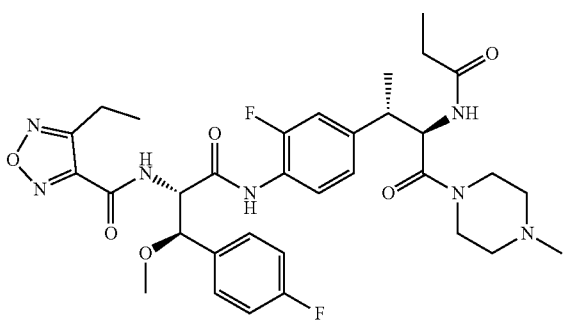
611
(m/z = 670.5)
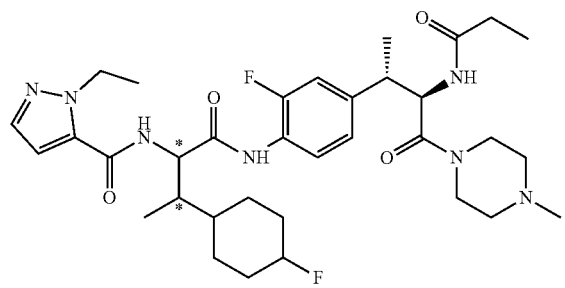
612
(m/z = 654.7)
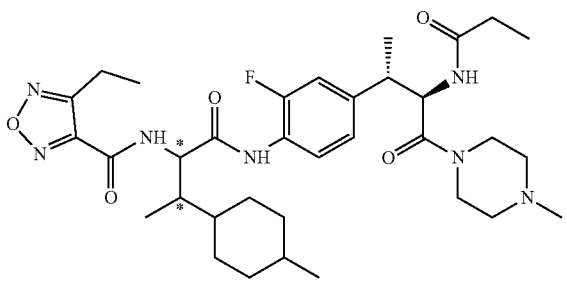
613
(m/z = 656.4)
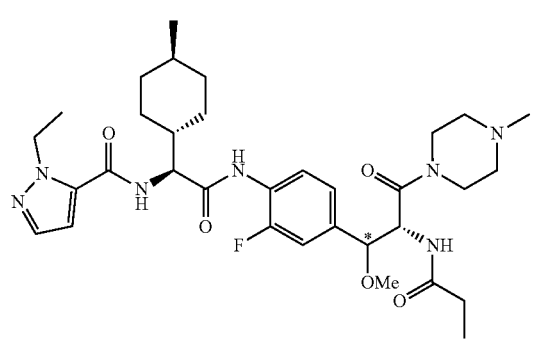
614
(m/z = 642.6)
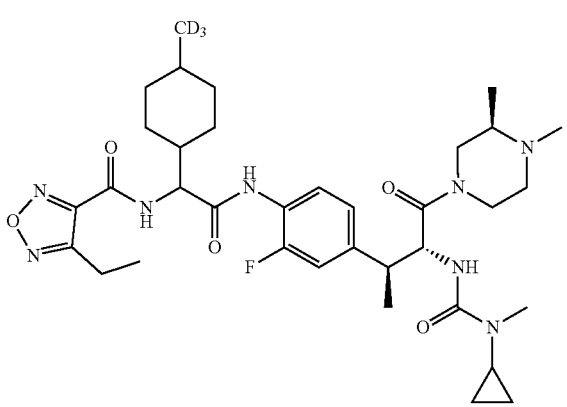
615
(m/z = 686.5)

-continued
616
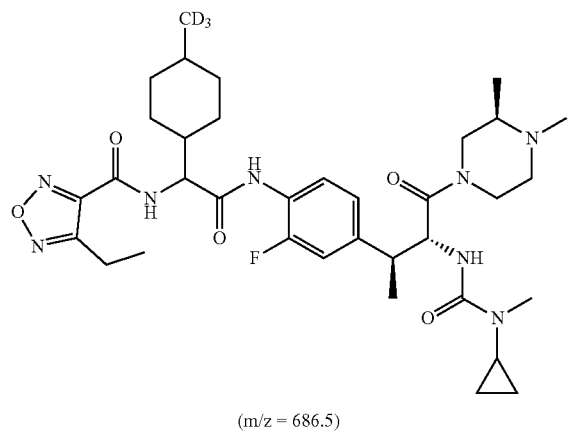
(m/z = 686.5)
617
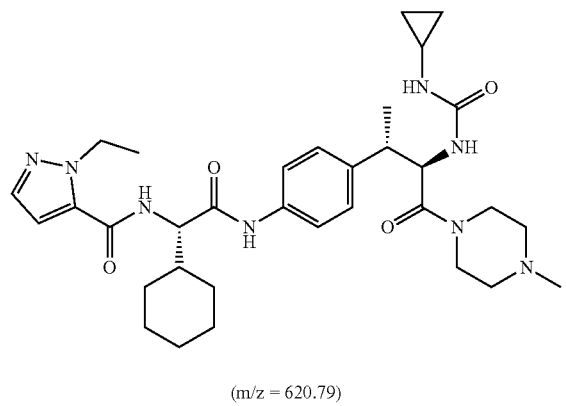
(m/z = 620.79)
620
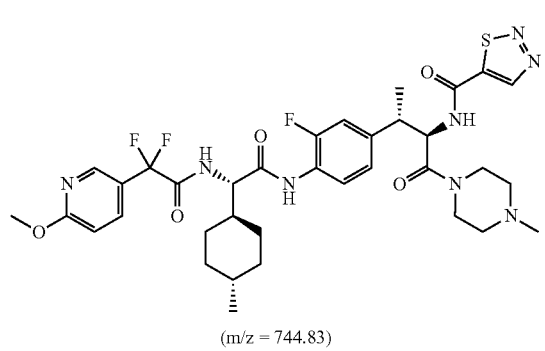
(m/z = 744.83)
621
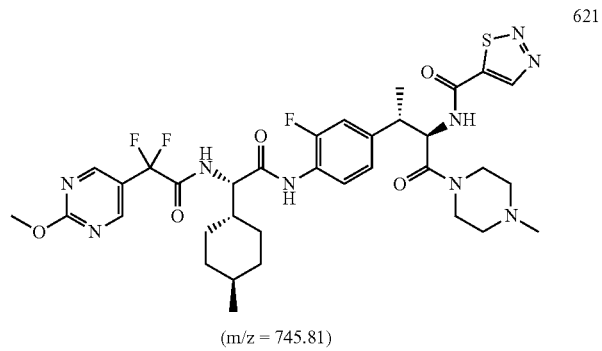
(m/z = 745.81)
622
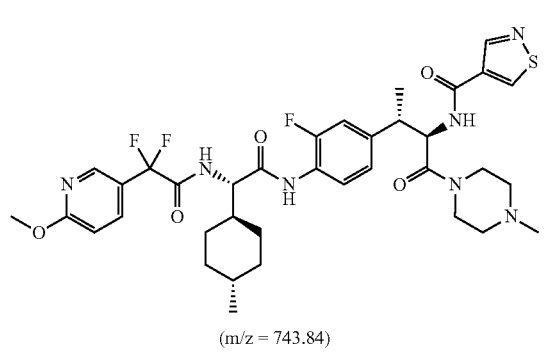
(m/z = 743.84)
623
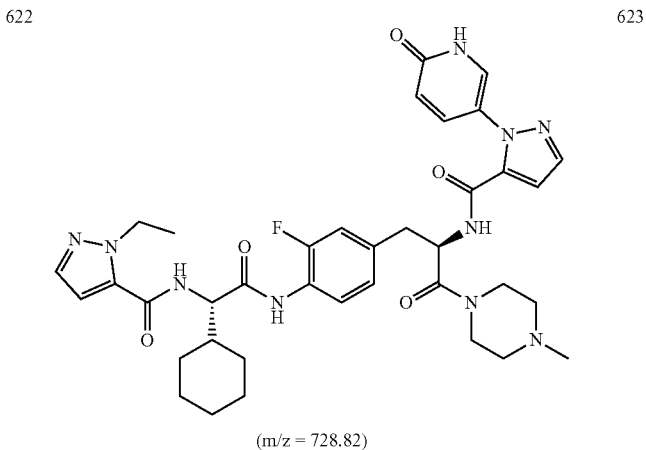
(m/z = 728.82)
624
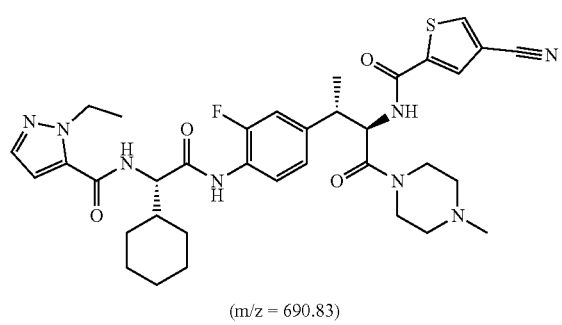
(m/z = 690.83)
625
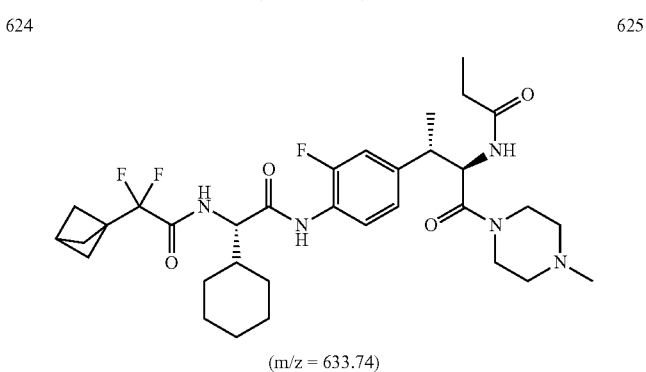
(m/z = 633.74)

-continued
626
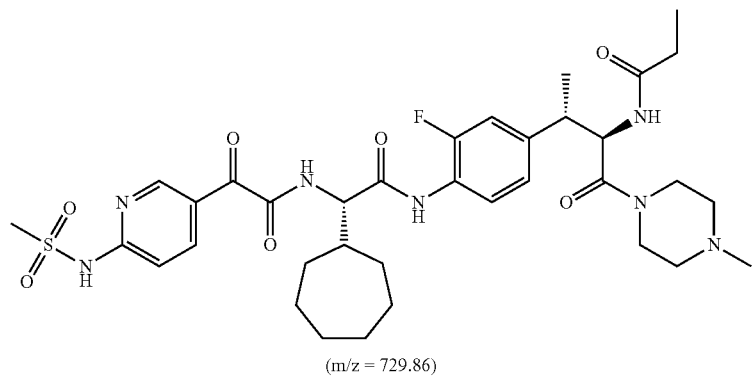
(m/z = 729.86)
627
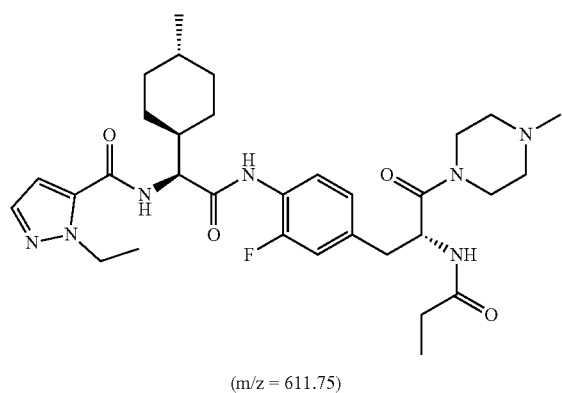
(m/z = 611.75)
628
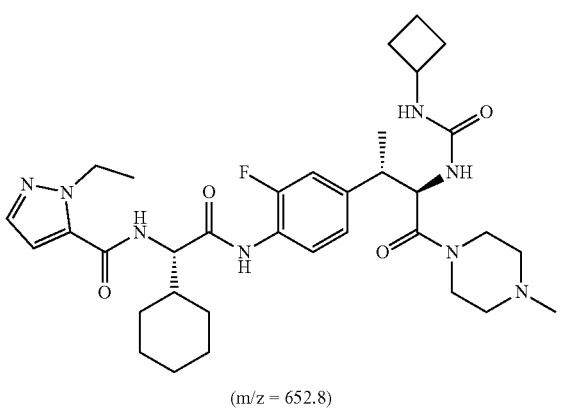
(m/z = 652.8)
629
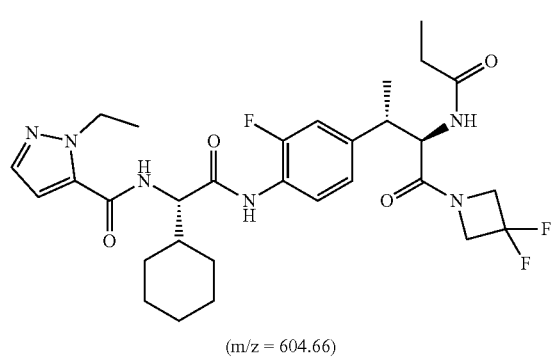
(m/z = 604.66)
630
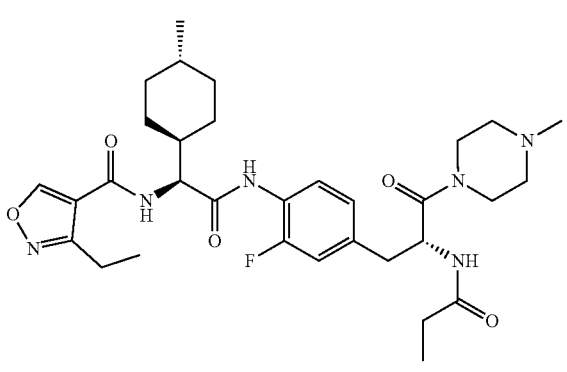
(m/z = 612.74)
631
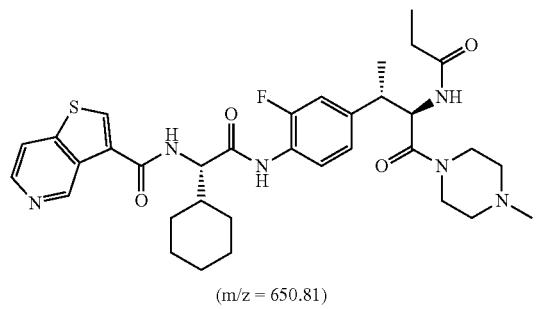
(m/z = 650.81)
632
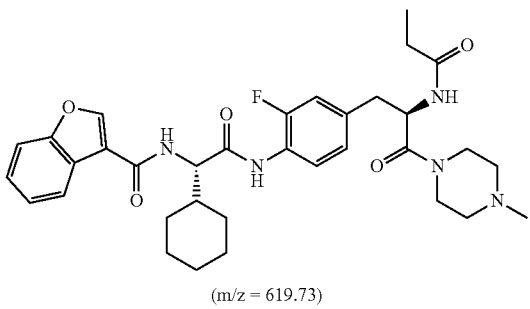
(m/z = 619.73)

| 633 | 634 |
|---|---|
| 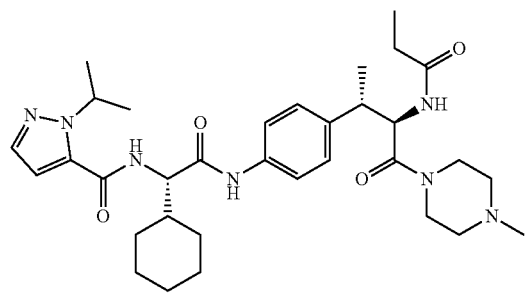 (m/z = 607.79) | 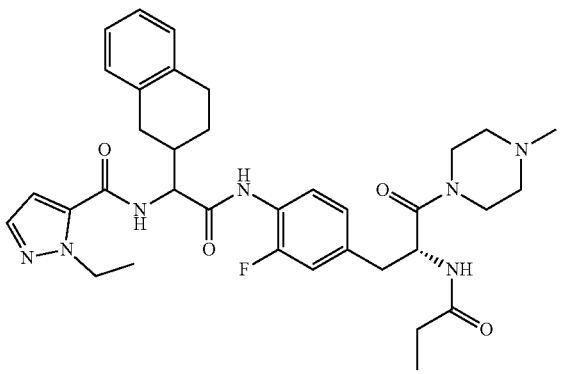 (m/z = 645.77) |
| 635 | 636 |
| 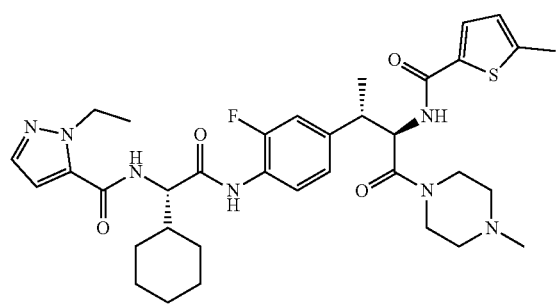 (m/z = 679.85) | 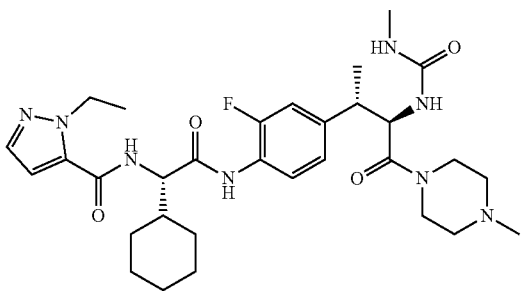 (m/z = 612.74) |
| 637 | 638 |
| 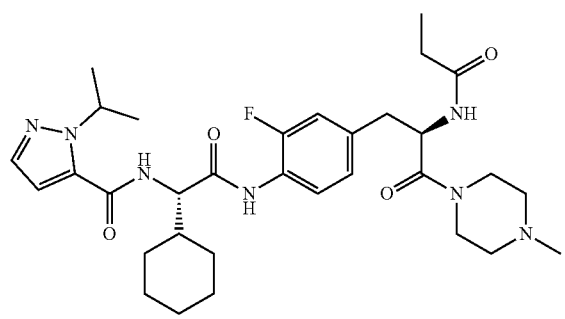 (m/z = 611.75) | 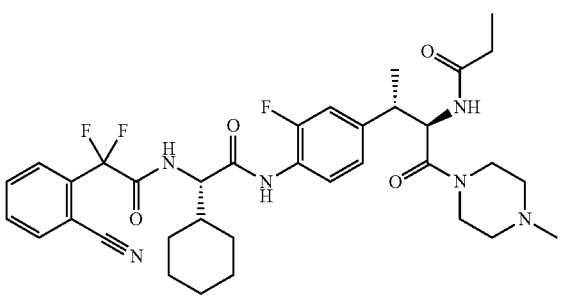 (m/z = 668.75) |
| 639 | 640 |
| 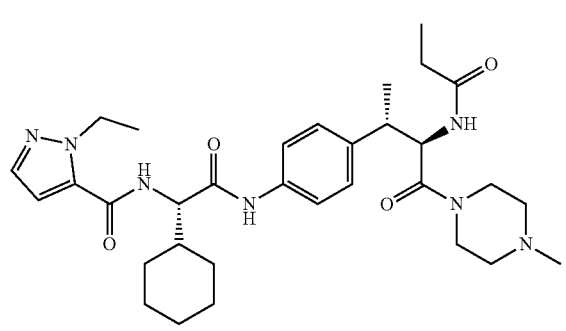 (m/z = 593.76) | 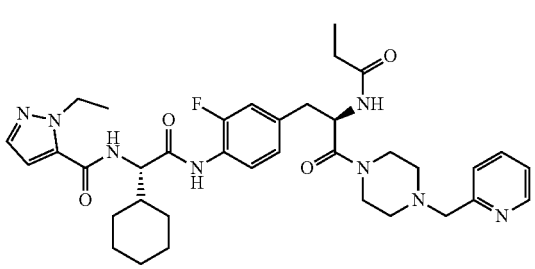 (m/z = 674.81) |

-continued
641
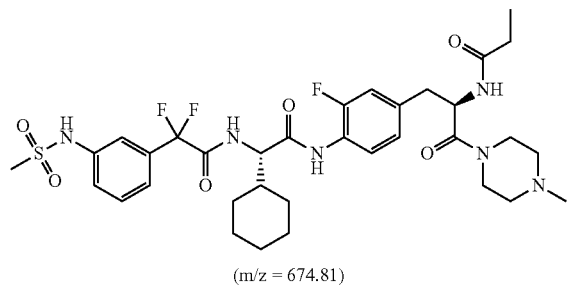
(m/z = 674.81)
642
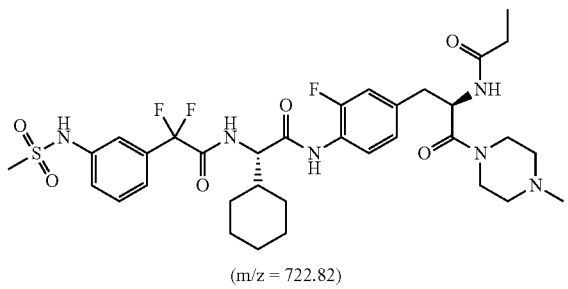
(m/z = 722.82)
643
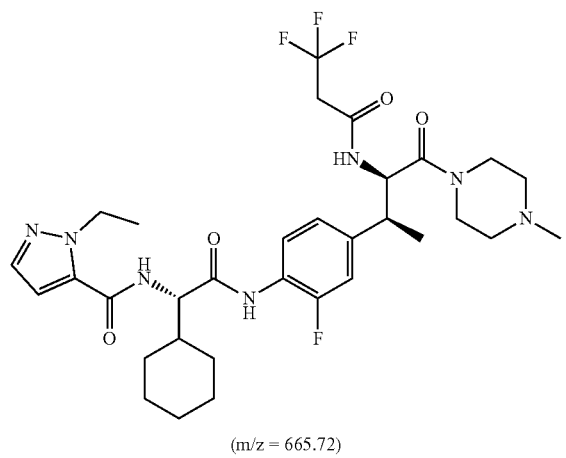
(m/z = 665.72)
644
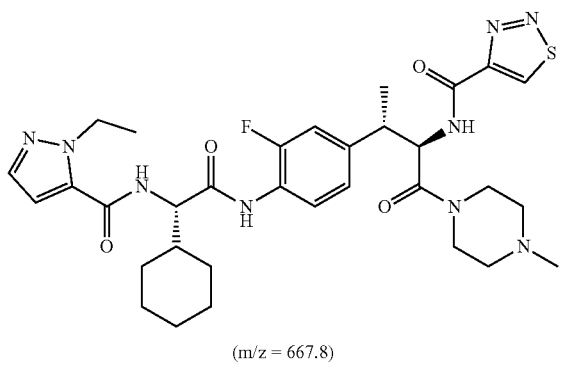
(m/z = 667.8)
645
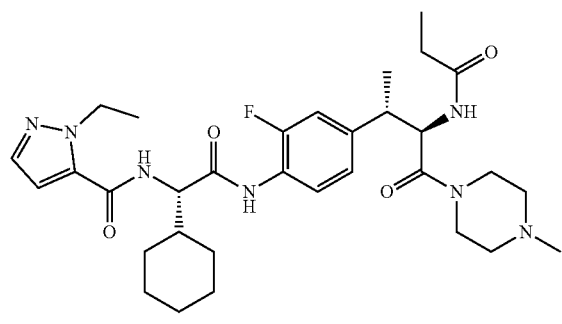
(m/z = 597.72)
646
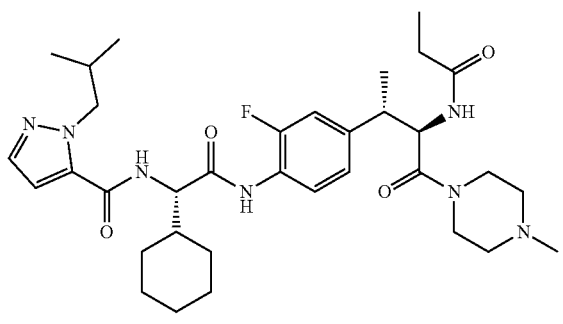
(m/z = 625.78)
647
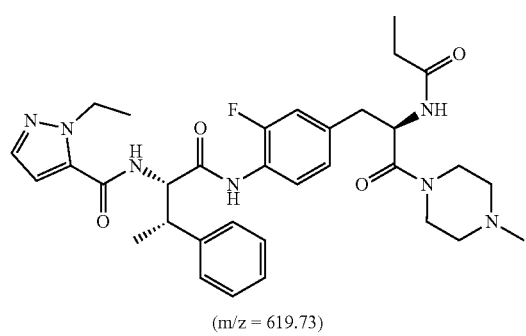
(m/z = 619.73)
648
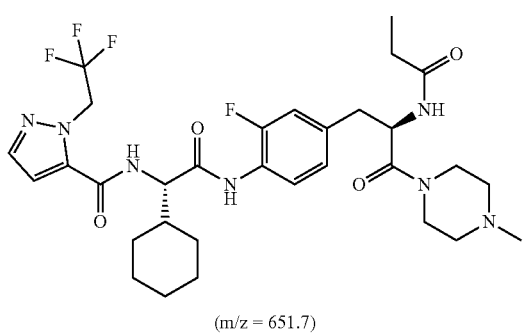
(m/z = 651.7)

-continued
649
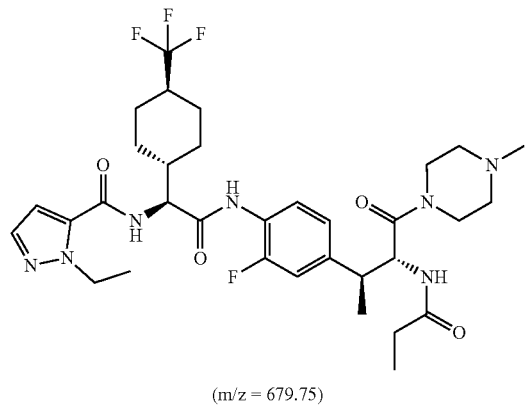
(m/z = 679.75)
650
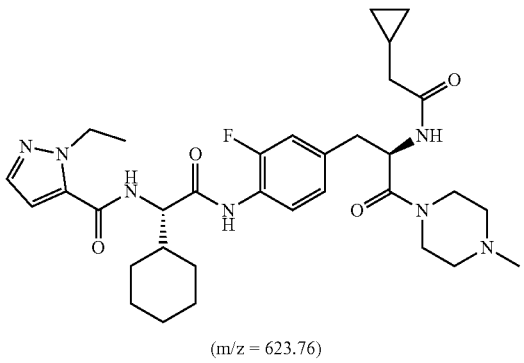
(m/z = 623.76)
651
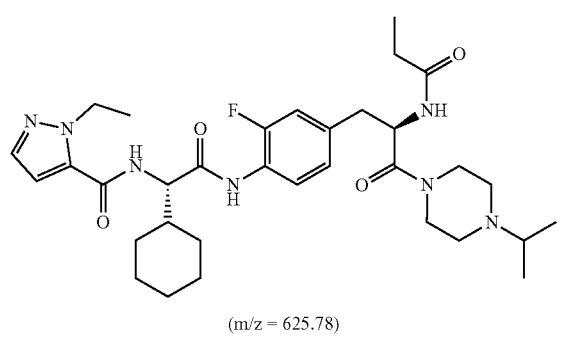
(m/z = 625.78)
652
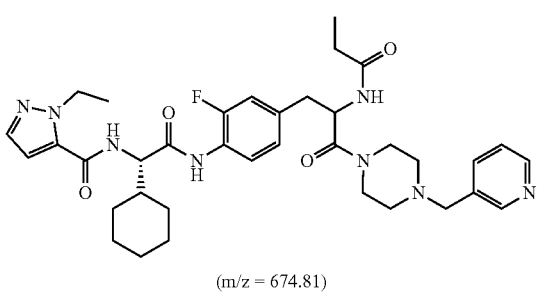
(m/z = 674.81)
653
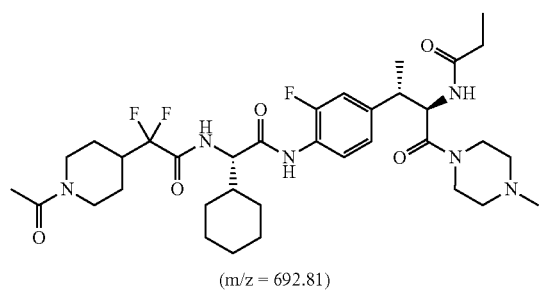
(m/z = 692.81)
654
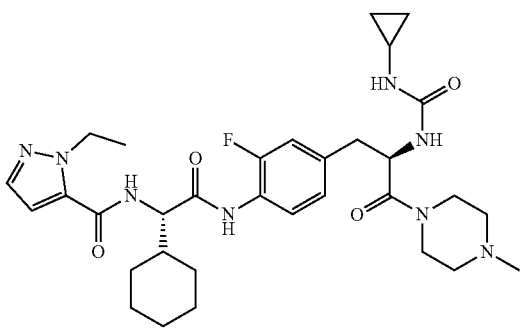
(m/z = 624.75)
655
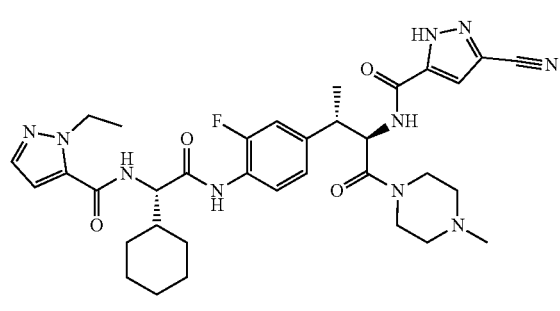
(m/z = 674.77)
656
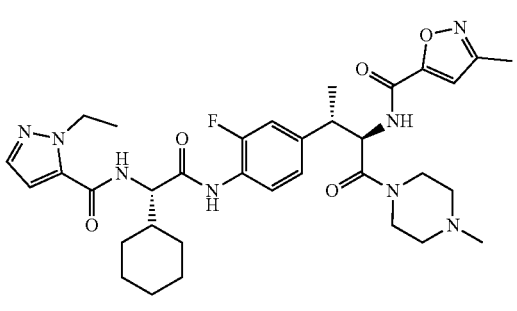
(m/z = 664.77)

259                                                                 260
-continued
657
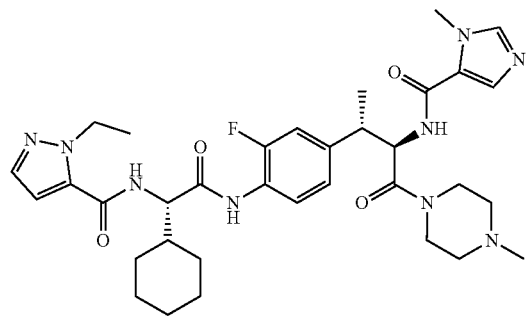
(m/z = 663.79)
658
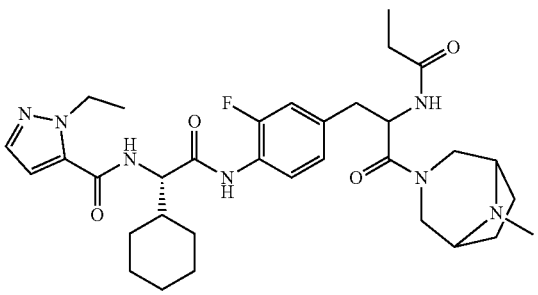
(m/z = 623.76)
659
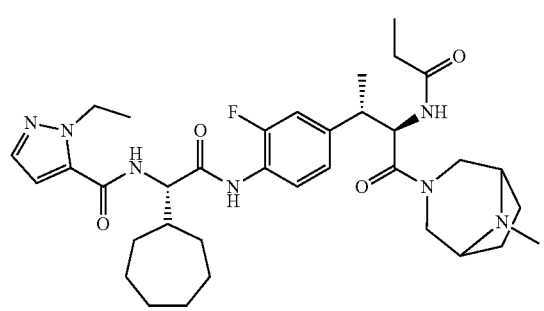
(m/z = 651.81)
660
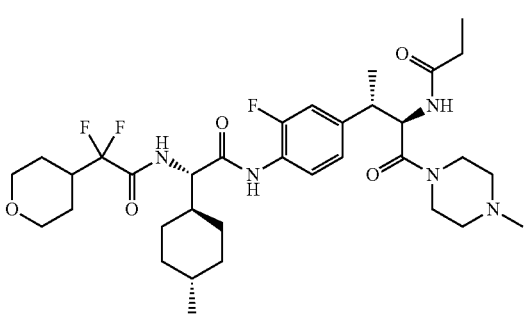
(m/z = 665.79)
661
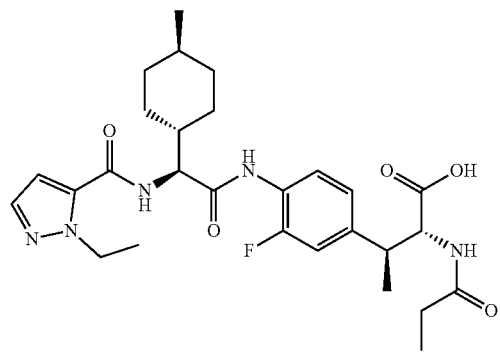
(m/z = 543.63)
662
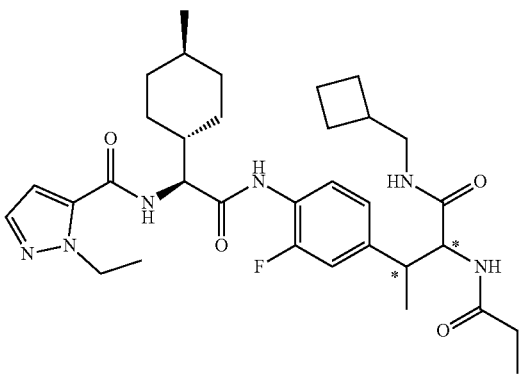
(m/z = 610.76)
663
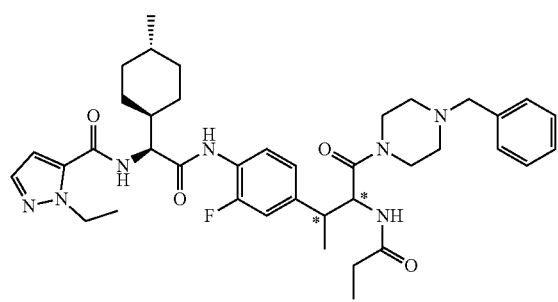
(m/z = 701.87)
664
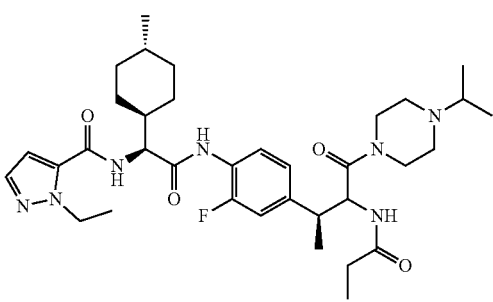
(m/z = 653.83)

-continued
665
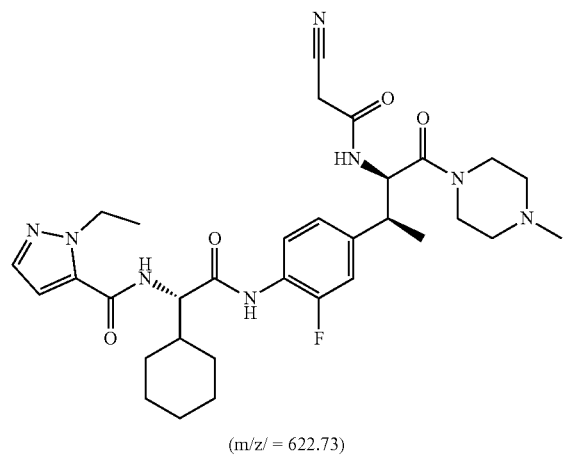
(m/z/ = 622.73)
666
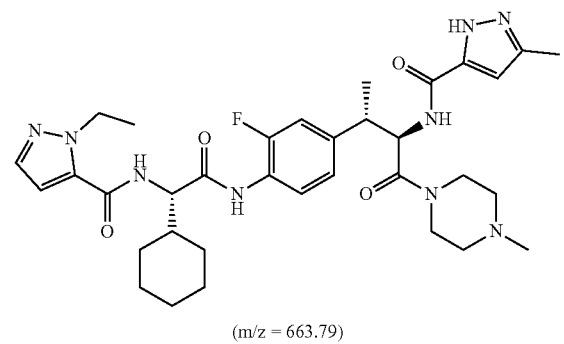
(m/z = 663.79)
667
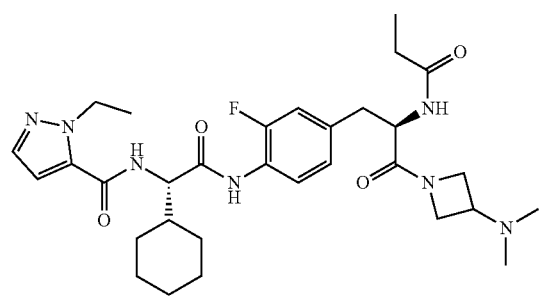
(m/z = 597.72)
669
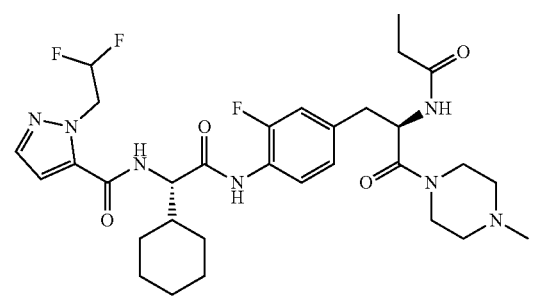
(m/z = 633.7)
670
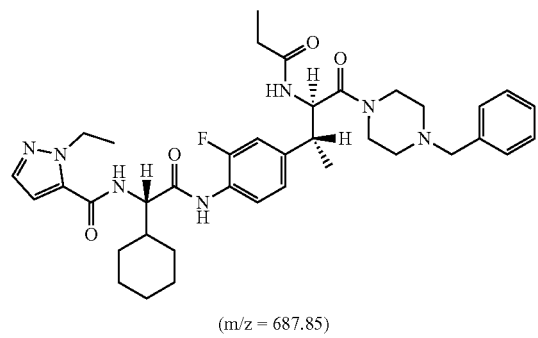
(m/z = 687.85)
671
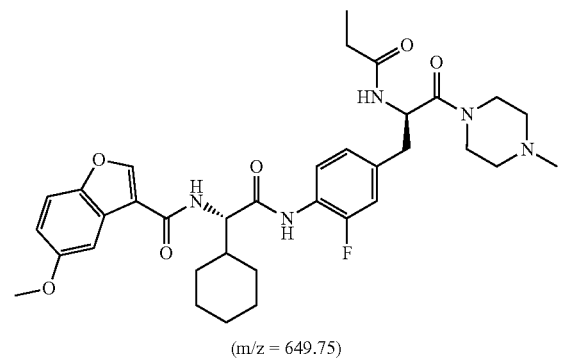
(m/z = 649.75)
672
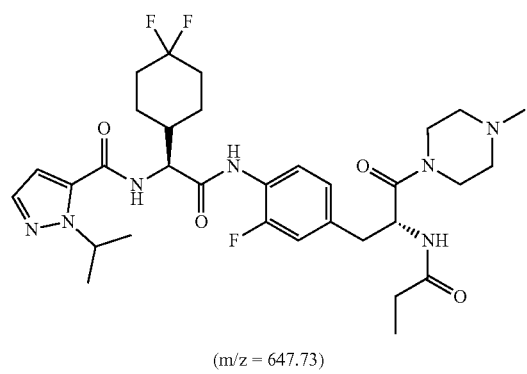
(m/z = 647.73)
674
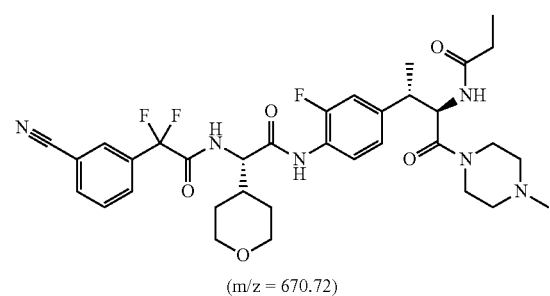
(m/z = 670.72)

-continued
675
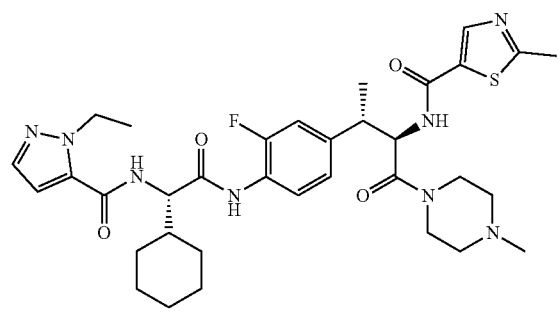
(m/z = 680.84)
676
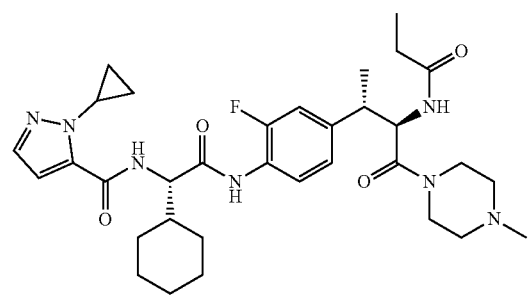
(m/z = 609.73)
677
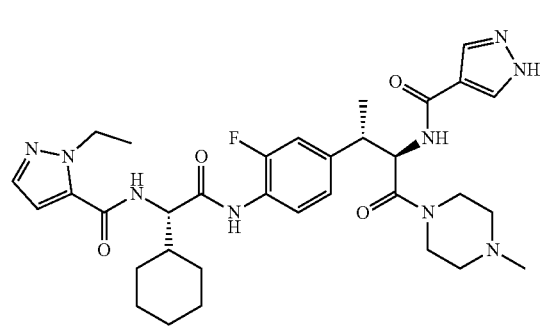
(m/z = 649.76)
678
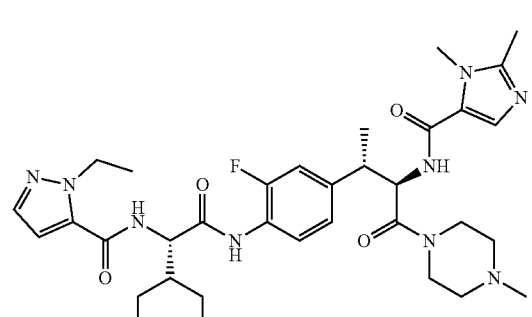
(m/z = 677.81)
679
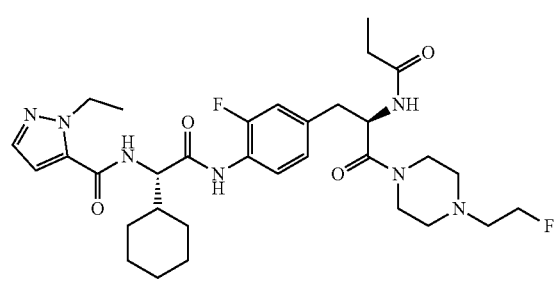
(m/z = 629.74)
680
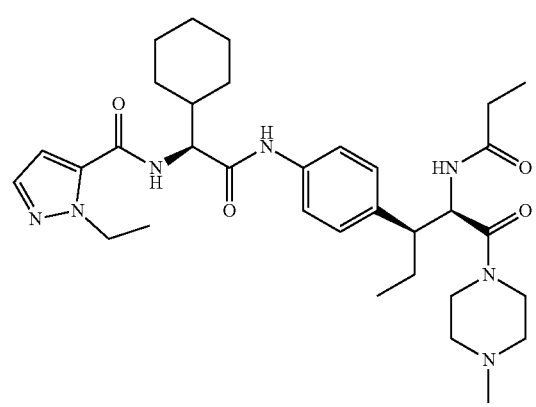
(m/z = 607.79)
681
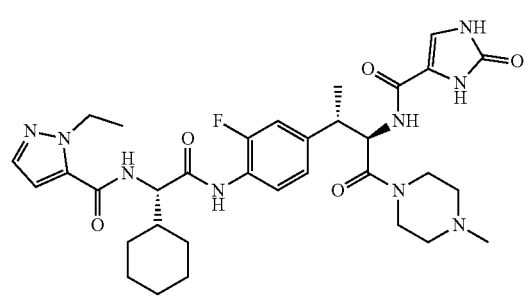
(m/z = 665.76)
682
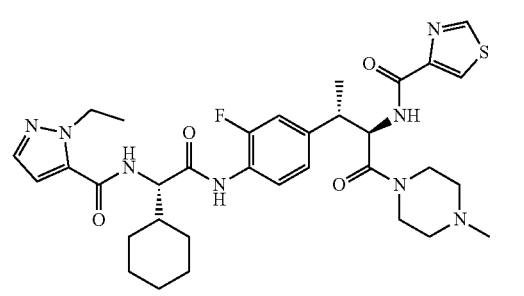
(m/z = 666.81)

-continued
683
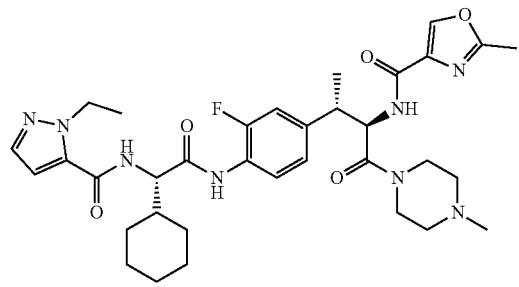
(m/z = 664.77)
684
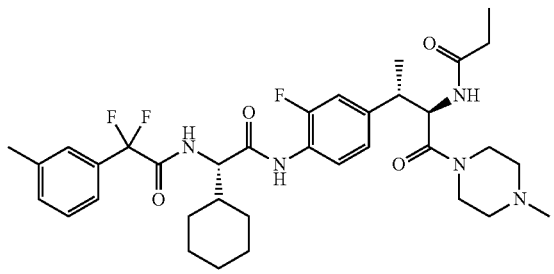
(m/z = 657.77)
685
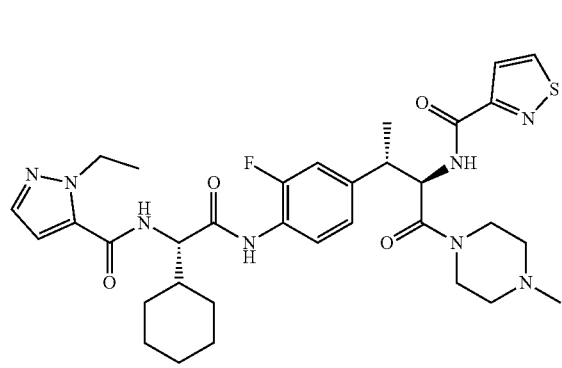
(m/z = 666.81)
686
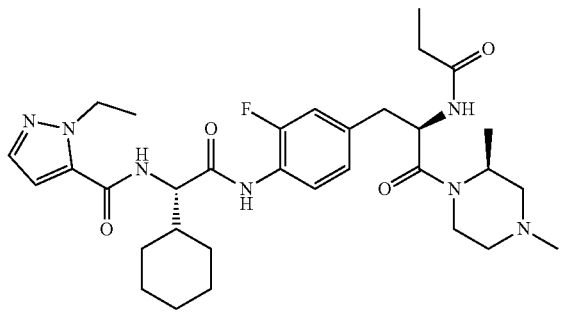
(m/z = 611.75)
687
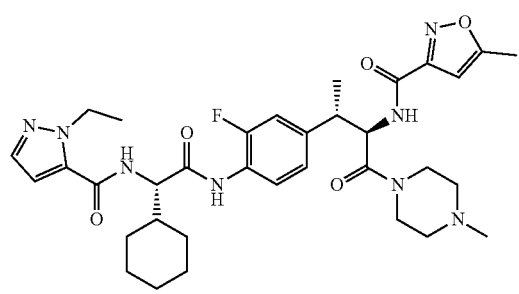
(m/z = 664.77)
688
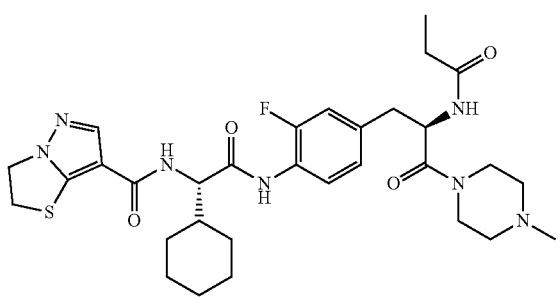
(m/z = 627.77)
689
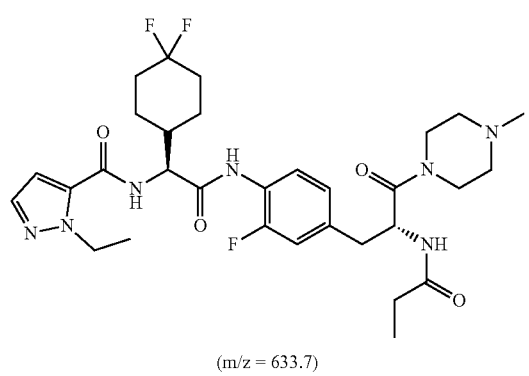
(m/z = 633.7)
690
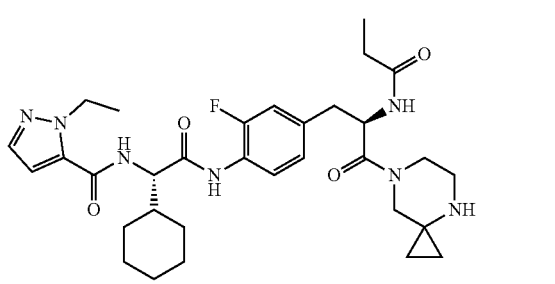
(m/z = 609.73)

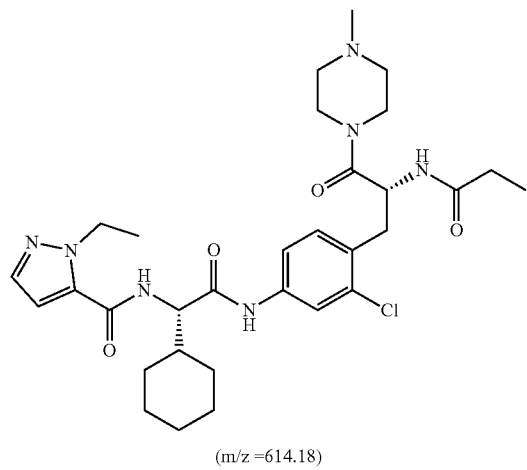
(m/z =614.18)
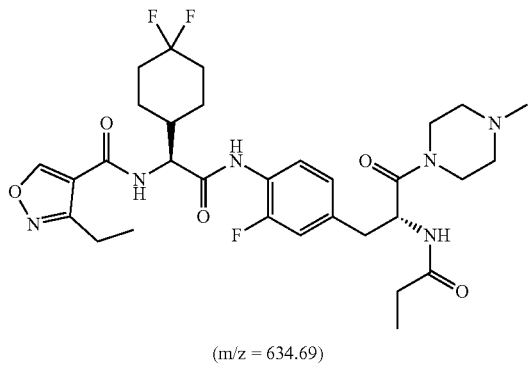
(m/z = 634.69)
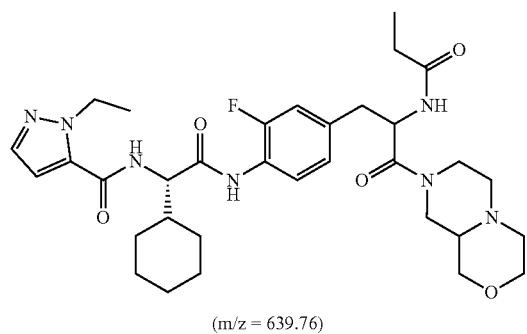
(m/z = 639.76)
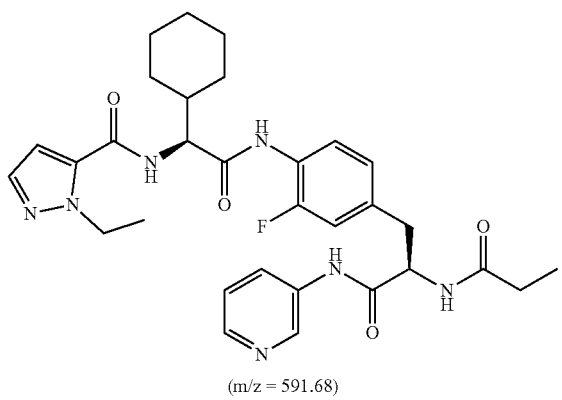
(m/z = 591.68)
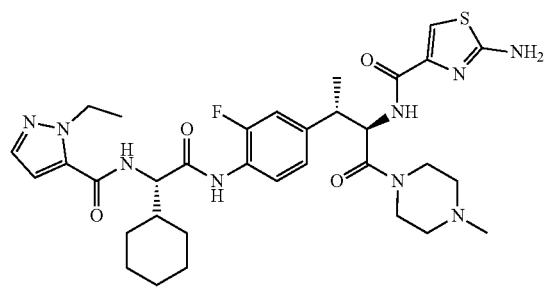
(m/z = 691.82)
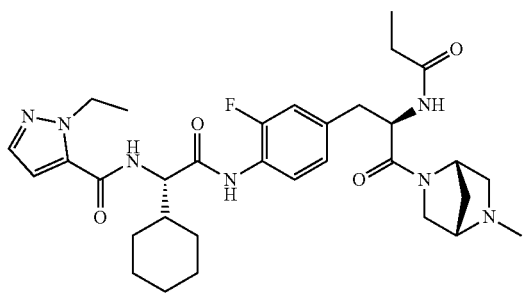
(m/z = 609.73)
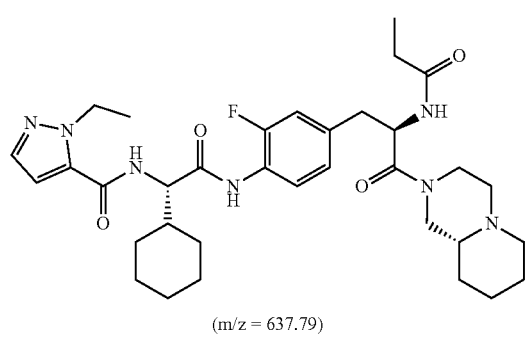
(m/z = 637.79)
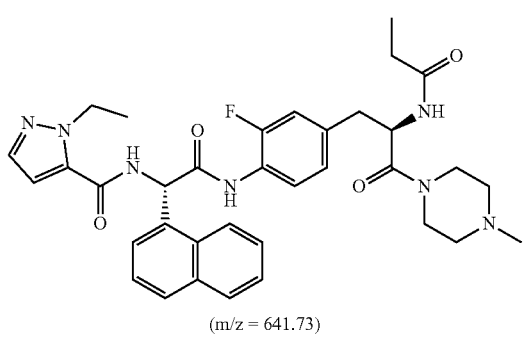
(m/z = 641.73)

-continued
699
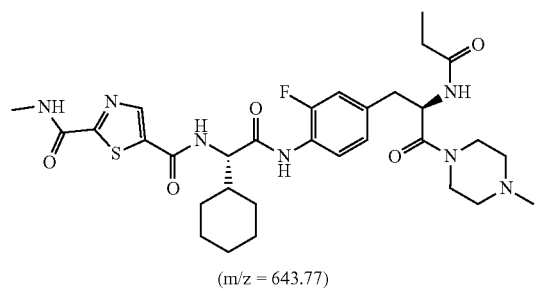
(m/z = 643.77)
700
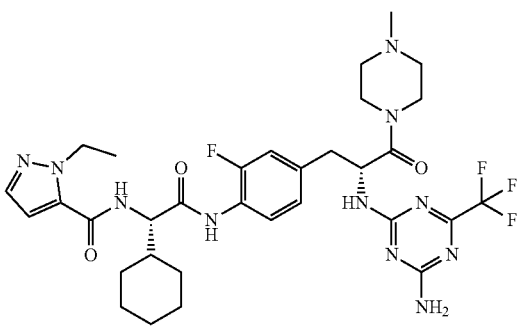
(m/z = 703.73)
701
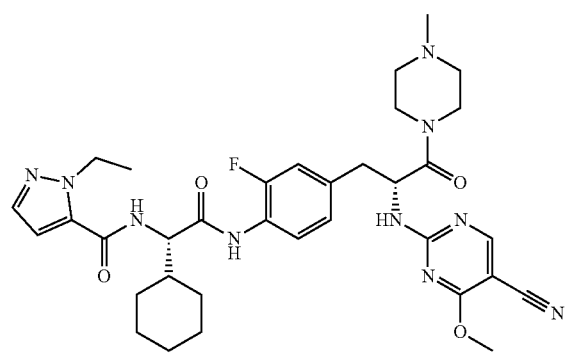
(m/z = 674.77)
702
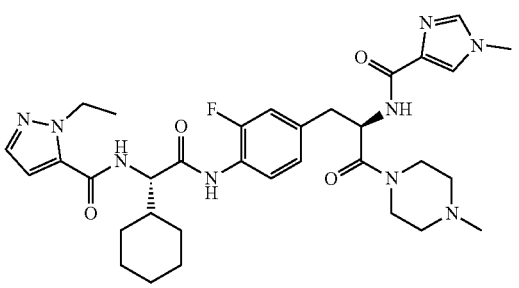
(m/z = 649.76)
703
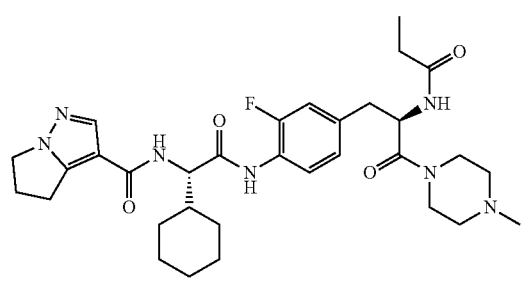
(m/z = 609.73)
704
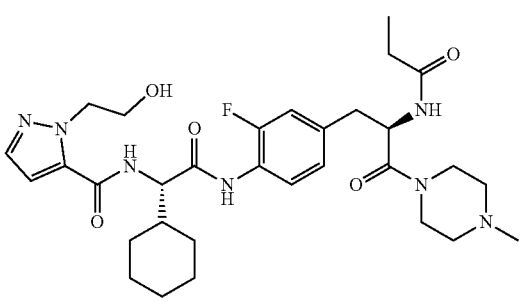
(m/z = 613.72)
705
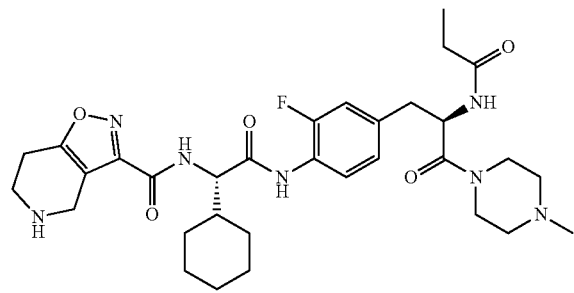
(m/z = 625.73)
706
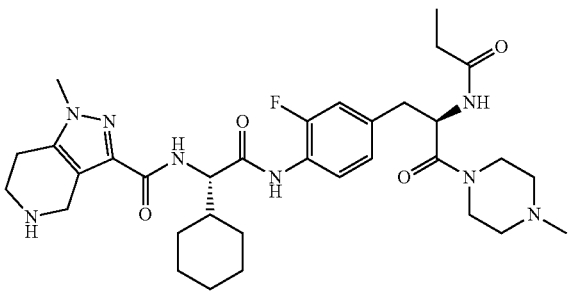
(m/z = 638.78)

-continued
707
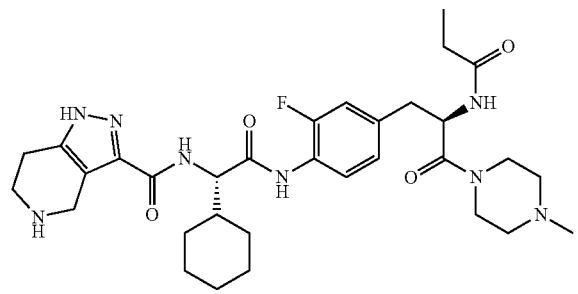
(m/z = 624.75)
708
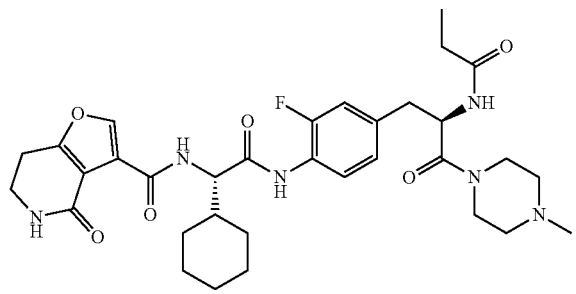
(m/z = 638.73)
709
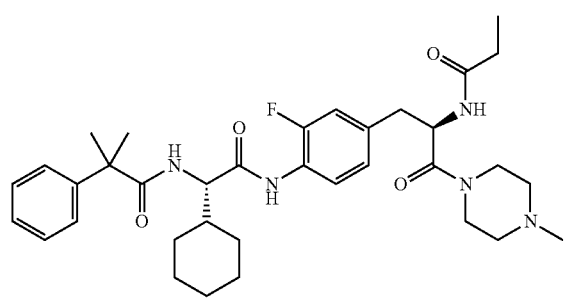
(m/z = 621.79)
710
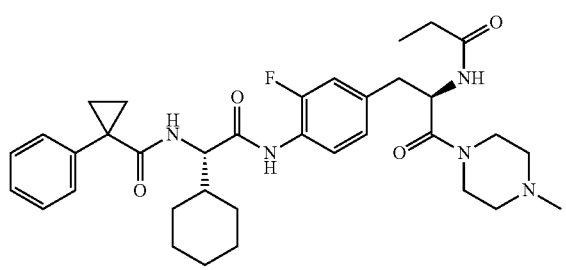
(m/z = 619.77)
711
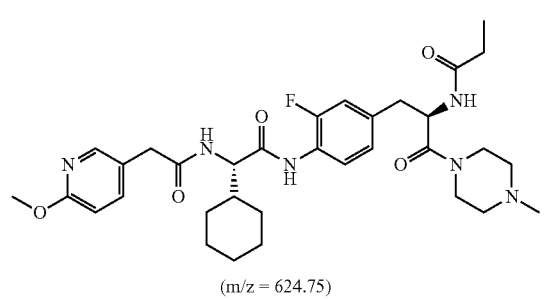
(m/z = 624.75)
712
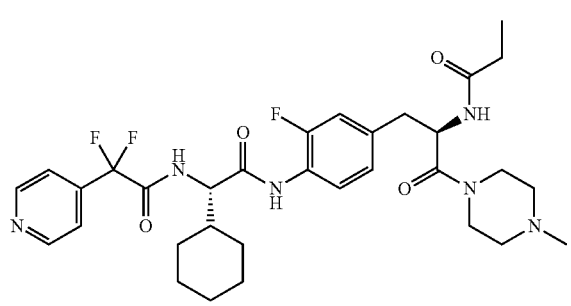
(m/z = 630.7)
713
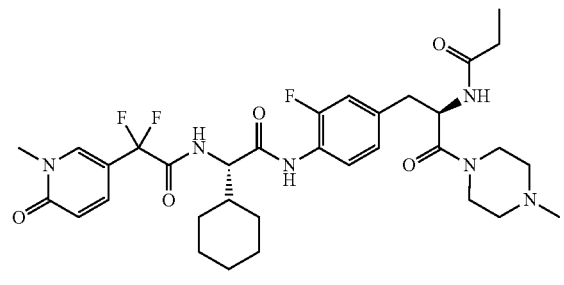
(m/z = 660.73)
715
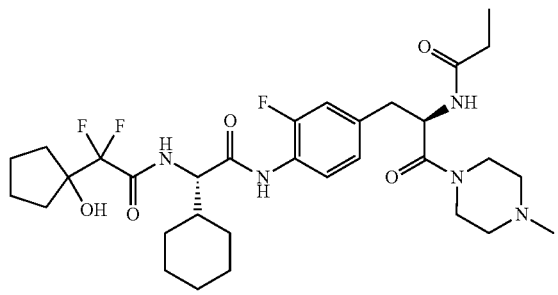
(m/z = 637.73)

-continued
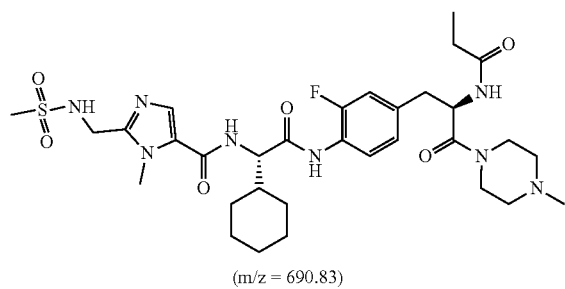
(m/z = 690.83)
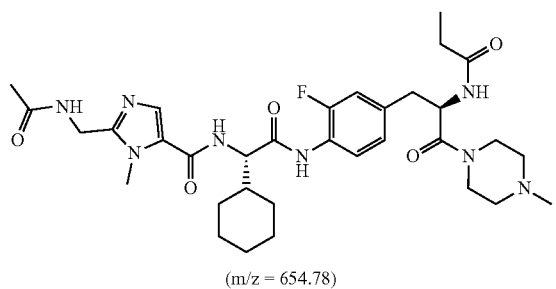
(m/z = 654.78)
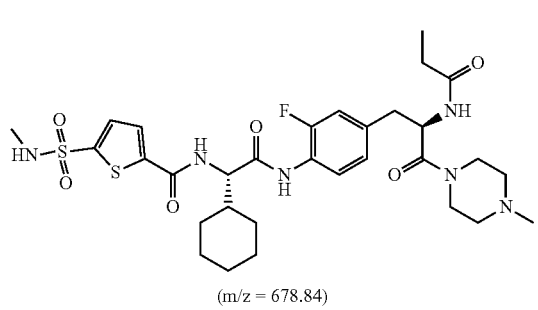
(m/z = 678.84)
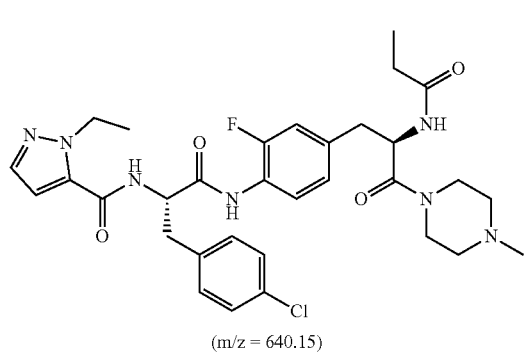
(m/z = 640.15)
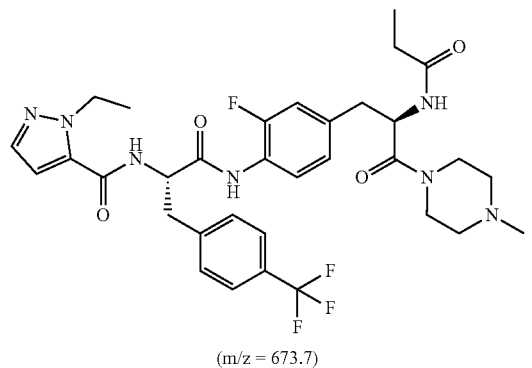
(m/z = 673.7)
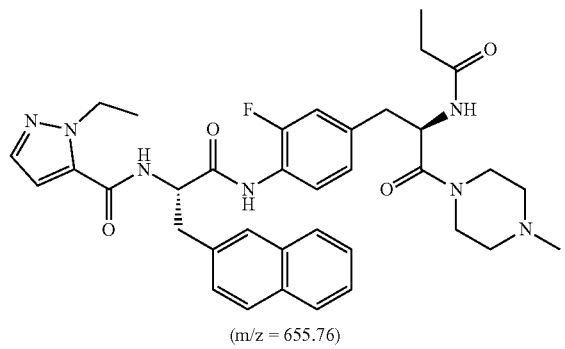
(m/z = 655.76)
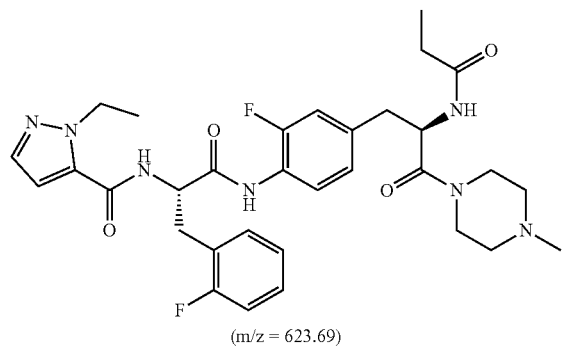
(m/z = 623.69)
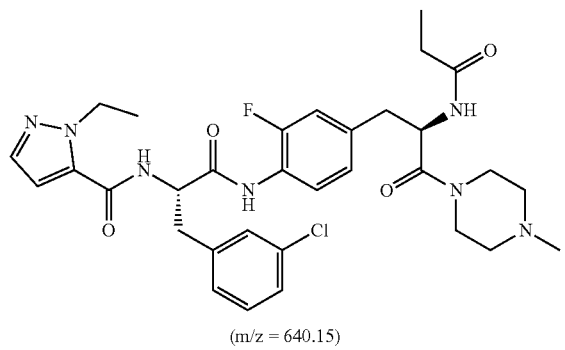
(m/z = 640.15)

-continued
727
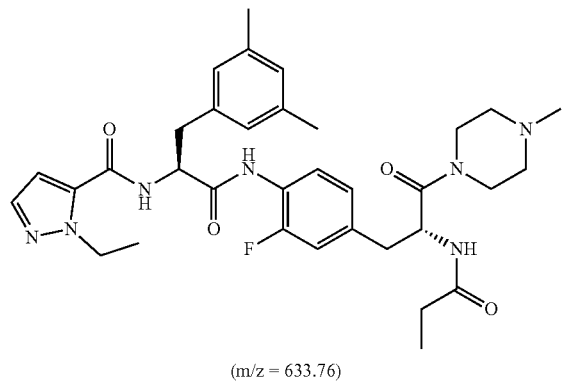
(m/z = 633.76)
728
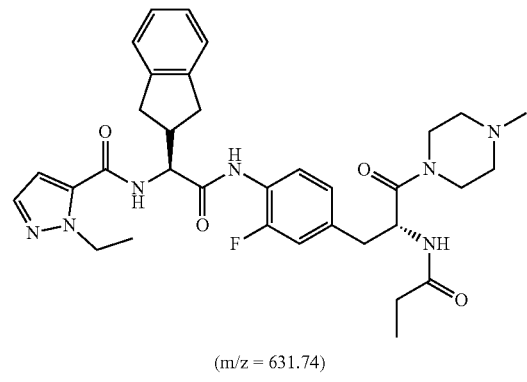
(m/z = 631.74)
729
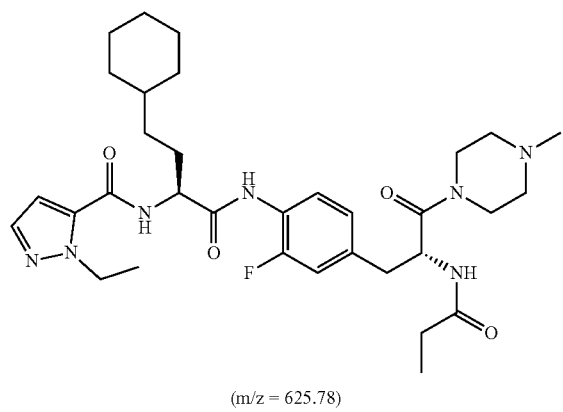
(m/z = 625.78)
730
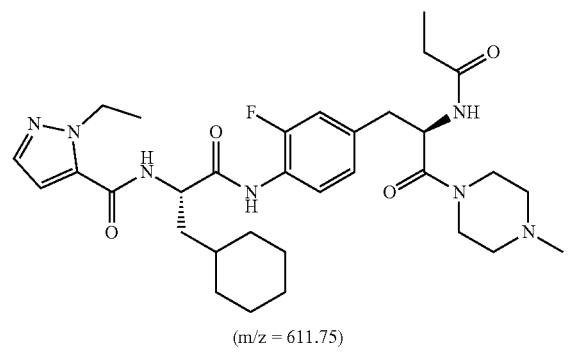
(m/z = 611.75)
731
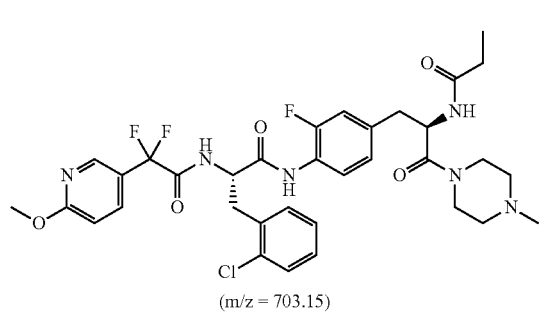
(m/z = 703.15)
732
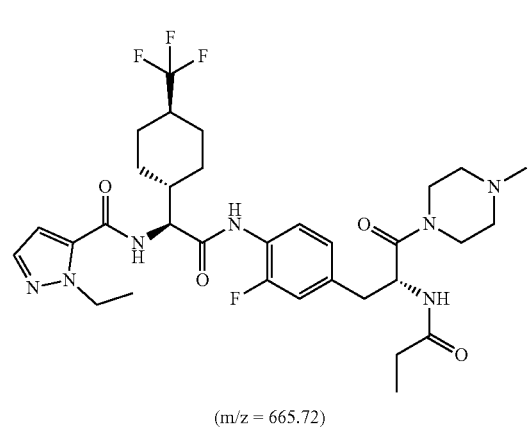
(m/z = 665.72)
733
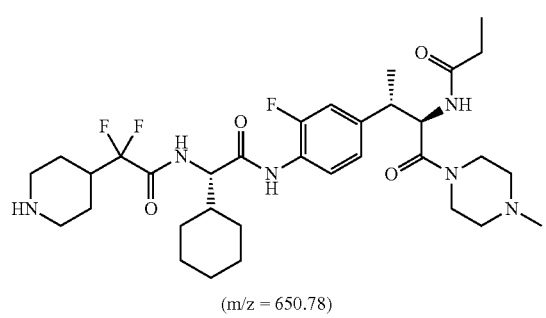
(m/z = 650.78)
734
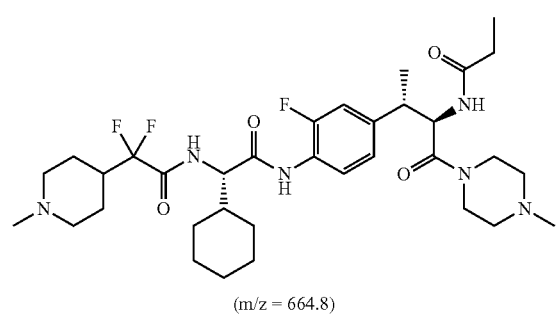
(m/z = 664.8)

-continued
735
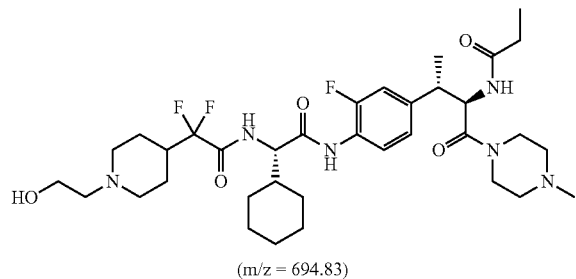
(m/z = 694.83)
738
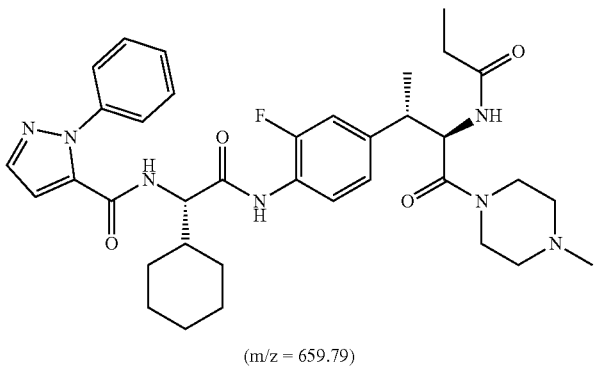
(m/z = 659.79)
741
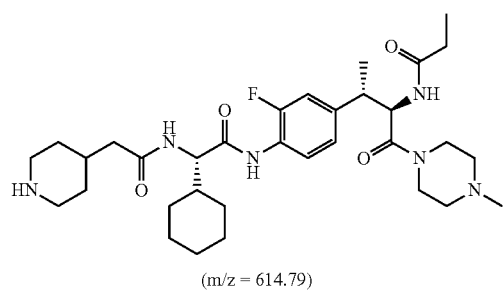
(m/z = 614.79)
742
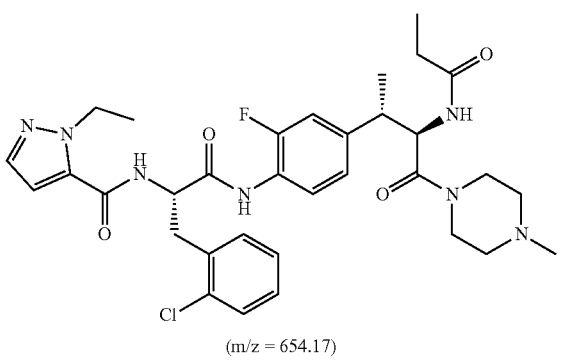
(m/z = 654.17)
743
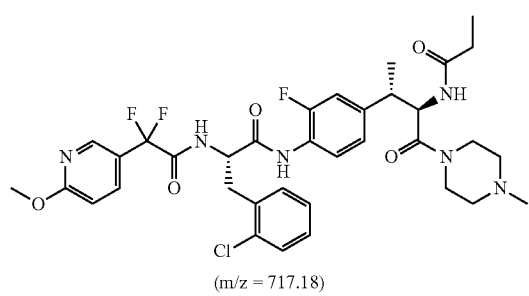
(m/z = 717.18)
744
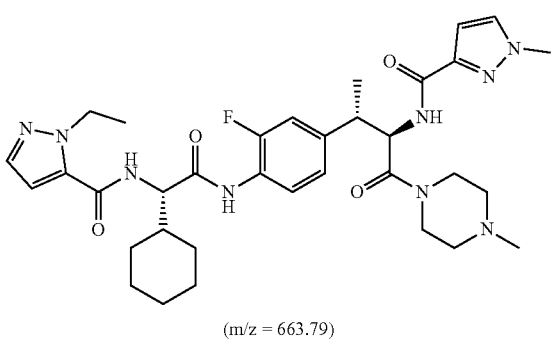
(m/z = 663.79)
745
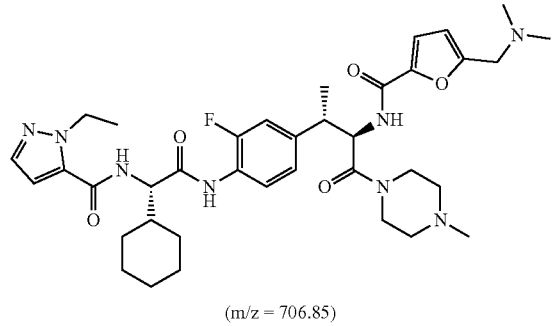
(m/z = 706.85)
746
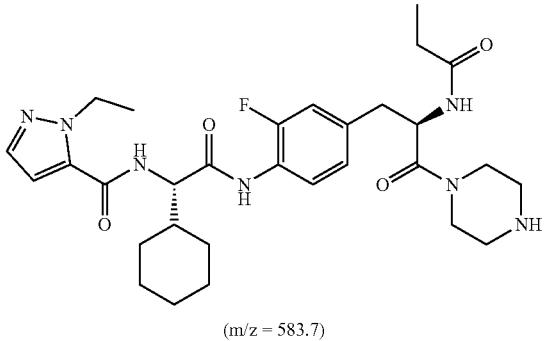
(m/z = 583.7)

-continued
747
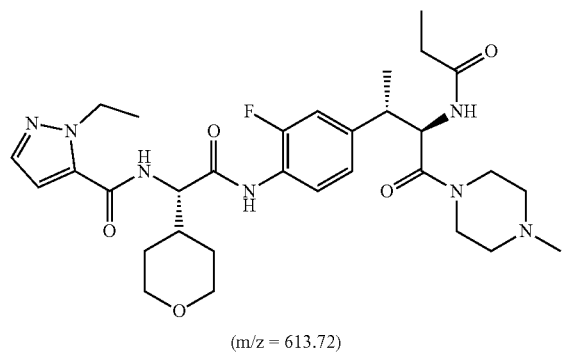
(m/z = 613.72)
748
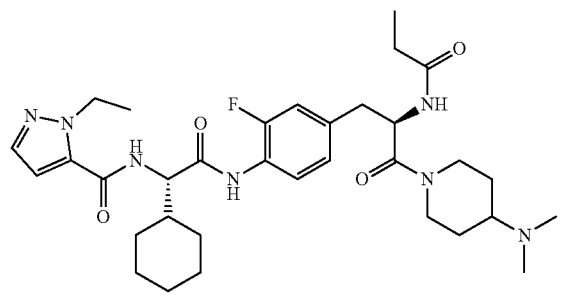
(m/z = 625.78)
749
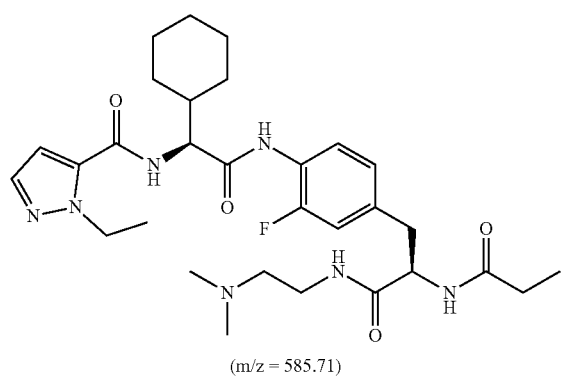
(m/z = 585.71)
750
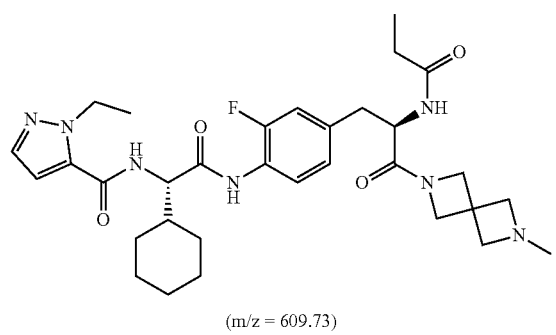
(m/z = 609.73)
751
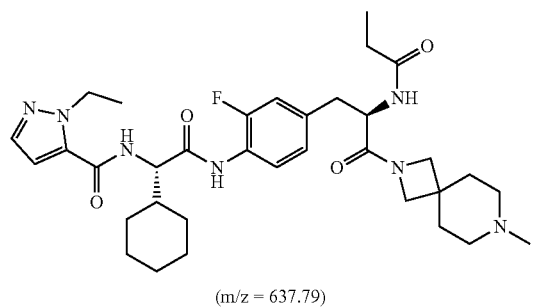
(m/z = 637.79)
752
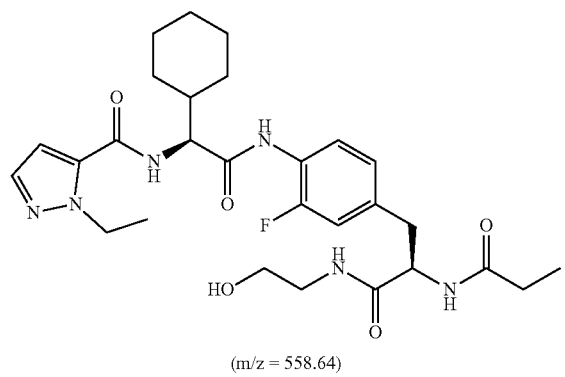
(m/z = 558.64)
753
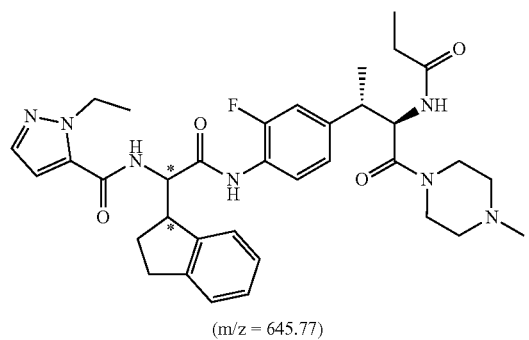
(m/z = 645.77)
754
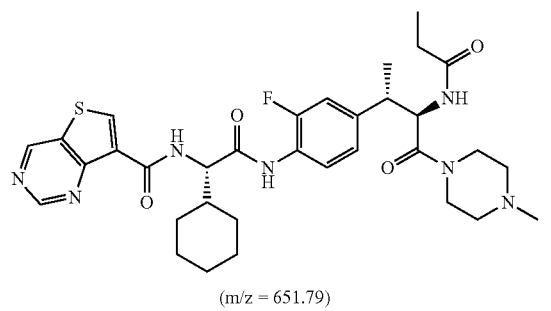
(m/z = 651.79)

-continued
757
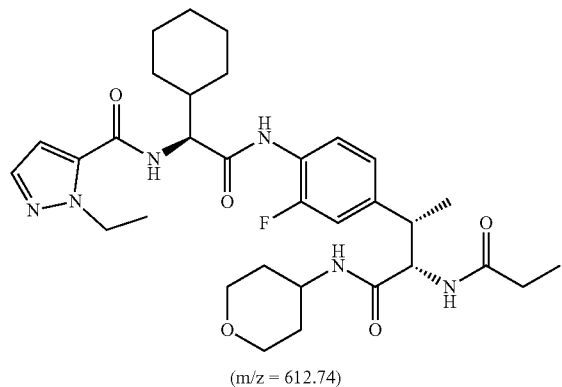
(m/z = 612.74)
758
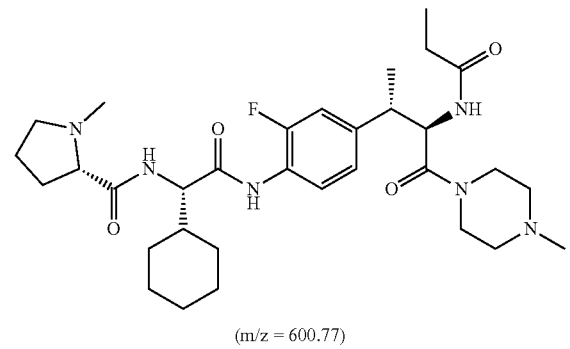
(m/z = 600.77)
760
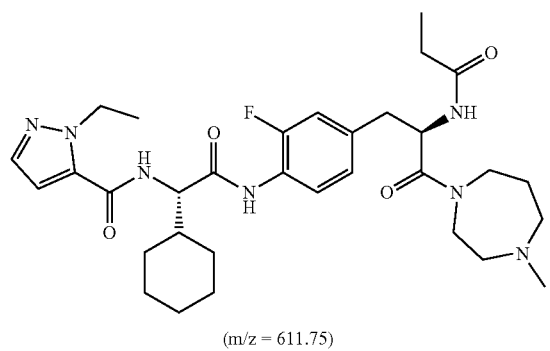
(m/z = 611.75)
761
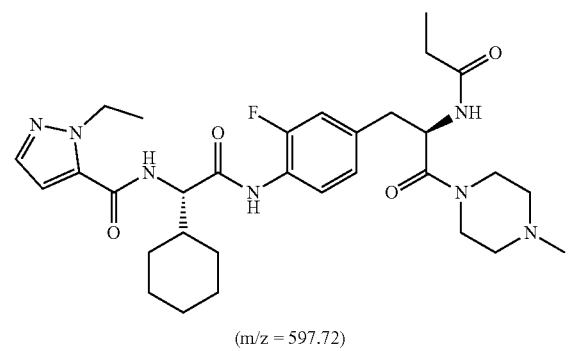
(m/z = 597.72)
763
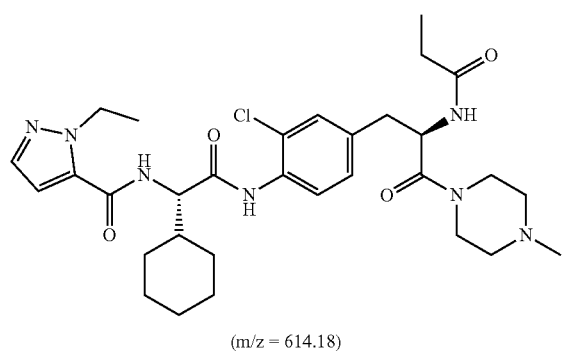
(m/z = 614.18)
764
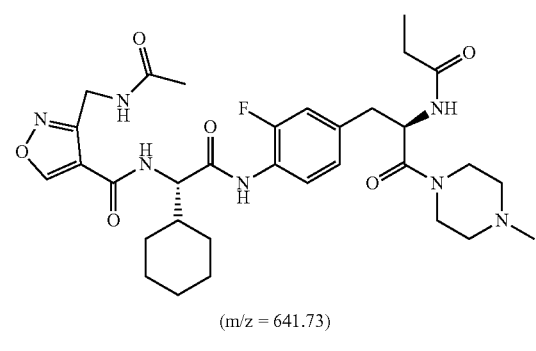
(m/z = 641.73)
765
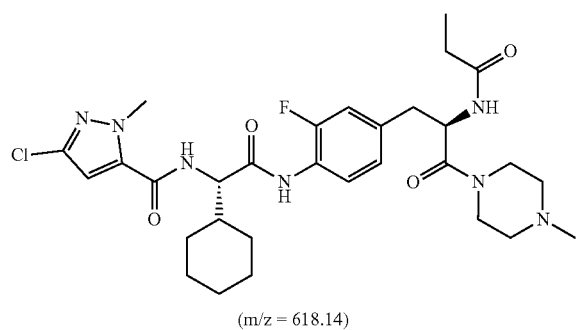
(m/z = 618.14)
766
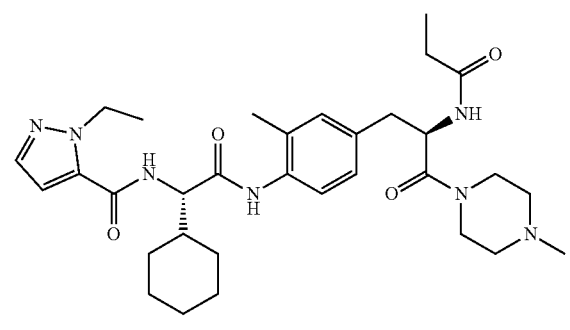
(m/z = 593.76)

767
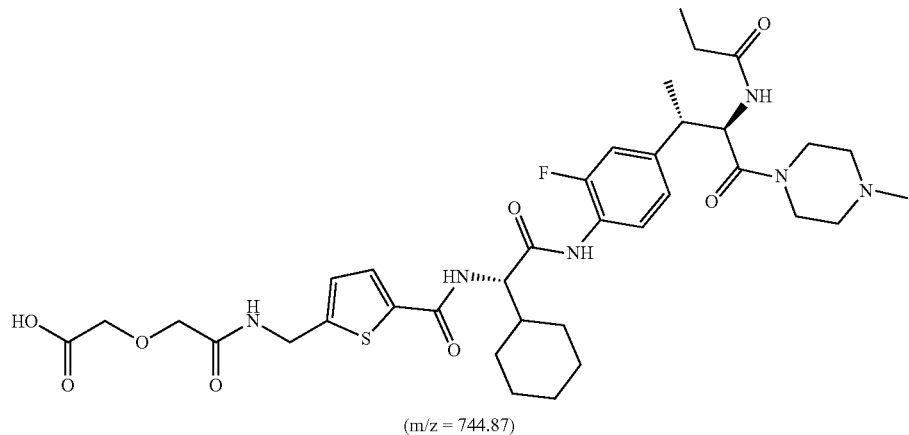
(m/z = 744.87)
768
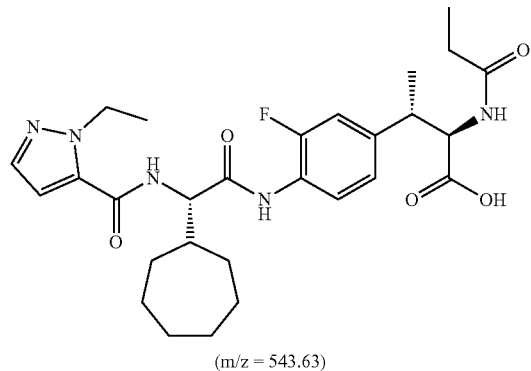
(m/z = 543.63)
769
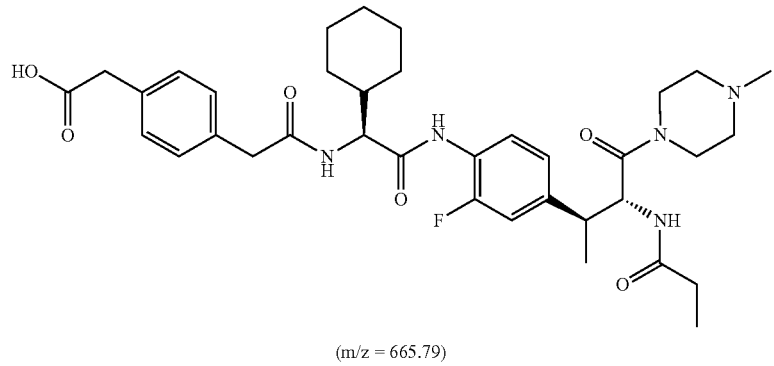
(m/z = 665.79)
770
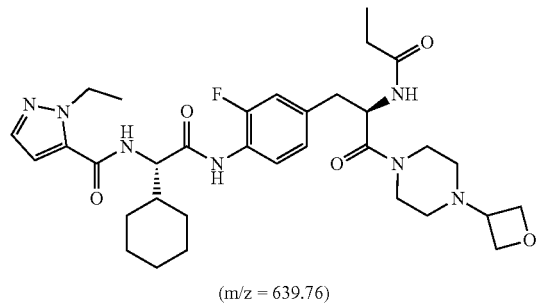
(m/z = 639.76)
771
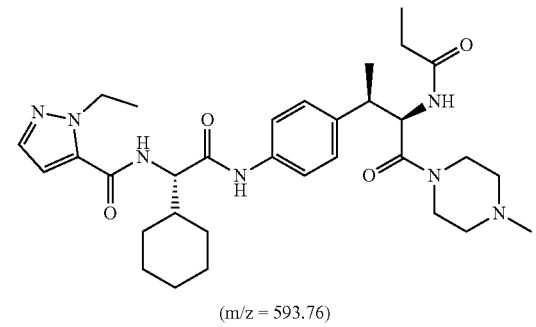
(m/z = 593.76)

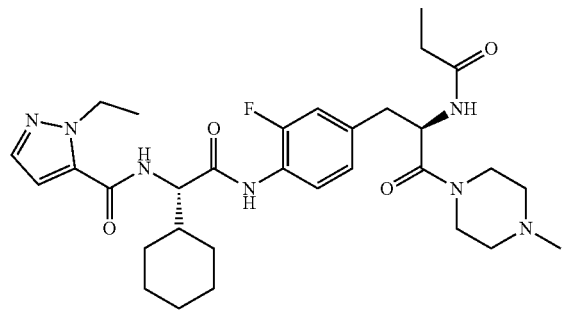
(m/z = 597.72)
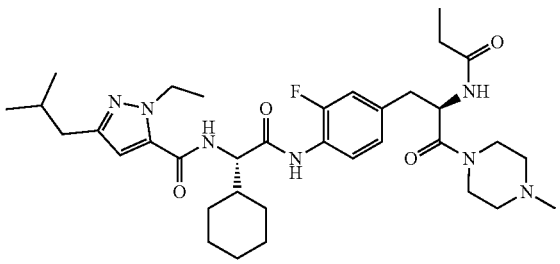
(m/z = 653.83)
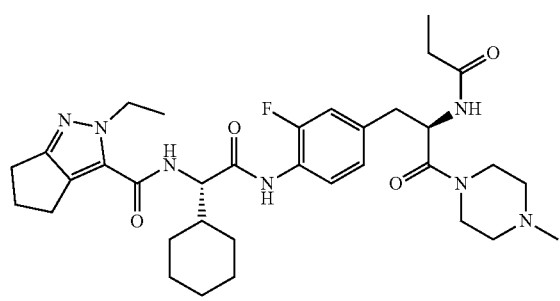
(m/z = 637.79)
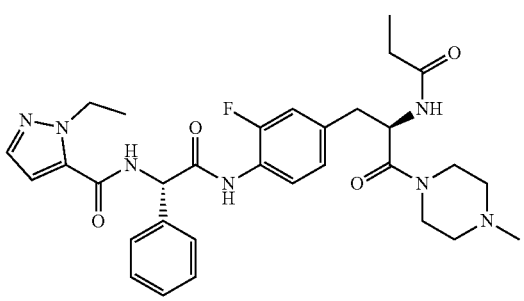
(m/z = 591.68)
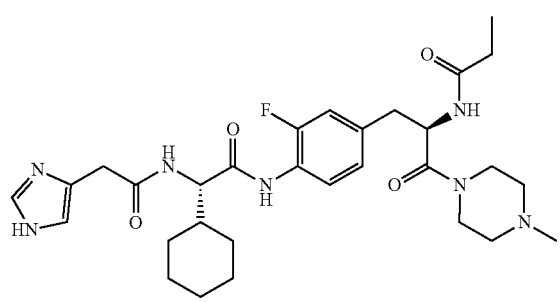
(m/z = 583.7)
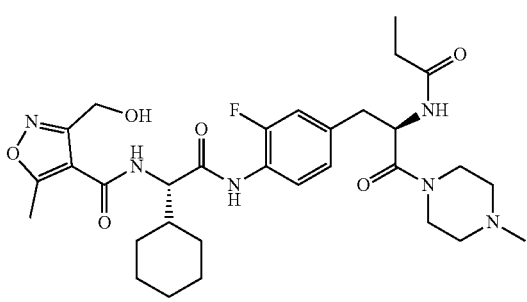
(m/z = 614.71)
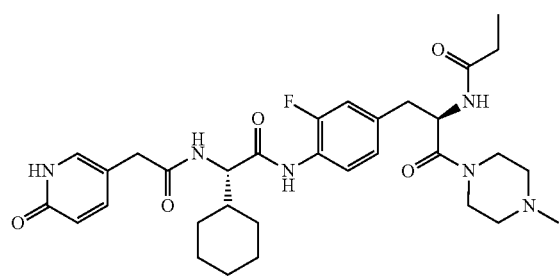
(m/z = 610.72)
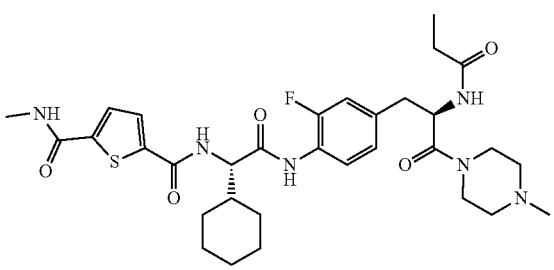
(m/z = 642.78)

287 288
-continued
780
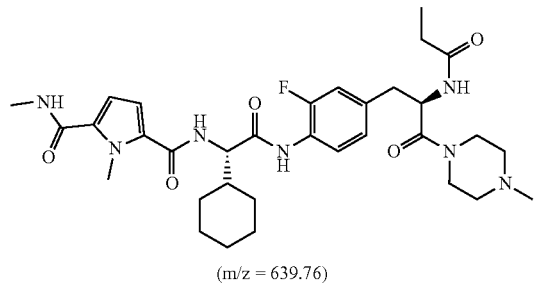
(m/z = 639.76)
781
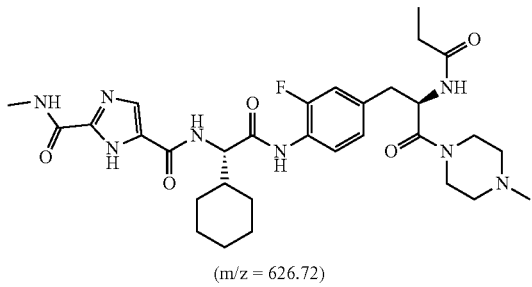
(m/z = 626.72)
782
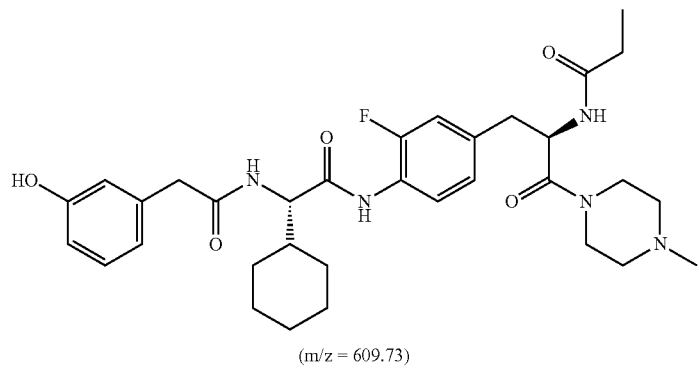
(m/z = 609.73)
783
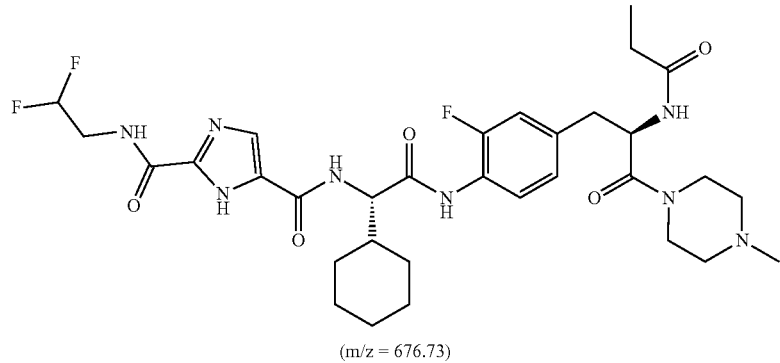
(m/z = 676.73)
785
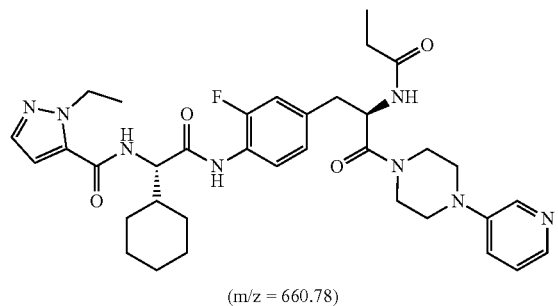
(m/z = 660.78)
786
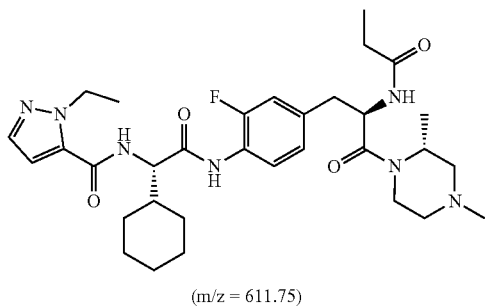
(m/z = 611.75)

787
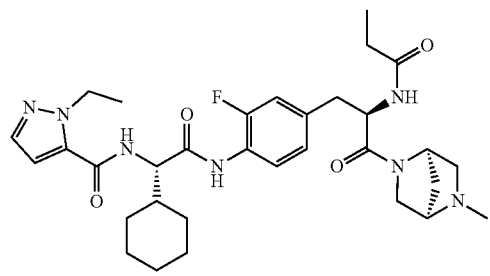
(m/z = 609.73)
788
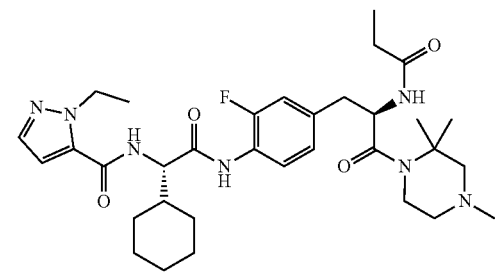
(m/z = 625.78)
789
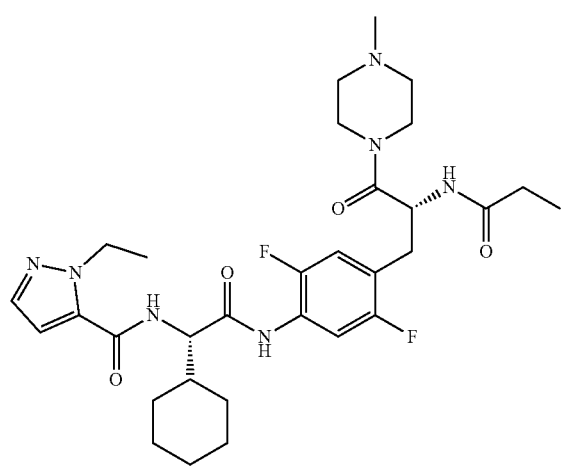
(m/z = 615.71)
790
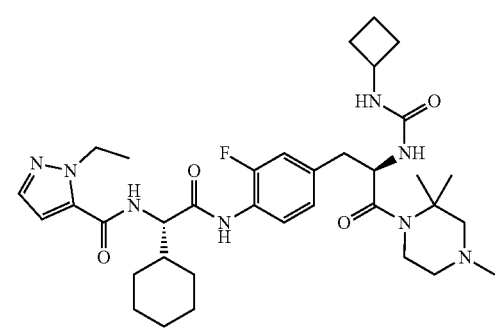
(m/z = 638.78)
791
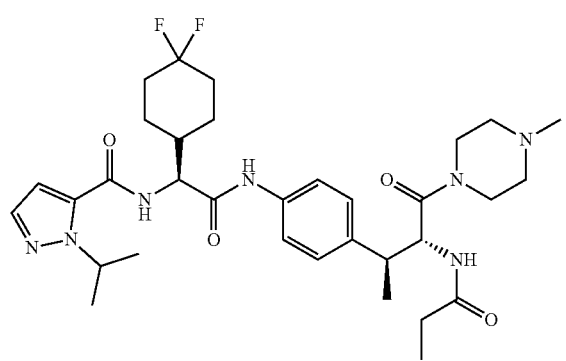
(m/z = 643.77)
792
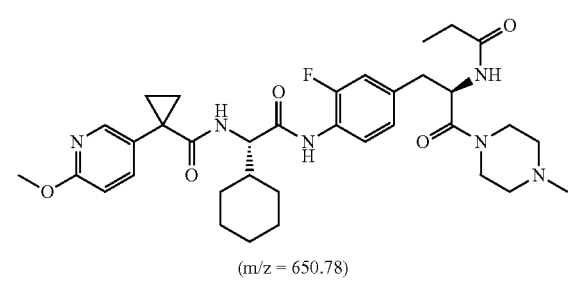
(m/z = 650.78)
793
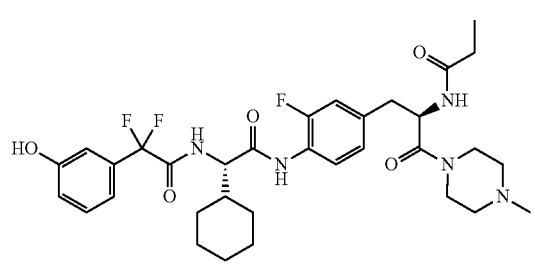
(m/z = 645.71)
794
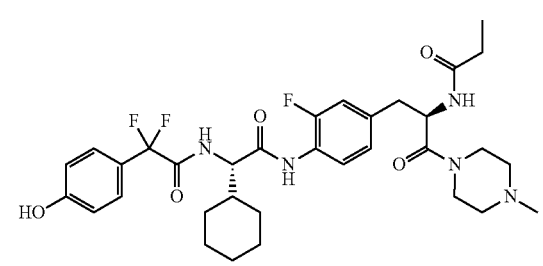
(m/z = 645.71)

-continued
291
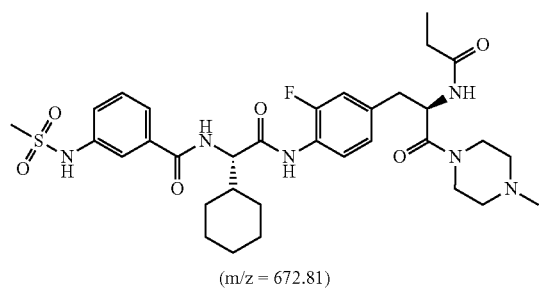
(m/z = 672.81)
292
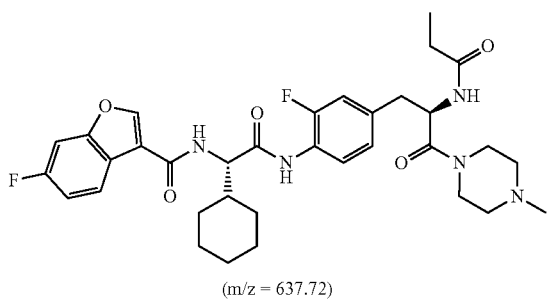
(m/z = 637.72)
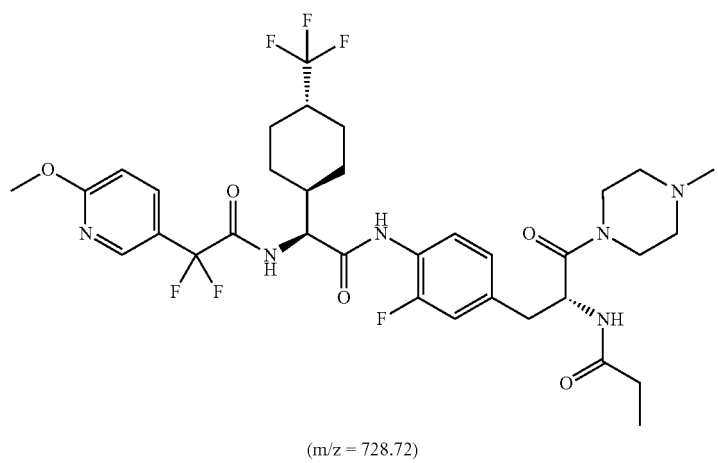
(m/z = 728.72)
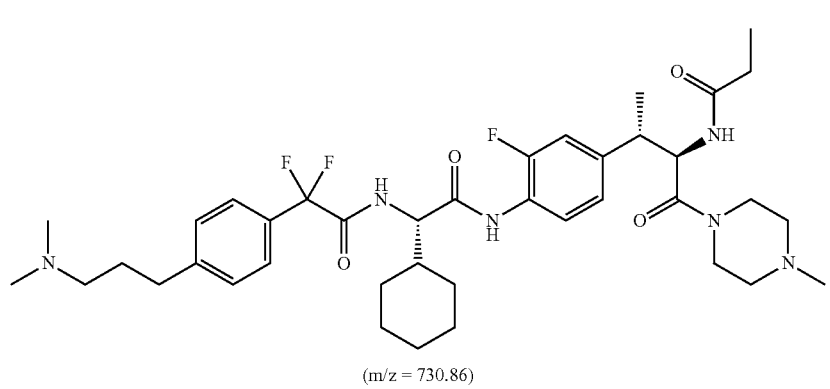
(m/z = 730.86)
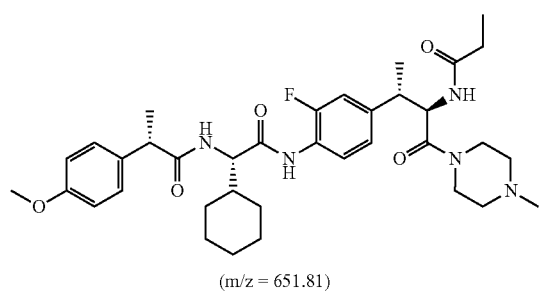
(m/z = 651.81)
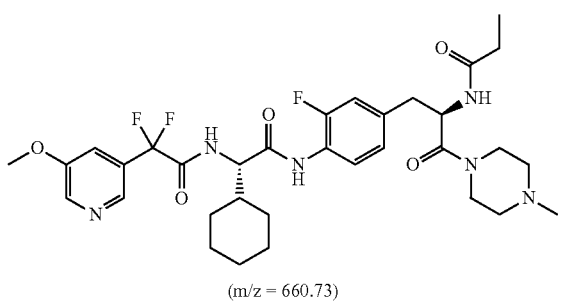
(m/z = 660.73)

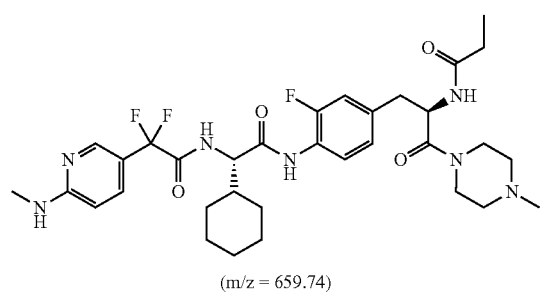
802
(m/z = 659.74)
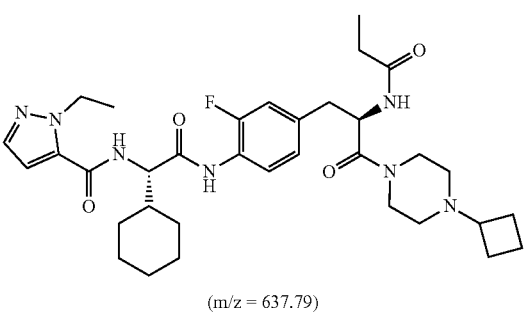
803
(m/z = 637.79)
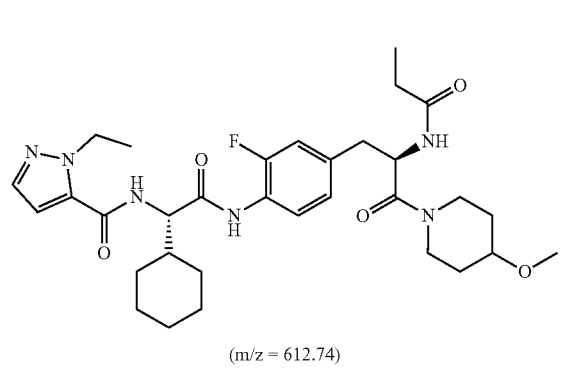
804
(m/z = 612.74)
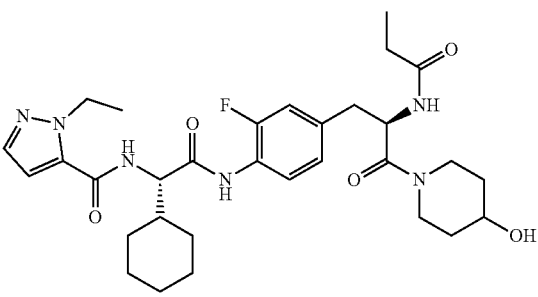
805
(m/z = 598.71)
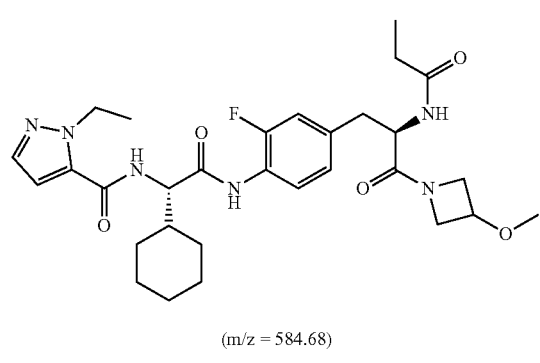
806
(m/z = 584.68)
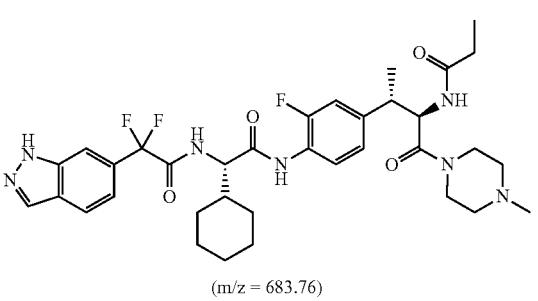
807
(m/z = 683.76)
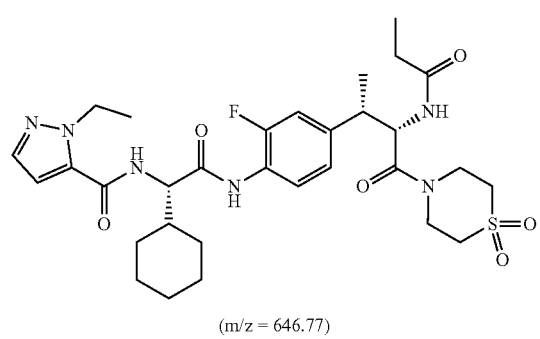
808
(m/z = 646.77)
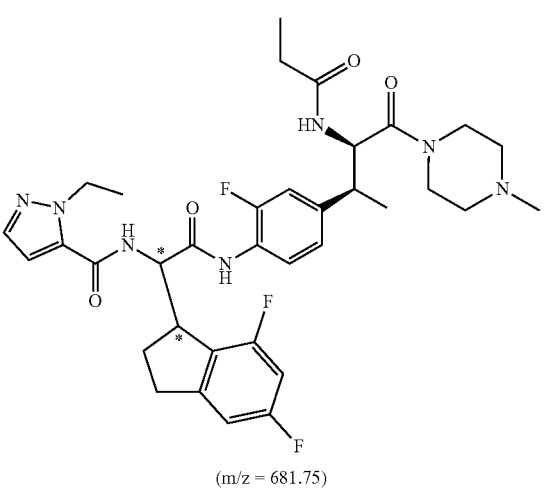
809
(m/z = 681.75)

-continued

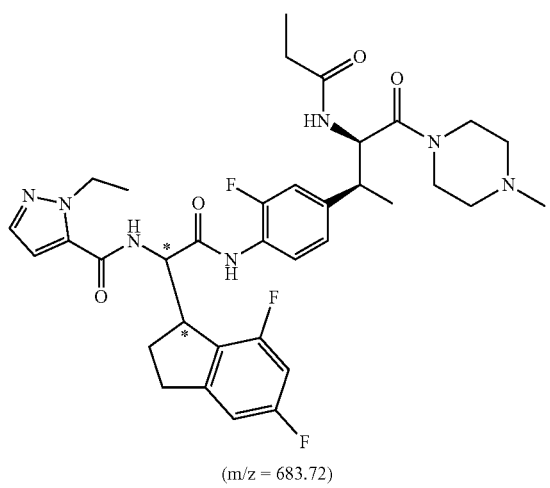

(m/z = 683.72)

Example 40: IL-17A/A HEK-Blue Cell Assay

The HEK-Blue IL-17A reporter cell line (Fisher #NC1408637) was used for cell-based IL-17A/A inhibition assays. Cells were grown and prepared for assays according to the manufacturer's instructions. This cell line consists of THEK 293 cells that were designed to expressed IL-17RA, IL-17RC, and the ActI adapter molecule, the combination of which, when stimulated by IL-17A/A activates a NFκB promoter and drives expression of a recombinant Secreted Alkaline Phosphatase (SEAP) geneprotein. Media from the cells is then added to a development reagent (Quanti-Blue Substrate, Fisher #NC9711613), and read at $A_{630}$.

Compounds were titrated in DMSO, with a top final compound concentration of 10 uM, 1 uM, or 0.3 uM, and added to the cells immediately before adding IL-17A/A (Genscript #Z03228). The cells, compound, and IL-17A/A were then incubated for 20 hours before media was removed for SEAP analysis. The resulting inhibition curve was then analyzed using Graphpad Prism 7.0, and $IC_{50}$ values were determined using a 4-parameter nonlinear fit. DMSO was added to a universal final concentration of 0.1% to optimize background.

Table 1 includes $pIC_{50}$ values for IL-17A/A inhibition of selected compounds; with compounds having a $pIC_{50}$ of greater than or equal 8 as A; 8>B≥7 as B; and 7>C≥5. Table 2 also includes $pIC_{50}$ values for IL-17A/A inhibition of selected compounds; with compounds categorized in the following activity categories:

X1a: compounds were evaluated up to 10 uM and did not inhibit activity by >80%, however they showed some activity at 10 uM (less than 80% and more than 20%);

X1b: compounds were evaluated up to 10 uM and inhibited activity at 10 uM by less than 20%;

X2a: compounds were evaluated up to 1 uM and did not inhibit activity by >80%, however they showed some activity at 1 uM (less than 80% and more than 20%);

X2b: compounds were evaluated up to 1 uM and inhibited activity at 1 uM by less than 20%;

X3a: compounds were evaluated up to 0.3 uM and did not inhibit activity by >80%, however they showed some activity at 0.3 uM (less than 80% and more than 20%);

X3b: compounds were evaluated up to 0.3 uM and inhibited activity at 0.3 uM by less than 20%;

TABLE 1

IL-17A/A $pIC_{50}$ inhibition values for selected compounds

| Compound. No. | IL-17A/A inhibition |
|---|---|
| 203 | C |
| 204 | C |
| 205 | C |
| 206 | C |
| 207 | C |
| 208 | C |
| 210 | C |
| 211 | C |
| 213 | C |
| 214 | B |
| 215 | C |
| 216 | C |
| 217 | C |
| 218 | B |
| 219 | B |
| 220 | B |
| 221 | B |
| 222 | B |
| 223 | C |
| 224 | A |
| 227 | B |
| 228 | A |
| 229 | B |
| 230 | A |
| 231 | A |
| 232 | B |
| 234 | B |
| 235 | B |
| 236 | B |
| 237 | B |
| 238 | B |
| 239 | B |
| 240 | B |
| 241 | A |
| 242 | X2b |
| 243 | B |
| 244 | B |
| 245 | B |
| 246 | B |
| 247 | B |
| 248 | B |
| 249 | B |
| 250 | B |
| 251 | B |
| 252 | B |
| 253 | A |
| 254 | B |
| 255 | B |

TABLE 1-continued

IL-17A/A pIC$_{50}$ inhibition values for selected compounds

| Compound. No. | IL-17A/A inhibition |
| --- | --- |
| 256 | B |
| 257 | A |
| 258 | A |
| 259 | A |
| 260 | A |
| 261 | A |
| 262 | B |
| 263 | A |
| 264 | B |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | B |
| 277 | A |
| 278 | A |
| 279 | B |
| 280 | B |
| 281 | B |
| 282 | A |
| 283 | A |
| 284 | A |
| 285 | B |
| 286 | B |
| 287 | A |
| 288 | B |
| 289 | B |
| 290 | A |
| 291 | B |
| 292 | B |
| 293 | B |
| 294 | B |
| 295 | A |
| 296 | B |
| 297 | B |
| 298 | B |
| 299 | B |
| 300 | B |
| 301 | A |
| 302 | B |
| 303 | B |
| 304 | B |
| 305 | B |
| 306 | B |
| 307 | B |
| 308 | A |
| 309 | B |
| 310 | B |
| 311 | A |
| 312 | A |
| 313 | B |
| 314 | B |
| 315 | A |
| 316 | A |
| 317 | B |
| 318 | B |
| 319 | B |
| 320 | B |
| 321 | B |
| 322 | B |
| 323 | B |
| 324 | B |
| 325 | B |
| 326 | B |
| 327 | B |
| 328 | B |
| 329 | A |
| 330 | A |
| 331 | A |
| 332 | A |
| 333 | A |
| 334 | A |
| 335 | A |
| 336 | A |
| 337 | A |
| 338 | A |
| 339 | A |
| 340 | A |
| 341 | B |
| 342 | B |
| 343 | B |
| 344 | B |
| 345 | B |
| 346 | B |
| 347 | A |
| 348 | A |
| 349 | A |
| 350 | A |
| 351 | B |
| 352 | B |
| 353 | B |
| 354 | A |
| 355 | A |
| 356 | B |
| 357 | A |
| 358 | B |
| 359 | B |
| 360 | B |
| 361 | B |
| 362 | B |
| 363 | A |
| 364 | A |
| 365 | B |
| 366 | A |
| 367 | B |
| 368 | B |
| 369 | B |
| 370 | B |
| 371 | B |
| 372 | B |
| 373 | B |
| 374 | B |
| 375 | B |
| 376 | B |
| 377 | B |
| 378 | B |
| 380 | B |
| 381 | B |
| 382 | B |
| 383 | B |
| 384 | B |
| 385 | B |
| 386 | B |
| 388 | B |
| 389 | B |
| 390 | A |
| 391 | A |
| 392 | B |
| 393 | B |
| 394 | A |
| 395 | B |
| 396 | B |
| 397 | B |
| 398 | A |
| 399 | A |
| 400 | A |
| 402 | B |
| 404 | B |
| 405 | B |
| 406 | B |
| 407 | A |
| 408 | A |
| 409 | B |
| 410 | B |
| 414 | A |

TABLE 1-continued

IL-17A/A pIC$_{50}$ inhibition values for selected compounds

| Compound. No. | IL-17A/A inhibition |
|---|---|
| 417 | A |
| 418 | B |
| 419 | B |
| 420 | A |
| 421 | B |
| 422 | B |
| 423 | B |
| 424 | B |
| 425 | B |
| 426 | A |
| 427 | A |
| 428 | B |
| 429 | A |
| 430 | A |
| 431 | A |
| 432 | A |
| 433 | A |
| 434 | A |
| 435 | A |
| 436 | A |
| 437 | A |
| 438 | B |
| 439 | B |
| 440 | A |
| 441 | A |
| 442 | B |
| 443 | A |
| 444 | B |
| 445 | B |
| 446 | A |
| 447 | B |
| 448 | A |
| 449 | A |
| 450 | A |
| 451 | A |
| 452 | A |
| 454 | C |
| 455 | C |
| 456 | A |
| 457 | A |
| 458 | A |
| 460 | A |
| 462 | A |
| 464 | A |
| 465 | A |
| 466 | A |
| 467 | A |
| 468 | B |
| 469 | B |
| 470 | B |
| 471 | B |
| 472 | B |
| 473 | B |
| 474 | B |
| 476 | A |
| 477 | B |
| 478 | B |
| 479 | A |
| 480 | A |
| 481 | A |
| 482 | B |
| 483 | B |
| 484 | B |
| 485 | B |
| 486 | B |
| 487 | B |
| 488 | A |
| 489 | B |
| 490 | B |
| 491 | B |
| 492 | A |
| 493 | B |
| 494 | A |
| 495 | B |
| 497 | A |
| 498 | B |

TABLE 1-continued

IL-17A/A pIC$_{50}$ inhibition values for selected compounds

| Compound. No. | IL-17A/A inhibition |
|---|---|
| 499 | A |
| 500 | A |
| 501 | B |
| 502 | A |
| 503 | B |
| 504 | A |
| 505 | B |
| 506 | A |
| 507 | B |
| 508 | A |
| 509 | B |
| 510 | B |
| 511 | A |
| 512 | B |
| 513 | A |
| 514 | A |
| 515 | B |
| 516 | A |
| 517 | A |
| 518 | B |
| 519 | X3a |
| 520 | X1b |
| 521 | C |
| 522 | X1b |
| 523 | A |
| 524 | B |
| 525 | B |
| 526 | B |
| 527 | B |
| 530 | A |
| 531 | B |
| 532 | B |
| 533 | A |
| 534 | B |
| 535 | A |
| 536 | B |
| 537 | B |
| 538 | A |
| 539 | A |
| 540 | X2b |
| 541 | X3b |
| 542 | X3b |
| 543 | X3b |
| 544 | X3a |
| 545 | B |
| 546 | B |
| 547 | X3b |
| 548 | X2b |
| 549 | A |
| 550 | A |
| 551 | B |
| 552 | B |
| 553 | X2a |
| 554 | C |
| 555 | A |
| 556 | X2a |
| 557 | C |
| 558 | A |
| 559 | X2b |
| 560 | X2b |
| 561 | A |
| 562 | B |
| 563 | X2b |
| 564 | X2a |
| 565 | A |
| 566 | B |
| 567 | X2b |
| 568 | A |
| 569 | C |
| 570 | A |
| 571 | X2a |
| 572 | C |
| 573 | A |
| 574 | A |
| 575 | X3a |
| 576 | B |

TABLE 1-continued

IL-17A/A pIC$_{50}$ inhibition values for selected compounds

| Compound. No. | IL-17A/A inhibition |
|---|---|
| 577 | B |
| 578 | X3b |
| 579 | B |
| 580 | X3a |
| 581 | B |
| 582 | B |
| 583 | A |
| 584 | X2b |
| 585 | X2a |
| 586 | A |
| 587 | B |
| 588 | X3b |
| 589 | X3b |
| 590 | X3b |
| 591 | X3b |
| 592 | B |
| 593 | B |
| 594 | A |
| 595 | B |
| 596 | B |
| 597 | B |
| 598 | B |
| 599 | A |
| 600 | A |
| 601 | A |
| 602 | A |
| 603 | A |
| 604 | A |
| 605 | B |
| 606 | B |
| 607 | B |
| 608 | X3b |
| 609 | X2b |
| 610 | C |
| 611 | B |
| 612 | X2b |
| 613 | X2b |
| 614 | C |
| 615 | A |
| 616 | A |
| 617 | B |
| 620 | A |
| 621 | B |
| 622 | B |
| 623 | C |
| 624 | C |
| 625 | C |
| 626 | C |
| 627 | C |
| 628 | C |
| 629 | C |
| 630 | C |
| 631 | C |
| 632 | C |
| 633 | C |
| 634 | C |
| 635 | C |
| 636 | C |
| 637 | C |
| 638 | C |
| 639 | C |
| 640 | C |
| 642 | C |
| 643 | C |
| 644 | C |
| 645 | C |
| 646 | C |
| 647 | C |
| 648 | C |
| 649 | C |
| 650 | C |
| 651 | C |
| 652 | C |
| 653 | C |
| 654 | C |
| 655 | C |
| 656 | C |
| 657 | C |
| 658 | C |
| 659 | X3a |
| 660 | X3a |
| 661 | X3b |
| 662 | X3a |
| 663 | X3b |
| 664 | X3b |
| 665 | C |
| 666 | C |
| 667 | C |
| 669 | C |
| 670 | C |
| 671 | C |
| 672 | C |
| 674 | C |
| 675 | C |
| 676 | C |
| 677 | C |
| 678 | C |
| 679 | C |
| 680 | C |
| 681 | C |
| 682 | C |
| 683 | C |
| 684 | C |
| 685 | C |
| 686 | C |
| 687 | C |
| 688 | C |
| 689 | C |
| 690 | C |
| 691 | C |
| 692 | C |
| 693 | C |
| 694 | C |
| 695 | C |
| 696 | X2a |
| 697 | X2a |
| 698 | X2b |
| 699 | X2b |
| 700 | X2a |
| 701 | X2a |
| 702 | X2b |
| 703 | X2a |
| 704 | X2a |
| 705 | X2b |
| 706 | X2b |
| 707 | X2b |
| 708 | X2b |
| 709 | X2b |
| 710 | X2b |
| 711 | X2a |
| 712 | X2a |
| 713 | X2b |
| 715 | X2b |
| 716 | X2b |
| 717 | X2b |
| 718 | X2a |
| 722 | X2b |
| 723 | X2b |
| 724 | X2b |
| 725 | X2b |
| 726 | X2b |
| 727 | X2b |
| 728 | X2a |
| 729 | X2b |
| 730 | X2b |
| 731 | X2b |
| 732 | X2a |
| 733 | X2b |
| 734 | X2a |
| 735 | X2a |
| 738 | X2a |
| 741 | X2b |

TABLE 1-continued

IL-17A/A pIC$_{50}$ inhibition values for selected compounds

| Compound. No. | IL-17A/A inhibition |
|---|---|
| 742 | X2a |
| 743 | X2a |
| 744 | X2a |
| 745 | X2b |
| 746 | X2b |
| 747 | X2b |
| 748 | X2a |
| 749 | X2a |
| 750 | X2b |
| 751 | X2b |
| 752 | X2b |
| 753 | X2b |
| 754 | X2b |
| 757 | X2b |
| 758 | X2b |
| 760 | C |
| 761 | C |
| 763 | C |
| 764 | C |
| 765 | C |
| 766 | C |
| 767 | C |
| 768 | C |
| 769 | C |
| 770 | C |
| 771 | X1a |
| 772 | X1a |
| 773 | X1b |
| 774 | X1b |
| 775 | X1b |
| 776 | X1b |
| 777 | X1b |
| 778 | X1b |
| 779 | X1a |
| 780 | X1b |
| 781 | X1b |
| 782 | X1b |
| 783 | X1b |
| 809 | A |
| 810 | A |

What is claimed is:

1. A compound represented by the structure of Formula (I):

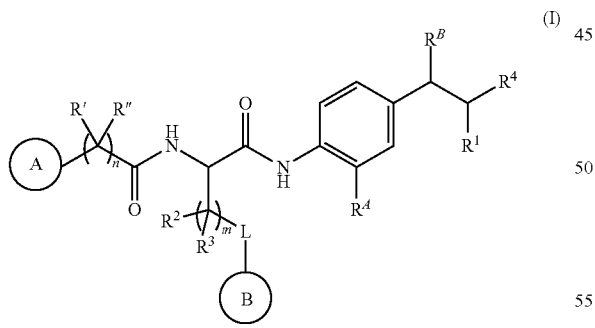

or a pharmaceutically acceptable salt thereof, wherein:

Ring A is $C_{3-12}$ carbocycle or 3- to 12-membered heterocycle;
  wherein Ring A is optionally substituted with one or more substituents independently selected from the group consisting of halogen, —CN, —NO$_2$, $C_{1-10}$ alkyl, $C_{2-10}$ alkenyl, $C_{2-10}$ alkynyl, —C(O)R$^{11}$, —C(O)N(R$^{11}$)$_2$, —C(O)OR$^{11}$, —N(R$^{11}$)$_2$, —NR$^{11}$C(O)R$^{11}$, —NR$^{11}$S(O)$_2$R$^{11}$, =NR$^{11}$, —OR$^{11}$, —OC(O)R$^{11}$, =O, —SR$^{11}$, —S(O)R$^{11}$, —S(O)$_2$R$^{11}$, =S, $C_{3-12}$ carbocycle, and 3- to 12-membered heterocycle;
  wherein each $C_{1-10}$ alkyl, $C_{2-10}$ alkenyl, and $C_{2-10}$ alkynyl substituent of Ring A is optionally and independently substituted with one or more substituents independently selected from the group consisting of halogen, —CN, —NO$_2$, —C(O)R$^{11}$, —C(O)N(R$^{11}$)$_2$, —C(O)OR$^{11}$, —N(R$^{11}$)$_2$, —NR$^{11}$C(O)R$^{11}$, =NR$^{11}$, —OR$^{18}$, —OC(O)R$^{11}$, =O, —SR$^{11}$, —S(O)R$^{11}$, —S(O)$_2$R$^{11}$, =S, $C_{3-10}$ carbocycle, and 3- to 10-membered heterocycle;
  wherein each $C_{3-10}$ carbocycle and 3- to 10-membered heterocycle substituent of each $C_{1-10}$ alkyl, $C_{2-10}$ alkenyl, and $C_{2-10}$ alkynyl substituent of Ring A is optionally and independently substituted with one or more substituents independently selected from the group consisting of halogen, —CN, —NO$_2$, —C(O)R$^{11}$, —C(O)N(R$^{11}$)$_2$, —C(O)OR$^{11}$, —N(R$^{11}$)$_2$, —NR$^{11}$C(O)R$^{11}$, =NR$^{11}$, —OR$^{11}$, —OC(O)R$^{11}$, and =O; and
  wherein each $C_{3-12}$ carbocycle and 3- to 12-membered heterocycle substituent of Ring A is optionally and independently substituted with one or more substituents independently selected from the group consisting of halogen, —CN, —NO$_2$, $C_{1-6}$ alkyl, $C_{1-6}$ haloalkyl, —C(O)R$^{11}$, —C(O)N(R$^{11}$)$_2$, —C(O)OR$^{11}$, —N(R$^{11}$)$_2$, —NR$^{11}$C(O)R$^{11}$, —OR$^{11}$, —OC(O)R$^{11}$, and —SR$^{11}$;

Ring B is $C_{3-10}$ carbocycle or 3- to 12-membered heterocycle;
  wherein Ring B is optionally substituted with one or more substituents independently selected from the group consisting of halogen, —CN, —NO$_2$, $C_{1-10}$ alkyl, $C_{2-10}$ alkenyl, $C_{2-10}$ alkynyl, —C(O)R$^{12}$, —C(O)N(R$^{12}$)$_2$, —C(O)OR$^{12}$, —N(R$^{12}$)$_2$, —NR$^{12}$C(O)R$^{12}$, =NR$^{12}$, —OR$^{12}$, —OC(O)R$^{12}$, =O, —SR$^{12}$, —S(O)R$^{12}$, —S(O)$_2$R$^{12}$, and =S;
  wherein each $C_{1-10}$ alkyl, $C_{2-10}$ alkenyl, and $C_{2-10}$ alkynyl substituent of Ring B is optionally and independently substituted with one or more substituents independently selected from the group consisting of halogen, —CN, —NO$_2$, —C(O)R$^{12}$, —C(O)N(R$^{12}$)$_2$, —C(O)OR$^{12}$, —N(R$^{12}$)$_2$, —NR$^{12}$C(O)R$^{12}$, =NR$^{12}$, —OR$^{12}$, —OC(O)R$^{12}$, =O, —SR$^{12}$, —S(O)R$^{12}$, —S(O)$_2$R$^{12}$, =S, $C_{3-10}$ carbocycle, and 3- to 10-membered heterocycle; and
  wherein each $C_{3-10}$ carbocycle and 3- to 10-membered heterocycle substituent of each $C_{1-10}$ alkyl, $C_{2-10}$ alkenyl, and $C_{2-10}$ alkynyl substituent of Ring B is optionally and independently substituted with one or more substituents independently selected from the group consisting of halogen, —CN, —NO$_2$, —C(O)R$^{12}$, —C(O)N(R$^{12}$)$_2$, —C(O)OR$^{12}$, —N(R$^{12}$)$_2$, —NR$^{12}$C(O)R$^{12}$, =NR$^{12}$, —OR$^{12}$, —OC(O)R$^{12}$, and =O;

each R$^{11}$ is independently hydrogen, $C_{1-6}$ alkyl, $C_{3-12}$ carbocycle, or 3- to 12-membered heterocycle;
  wherein each $C_{1-6}$ alkyl of R$^{11}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, $C_{3-10}$ carbocycle, and 3- to 10-membered heterocycle;

wherein each $C_{3-10}$ carbocycle and 3- to 10-membered heterocycle substituent of each $C_{1-6}$ alkyl of $R^{11}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

wherein each $C_{3-12}$ carbocycle and 3- to 12-membered heterocycle of $R^{11}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and wherein each $C_{1-6}$ alkyl substituent of each $C_{3-12}$ carbocycle and 3- to 12-membered heterocycle of $R^{11}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

each $R^{12}$ is independently hydrogen, C$_{1-6}$ alkyl, C$_{3-12}$ carbocycle, or 3- to 12-membered heterocycle;

wherein each $C_{1-6}$ alkyl of $R^{12}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;

wherein each $C_{3-10}$ carbocycle and 3- to 10-membered heterocycle substituent of each $C_{1-6}$ alkyl of $R^{12}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

wherein each $C_{3-12}$ carbocycle and 3- to 12-membered heterocycle of $R^{12}$ is optionally and independently substituted with one or more substituents independently selected from the group consisting of halogen, —CN, —NO$_2$, —C$_{1-6}$ alkyl, —NH$_2$, —OH, —OC$_{1-6}$ alkyl, —OC$_{1-6}$ haloalkyl, and =O; and wherein each $C_{1-6}$ alkyl substituent of each $C_{3-12}$ carbocycle and 3- to 12-membered heterocycle of $R^{12}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

$R^A$ is hydrogen, halogen, —CN, —NO$_2$, C$_{1-6}$ alkyl, —C(O)R$^{14}$, —C(O)N(R$^{14}$)$_2$, —C(O)OR$^{14}$, —N(R$^{14}$)$_2$, —NR$^{14}$C(O)R$^{14}$, —OR$^{14}$, or —OC(O)R$^{14}$, wherein the C$_{1-6}$ alkyl is optionally substituted with one or more substituents independently selected from the group consisting of halogen, —CN, —NO$_2$, —C(O)R$^{14}$, —N(R$^{14}$)$_2$, —OR$^{14}$, and =O;

$R^B$ is hydrogen, halogen, —CN, —NO$_2$, —C$_{1-6}$ alkyl, —C(O)R$^{15}$, —C(O)N(R$^{15}$)$_2$, —C(O)OR$^{15}$, —N(R$^{15}$)$_2$, —NR$^{11}$C(O)R$^{15}$, —OR$^5$, or —OC(O)R$^{15}$, wherein the C$_{1-6}$ alkyl is optionally substituted with one or more substituents independently selected from the group consisting of halogen, —CN, —NO$_2$, —C(O)R$^{15}$, —N(R$^{15}$)$_2$, —OR$^5$, and =O;

each $R^{14}$ is independently hydrogen, C$_{1-6}$ alkyl, C$_{3-12}$ carbocycle, or 3- to 12-membered heterocycle;

wherein each $C_{1-6}$ alkyl of $R^{14}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;

wherein each $C_{3-10}$ carbocycle and 3- to 10-membered heterocycle substituent of each $C_{1-6}$ alkyl of $R^{14}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

wherein each $C_{3-12}$ carbocycle and 3- to 12-membered heterocycle of $R^{14}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and wherein each $C_{1-6}$ alkyl substituent of each $C_{3-12}$ carbocycle and 3- to 12-membered heterocycle of $R^{14}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

each $R^{11}$ is independently hydrogen, C$_{1-6}$ alkyl, C$_{3-12}$ carbocycle, or 3- to 12-membered heterocycle;

wherein each $C_{1-6}$ alkyl of $R^{15}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;

wherein each $C_{3-10}$ carbocycle and 3- to 10-membered heterocycle substituent of each $C_{1-6}$ alkyl of $R^{15}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

wherein each $C_{3-12}$ carbocycle and 3- to 12-membered heterocycle of $R^{15}$ is optionally and independently substituted with one or more substituents independently selected from the group consisting of halogen, —CN, —NO$_2$, —C$_{1-6}$ alkyl, —NH$_2$, —OH, —OC$_{1-6}$ alkyl, —OC$_{1-6}$ haloalkyl, and =O; and wherein each $C_{1-6}$ alkyl substituent of each $C_{3-12}$ carbocycle and 3- to 12-membered heterocycle of $R^{14}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

R' is hydrogen, halogen, C$_{1-6}$ alkyl, or —OR$^{16}$, wherein the C$_{1-6}$ alkyl is optionally substituted with one or more substituents independently selected from the group consisting of halogen, —CN, —NO$_2$, —C(O)R$^{16}$, —N(R$^{16}$)$_2$, —OR$^{16}$, and =O;

R" is hydrogen, halogen, C$_{1-6}$ alkyl, or —OR$^{16}$, wherein the C$_{1-6}$ alkyl is optionally substituted with one or more substituents independently selected from the group consisting of halogen, —CN, —NO$_2$, —C(O)R$^{16}$, —N(R$^{16}$)$_2$, —OR$^{16}$, and =O;
  each R$^{16}$ is independently hydrogen, C$_{1-6}$ alkyl, C$_{3-12}$ carbocycle, or 3- to 12-membered heterocycle;
    wherein each C$_{1-6}$ alkyl of R$^{16}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;
    wherein each C$_{3-10}$ carbocycle and 3- to 10-membered heterocycle substituent of each C$_{1-6}$ alkyl of R$^{16}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
    wherein each C$_{3-12}$ carbocycle and 3- to 12-membered heterocycle of R$^{16}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and
    wherein each C$_{1-6}$ alkyl substituent of each C$_{3-12}$ carbocycle and 3- to 12-membered heterocycle of R$^{16}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
  R$^1$ is —NR$^{21}$R$^{22}$, —NR$^{21}$C(O)R$^{22}$, —NR$^{21}$C(O)NR$^{21}$R$^{22}$, —NR$^{21}$C(O)OR$^{22}$, —NR$^{21}$S(O)$_2$R$^{22}$, —NR$^{21}$S(O)$_2$NR$^{21}$R$^{22}$, or —OR$^{21}$;
  each R$^{21}$ is independently hydrogen or C$_{1-6}$ alkyl, wherein each C$_{1-6}$ alkyl is optionally and independently substituted with one or more substituents independently selected from the group consisting of halogen, —CN, —NO$_2$, —C(O)R$^{17}$, —N(R$^{17}$)$_2$, —OR$^{17}$, and =O;
  R$^{22}$ is C$_{1-10}$ alkyl, C$_{2-10}$ alkenyl, C$_{2-10}$ alkynyl, C$_{3-12}$ carbocycle, or 3- to 12-membered heterocycle;
    wherein the C$_{1-10}$ alkyl, C$_{2-10}$ alkenyl, or C$_{2-10}$ alkynyl of R$^{22}$ is optionally substituted with one or more substituents independently selected from the group consisting of halogen, —CN, —NO$_2$, —C(O)R$^{18}$, —C(O)N(R$^{18}$)$_2$, —C(O)OR$^{18}$, —N(R$^{18}$)$_2$, —NR$^{18}$C(O)R$^{18}$, =NR$^{18}$, —OR$^{18}$, —OC(O)R$^{18}$, =O, —SR$^{18}$, —S(O)R$^{18}$, —S(O)$_2$R$^{18}$, =S, C$_{3-10}$ carbocycle, and 3- to 10-membered heterocycle;
    wherein each C$_{3-10}$ carbocycle and 3- to 10-membered heterocycle substituent of the C$_{1-10}$ alkyl, C$_{2-10}$ alkenyl, or C$_{2-10}$ alkynyl of R$^{22}$ is optionally and independently substituted with one or more substituents independently selected from the group consisting of halogen, —CN, —NO$_2$, —C(O)R$^{18}$, —C(O)N(R$^{18}$)$_2$, —C(O)OR$^{18}$, —N(R$^{18}$)$_2$, —NR$^{18}$C(O)R$^{18}$, =NR$^{18}$, —OR$^{18}$, —OC(O)R$^{18}$, and =O;
    wherein the C$_{3-12}$ carbocycle or 3- to 12-membered heterocycle of R$^{22}$ is optionally substituted with one or more substituents independently selected from the group consisting of halogen, —CN, —NO$_2$, C$_{1-10}$ alkyl, C$_{2-10}$ alkenyl, C$_{2-10}$ alkynyl, —C(O)R$^{18}$, —C(O)N(R$^{18}$)$_2$, —C(O)OR$^{18}$, —N(R$^{18}$)$_2$, —NR$^{18}$C(O)R$^{18}$, =NR$^{18}$, —OR$^{18}$, —OC(O)R$^{18}$, =O, —SR$^{18}$, —S(O)R$^{18}$, —S(O)$_2$R$^{18}$, =S, C$_{3-10}$ carbocycle, and 3- to 10-membered heterocycle;
    wherein each C$_{1-10}$ alkyl, C$_{2-10}$ alkenyl, and C$_{2-10}$ alkynyl substituent of the C$_{3-12}$ carbocycle or 3- to 12-membered heterocycle of R$^{22}$ is optionally and independently substituted with one or more substituents independently selected from the group consisting of halogen, —CN, —NO$_2$, —C(O)R$^{18}$, —C(O)N(R$^{18}$)$_2$, —C(O)OR$^{18}$, —N(R$^{18}$)$_2$, —NR$^{18}$C(O)R$^{18}$, =NR$^{18}$, —OR$^{18}$, —OC(O)R$^{18}$, =O, —SR$^{18}$, —S(O)R$^{18}$, —S(O)$_2$R$^{18}$, =S, C$_{3-10}$ carbocycle, and 3- to 10-membered heterocycle;
    wherein each C$_{3-10}$ carbocycle and 3- to 10-membered heterocycle substituent of each C$_{1-10}$ alkyl, C$_{2-10}$ alkenyl, and C$_{2-10}$ alkynyl substituent of the C$_{3-12}$ carbocycle or 3- to 12-membered heterocycle of R$^{22}$ is optionally and independently substituted with one or more substituents independently selected from the group consisting of halogen, —CN, —NO$_2$, —C(O)R$^{18}$, —C(O)N(R$^{18}$)$_2$, —C(O)OR$^{18}$, —N(R$^{18}$)$_2$, —NR$^{18}$C(O)R$^{18}$, =NR$^{18}$, —OR$^{18}$, —OC(O)R$^{18}$, and =O; and
    wherein each C$_{3-10}$ carbocycle and 3- to 10-membered heterocycle substituent of the C$_{3-12}$ carbocycle or 3- to 12-membered heterocycle of R$^{22}$ is optionally and independently substituted with one or more substituents independently selected from the group consisting of halogen, —CN, —NO$_2$, —C(O)R$^{18}$, —C(O)N(R$^{18}$)$_2$, —C(O)OR$^{18}$, —N(R$^{18}$)$_2$, —NR$^{18}$C(O)R$^{18}$, =NR$^{18}$, —OR$^{18}$, —OC(O)R$^{18}$, and =O;
  each R$^{18}$ is independently hydrogen, C$_{1-6}$ alkyl, C$_{3-12}$ carbocycle, or 3- to 12-membered heterocycle;
    wherein each C$_{1-6}$ alkyl of R$^{18}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;
    wherein each C$_{3-10}$ carbocycle and 3- to 10-membered heterocycle substituent of each C$_{1-6}$ alkyl of R$^{18}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
    wherein each C$_{3-12}$ carbocycle and 3- to 12-membered heterocycle of R$^{18}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and
    wherein each C$_{1-6}$ alkyl substituent of each C$_{3-12}$ carbocycle and 3- to 12-membered heterocycle of R$^{18}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
  each R$^2$ is independently hydrogen, halogen, C$_{1-6}$ alkyl, —OR$^{17}$, or C$_{3-6}$ cycloalkyl, wherein each C$_{1-6}$ alkyl and C$_{3-6}$ cycloalkyl is optionally and independently substituted with one or more substituents independently selected from the group consisting of halogen, —CN, —NO$_2$, —C(O)R$^{17}$, —N(R$^{17}$)$_2$, —OR$^{17}$, and =O;

each R$^3$ is independently hydrogen, halogen, C$_{1-6}$ alkyl, —OR$^{17}$, or C$_{3-6}$ cycloalkyl, wherein each C$_{1-6}$ alkyl and C$_{3-6}$ cycloalkyl is optionally and independently substituted with one or more substituents independently selected from the group consisting of halogen, —CN, —NO$_2$, —C(O)R$^{17}$, —N(R$^{17}$)$_2$, —OR$^{17}$, and =O; or each R$^2$ and R$^3$, together with the carbon atom to which they are bound, independently forms a C$_{3-6}$ cycloalkyl, wherein each C$_{3-6}$ cycloalkyl is optionally and independently substituted with one or more substituents independently selected from the group consisting of halogen, —CN, —NO$_2$, —C(O)R$^{17}$, —N(R$^{17}$)$_2$, —OR$^{17}$, and =O;

each R$^{17}$ is independently hydrogen, C$_{1-6}$ alkyl, C$_{3-12}$ carbocycle, or 3- to 12-membered heterocycle;
  wherein each C$_{1-6}$ alkyl of R$^{17}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;
  wherein each C$_{3-10}$ carbocycle and 3- to 10-membered heterocycle substituent of each C$_{1-6}$ alkyl of R$^{17}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
  wherein each C$_{3-12}$ carbocycle and 3- to 12-membered heterocycle of R$^{17}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and
  wherein each C$_{1-6}$ alkyl substituent of each C$_{3-12}$ carbocycle and 3- to 12-membered heterocycle of R$^{17}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

R$^4$ is —C(O)NR$^{23}$R$^{24}$ or

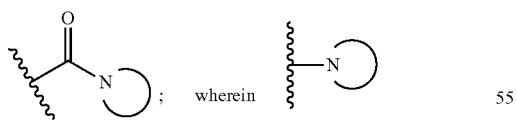

; wherein is 4- to 9-membered heterocycle, wherein the 4- to 9-membered heterocycle is optionally substituted with one or more substituents independently selected from the group consisting of halogen, —CN, —NO$_2$, C$_{1-10}$ alkyl, C$_{2-10}$ alkenyl, C$_{2-10}$ alkynyl, —C(O)R$^{13}$, —C(O)N(R$^{13}$)$_2$, —C(O)OR$^{13}$, —N(R$^{13}$)$_2$, —NR$^{13}$C(O)R$^{13}$, =NR$^{13}$, —OR$^{13}$, —OC(O)R$^{13}$, =O, —SR$^{13}$, —S(O)R$^{13}$, —S(O)$_2$R$^{13}$ and =S;
  wherein each C$_{1-10}$ alkyl, C$_{2-10}$ alkenyl, and C$_{2-10}$ alkynyl substituent of the 4- to 9-membered heterocycle is optionally and independently substituted with one or more substituents independently selected from the group consisting of halogen, —CN, —NO$_2$, —C(O)R$^{13}$, —C(O)N(R$^{13}$)$_2$, —C(O)OR$^{13}$, —N(R$^{13}$)$_2$, —NR$^{13}$C(O)R$^{13}$, =NR$^{13}$, —OR$^{13}$, —OC(O)R$^{13}$, =O, —SR$^{13}$, —S(O)R$^{13}$, —S(O)$_2$R$^{11}$, =S, C$_{3-10}$ carbocycle, and 3- to 10-membered heterocycle; and
  wherein each C$_{3-10}$ carbocycle and 3- to 10-membered heterocycle substituent of each C$_{1-10}$ alkyl, C$_{2-10}$ alkenyl, and C$_{2-10}$ alkynyl substituent of the 4- to 9-membered heterocycle is optionally and independently substituted with one or more substituents independently selected from the group consisting of halogen, —CN, —NO$_2$, —C(O)R$^{13}$, —C(O)N(R$^{13}$)$_2$, —C(O)OR$^{13}$, —N(R$^{13}$)$_2$, —NR$^{13}$C(O)R$^{13}$, =NR$^{13}$, —OR$^{13}$, —OC(O)R$^{13}$, and =O;

each R$^{13}$ is independently hydrogen, C$_{1-6}$ alkyl, C$_{3-12}$ carbocycle, or 3- to 12-membered heterocycle;
  wherein each C$_{1-6}$ alkyl of R$^{13}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;
  wherein each C$_{3-10}$ carbocycle and 3- to 10-membered heterocycle substituent of each C$_{1-6}$ alkyl of R$^{13}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
  wherein each C$_{3-12}$ carbocycle and 3- to 12-membered heterocycle of R$^{13}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and
  wherein each C$_{1-6}$ alkyl substituent of each C$_{3-12}$ carbocycle and 3- to 12-membered heterocycle of R$^{13}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

R$^{23}$ is C$_{1-6}$ alkyl, C$_{3-12}$ carbocycle, or 3- to 12-membered heterocycle;
  wherein the C$_{1-6}$ alkyl is optionally substituted with one or more substituents independently selected from the group consisting of halogen, —CN, —NO$_2$, —N(R$^{19}$)$_2$, —OR$^{19}$, —SR$^{19}$, C$_{3-10}$ carbocycle, and 3- to 10-membered heterocycle;
  wherein each C$_{3-10}$ carbocycle and 3- to 10-membered heterocycle substituent of the C$_{1-6}$ alkyl of R$^{23}$ is optionally and independently substituted with one or more substituents independently selected from the group consisting of halogen, —CN, C$_{1-6}$ alkyl, C$_{1-6}$ haloalkyl, —N(R$^{19}$)$_2$, —OR$^{19}$, and =O; and
  wherein the C$_{3-12}$ carbocycle or 3- to 12-membered heterocycle of R$^{23}$ is optionally substituted with one or more substituents independently selected from the group consisting of halogen, —CN, —C$_{1-6}$ alkyl, —C$_{1-6}$ haloalkyl, —N(R$^{19}$)$_2$, —OR$^{19}$, and =O;

R$^{24}$ is hydrogen or C$_{1-6}$ alkyl;
wherein the C$_{1-6}$ alkyl is optionally substituted with one or more substituents independently selected from the group consisting of halogen, —CN, —NO$_2$, —N(R$^{19}$)$_2$, —OR$^{19}$, —SR$^{19}$, C$_{3-6}$ carbocycle, and 3- to 6-membered heterocycle;

each R$^{19}$ is independently hydrogen, C$_{1-6}$ alkyl, C$_{3-12}$ carbocycle, or 3- to 12-membered heterocycle;
wherein each C$_{1-6}$ alkyl of R$^{19}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, =O, C$_{3-10}$ carbocycle, and 3- to 10-membered heterocycle;
wherein each C$_{3-10}$ carbocycle and 3- to 10-membered heterocycle substituent of each C$_{1-6}$ alkyl of R$^{19}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;
wherein each C$_{3-12}$ carbocycle and 3- to 12-membered heterocycle of R$^{19}$ is optionally and independently substituted with one or more substituents independently selected from the group consisting of halogen, —CN, —NO$_2$, C$_{1-6}$ alkyl, —NH$_2$, —OH, —OC$_{1-6}$ alkyl, —OC$_{1-6}$ haloalkyl, and =O; and
wherein each C$_{1-6}$ alkyl substituent of each C$_{3-12}$ carbocycle and 3- to 12-membered heterocycle of R$^{19}$ is optionally and independently substituted with one or more substituents independently selected from the group consisting of halogen, —CN, —NO$_2$, —NH$_2$, —OH, —OC$_{1-6}$ alkyl, —OC$_{1-6}$ haloalkyl, and =O;

L is absent, —NH—, or —O—;
m is 0, 1, or 2; and
n is 0 or 1;
with the proviso that at least one of R$^A$ and R$^B$ is not hydrogen.

2. The compound of claim 1, or a pharmaceutically acceptable salt thereof, wherein Ring A is C$_{3-6}$ carbocycle, 8-membered heterocycle, 9-membered heterocycle, 5-membered heteroaryl, or 6-membered heteroaryl;
wherein Ring A is optionally substituted with one or more substituents independently selected from the group consisting of halogen, —CN, —NO$_2$, C$_{1-6}$ alkyl, —N(R$^{11}$)$_2$, —NR$^{11}$S(O)$_2$R$^{11}$, —OR$^{11}$, C$_{3-5}$ carbocycle, and 3- to 5-membered heterocycle; and
wherein each C$_{1-6}$ alkyl substituent of Ring A is optionally and independently substituted with one or more independently selected C$_{3-5}$ carbocycle substituents.

3. The compound of claim 1, or a pharmaceutically acceptable salt thereof, wherein:
Ring A is 5-membered heteroaryl;
wherein Ring A is optionally substituted with one or more substituents independently selected from the group consisting of halogen, —CN, C$_{1-10}$ alkyl, and —OR$^{11}$; and
each R$^{11}$ is independently a C$_{1-6}$ alkyl.

4. The compound of claim 1, or a pharmaceutically acceptable salt thereof,

Ring A is pyrrolyl, furanyl, thiophenyl, pyrazolyl, isoxazolyl, oxazolyl, thiazolyl, triazolyl, oxadiazolyl, or thiadiazolyl;
wherein Ring A is optionally substituted with one or more substituents independently selected from the group consisting of halogen, —CN, C$_{1-10}$ alkyl, and —OR$^{11}$; and
each R$^{11}$ is independently a C$_{1-6}$ alkyl.

5. The compound of claim 1, or a pharmaceutically acceptable salt thereof, wherein Ring A is pyrrolyl, furanyl, pyrazolyl, isoxazolyl, oxadiazolyl, or tetrazolyl;
wherein Ring A is optionally substituted with one or more substituents independently selected from the group consisting of C$_{1-6}$ alkyl, —OR$^{11}$, C$_{3-5}$ carbocycle, and 3- to 5-membered heterocycle; and
wherein each C$_{1-6}$ alkyl substituent of Ring A is optionally and independently substituted with one or more independently selected C$_{3-5}$ carbocycle substituents.

6. The compound of claim 1, or a pharmaceutically acceptable salt thereof, wherein Ring A is:

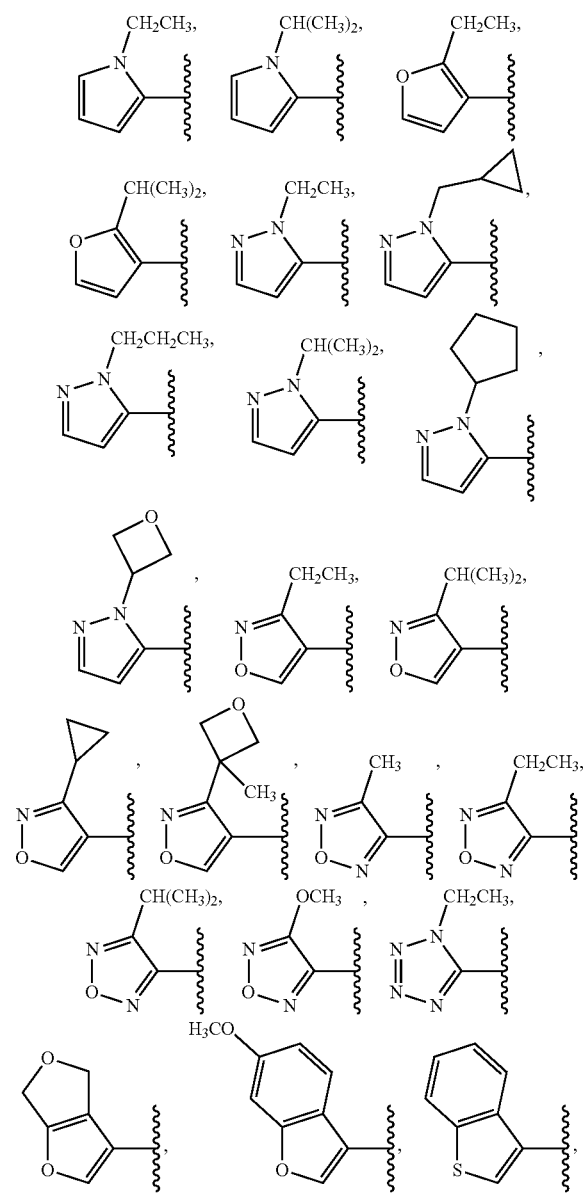

313

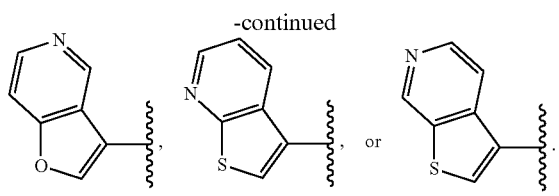

-continued

7. The compound of claim 1, or a pharmaceutically acceptable salt thereof, wherein Ring B is $C_{3-10}$ carbocycle or 3- to 12-membered heterocycle;
   wherein Ring B is optionally substituted with one or more substituents independently selected from the group consisting of halogen and $C_{1-10}$ alkyl.

8. The compound of claim 1, or a pharmaceutically acceptable salt thereof, wherein Ring B is monocyclic $C_{5-8}$ cycloalkyl, bicyclic 9-membered carbocycle, or bicyclic 10-membered carbocycle;
   wherein Ring B is optionally substituted with one or more substituents independently selected from the group consisting of halogen and $C_{1-6}$ alkyl; and
   wherein each $C_{1-6}$ alkyl substituent of Ring B is optionally and independently substituted with one or more independently selected halogen substituents.

9. The compound of claim 1, or a pharmaceutically acceptable salt thereof, wherein Ring B is:

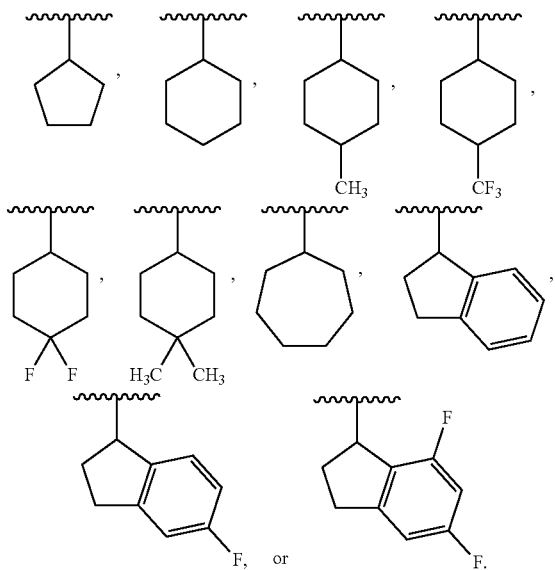

10. The compound of claim 1, or a pharmaceutically acceptable salt thereof, wherein $R^A$ is hydrogen, halogen, —CN, $C_{1-6}$ alkyl, —C(O)N($R^{14}$)$_2$, —C(O)O$R^{14}$, —N($R^{14}$)$_2$, or —O$R^{14}$, wherein the $C_{1-6}$ alkyl is optionally substituted with one or more substituents independently selected from the group consisting of halogen, CN, C(O)$R^{14}$, N($R^{14}$)$_2$, O$R^{14}$, and =O.

11. The compound of claim 1, or a pharmaceutically acceptable salt thereof, wherein $R^A$ is hydrogen or halogen.

12. The compound of claim 1, or a pharmaceutically acceptable salt thereof, wherein $R^B$ is hydrogen or $C_{1-6}$ alkyl, wherein the $C_{1-6}$ alkyl is optionally substituted with one or more substituents independently selected from the group consisting of halogen, —CN, —NO$_2$, —C(O)$R^{15}$, —N($R^{15}$)$_2$, —O$R^{15}$, and =O.

13. The compound of claim 1, or a pharmaceutically acceptable salt thereof, wherein $R^B$ is hydrogen or $C_{1-6}$ alkyl, wherein the $C_{1-6}$ alkyl is optionally substituted with one or more substituents independently selected from the group consisting of halogen, —CN, C(O)$R^{15}$, —N($R^{15}$)$_2$, —O$R^{15}$, and =O.

14. The compound of claim 1, or a pharmaceutically acceptable salt thereof, wherein $R^1$ is —NR$^{21}$C(O)R$^{22}$, —NR$^{21}$C(O)NR$^{21}$R$^{22}$, or —NR$^{21}$C(O)OR$^{22}$.

15. The compound of claim 1, or a pharmaceutically acceptable salt thereof, wherein $R^1$ is —NR$^{21}$C(O)R$^{22}$.

16. The compound of claim 1, or a pharmaceutically acceptable salt thereof, wherein $R^1$ is:

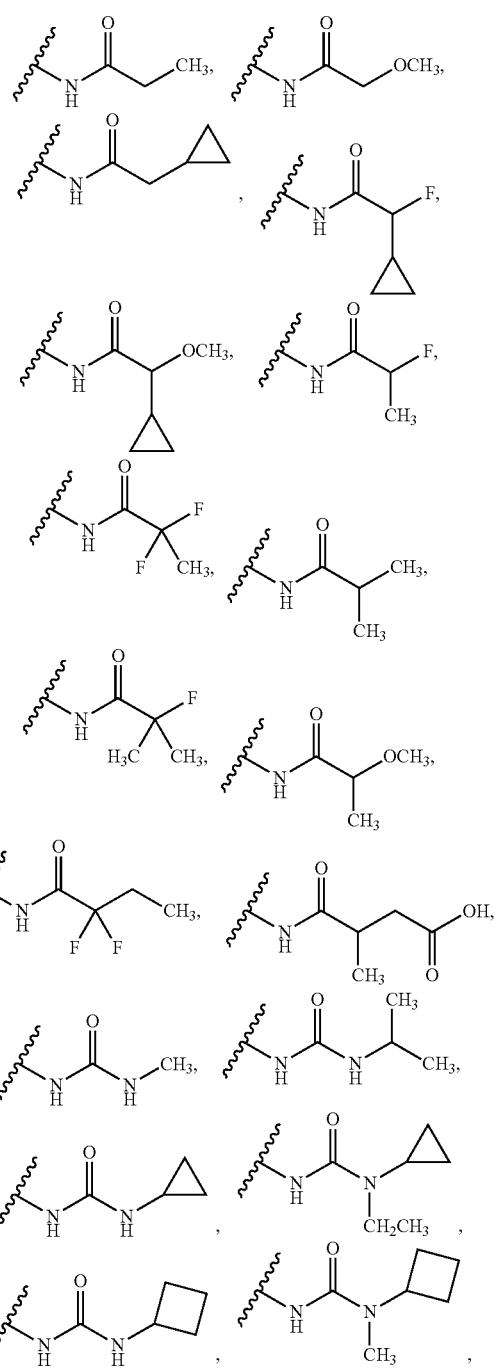

-continued

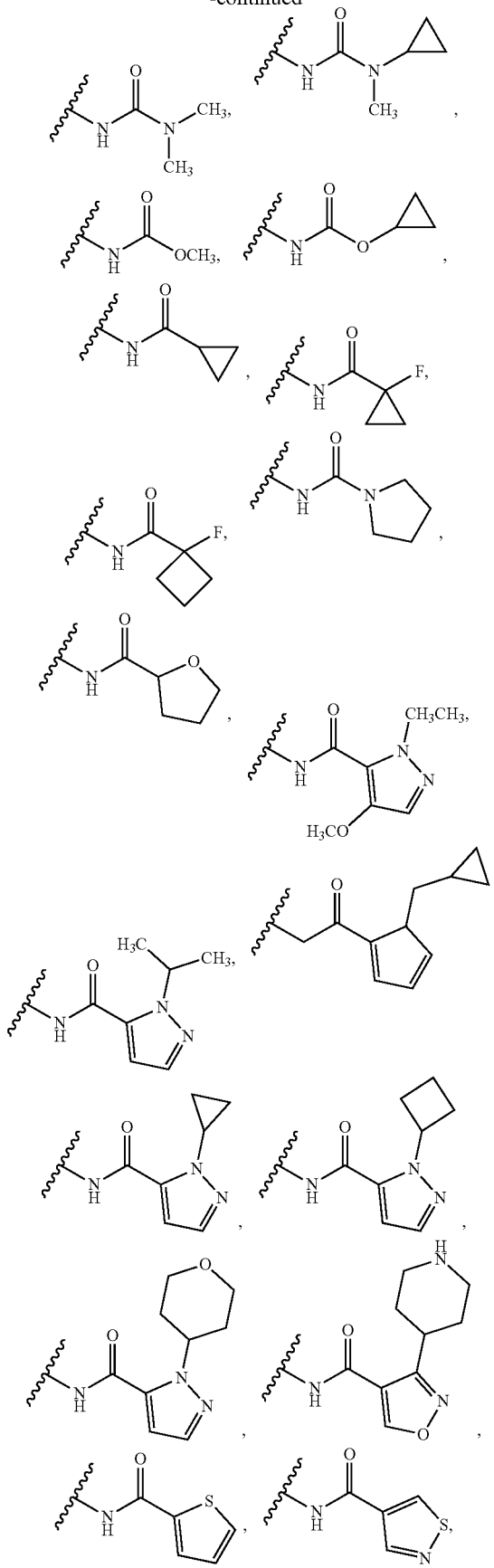

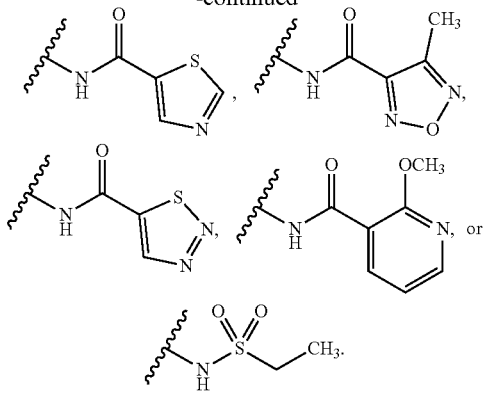

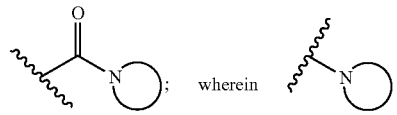

17. The compound of claim 1, or a pharmaceutically acceptable salt thereof, wherein $R^4$ is $-C(O)NR^{23}R^{24}$.

18. The compound of claim 1, or a pharmaceutically acceptable salt thereof, wherein $R^4$ is

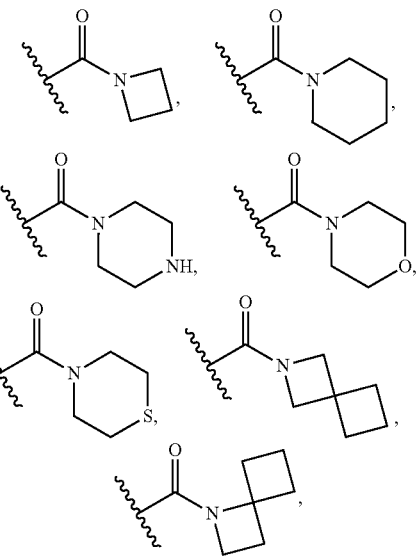

is 4- to 9-membered heterocycle, wherein the 4- to 9-membered heterocycle is optionally substituted with one or more independently selected from $C_{1-10}$alkyl.

19. The compound of claim 1, or a pharmaceutically acceptable salt thereof, wherein $R^4$ is:

wherein $R^4$ is optionally substituted with one or more substituents independently selected from the group consisting of halogen, $-CN$, $-NO_2$, $C_{1-10}$ alkyl, $C_{2-10}$ alkenyl, $-C_{2-10}$ alkynyl, $-C(O)R^{13}$, $-C(O)N(R^{13})_2$, $-C(O)OR^{13}$, $-N(R^{13})_2$, $-NR^{13}C(O)R^{13}$, $=NR^{13}$, $-OR^{13}$, $-OC(O)R^{13}$, $=O$, $-SR^{13}$, $-S(O)R^{13}$, $-S(O)_2R^{13}$, and $=S$;

wherein each $C_{1-10}$ alkyl, $C_{2-10}$ alkenyl, and $C_{2-10}$ alkynyl substituent of $R^4$ is optionally and independently substituted with one or more substituents independently selected from the group consisting of halogen, —CN, —NO$_2$, —C(O)R$^{13}$, —C(O)N(R$^{13}$)$_2$, —C(O)OR$^{13}$, —N(R$^{13}$)$_2$, —NR$^{13}$C(O)R$^{13}$, =NR$^{13}$, —OR$^{13}$, —OC(O)R$^{13}$, =O, —SR$^{13}$, —S(O)R$^{13}$, —S(O)$_2$R$^{13}$, =S, C$_{3-10}$ carbocycle, and 3- to 10-membered heterocycle; and wherein each C$_{3-10}$ carbocycle and 3- to 10-membered heterocycle substituent of each C$_{1-10}$ alkyl, C$_{2-10}$ alkenyl, and C$_{2-10}$ alkynyl substituent of R$^4$ is optionally and independently substituted with one or more substituents independently selected from the group consisting of halogen, —CN, —NO$_2$, —C(O)R$^{13}$, —C(O)N(R$^{13}$)$_2$, —C(O)OR$^{13}$, —N(R$^{13}$)$_2$, —NR$^{13}$C(O)R$^{13}$, =NR$^{13}$, —OR$^{13}$, —OC(O)R$^{13}$, and =O.

20. The compound of claim 1, or a pharmaceutically acceptable salt thereof, wherein R$^4$ is:

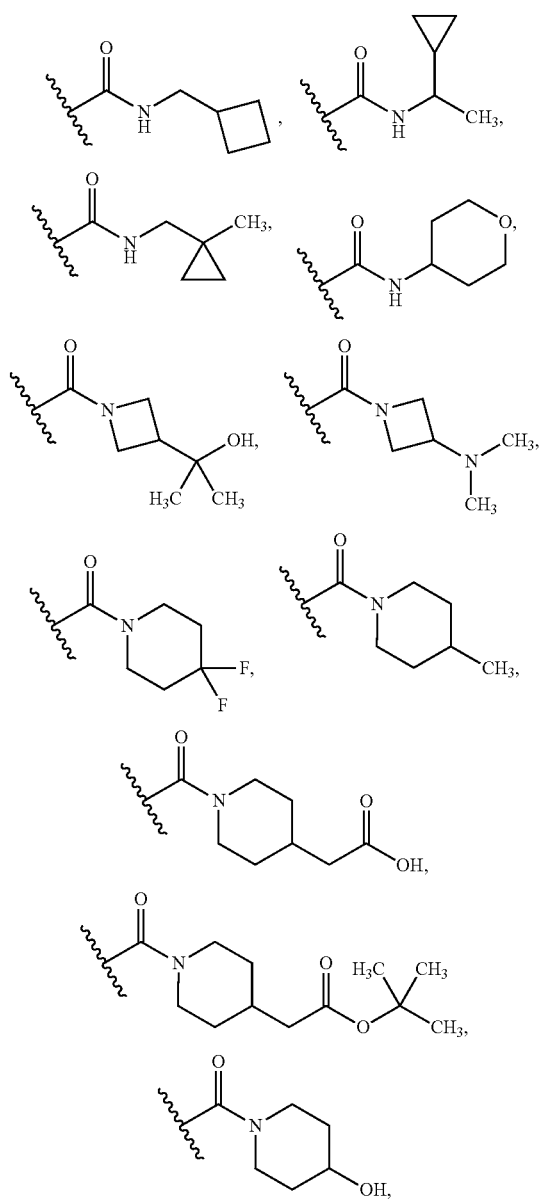

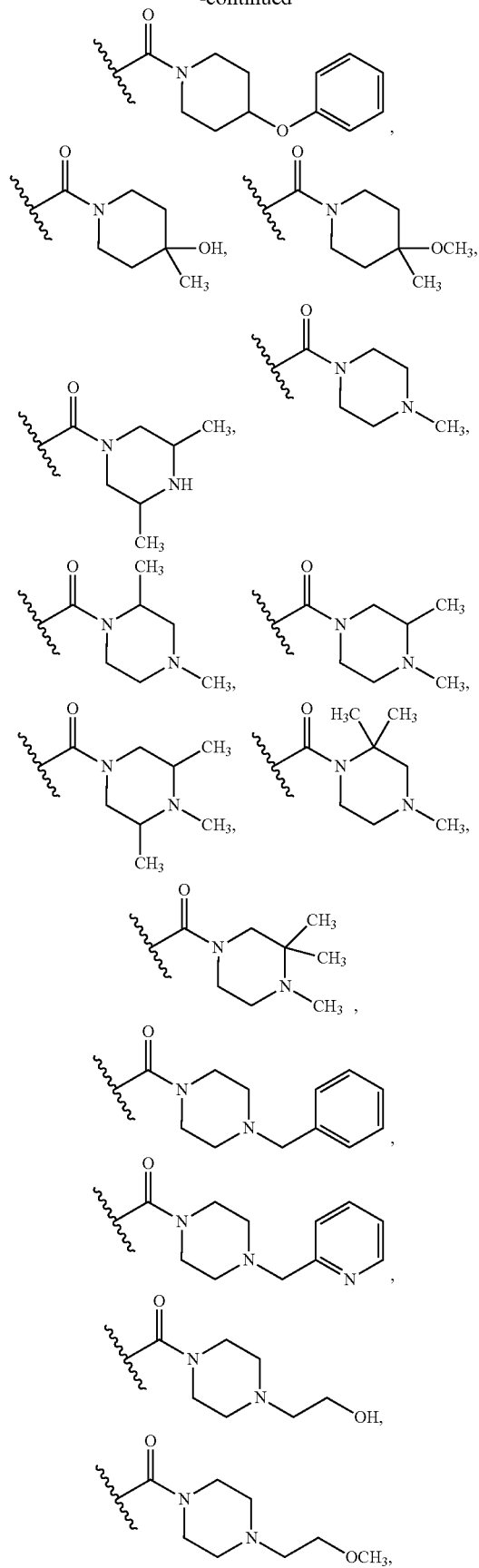

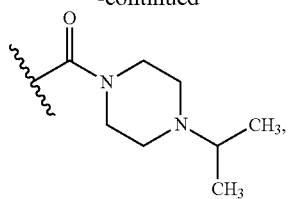

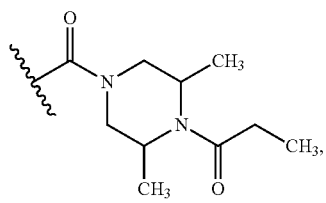

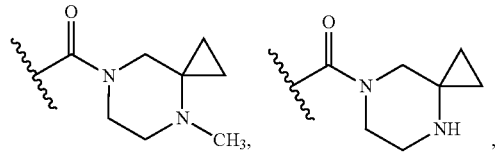

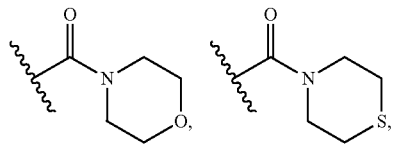

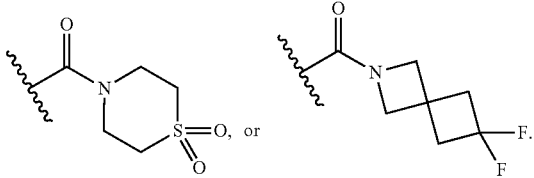

21. The compound of claim 1, or a pharmaceutically acceptable salt thereof, wherein:

R' is halogen;

R" is halogen; and n is 1.

22. The compound of claim 1, or a pharmaceutically acceptable salt thereof, wherein:

Ring A is $C_{3-6}$ cycloalkyl, bicyclic 8-membered heterocycle, bicyclic 9-membered heterocycle, phenyl, 5-membered heteroaryl, or 6-membered heteroaryl;

wherein Ring A is optionally substituted with one or more substituents independently selected from the group consisting of halogen, —CN, —NO$_2$, $C_{1-6}$ alkyl, —N(R$^{11}$)$_2$, —NR$^{11}$S(O)$_2$R$^{11}$, and —OR$^{11}$;

R' is hydrogen or halogen;

R" is hydrogen or halogen; and n is 1.

23. The compound of claim 1, or a pharmaceutically acceptable salt thereof, wherein

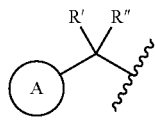

is:

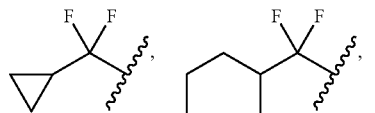

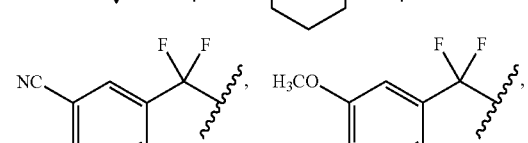

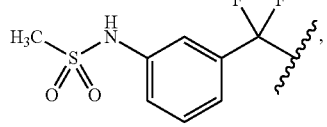

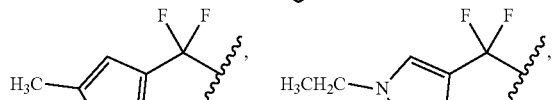

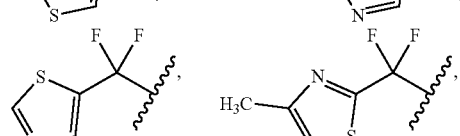

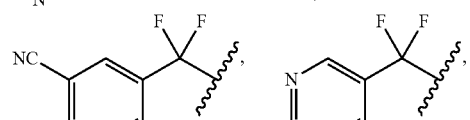

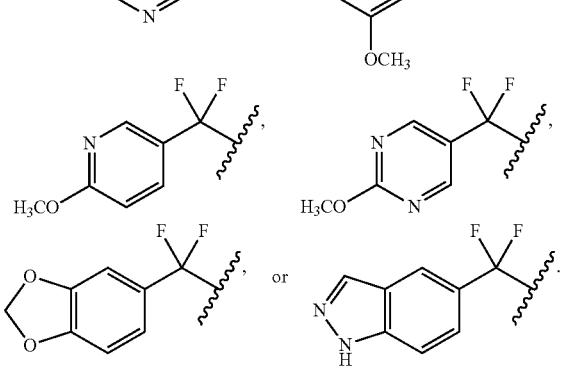

24. The compound of claim 1, or a pharmaceutically acceptable salt thereof, wherein:

Ring B is a monocyclic $C_{5-8}$ carbocycle;

wherein Ring B is optionally substituted with one or more substituents independently selected from the group consisting of halogen, $C_{1-6}$ alkyl, and —OR$^{12}$;

wherein each $C_{1-6}$ alkyl substituent of Ring B is optionally and independently substituted with one or more independently selected halogen substituents;

each R$^2$ is independently hydrogen, $C_{1-6}$ alkyl, —OR$^{17}$, or $C_{3-6}$ cycloalkyl, wherein each $C_{1-6}$ alkyl and $C_{3-6}$ cycloalkyl is optionally and independently substituted with one or more substituents independently selected from the group consisting of halogen, —CN, —NO₂, —C(O)R¹⁷, —N(R¹⁷)₂, —OR¹⁷, and =O;

each R³ is independently hydrogen, $C_{1-6}$ alkyl, —OR¹⁷, or $C_{3-6}$ cycloalkyl, wherein each $C_{1-6}$ alkyl and $C_{3-6}$ cycloalkyl is optionally and independently substituted with one or more substituents independently selected from the group consisting of halogen, —CN, —NO₂, —C(O)R¹⁷, —N(R¹⁷)₂, —OR¹⁷, and =O; and m is 1.

25. The compound of claim 1, or a pharmaceutically acceptable salt thereof, wherein

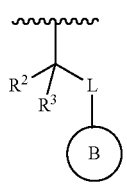

is:

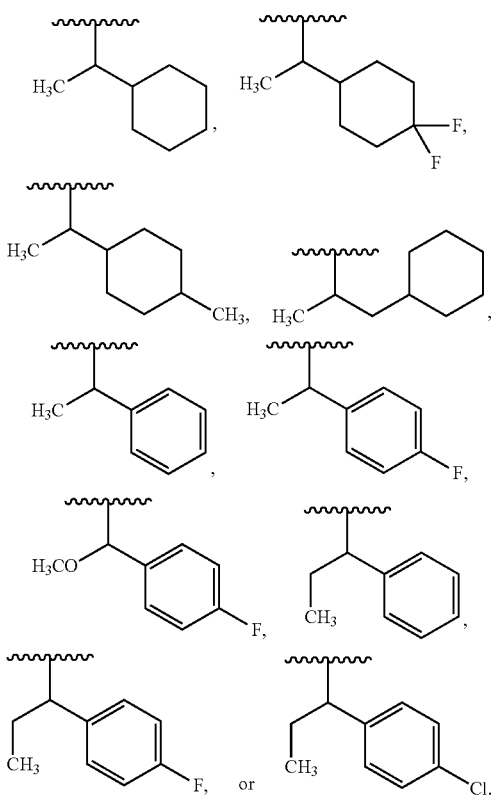

26. The compound of claim 1, or a pharmaceutically acceptable salt thereof, wherein:

L is absent; and m is 0.

27. The compound of claim 1, wherein the compound is:

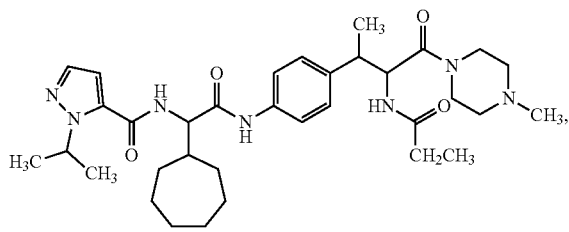 [SMILES: CCC(=O)NC(C(=O)N1CCN(C)CC1)C(C)c1ccc(NC(=O)C(NC(=O)c2ccnn2C(C)C)C2CCCCCC2)cc1]

or a pharmaceutically acceptable salt thereof.

28. The compound of claim 1, wherein the compound is:

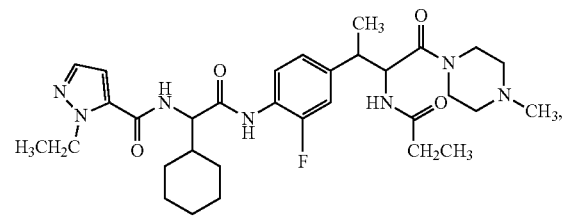

or a pharmaceutically acceptable salt thereof.

29. The compound of claim 1, wherein the compound is:

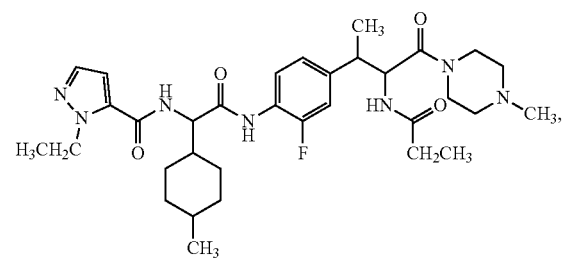

or a pharmaceutically acceptable salt thereof.

30. The compound of claim 1, wherein the compound is:

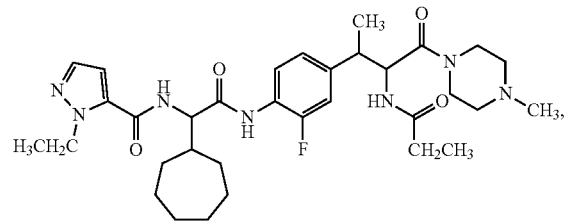

or a pharmaceutically acceptable salt thereof.

31. The compound of claim 1, wherein the compound is:

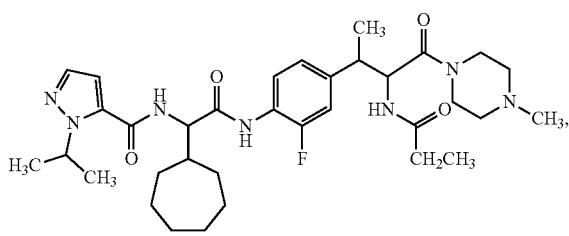 [SMILES: CCC(=O)NC(C(=O)N1CCN(C)CC1)C(C)c1ccc(NC(=O)C(NC(=O)c2ccnn2C(C)C)C2CCCCCC2)c(F)c1]

or a pharmaceutically acceptable salt thereof.

32. The compound of claim 1, wherein the compound is:

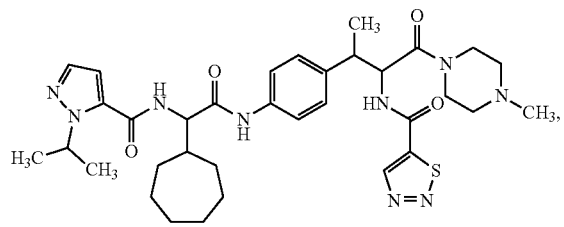 [SMILES: CC(c1ccc(NC(=O)C(NC(=O)c2ccnn2C(C)C)C2CCCCCC2)cc1)C(NC(=O)c1cnns1)C(=O)N1CCN(C)CC1]

or a pharmaceutically acceptable salt thereof.

33. The compound of claim 1, wherein the compound is:

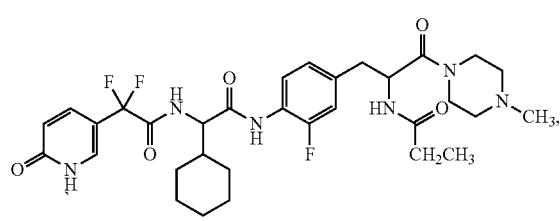

or a pharmaceutically acceptable salt thereof.

34. The compound of claim 1, wherein the compound is:

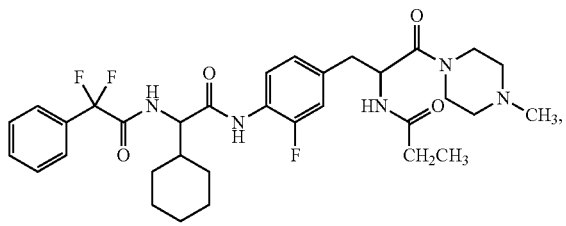 [SMILES: CCC(=O)NC(Cc1ccc(NC(=O)C(NC(=O)C(F)(F)c2ccccc2)C2CCCCC2)c(F)c1)C(=O)N1CCN(C)CC1]

or a pharmaceutically acceptable salt thereof.

35. The compound of claim 1, wherein the compound is:

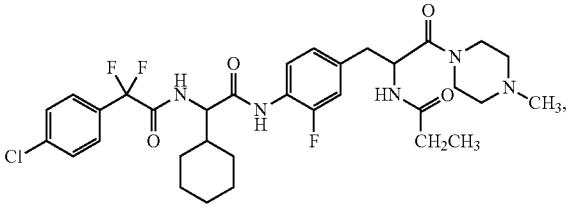 [SMILES: CCC(=O)NC(Cc1ccc(NC(=O)C(NC(=O)C(F)(F)c2ccc(Cl)cc2)C2CCCCC2)c(F)c1)C(=O)N1CCN(C)CC1]

or a pharmaceutically acceptable salt thereof.

36. The compound of claim 1, wherein the compound is:

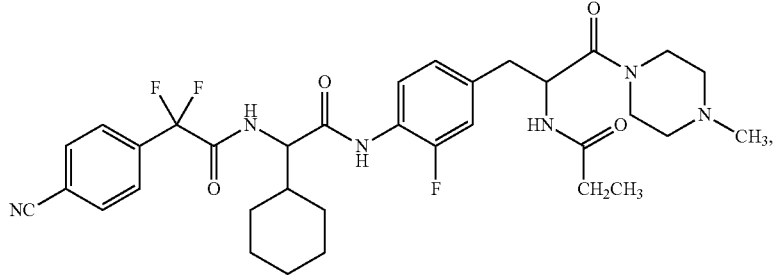 [SMILES: CCC(=O)NC(Cc1ccc(NC(=O)C(NC(=O)C(F)(F)c2ccc(C#N)cc2)C2CCCCC2)c(F)c1)C(=O)N1CCN(C)CC1]

or a pharmaceutically acceptable salt thereof.

37. The compound of claim 1, wherein the compound is:

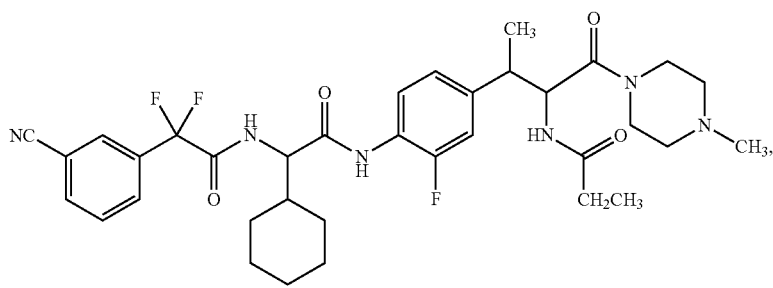 [SMILES: CCC(=O)NC(C(=O)N1CCN(C)CC1)C(C)c1ccc(NC(=O)C(NC(=O)C(F)(F)c2cccc(C#N)c2)C2CCCCC2)c(F)c1]

or a pharmaceutically acceptable salt thereof.

38. The compound of claim 1, wherein the compound is:

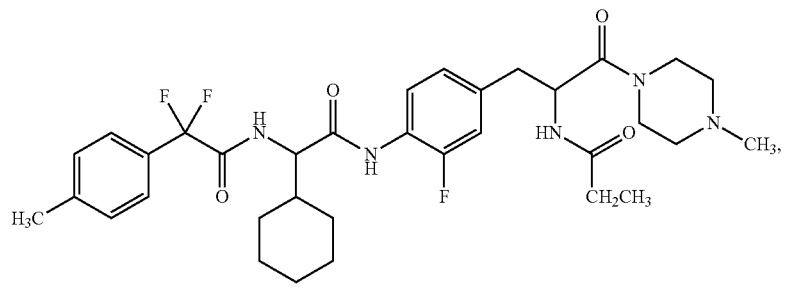 [SMILES: CCC(=O)NC(Cc1ccc(NC(=O)C(NC(=O)C(F)(F)c2ccc(C)cc2)C2CCCCC2)c(F)c1)C(=O)N1CCN(C)CC1]

or a pharmaceutically acceptable salt thereof.

39. The compound of claim 1, wherein the compound is:

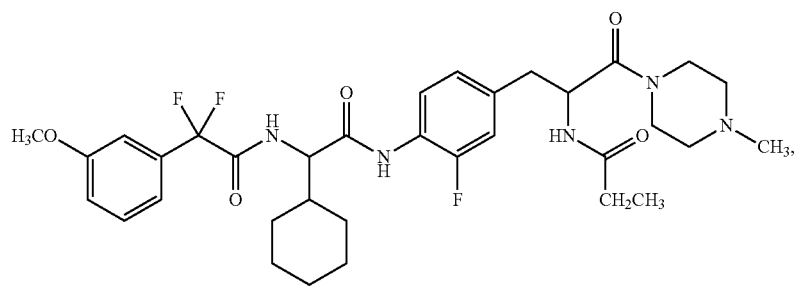 [SMILES: CCC(=O)NC(Cc1ccc(NC(=O)C(NC(=O)C(F)(F)c2cccc(OC)c2)C2CCCCC2)c(F)c1)C(=O)N1CCN(C)CC1]

or a pharmaceutically acceptable salt thereof.

40. The compound of claim 1, wherein the compound is:

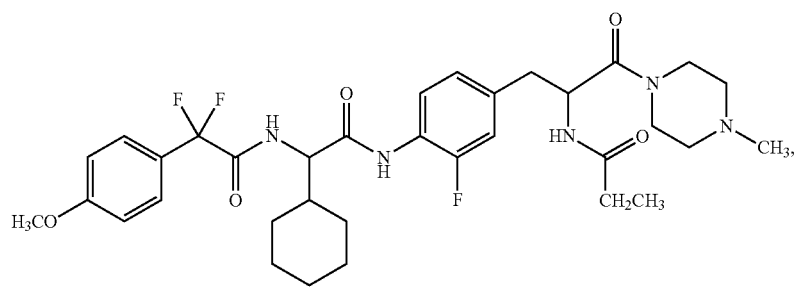 [SMILES: CCC(=O)NC(Cc1ccc(NC(=O)C(NC(=O)C(F)(F)c2ccc(OC)cc2)C2CCCCC2)c(F)c1)C(=O)N1CCN(C)CC1]

or a pharmaceutically acceptable salt thereof.

41. The compound of claim 1, wherein the compound is:

42. The compound of claim 1, wherein the compound is:

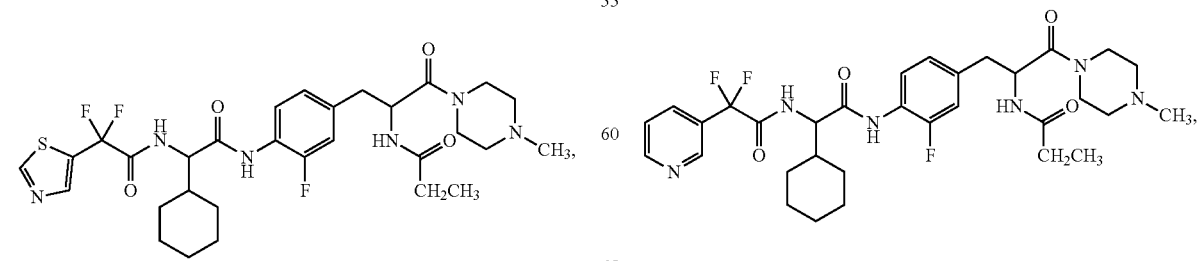

or a pharmaceutically acceptable salt thereof.

or a pharmaceutically acceptable salt thereof.

43. The compound of claim 1, wherein the compound is:

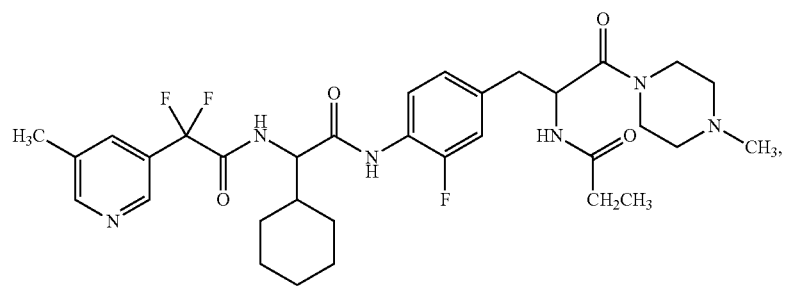 [SMILES: CCC(=O)NC(Cc1ccc(NC(=O)C(NC(=O)C(F)(F)c2cncc(C)c2)C2CCCCC2)c(F)c1)C(=O)N1CCN(C)CC1]

or a pharmaceutically acceptable salt thereof.

44. The compound of claim 1, wherein the compound is:

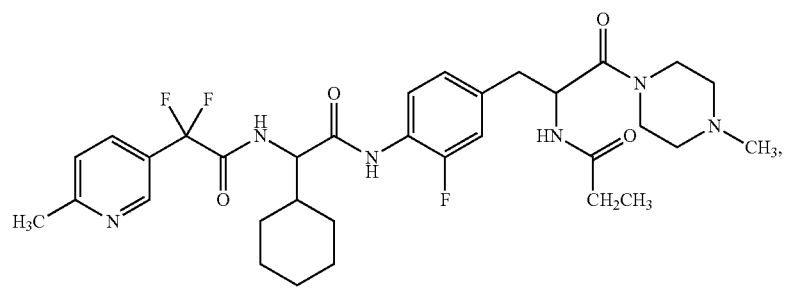 [SMILES: CCC(=O)NC(Cc1ccc(NC(=O)C(NC(=O)C(F)(F)c2ccc(C)nc2)C2CCCCC2)c(F)c1)C(=O)N1CCN(C)CC1]

or a pharmaceutically acceptable salt thereof.

45. The compound of claim 1, wherein the compound is:

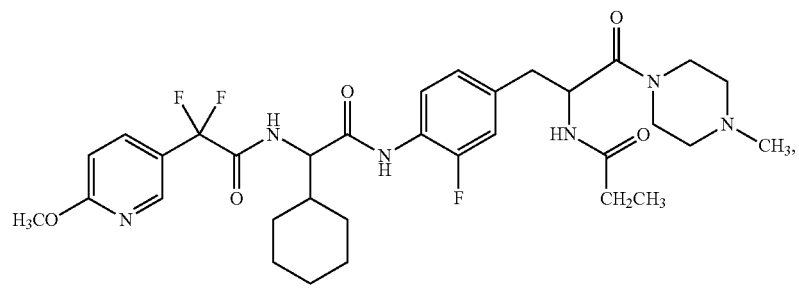 [SMILES: CCC(=O)NC(Cc1ccc(NC(=O)C(NC(=O)C(F)(F)c2ccc(OC)nc2)C2CCCCC2)c(F)c1)C(=O)N1CCN(C)CC1]

or a pharmaceutically acceptable salt thereof.

46. The compound of claim 1, wherein the compound is:

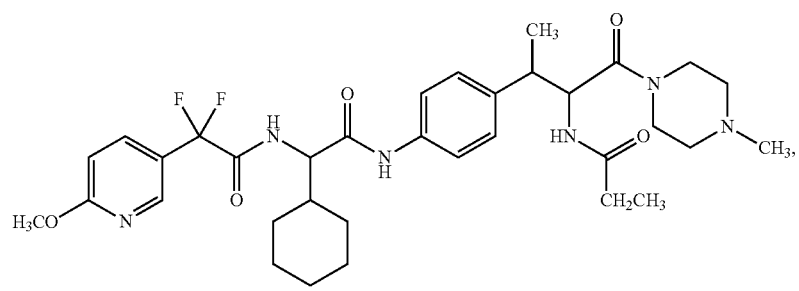 [SMILES: CCC(=O)NC(C(=O)N1CCN(C)CC1)C(C)c1ccc(NC(=O)C(NC(=O)C(F)(F)c2ccc(OC)nc2)C2CCCCC2)cc1]

or a pharmaceutically acceptable salt thereof.

47. The compound of claim 1, wherein the compound is:

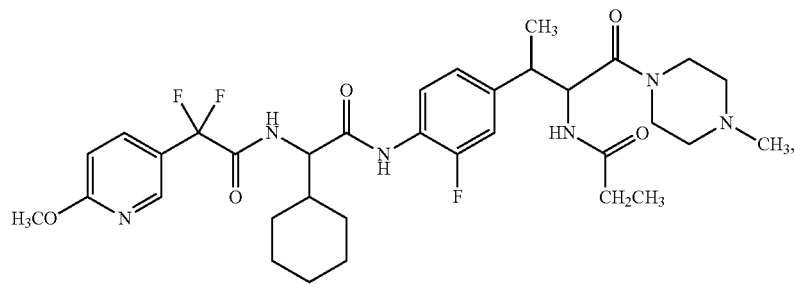 [SMILES: CCC(=O)NC(C(=O)N1CCN(C)CC1)C(C)c1ccc(NC(=O)C(NC(=O)C(F)(F)c2ccc(OC)nc2)C2CCCCC2)c(F)c1]

15 or a pharmaceutically acceptable salt thereof.

48. The compound of claim 1, wherein the compound is:

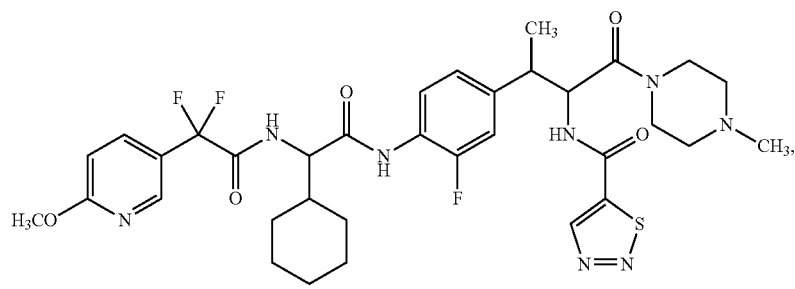 [SMILES: COc1ccc(C(F)(F)C(=O)NC(C(=O)Nc2ccc(C(C)C(NC(=O)c3cnns3)C(=O)N3CCN(C)CC3)cc2F)C2CCCCC2)cn1]

30 or a pharmaceutically acceptable salt thereof.

49. The compound of claim 1, wherein the compound is:

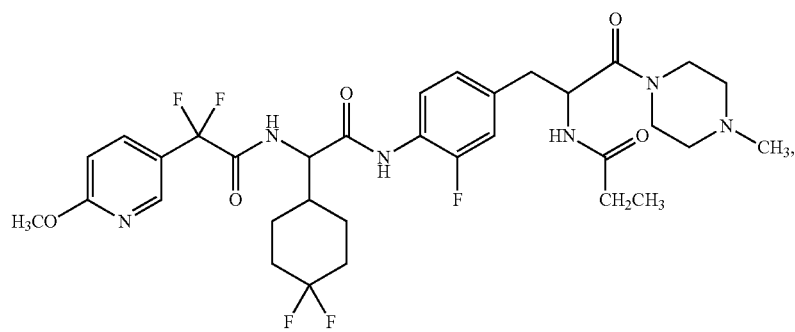 [SMILES: CCC(=O)NC(Cc1ccc(NC(=O)C(NC(=O)C(F)(F)c2ccc(OC)nc2)C2CCC(F)(F)CC2)c(F)c1)C(=O)N1CCN(C)CC1]

or a pharmaceutically acceptable salt thereof.

50. The compound of claim 1, wherein the compound is:

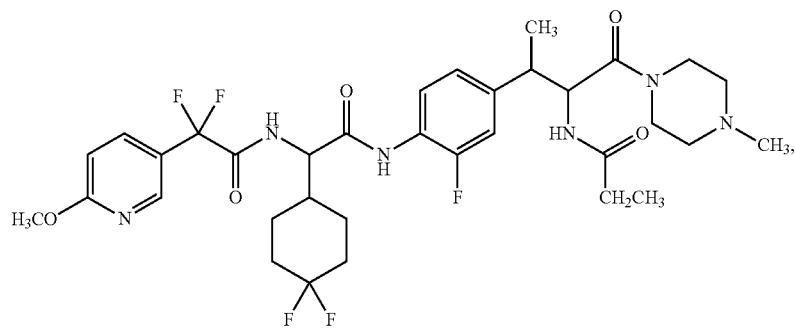 [SMILES: CCC(=O)NC(C(=O)N1CCN(C)CC1)C(C)c1ccc(NC(=O)C(NC(=O)C(F)(F)c2ccc(OC)nc2)C2CCC(F)(F)CC2)c(F)c1]

or a pharmaceutically acceptable salt thereof.

51. The compound of claim 1, wherein the compound is:

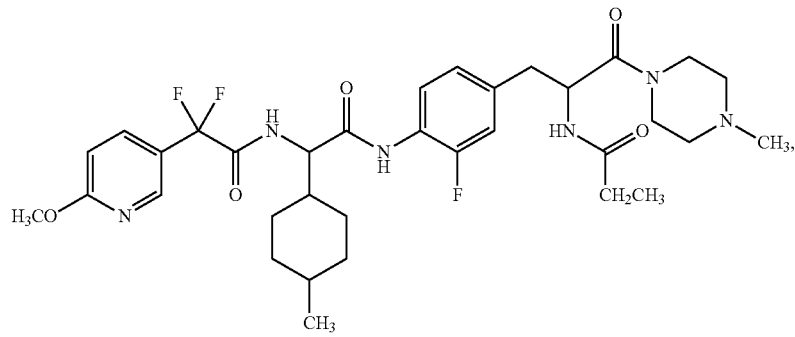 [SMILES: CCC(=O)NC(Cc1ccc(NC(=O)C(NC(=O)C(F)(F)c2ccc(OC)nc2)C2CCC(C)CC2)c(F)c1)C(=O)N1CCN(C)CC1]

or a pharmaceutically acceptable salt thereof.

52. The compound of claim 1, wherein the compound is:

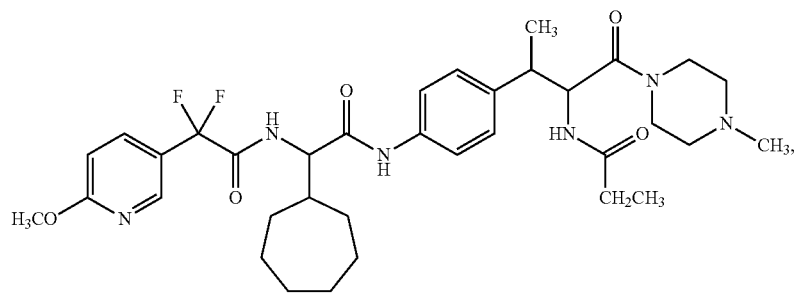 [SMILES: CCC(=O)NC(C(=O)N1CCN(C)CC1)C(C)c1ccc(NC(=O)C(NC(=O)C(F)(F)c2ccc(OC)nc2)C2CCCCCC2)cc1]

or a pharmaceutically acceptable salt thereof.

53. The compound of claim 1, wherein the compound is:

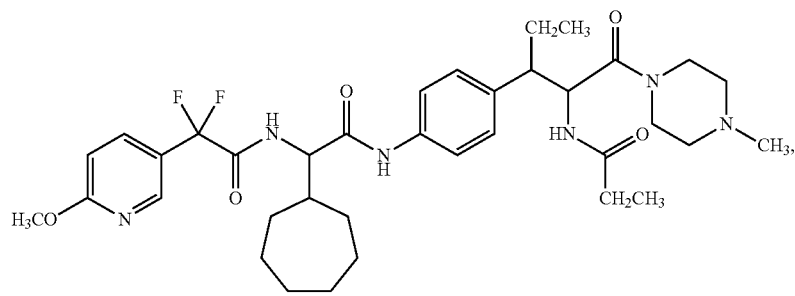 [SMILES: CCC(=O)NC(C(=O)N1CCN(C)CC1)C(CC)c1ccc(NC(=O)C(NC(=O)C(F)(F)c2ccc(OC)nc2)C2CCCCCC2)cc1]

or a pharmaceutically acceptable salt thereof.

54. The compound of claim 1, wherein the compound is:

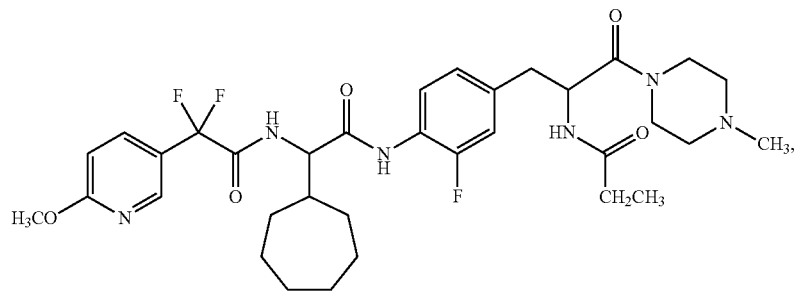 [SMILES: CCC(=O)NC(Cc1ccc(NC(=O)C(NC(=O)C(F)(F)c2ccc(OC)nc2)C2CCCCCC2)c(F)c1)C(=O)N1CCN(C)CC1]

or a pharmaceutically acceptable salt thereof.

55. The compound of claim 1, wherein the compound is:

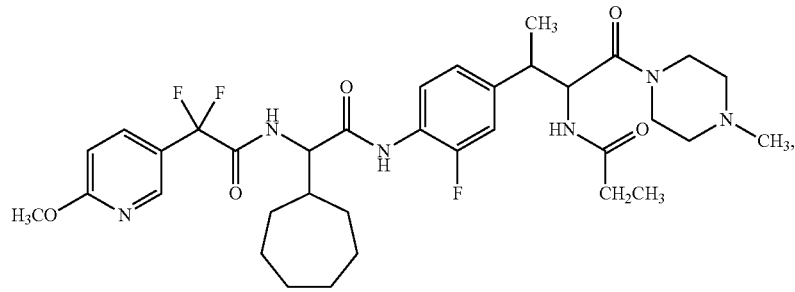 [SMILES: CCC(=O)NC(C(=O)N1CCN(C)CC1)C(C)c1ccc(NC(=O)C(NC(=O)C(F)(F)c2ccc(OC)nc2)C2CCCCCC2)c(F)c1]

or a pharmaceutically acceptable salt thereof.

56. A pharmaceutical composition comprising a pharmaceutically acceptable excipient and the compound of claim 1, or a pharmaceutically acceptable salt thereof.

57. A method of inhibiting interleukin-17A activity in a subject in need thereof, wherein the method comprises administering to the subject a compound of claim 1, or a pharmaceutically acceptable salt thereof, or the pharmaceutical composition of claim 56.

58. A method of treating an inflammatory disease or an inflammatory condition in a subject in need thereof, wherein the method comprises administering to the subject a compound of claim 1, or a pharmaceutically acceptable salt thereof, or the pharmaceutical composition of claim 56.

59. The method of claim 58, wherein the inflammatory disease or the inflammatory condition is selected from the group consisting of ankylosing spondylitis, aspsoriatic arthritis, erythrodermic psoriasis, guttate psoriasis, hidradenitis suppurutiva, inverse psoriasis, non-infectious uveitis, palmoplantar psoriasis, plaque psoriasis, pustular psoriasis, rheumatoid arthritis, and spondyloarthritis.

60. The method of claim 59, wherein the inflammatory disease or the inflammatory condition is selected from the group consisting of erythrodermic psoriasis, guttate psoriasis, inverse psoriasis, plaque psoriasis, and pustular psoriasis.

* * * * *